(12) United States Patent
Turner et al.

(10) Patent No.: US 6,248,739 B1
(45) Date of Patent: Jun. 19, 2001

(54) QUINOLINECARBOXAMIDES AS ANTIVIRAL AGENTS

(75) Inventors: Steven Ronald Turner, Kalamazoo; Joseph Walter Strohbach, Mendon; Suvit Thaisrivongs, Kalamazoo; Valerie A. Vaillancourt, Kalamazoo; Mark E. Schnute, Kalamazoo, all of MI (US); John Alan Tucker, South San Francisco, CA (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/466,712

(22) Filed: Dec. 17, 1999

Related U.S. Application Data

(60) Provisional application No. 60/140,610, filed on Jun. 23, 1999, and provisional application No. 60/115,301, filed on Jan. 8, 1999.

(51) Int. Cl.[7] .......... A61K 31/535; A61K 31/47; C07D 413/00; C07D 215/16
(52) U.S. Cl. .......... 514/235.2; 514/312; 544/128; 546/157
(58) Field of Search .......... 546/157; 514/312, 514/235.2; 544/128

(56) References Cited

U.S. PATENT DOCUMENTS 5,753,666 * 5/1998 Beasley .................. 514/258
5,891,878 * 4/1999 Beasley .................. 514/247

FOREIGN PATENT DOCUMENTS

| 2-124871 | 5/1990 | (JP) | .............. C07D/213/81 |
| WO97/04779 | 2/1997 | (WO) | .............. A61K/31/47 |
| WO98/11073 | 3/1998 | (WO) | .............. C07D/215/48 |

OTHER PUBLICATIONS

J. Med. Chem. 1993,36,1580–1596—3–Quinolinecarboxamides. A Series of Novel Orally–Active Antiherpetic Agents.

* cited by examiner

*Primary Examiner*—D. Margaret Seaman
(74) *Attorney, Agent, or Firm*—Lucy X. Yang

(57) ABSTRACT

The present invention provides a compound of formula I

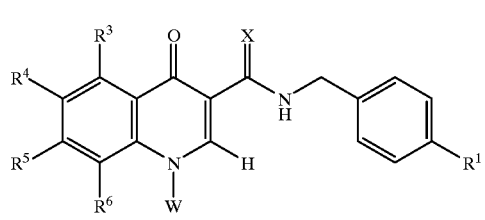

which is useful as antiviral agents, in particular, as agents against viruses of the herpes family.

81 Claims, No Drawings

QUINOLINECARBOXAMIDES AS ANTIVIRAL AGENTS

CROSS REFERENCE TO RELATED APPLICATIONS

This application claims the benefit of the following provisional applications: U.S. Ser. No. 60/140,610, filed Jun. 23, 1999; and U.S. Ser. No. 60/115,301, filed Jan. 8, 1999, under 35 USC §119(e)(1).

FIELD OF THE INVENTION

The present invention provides 4-oxo-1,4-dihydro-3-quinolinecarboxamide derivatives. These compounds are useful as antiviral agents, in particular, as agents against viruses of the herpes family.

BACKGROUND OF THE INVENTION

The herpesviruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), epstein-Barr virus (EBV), and human herpes viruses 6, 7, and 8 (HHV-6, HHV-7, and (HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causitive agent of chicken pox and shingles. EBV causes infectious mononucleosis. It can also cause lymphomas in immunocompromised patients and has been associated with Burkitt's lymphoma, nasopharyngeal carcinoma, and Hodgkins disease. HHV-6 is the causitive agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

Compounds of the present invention are distinct from other hydroxyquinoline antiviral agents in that the 4-substituent on the benzyl amide of the present invention (i.e. the chloro, bromo, cyano, or nitro substituent) provides significantly improved antiviral activity. Certain compounds of formula (I) also possess unique substituents $R^4$ that provide improved antiviral activity.

INFORMATION DISCLOSURE

U.S. Pat. No. 5,891,878 and WO 97/04775 disclose compounds that are reported to be useful in the treatment of a disease state capable of being modulated by inhibition of production of phosphodiesterase IV or tumor necrosis factor. The genera of compounds disclosed in these applications are believed to overlap with the compounds of formula I disclosed herein. However, no specific compounds are prepared in these PCT applications having the 4-substitutedbenzamide group of the compounds of formula I herein.

U.S. Pat. No. 3,960,868 discloses derivatives of 6, 7, or 8 cycloalkyl-4-oxoquinoline-3-carboxylic acid that are reported to possess analgesic, anti-inflammatory, anti-microbial, and histamine liberating properties. The structure of these compounds differs from the structure of the compounds of formula I by requiring a cycloalkyl substituent at the 6, 7, or 8 position of the quinoline ring.

U.S. Pat. No. 4,959,363 discloses quinolonecarboxamide compounds that are reported to possess antiviral activity. The structure of these compounds differs from the structure of the compounds of formula I disclosed herein at the 3-position by not including a 4-substitutedbenzamide, and at the 6-position by requiring a hydrogen or fluoro substituent.

U.S. Pat. No. 5,175,151, discloses quinolone compounds that are reported to possess antihypertensive and antiviral activity. The structure of these compounds differs from the structure of the compounds of formula I disclosed herein at the 3-position by not including a 4-substitutedbenzamide, and at the 2-position by requiring an oxygen linked substituent.

U.K. Patent Application 1,191,443 discloses quinoline derivatives that are reported to possess antiviral activity. The structure of these compounds differs from the structure of the compounds of formula I disclosed herein by not including a 4-substitutedbenzamide at the 3-position, and by requiring a fused furan heterocyclic ring at the 5,6-, 6,7-, or 7,8-position of the quinolone.

WO 97/14682 discloses quinoline derivatives that are reported to be useful to treat specific hormone dependent diseases. The structure of these compounds differs from the structure of the compounds of formula I disclosed herein at the 3-position by not including a 4-substitutedbenzamide, at the 1-position, by requiring a halogenoaralkyl, and at the 7-position by requiring an acylaminoaryl group.

U.S. Pat. No. 4,786,644, discloses 1-aryl-3-quinolinecarboxamides that are reported to be useful to treat pain and inflammation. The structure of these compounds differs from the structure of the compounds of formula I disclosed herein at the 3-position by not including a 4-substitutedbenzamide, and at the 1-position by requiring an optionally substituted phenyl substituent.

U.S. Pat. No. 4,835,163, discloses N-alkoxyalkyl derivatives of quinolone carboxamides that are reported to possess anticonvulsive and psychotonic activity. The structure of these compounds differs from the structure of the compounds of formula I disclosed herein at the 3-position by not including a 4-substitutedbenzamide substituent.

U.S. Pat. No. 5,096,901; U.K. Application Number 2 236 751; and T. J. Ward et al., Med. Chem. Res. (1993), 4, 267–272 disclose quinolone-3-(azabicyclo)carboxamides that are reported to possess 5-HT3 activity and to be useful to treat neuro-psychiatric disorders. The structure of these compounds differs from the structure of the compounds of formula I disclosed herein by requiring an azabicyclo containing substituent at the 3-position.

JP 02124871 discloses quinolone compounds that are reported to possess 5-lipoxygenase activity. The structure of these compounds differs from the structure of the compounds of formula I disclosed herein at the 3-position by not including a 4-substitutedbenzamide substituent.

EP 0 332 930A2, discloses quinolone compounds that are reported to possess antibacterial antiviral activity. The structure of these compounds differs from the structure of the compounds of formula I disclosed herein at the 3-position by not including a 4-substitutedbenzamide, and at the 6-position by requiring a hydrogen, halo, or nitro substituent.

Chem. Abstracts (1969), 71, 101735q, discloses quinolone compounds that are reported to possess antiinflamatory activity. The structure of these compounds differs from the structure of the compounds of formula I disclosed herein at the 3-position by not including a 4-substitutedbenzamide substituent.

U.S. Pat. Nos. 5,051,418 and 4,908,366, disclose 8-cyano-quinolone compounds that are reported to possess antibacterial activity. The structure of these compounds differs from the structure of the compounds of formula I disclosed herein at the 3-position by not including a 4-substitutedbenzamide, and at the 8-position by requiring a cyano substituent.

EP 0 370 686, discloses a process for preparing quinolone carboxylic acid intermediates. The structure of the disclosed compounds differs from the structure of the compounds of formula I disclosed herein at the 3-position by not including a 4-substitutedbenzamide, and at the 6-position by requiring a fluoro substituent.

U.S. Pat. No. 4,621,088, discloses quinolone amino acid derivatives that are reported to possess antiallergic activity, central nervous system activity and cardiovascular activity. The structure of these compounds differs from the structure of the compounds of formula I disclosed herein at the 3-position by not including a 4-substitutedbenzamide.

U.S. Pat. No. 5,328,887 discloses an array of compounds including numerous quinolone compounds that are reported to be useful as fluorescent donor elements for use in a thermal transfer possess. The single specific 4-quinolone compound prepared and tested in the application differs from the compounds of formula I disclosed herein at the 3-position by not including a 4-substitutedbenzamide, at the 2-position by having a phenyl substituent, at the 6-position by having a hydrogen, and at the 1-position by being unsubstituted.

U.S. Pat. No. 4,855,291, discloses quinolone compounds that are reported to possess antihypertensive activity. The structure of these compounds differs from the structure of the compounds of formula I disclosed herein at the 3-position by not including a 4-substitutedbenzamide.

U.S. Pat. No. 3,524,858, discloses quinolone compounds that are reported to possess anti-microbial activity. The structure of these compounds differs from the structure of the compounds of formula I disclosed herein at the 3-position by not including a 4-substitutedbenzamide, and at the 6,7-positions by requiring a methylenedioxy substituent.

WO 98/23608 discloses quinolone compounds that are reported to possess integrin antagonist activity. The structure of these compounds differs from the structure of the compounds of formula I disclosed herein at the 3-position by not including a 4-substitutedbenzamide.

U.S. Pat. No. 5,026,856, discloses isoindoline compounds that are reported to possess antibacterial activity. The structure of these compounds differs from the structure of the compounds of formula I disclosed herein at the 3-position by not including a 4-substitutedbenzamide, and at the 6-position by requiring a halo, hydroxy, or loweralkoxy substituent.

U.S. Pat. No. 5,563,141, discloses an array of compounds that are reported to inhibit cell adhesion. Although the disclosed genus of compounds may include 3aminocarbonyl-4-quinolones, these compounds do not comprise a 4-substituted-benzamide at the 3-position. All of final compounds specifically prepared in the patent comprise a 4-pyridyl(piperazin-1-yl) ring system.

WO 9932450 discloses compounds of the following generic formula which are useful for the treatment of herpesvirus infections.

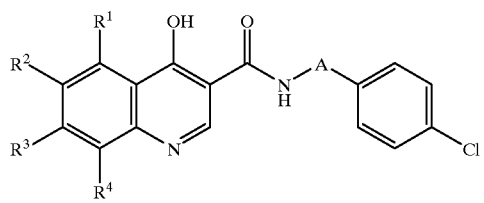

Liebigs Ann. Chem. 1987, 871–879 describes the synthesis of the following structure through the combination of an aryl acid chloride and a β-hydrazidoalkenyl amide.

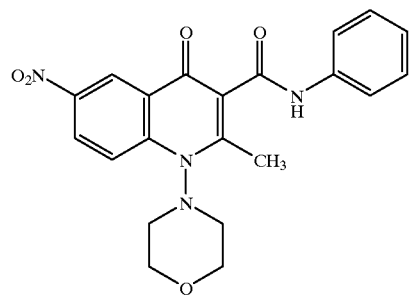

EP 343560 discloses antibacterial agents having the following structure.

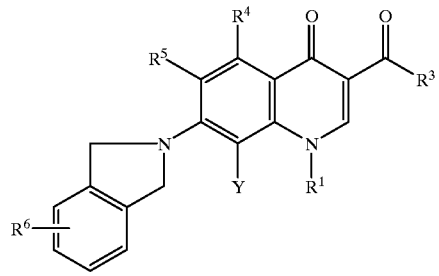

JP 02040379 discloses compounds useful as antibacterials having generic structure.

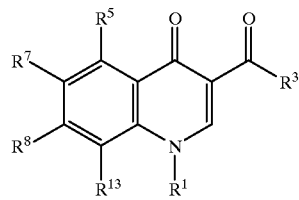

U.S. Pat. No. 5,412,104 discloses the following generic structure as being useful as antiviral agents against DNA containing viruses such as herpes group viruses.

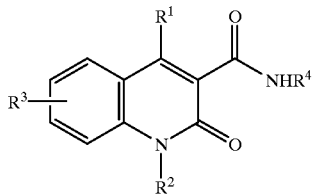

SUMMARY OF THE INVENTION

The present invention provides a compound of formula I,

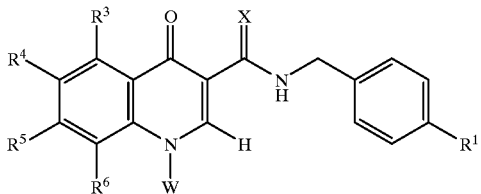

or a pharmaceutically acceptable salt thereof wherein,

X is
a) O, or
b) S;

W is
a) $R^2$;
b) $NR^7R^8$,
c) $OR^9$, or
d) $SO_tR^9$;

$R^1$ is
a) Cl,
b) F,
c) Br,
d) CN, or
e) $NO_2$;

$R^2$ is
a) $(CH_2CH_2O)_mR^{10}$,
b) het, wherein said het is bonded via a carbon atom,
c) $C_{1-7}$ alkyl which may be partially unsaturated and is optionally substituted by one or more substituents selected from a group consisting of $NR^7R^8$, $R^{11}$, CN, $SO_tR^9$, or $OC_{2-4}$ alkyl which is further substituted by het, $OR^{10}$, OC(=O)aryl, or $NR^7R^8$, or
d) $C_{3-8}$ cycloalkyl, which may be partially unsaturated and is optionally substituted by $R^{11}$, $NR^7R^8$, $SO_tR^9$, or $C_{1-7}$ alkyl optionally substituted by $R^{11}$, $NR^7R^8$, or $SO_tR^9$;

$R^3$ is
a) H,
b) halo, or
c) $C_{1-4}$ alkyl, optionally substituted by one to three halo;

$R^4$ is
a) H,
b) aryl,
c) het,
d) $SO_2NHR^{12}$,
e) $CONHR^{12}$,
f) $NR^7R^8$,
g) $NHCOR^{12}$,
h) $NHSO_2R^{12}$,
i) $OC_{2-7}$ alkyl optionally substituted by —OH,
j) $SC_{2-7}$ alkyl optionally substituted by OH, or
k) $C_{1-8}$ alkyl which may be partially unsaturated and is optionally substituted by one or more substituents selected from a group consisting of $N_3$, $OR^{10}$, $NR^7R^8$, halo, $SO_tR^9$, $OR^{13}$ or $R^{11}$;

$R^5$ is
a) H,
b) halo,
c) $C{\equiv}CR^{14}$,
d) $NR^7R^8$,
e) $SO_2NHR^{12}$,
f) het, or
g) $C_{1-7}$ alkyl, optionally substituted by OH;

$R^6$ is
a) H,
b) halo,
c) $SC_{1-7}$ alkyl,
d) $C_{1-7}$ alkoxy, optionally substituted by one or more halo or OH, or
e) $C_{1-7}$ alkyl, which may be partially unsaturated and is optionally substituted by halo, $NR^{10}R^{10}$, $(CH_2)_nOR^{13}$, $R^{11}$, $OC_{1-7}$ alkyl which is further substituted with het, $NR^7R^8$, or $SO_tR^9$;

$R^7$ and $R^8$ are independently
a) H,
b) aryl,
c) $C_{1-7}$alkyl which may be partially unsaturated and is optionally substituted by one or more substituents selected from a group consisting of $NR^{10}OR^{10}$, $CONR^{10}R^{10}$, $R^{11}$, $SO_tR^9$, halo; or
d) $R^7$ and $R^8$ together with the nitrogen to which they are attached to form a het;

$R^9$ is
a) aryl,
b) het,
c) $C_{3-8}$cycloalkyl, or
d) $C_{1-7}$alkyl which may be partially unsaturated and optionally substituted by one or more $OR^{10}$, Oaryl, het, aryl, $NR^{10}R^{10}$, CN, SH, $SO_tC_{1-6}$ alkyl, $SO_t$aryl, halo, or $CONR^{10}R^{10}$;

$R^{10}$ is
a) H, or
b) $C_{1-7}$ alkyl, optionally substituted by OH;

$R^{11}$ is
a) $OR^{10}$,
b) Ohet,
c) Oaryl,
d) $CO_2R^{10}$,
e) het,
f) aryl, or
g) CN;

$R^{12}$ is
a) H,
b) het,
c) aryl,
d) $C_{3-8}$ cycloalkyl, or
e) $C_{1-7}$ alkyl optionally substituted by $NR^7R^8$, or $R^{11}$;

$R^{13}$ is
a) $(P{=}O)(OH)_2$,
b) $(P{=}O)(C_{1-7}$ alkoxy$)_2$,
c) $CO(CH_2)_nCON(CH_3)(CH_2)_nSO_3^-M^+$,
d) an amino acid,
e) C(=O)aryl,
f) C(=O)$C_{1-6}$alkyl, optionally substituted by $NR^{10}R^{10}$, or
g) $CO(CH_2)_nCO_2H$;

$R^{14}$ is
  a) het,
  b) $(CH_2)_nOR^3$, or
  c) $C_{1-7}$ alkyl substituted by one or more substituents selected from a group consisting of $R^{11}$, $OC_{1-7}$ alkyl which is further substituted with het, $NR^7R^8$, or $SO_iR^9$; aryl is a phenyl radical or an ortho-fused bicyclic carbocyclic radical wherein at least one ring is aromatic;
    het is a four- (4), five- (5), six- (6), or seven- (7) membered saturated or unsaturated heterocyclic ring having 1, 2, or 3 heteroatoms selected from the group consisting of oxygen, sulfur, and nitrogen, which is optionally fused to a benzene ring, or any bicyclic heterocycle group;
    wherein any aryl is optionally substituted with one or more substituents selected from the group consisting of halo, OH, $CF_3$, $C_{1-6}$alkoxy, and $C_{1-6}$ alkyl which maybe further substituted by one to three $SR^{10}$, $NR^{10}R^{10}$, $OR^{10}$, or $CO_2R^{10}$;
    wherein any het is optionally substituted with one or more substituents selected from the group consisting of halo, OH, $CF_3$, $C_{1-6}$alkoxy, oxo, oxine, and $C_{1-6}$ alkyl which maybe further substituted by one to three $SR^{10}$, $NR^{10}R^{10}$, $OR^{10}$, or $CO_2R^{10}$;
    i is 0, 1, or 2;
    m is 1, 2, or 3;
    n is 1, 2, 3, 4, 5, or 6; and
    M is sodium, potassium, or lithium;

With the proviso that $R^1$ is not Cl, Br, F, or CN; when X is O;
  $R^2$ is $C_{1-7}$ alkyl optionally substituted by $R^{15}$;
  $R^3$ is H, methyl, or halo;
  $R^4$ is H, $CONH(C_{1-7}alkyl)$, $NR^{16}R^{17}$, or $C_{1-7}$ alkyl optionally substituted by $OR^{10}$, CN, COOH, or $NR^{16}R^{17}$;
  $R^5$ is H, halo, $SO_2NHR^{10}$, $NR^{16}R^{17}$, or $C_{1-7}$ alkyl optionally substituted by $OR^{10}$;
  $R^6$ is H, halo, $C_{1-7}$ alkoxy, or $C_{1-7}$ alkyl optionally substituted by halo, $OR^{10}$, $CO_2R^{10}$ or $NR^{16}R^{17}$;
  $R^{15}$ is $NR^{16}R^{17}$, $OR^{10}$, CN, or $CO_2R^{10}$; and
  $R^{16}$ and $R^{17}$ are independently H or $C_{1-7}$alkyl; or $NR^{16}R^{17}$ together with the nitrogen to which they are attached form a 5- or 6-membered ring such as pyrrolidine, piperidine, morpholine, or piperazine.

In another aspect, the present invention also provides:
a pharmaceutical composition comprising a compound of formula I, or a pharmaceutically acceptable salt thereof, and a pharmaceutically acceptable carrier,
a method of treating or preventing a herpesviral infection, comprising administering to a mammal in need of such treatment, a compound of formula (I) or a pharmaceutically acceptable salt thereof,
a compound of formula (I) or a pharmaceutically acceptable salt thereof for use in medical treatment or prevention of a herpesviral infection,
the use of a compound of formula (I) or a pharmaceutically acceptable salt thereof to prepare a medicament for treating or preventing a herpesviral infection in a mammal, and
a method for inhibiting a viral DNA polymerase, comprising contacting (in vitro or in vivo) the polymerase with an effective inhibitory amount of a compound of formula I, or a pharmaceutically acceptable salt thereof.

The invention also provides novel intermediates and processes disclosed herein that are useful for preparing compounds of formula I.

DETAILED DESCRIPTION OF THE INVENTION

The following definitions are used, unless otherwise described. Halo denotes fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

Aryl denotes a phenyl radical or an ortho-fused bicyclic carbocyclic radical wherein at least one ring is aromatic. Aryl is optionally substituted with one or more substituents selected from the group consisting of halo, OH, $CF_3$, $C_{1-6}$alkoxy, and $C_{1-6}$ alkyl which maybe further substituted by one to three $SR^{10}$, $NR^{10}R^{10}$, $OR^{10}$, or $CO_2R^{10}$;

Het denotes a four- (4), five- (5), six- (6), or seven- (7) membered saturated or unsaturated heterocyclic ring having 1, 2, or 3 heteroatoms selected from the group consisting of oxygen, sulfur, and nitrogen, which is optionally fused to a benzene ring, or any bicyclic heterocycle group. Het is optionally substituted with one or more substituents selected from the group consisting of halo, OH, $CF_3$, $C_{1-6}$alkoxy, oxo, oxine, and $C_{1-6}$ alkyl which maybe further substituted by one to three $SR^{10}$, $NR^{10}R^{10}$, $OR^{10}$, or $CO_2R^{10}$;

"Amino acid," includes a residue of natural amino acid (e.g. Ala, Arg, Asn, Asp, Cys, Glu, Gln, Gly, His, Hyl, Hyp, Ile, leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, -methyl-alanine, para-benzoylphenylalanine, phenylglycine, propargylglycine, sarcosine, and tert-butylglycine). An amino acid can conveniently be linked to the remainder of a compound of formula I through the carboxy terminus, the amino terminus, or through any other convenient point of attachment, such as, for example, through the sulfur of cysteine. In particular, an amino acid can conveniently be linked to the remainder of a compound of formula I through the carboxy terminus.

Mammal denotes human and animals.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents Specifically, alkyl can be methyl, ethyl, propyl, isopropyl, butyl, iso-butyl, sec-butyl, pentyl, 3-pentyl, hexyl, heptyl, etc.; $C_{3-8}$cycloalkyl can be cyclopropyl, cyclobutyl, cyclopentyl, cyclohexyl, cycloheptyl, or cyclooctyl; alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; het can be azetidinyl, 3,3-dihydroxy-1-azetinyl, pyrrolidino, piperidino, morpholino, thiomorpholino, or heteroaryl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R^1$ is Cl.

A specific value for $R^1$ is F.

A specific value for $R^1$ is CN, or $NO_2$.

A specific value for $R^2$ is $(CH_2CH_2O)_mH$, or $(CH_2CH_2)_mC_{1-4}$ alkyl, wherein m is 2, or 3.

A specific value for $R^2$ is $C_{3-8}$cycloalkyl optionally substituted by $R^{11}$, $NR^7R^8$, $SO_iR^9$, or $C_{1-7}$ alkyl optionally substituted by $R^{11}$, $NR^7R^8$, or $SO_iR^9$; wherein $R^7$, $R^8$, $R^9$, $R^{11}$ and i are the same as defined above.

A specific value for $R^2$ is cyclopropyl.

A specific value for $R^2$ is het wherein said het is bonded via a carbon atom and is the same as defined above.

A specific value for $R^2$ is tetrahydro-2H-pyranyl, piperdinyl, 1-methyl-piperidinyl, or 1,1-dioxo-tetrahydro-2H-thiopyran.

A specific value for $R^2$ is $C_{2-7}$ alkyl which is partially unsaturated and optionally substituted by $NR^7R^8$, $R^{11}$, $SO_iR^9$, or $OC_{2-4}$ alkyl which is further substituted by het, $OR^{10}$, or $OC(=O)$aryl; wherein $R^7$, $R^8$, $R^9$, $R^{10}$ are the same as defined above.

A specific value for $R^2$ is (Z or E)-CH=$CHR^{10}$, or —C—C≡$CR^{10}$; wherein said $R^{10}$ is H, or $C_{1-7}$ alkyl optionally substituted by OH.

A specific value for $R^2$ is $C_{1-7}$ alkyl substituted by $NR^7R^8$, $R^{11}$, $SO_iR^9$, or $OC_{2-4}$ alkyl which is further substituted by het, $OR^{10}$, or $OC(=O)$aryl wherein $R^7$, $R^8$, $R^9$, $R^{10}$ and $R^{11}$ are the same as defined above.

A specific value for $R^2$ is $C_{1-7}$ alkyl substituted by $OC_{2-4}$ alkyl which is further substituted by het, OH, $OC_{1-4}$ alkyl, or $OC(=O)$aryl.

A specific value for $R^2$ is $C_{1-7}$ alkyl substituted by $SO_iR^9$ wherein $R^9$ and i are the same as defined above.

A specific value for $R^2$ is $C_{1-7}$ alkyl substituted by $SO_iR^9$; wherein $R^9$ is $C_{1-4}$ alkyl, optionally substituted by OH, or $R^9$ is phenyl, optionally substituted by Cl; wherein i is 0, 1, or 2.

A specific value for $R^2$ is methyl.

A specific value for W is $NR^7R^8$, wherein $R^7$ and $R^8$ are the same as defined above.

A specific value for W is $NR^7R^8$, wherein $R^7$ and $R^8$ together with the nitrogen to which they are attached to form a het wherein said het is the same as defined above.

A specific value for W is morpholine, piperidine, pyrrolidine, piperazine, or 4-methyl-piperazine.

A specific value for W is $NR^7R^8$, wherein $R^7$ and $R^8$ are independently H or $C_{1-4}$ alkyl optionally substituted by OH.

A specific value for W is morpholine.

A specific value for W is $OR^9$, or $SO_iR^9$ wherein $R^9$ is $C_{1-6}$alkyl which may be partially unsaturated and optionally substituted by $OR^{10}$, Oaryl, het, aryl, $NR^{10}R^{10}$, CN, $CONR^{10}R^{10}$, or halo; wherein $R^{10}$ is H or $C_{1-4}$ alkyl.

A specific value for $R^3$ is H.

A specific value for is $CF_3$, or halo.

A specific value for $R^4$ is aryl or het.

A specific value for $R^4$ is $SO_2NHR^{12}$, $CONHR^{12}$, $NHCOR^{12}$, or $NHSO_2R^{12}$, wherein $R^{12}$ is the same as defined above.

A specific value for $R^4$ is $C_{2-8}$ alkyl which is partially unsaturated and optionally substituted by $OR^{10}$, $NR^7R^8$, halo, $SO_iR^9$, $OR^{13}$ or $R^{11}$, wherein $R^7$, $R^8$, $R^9$, $R^{10}$, $R^{11}$ and $R^{13}$ are the same as defined above.

A specific value for $R^4$ is (Z or E)-CH=$CHC_{1-4}$ alkyl, optionally substituted by OH.

A specific value for $R^4$ is ≡C—$CC_{1-4}$ alkyl, optionally substituted by OH or $OR^{13}$, wherein $R^{13}$ is $(P=O)(OH)_2$, $(P=O)(C_{1-7}$ alkoxy$)_2$, or $CO(CH_2)_6CON(CH_3)(CH_2)_nSO_3^-M^+$.

A specific value for $R^4$ is $C_{1-8}$ alkyl substituted by $OR^{13}$ wherein $R^{13}$ is $(P=O)(OH)_2$, $(P=O)(C_{1-7}$ alkoxy$)_2$, or $CO(CH_2)_nCON(CH_3)(CH_2)_6SO_3^-M^+$.

A specific value for $R^4$ is $C_{1-8}$ alkyl substituted by $SO_iR^9$, wherein $R^9$ is the same as defined above.

A specific value for $R^4$ is $NR^7R^8$, wherein $R^7$ and $R^8$ are the same as defined above.

A specific value for $R^4$ is $C_{1-8}$ alkyl substituted by $NR^7R^8$, wherein $R^7$ and $R^8$ are the same as defined above.

A specific value for $R^4$ is $C_{1-8}$ alkyl substituted by $NR^7R^8$, wherein $R^7$ and $R^8$ together with the nitrogen to which they are attached to form a het, wherein het is the same as defined above.

A specific value for $R^4$ is $C_{1-8}$ alkyl substituted by $NR^7R^8$, wherein $R^7$ and R 8 are independently $C_{1-6}$ alkyl, optionally substituted by one or more substituents selected from a group consisting of OH, aryl, or CN wherein aryl is the same as defined above.

A specific value for $R^4$ is $C_{1-8}$ alkyl substituted by $N_3$.

A specific value for $R^4$ is $C_{1-8}$ alkyl substituted by bet wherein bet is the same as defined above.

A specific value for $R^4$ is 4morpholine methyl.

A specific value for $R^4$ is $C_{1-7}$ alkyl substituted by $R^{11}$, wherein $R^{11}$ is the same as defined above.

A specific value for $R^5$ is H or $C_{1-7}$ alkyl optionally substituted by one or more OH.

A specific value for $R^6$ is $OC_{1-7}$ alkyl optionally substituted by one or more OH.

A specific value for $R^6$ is halo.

A specific value for $R^6$ is C≡$CC_{1-7}$ alkyl substituted by one or more OH, or $C_{2-7}$ alkoxy substituted by one or more OH.

A specific value for $R^6$ is H or $C_{1-7}$ alkyl, optionally substituted by halo, $NR^{10}R^{10}$, OH, $CO_2R^{10}$, or het; wherein $R^{10}$ and het are the same as defined above.

A specific value for M is sodium, potassium, or lithium.

A specific value is where X is S; W, $R^1$, $R^2$, $R^3$, $R^4$, $R^5$, $R^6$ are the same as defined above.

A specific value is where X is O; $R^1$, $R^3$, $R^4$, $R^5$, $R^6$ are the same as defined above, W is $NR^7R^8$, $OR^9$, $SO_tR^9$ or $R^2$; wherein $R^2$ is:

a) $(CH_2CH_2O)_nR^{10}$,
b) het, wherein said het is bonded via a carbon atom,
c) $C_{1-7}$ alkyl which is partially unsaturated and optionally substituted by OH,
d) $C_{3-8}$ cycloalkyl, or
e) $C_{1-7}$ alkyl which is optionally substituted by one or more substituents selected from a group consisting of Ohet, Oaryl, $SO_tR^9$, or $OC_{2-4}$ alkyl which is further substituted by het, $OR^{10}$, or OC(=O)aryl; wherein $R^7$, $R^8$, $R^9$, $R^{10}$ and n are the same as defined above.

A specific value is where X is O or S; $R^1$ is Cl; $R^3$ is H; $R^5$ is H; $R^6$ is H or F; $R^4$ is 4-morpholinylmethyl; and $R^2$ is:

a) $C_{1-4}$ alkyl substituted by $SO_tR^9$, or $C_{1-4}$ alkoxy which is further substituted by OH, het, $OC_{1-4}$ alkyl, or OC(=O)pheyl,
b) $(CH_2CH_2O)_2C_{1-4}$alkyl,
c) $C_{1-6}$alkyl which is partially unsaturated and optionally substituted by OH,
d) cyclopropyl, tetrahydro-2H-pyranyl, piperdinyl, mopholinyl, 1-methyl-piperidinyl, or 1,1-dioxotetrahydro-2H-thiopyran; wherein $R^9$ is phenyl optionally substituted by Cl, or $R^9$ is $C_{1-6}$alkyl optionally substituted by OH.

A specific value is where X is O or S; $R^1$ is Cl; $R^3$ is H; $R^5$ is H; $R^6$ is H or F; $R^4$ is $C_{1-6}$alkyl which is partially unsaturated and optionally substituted by OH or $OR^{13}$; or $R^4$ is $C_{1-4}$alkyl substituted with $OR^{13}$; W is $NR^{10}R^{10}$, cyclopropyl, $(CH_2CH_2O)_2OR^{10}$, or $C_{1-6}$ alkyl which may be partially unsaturated and is optionally substituted by OH, mopholinyl, $NR^{10}R^{10}$; C(=O)$OC_{1-4}$alkyl, wherein $R^{10}$ is H or $C_{1-4}$alkyl; $R^{13}$ is (P=O)$(C_{1-7}$ alkoxy)$_2$, CO$(CH_2)_n$CON$(CH_3)(CH_2)_nSO_3^-M^+$, or (P=O)$(OH)_2$.

A specific value is where X is O or S; $R^1$ is Cl; $R^3$ is H; $R^5$ is H; $R^6$ is C≡C$C_{1-4}$ alkyl optionally substituted by OH; $R^4$ is H or $C_{1-4}$alkyl which may be partially unsaturated and optionally substituted by OH, and W is $C_{1-4}$ alkyl optionally substituted by OH.

When alkyl is partially unsaturated, it can be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl;

Examples of the present invention are (1) N-(4-chlorobenzyl)-6-(3-hydroxy-1-propynyl)-1-isopropyl-4-oxo-1,4-dihydro-3-quinolinecarboxamide;
(2) 1-(sec-butyl)-N-(4-chlorobenzyl)-6-(3-hydroxy-1-propynyl)-4-oxo-1,4-dihydro-3-quinolinecarboxamid;
(3) 1-(sec-butyl)-N-(4-chlorobenzyl)-6-(3-hydroxy-1-propynyl)-8-methoxy4-oxo-1,4-dihydro-3-quinolinecarboxamide;
(4) N-(4-chlorobenzyl)-8-(2-hydroxyethoxy)-6-(3-hydroxypropyl)-1-methyl-4-oxo-1,4-dihydro-3-quinolinecarboxamide;
(5) N-(4-chlorobenzyl)-8-[2-hydroxy-1-(hydroxymethyl)ethoxy]-6-(3-hydroxypropyl)-1-methyl-4-oxo-1,4-dihydro-3-quinolinecarboxamide;
(6) N-(4-chlorobenzyl)-8-fluoro-6-(hydroxymethyl)-4-oxo-1-[3-(tetrahydro-2H-pyran-2-yloxy)propyl]-1,4-dihydro-3-quinolinecarboxamide;
(7) N-(4-chlorobenzyl)-6-[3-hydroxy-1-propenyl]-1-[2-(4-morpholinyl)ethyl]-4-oxo-1,4-dihydro-3-quinolinecarboxamide;
(8) N-(4-chlorobenzyl)-8-fluoro-6-(3-hydroxy-1-propynyl)-1-methyl-4-oxo-1,4-dihydro-3-quinolinecarboxamide;
(9) N-(4-chlorobenzyl)-8-fluoro-6-[(Z)-3-hydroxy-1-propenyl]-1-methyl-4-oxo-1,4-dihydro-3-quinolinecarboxamide;
(10) N-(4-chlorobenzyl)-1-[2-(diethylamino)ethyl]-8-fluoro-6-(3-hydroxy-1-propynyl)-4-oxo-1,4-dihydro-3-quinolinecarboxamide;
(11) N-(4-chlorobenzyl)-6-(3-hydroxy-1-propynyl)-4-oxo-1-propyl-1,4-dihydro-3-quinolinecarboxamide;
(12) N-(4-chlorobenzyl)-1-[2-(diethylamino)ethyl]-6-(3-hydroxy-1-propynyl)-4-oxo-1,4-dihydro-3-quinolinecarboxamide;
(13) N-(4-chlorobenzyl)-1-[2-(dimethylamino)ethyl]-6-(3-hydroxy-1-propynyl)-4-oxo-1,4-dihydro-3-quinolinecarboxarmide hydrochloride;
(14) N-(4-chlorobenzyl)-6-(3-hydroxy-1-propynyl)-4-oxo-1-[2-(1-piperidinyl)ethyl]-1,4-dihydro-3-quinolinecarboxamide;
(15) N-(4-chlorobenzyl)-6-(3-hydroxy-1-propynyl)-4-oxo-1-[3-(1-piperidinyl)propyl]-1,4-dihydro-3-quinolinecarboxamide;
(16) N-(4-chlorobenzyl)-6-(3-hydroxy-1-propynyl)-1-[2-(1-methyl-2-pyrrolidinyl)ethyl]4-oxo-1,4-dihydro-3-quinolinecarboxamide;
(17) N-(4-chlorobenzyl)-1-[2-(diisopropylamino)ethyl]-6-(3-hydroxy-1-propynyl)-4-oxo-1,4-dihydro-3-quinolinecarboxamide;
(18) N-(4-chlorobenzyl)-6-(3-hydroxy-1-propynyl)-4-oxo-1-[2-(1-pyrrolidinyl)ethyl]-1,4-dihydro-3-quinolinecarboxamide;
(19) N-(4-chlorobenzyl)-6-(3-hydroxy-1-propynyl)-1-[2-(4-morpholinyl)ethyl]-4-oxo-1,4-dihydro-3-quinolinecarboxamide;
(20) N-(4-chlorobenzyl)-1-[3-(dimethylamino)propyll-6-(3-hydroxy-1-propynyl)-4-oxo-1,4-dihydro-3-quinolinecarboxamide;
(21) N-(4-chlorobenzyl)-6-(3-hydroxy-1-propynyl)-4-oxo-1-vinyl-1,4-dihydro-3-quinolinecarboxamide;
(22) N-(4-chlorobenzyl)-6-[(E)-3-hydroxy-1-propenyl]-1-methyl-4-oxo-1,4-dihydro-3-quinolinecarboxamide;
(23) N-(4-chlorobenzyl)-6-[(Z)-3-hydroxy-1-propenyl]-1-methyl-4-oxo-1,4-dihydro-3-quinolinecarboxamide;
(24) N-(4-chlorobenzyl)-6-[ethyl(2-hydroxyethyl)amino]-1-methyl-4-oxo-1,4-dihydro-3-quinolinecarboxamide;
(25) N-(4-chlorobenzyl)-1-cyclopropyl-6-(3-hydroxy-1-propynyl)-4-oxo-1,4-dihydro-3-quinolinecarboxamide;
(26) N-(4-chlorobenzyl)-1-cyclopropyl-6-(3-hydroxypropyl)-4-oxo-1,4-dihydro-3-quinolinecarboxamide;
(27) N-(4-chlorobenzyl)-1-cyclopropyl-6-(4-morpholinylmethyl)-4-oxo-1,4-dihydro-3-quinolinecarboxamide;
(28) tert-butyl 2-[3-{[(4-chlorobenzyl)amino]carbonyl}-6-(3-hydroxy-1-propynyl)-4-oxo-1(4H)-quinolinyl]acetate;
(29) 2-[3-{[(4-chlorobenzyl)amino]carbonyl}-6-(3-hydroxy-1-propynyl)-4-oxo-1(4H)-quinolinyl]acetic acid;
(30) N-(4-chlorobenzyl)-1-(2-hydroxyethyl)-6-(3-hydroxy-1-propynyl)-4-oxo-1,4-dihydro-3-quinolinecarboxamide;
(31) N-(4-chlorobenzyl)-6-(3-hydroxy-1-propynyl)-1-methyl-4-oxo-1,4-dihydro-3-quinolinecarboxamide;
(32) di(tert-butyl)3-(3-{[(4chlorobenzyl)amino]carbonyl}-1-methyl-4-oxo-1,4-dihydro-6-quinolinyl)propyl phosphate;
(33) 3-(3-{[(4-chlorobenzyl)aminocarbonyl}-1-methyl-4-oxo-1,4-dihydro-6-quinolinyl)propyl dihydrogen phosphate;

(34) di(tert-butyl)3-(3-{(4chlorobenzyl)amino]carbonyll-1-cyclopropyl-4-oxo-1,4-dihydro-6-quinolinyl)propyl phosphate;
(35) sodium 2-[{8-[3-(3-{[(4-chlorobenzyl)amino]carbonyl}-1-cyclopropy-4-oxo-1,4-dihydro-6-quinolinyl)propoxy]-8-oxooctanoyl}(methyl)amino]-1-ethanesulfonate;
(36) sodium 2-[(8-([3-(3-{[(4-chlorobenzyl)amino]carbonyl}-1-methyl-4-oxo-1,4-dihydro-6-quinolinyl)-2-propynyl]oxy}-8-oxooctanoyl)(methyl)amino)-1-ethanesulfonate;
(37) sodium 2-[(8-{[3-(3-{[(4-chlorobenzyl)amino]carbonyl}-1-methyl-4-oxo-1,4-dihydro-6-quinolinyl)-2-propynyl]oxy}-8-oxooctanoyl)(methyl)amino]-1-ethanesulfonate;
(38) sodium 2-[(8-{13-(3-[{(4-chlorobenzyl)amino]carbonyl}-1-cyclopropyl-4-oxo-1,4-dihydro-6-quinolinyl)-2-propynyl]oxy}-8-oxooctanoyl)(methyl)amino]-1-ethanesulfonate;
(39) 1-(tert-butyl)-N-(4-chlorobenzyl)-6-(3-hydroxy-1-propynyl)-4-oxo-1,4-dihydro-3-quinolinecarboxamide;
(40) sodium 2-[{8-[3-(1-(tert-butyl)-3-{[(4-chlorobenzyl)amino]-carbonyl}4-oxo-1,4-dihydro-6-quinolinyl)propoxy]-8-oxooctanoyl}(methyl)amino]-1-ethanesulfonate;
(41) sodium 2-[(8-{[3-(1-(tert-butyl)-3-{[(4-chlorobenzyl)amino]-carbonyl}-4-oxo-1,4-dihydro-6-quinolinyl)-2-propynyl]oxy}-8-oxooctanoyl)(methyl)amino]-1-ethanesulfonate;
(42) N-(4-chlorobenzyl)-6-(3-hydroxy-1-propynyl)-1-[2-(2-methoxyethoxy)-ethyl]-4-oxo-1,4-dihydro-3-quinolinecarboxamide;
(43) N-(4-cyanobenzyl)-6-(3-hydroxy-1-propynyl)-1-methyl-4-oxo-1,4-dihydro-3-quinolinecarboxamide;
(44) 6-{[bis(2-hydroxyethyl)amino]methyl}-N-(4-chlorobenzyl)-1-methyl-4-oxo-1,4-dihydro-3-quinolinecarboxamide;
(45) N-(4-chlorobenzyl)-6-{[(2-hydroxyethyl)(methyl)amino]methyl}-1-methyl-4-oxo-1,4-dihydro-3-quinolinecarboxamide;
(46) N-(4-chlorobenzyl)-1-methyl-6-(1,4-oxazepan-4-ylmethyl)-4-oxo-1,4-dihydro-3-quinolinecarboxamide;
(47) N-(4-chlorobenzyl)-1-methyl-4-oxo-6-(1,4-thiazepan-4-ylmethyl)-1,4-dihydro3-quinolinecarboxamide;
(48) N-(4-chlorobenzyl)-1-methyl-6-(2-oxa-5-azabicyclo[2.2.1]hept-5-ylmethyl)-4-oxo-1,4-dihydro-3-quinolinecarboxamide;
(49) N-(4-chlorobenzyl)-6-(2,3-dihydro-4H-1,4-benzoxazin-4-ylmethyl)-1-methyl-4-oxo-1,4-dihydro-3-quinolinecarboxamide;
(50) 6-((benzyl(2-hydroxyethyl)amino)methyl)-N-(4-chlorobenzyl)-1-methyl-4-oxo-1,4-dihydro-3-quinolinecarboxamide;
(51) 6-(azidomethyl)-N-(4-chlorobenzyl)-1-methyl-4-oxo-1,4-dihydro-3-quinolinecarboxamide;
(52) N-(4-chlorobenzyl)-6-[(4,4-difluoro-1-piperidinyl)methyl]-1-methyl-4-oxo-1,4-dihydro-3-quinolinecarboxamide;
(53) N-(4-chlorobenzyl)-6-{[4-fluoro-3,6-dihydro-1(2H)-pyridinyl]methyl}-1-methyl-4-oxo-1,4-dihydro-3-quinolinecarboxamide;
(54) N-(4-chlorobenzyl)-1-methyl-4-oxo-6-vinyl-1,4-dihydro-3-quinoline-carboxamide;
(55) N-(4-chlorobenzyl)-1-[2-(2-hydroxyethoxy)ethyl]-6-(3-hydroxy-1-propynyl)-4-oxo-1,4-dihydro-3-quinolinecarboxamide;
(56) N-(4-chlorobenzyl)-1-{2-[2-(2-methoxyethoxy)ethoxy]ethyl}-6-(4-morpholinylmethyl)-4-oxo-1,4-dihydro-3-quinolinecarboxamide;
(57) N-(4-chlorobenzyl)-1-[2-(2-hydroxyethoxy)ethyl]-6-(4-morpholinylmethyl)-4-oxo-1,4-dihydro-3-quinolinecarboxamide;
(58) N-(4-chlorobenzyl)-1-[2-(2-ethoxyethoxy)ethyl]-6-(4-morpholinylmethyl)-4-oxo-1,4-dihydro-3-quinolinecarboxamide;
(59) N-(4-chlorobenzyl)-6-(4-morpholinylmethyl)-4-oxo-1-(2-propynyl)-1,4-dihydro-3-quinolinecarboxamide;
(60) N-(4-chlorobenzyl)-1-[2-(ethylsulfanyl)ethyl]-6-(4-morpholinylmethyl)-4-oxo-1,4-dihydro-3-quinolinecarboxamide;
(61) N-(4-chlorobenzyl)-1-[3-(methylsulfanyl)propyl]-6-(4-morpholinylmethyl)-4-oxo-1,4-dihydro-3-quinolinecarboxamide;
(62) N-(4-chlorobenzyl)-1-(4-hydroxy-2-butynyl)-6-(4-morpholinylmethyl)-4-oxo-1,4-dihydro-3-quinolinecarboxamide;
(63) N-(4chlorobenzyl)-6-{[(2-hydroxy-2-phenylethyl)(methyl)amino]methyl}-1-methyl-4-oxo-1,4-dihydro-3-quinolinecarboxamide;
(64) 1-{2-[bis(2-hydroxyetbyl)amino]ethyl}-N-(4-chlorobenzyl)-6-(4-morpholinylmethyl)-4-oxo-1,4-dihydro-3-quinolinecarboxamide;
(65) N-(4-chlorobenzyl)-1-[3-(methylsulfinyl)propyl]-6-(4-morpholinylmethyl)-4-oxo-1,4-dihydro-3-quinolinecarboxamide;
(66) N-(4-chlorobenzyl)-1-{3-[(3-hydroxypropyl)sulfanyl]propyl}-6-(4-morpholinylmethyl)-4-oxo-1,4-dihydro-3-quinolinecarboxamide;
(67) N-(4-chlorobenzyl)-1-[3-(methylsulfonyl)propyl]-6-(4-morpholinylmethyl)-4-oxo-1,4-dihydro-3-quinolinecarboxamide;
(68) N-(4-chlorobenzyl)-1-[2-(ethylsulfinyl)ethyl]-6-(4-morpholinylmethyl)-4-oxo-1,4-dihydro-3-quinolinecarboxamide;
(69) N-(4-chlorobenzyl)-1-[2-(ethylsulfonyl)ethyl]-6-(4-morpholinylmethyl)-4-oxo-1,4-dihydro-3-quinolinecarboxamide;
(70) N-(4-chlorobenzyl)-1-{3-[(3-hydroxypropyl)sulfinyl]propyl}-6-(4-morpholinylmethyl)-4-oxo-1,4-dihydro-3-quinolinecarboxamide;
(71) N-(4-chlorobenzyl)-1-{3-[(3-hydroxypropyl)sulfonyl]propyl}-6-(4-morpholinylmethyl)-4-oxo-1,4-dihydro-3-quinolinecarboxamide;
(72) N-(4-chlorobenzyl)-6-(4-morpholinylmethyl)-4-oxo-1-[2-(phenylsulfanyl)ethyl]-1,4-dihydro-3-quinolinecarboxamide;
(73) N-(4-chlorobenzyl)-1-[(methylsulfanyl)methyl]-6-(4-morpholinylmethyl)-4-oxo-1,4-dihydro-3-quinolinecarboxamide;
(74) N-(4-chlorobenzyl)-6-{[[2-hydroxy-2-(4-hydroxyphenyl)ethyl](methyl)-amino]methyl}-1-methyl-4-oxo-1,4-dihydro-3-quinolinecarboxamide;
(75) N-(4-chlorobenzyl)-6-[(3-hydroxy-1-azetidinyl)methyl]-1-methyl-4-oxo-1,4-dihydro-3-quinolinecarboxamide;
(76) N-(4-chlorobenzyl)-6-(4-morpholinylmethyl)-4-oxo-1-[(phenylsulfanyl)-methyl]-1,4-dihydro-3-quinolinecarboxamide;
(77) N-(4-chlorobenzyl)-6-{[[2-hydroxy-2-(4-hydroxy-3-methoxyphenyl)ethyl](methyl)amino]methyl}-1-methyl-4-oxo-1,4-dihydro-3-quinolinecarboxamide;
(78) N-(4-chlorobenzyl)-6-[(3,3-dihydroxy-1-azetidinyl)methyl]-1-methyl-4-oxo-1,4-dihydro-3-quinolinecarboxamide;
(79) N-(4-chlorobenzyl)-1-[(methylsulfinyl)methyl]-6-(4-morpholinylmethyl)-4-oxo-1,4-dihydro-3-quinolinecarboxamide;

(80) N-(4-chlorobenzyl)-1-[(methylsulfonyl)methyl]-6-(4-morpholinylmethyl)-4-oxo-1,4-dihydro-3-quinolinecarboxamide;
(81) N-(4-chlorobenzyl)-6-(4-morpholinylmethyl)-4-oxo-1-[(phenylsulfinyl)-methyl]-1,4-dihydro-3-quinolinecarboxamide;
(82) N-(4-chlorobenzyl)-6-(4-morpholinylmethyl)-4-oxo-1-[(phenylsulfonyl)-methyl]-1,4-dihydro-3-quinolinecarboxamide;
(83) N-(4-chlorobenzyl)-6-(3-hydroxypropyl)-1-[2-(2-methoxyethoxy)ethyl]-4-oxo-1,4-dihydro-3-quinolinecarboxamide;
(84) N-(4-chlorobenzyl)-1-[2-(2-methoxyethoxy)ethyl]-6-(4-morpholinylmethyl)-4-oxo-1,4-dihydro-3-quinolinecarboxamide;
(85) N-(4-chlorobenzyl)-1-[2-(2-methoxyethoxy)ethyl]-4-oxo-6-[(4-oxo-1-piperidinyl)methyl]-1,4-dihydro-3-quinolinecarboxamide;
(86) N-(4-chlorobenzyl)-6-{[(cyanomethyl)(methyl)amino]methyl}-1-[2-(2-methoxyethoxy)ethyl]-4-oxo-1,4-dihydro-3-quinolinecarboxamide;
(87) N-(4-chlorobenzyl)-6-{[(3R)-3-hydroxypyrrolidinyl]methyl}-1-[2-(2-methoxyethoxy)ethyl]-4-oxo-1,4-dihydro-3-quinolinecarboxamide;
(88) N-(4-chlorobenzyl)-1-[2-(2-methoxyethoxy)ethyl]-6-[(methylsulfanyl)methyl]-4-oxo-1,4-dihydro-3-quinolinecarboxamide;
(89) N-(4-chlorobenzyl)-6-{[[(1R,2S)-2-hydroxy-1-methyl-2-phenylethyl](methyl)-amino]methyl}-1-[2-(2-methoxyethoxy)ethyl]4-oxo-1,4-dihydro-3-quinolinecarboxamide;
(90) N-(4-chlorobenzyl)-6-{[(2-hydroxy-2-phenylethyl)(methyl)amino]methyl}-1-[2-(2-methoxyethoxy)ethyl]-4-oxo-1,4-dihydro-3-quinolinecarboxamide;
(91) N-(4-chlorobenzyl)-6-{[[2-hydroxy-2-(4-hydroxyphenyl)ethyl](methyl)amino]-methyl}-1-[2-(2-methoxyethoxy)ethyl]-4-oxo-1,4-dihydro-3-quinolinecarboxamide;
(92) 1-{2-[2-(tert-butoxy)ethoxy]ethyl-N-(4-chlorobenzyl)-6-(4-morpholinyl-methyl)-4-oxo-1,4-dihydro-3-quinolinecarboxamide;
(93) 1-{2-[2-(tert-butoxy)ethoxy]ethyl-N-(4-chlorobenzyl)-6-{[[2-hydroxy-2-(4-hydroxyphenyl)ethyl](methyl)amino]methyl-4-oxo-1,4-dihydro-3-quinolinecarboxamide;
(94) N-(4-chlorobenzyl)-6-(3-hydroxy-1-propynyl)-1-methyl-4-oxo-1,4-dihydro-3-quinolinecarbothioamide;
(95) N-(4-chlorobenzyl)-1-methyl-6-(4-morpholinylmethyl)-4-oxo-1,4-dihydro-3-quinolinecarbothioamide;
(96) N-(4-chlorobenzyl)-8-(3-hydroxy-1-propynyl)-1-methyl-4-oxo-1,4-dihydro-3-quinolinecarboxamide;
(97) N-(4-chlorobenzyl)-8-(4-hydroxy-1-butynyl)-1-methyl-4-oxo-1,4-dihydro-3-quinolinecarboxamide;
(98) N-(4-chlorobenzyl)-1-methyl-4-oxo-6-(tetrahydro-2H-pyran-4-ylmethyl)-1,4-dihydro-3-quinolinecarboxamide;
(99) N-(4-chlorobenzyl)-6-{[3-(hydroxyimino)-1-azetidinyl]methyl}-1-methyl-4-oxo-1,4-dihydro-3-quinolinecarboxamide;
(100) N-(4-chlorobenzyl)-1-{2-[2-(4-morpholinyl)ethoxy]ethyl}-6-(4-morpholinylmethyl)-4-oxo-1,4-dihydro-3-quinolinecarboxamide;
(101) N-(4-chlorobenzyl)-1-([(4-chlorophenyl)sulfanyl]methyl)-6-(4-morpholinylmethyl)-4-oxo-1,4-dihydro-3-quinolinecarboxamide;
(102) N-(4-chlorobenzyl)-1-([(4-chlorophenyl)sulfinyl]methyl)-6-(4-morpholinylmethyl)-4oxo-1,4-dihydro-3-quinolinecarboxainide;
(103) N-(4-chlorobenzyl)-1-([(4-chlorophenyl)sulfonyl]methyl)-6-(4-morpholinylmethyl)-4-oxo-1,4-dihydro-3-quinolinecarboxamide;
(104) N-(4-hlorobenzyl)-1-[(4-chlorophenoxy)methyl]-6-(4-morpholinylmethyl)-4-oxo-1,4-dihydro-3-quinolinecarboxamide;
(105) N-(4-chlorobenzyl)-1-[(2-methoxyethoxy)methyl]-6-(4-morpholinylmethyl)-4-oxo-1,4-dihydro-3-quinolinecarboxamide;
(106) 2-{[3-{[(4-chlorobenzyl)amino]carbonyl}-6-(4-morpholinylmethyl)-4-oxo-1(4H)-quinolinyl]methoxy}ethyl benzoate;
(107) N-(4-chlorobenzyl)-1-[(2-hydroxyethoxy)methyl]-6-(4-morpholinylmethyl)-4-oxo-1,4-dihydro-3-quinolinecarboxamide;
(108) N-(4-chlorobenzyl)-6-(4-morpholinylmethyl)-4-oxo-1-tetrahydro-2H-pyran-4-yl-1,4-dihydro-3-quinolinecarboxamide;
(109) N-(4-chlorobenzyl)-1-(1-methyl-4-piperidinyl)-6-(4-morpholinylmethyl)-4-oxo-1,4-dihydro-3-quinolinecarboxamide;
(110) N-(4-chlorobenzyl)-6-(4-morpholinylmethyl)-4-oxo-1-(4-piperidinyl)-1,4-dihydro-3-quinolinecarboxamide;
(111) N-(4-chlorobenzyl)-1-(1,1-dioxohexahydrothiopyran-4-yl)-6-(4-morpholinylmethyl)-4-oxo-1,4-dihydro-3-quinolinecarboxamide;
(112) N-(4-chlorobenzyl)-1-(4-morpholinyl)-6-(4-morpholinylmethyl)-4-oxo-1,4-dihydro-3-quinolinecarboxamide;
(113) N-(4-chlorobenzyl)-1-(4-methyl-1-piperazinyl)-6-(4-morpholinylmethyl)-4-oxo-1,4-dihydro-3-quinolinecarboxamide;
(114) N-(4-chlorobenzyl)-6-(4-morpholinylmethyl)-4-oxo-1-(1-piperidinyl)-1,4-dihydro-3-quinolinecarboxamide;
(115) N-(4-chlorobenzyl)-6-(4-morpholinylmethyl)-4-oxo-1-(1-pyrrolidinyl)-1,4-dihydro-3-quinolinecarboxamide;
(116) N-(4-chlorobenzyl)-1-(2R)-2-(methoxymethyl)pyrrolidinyl]-6-(4-morpholinylmethyl)-4-oxo-1,4-dihydro-3-quinolinecarboxamide;
(117) N-(4-chlorobenzyl)-1-(dimethylamino)-6-(4-morpholinylmethyl)-4-oxo-1,4-dihydro-3-quinolinecarboxamide;
(118) 1-amino-N-(4-chlorobenzyl)-6-(3-hydroxy-1-propynyl)-4-oxo-1,4-dihydro-3-quinolinecarboxamide;
(119) 1-amino-N-(4-chlorobenzyl)-6-(3-hydroxypropyl)-4-oxo-1,4-dihydro-3-quinolinecarboxamide;
(120) N-(4-chlorobenzyl)-1-(dimethylamino)-6-(3-hydroxy-1-propynyl)-4-oxo-1,4-dihydro-3-quinolinecarboxamide;
(121) N-(4-chlorobenzyl)-1-(dimethylamino)-4-oxo-1,4-dihydro-3-quinolinecarboxamide;
(122) 1-(Aalyloxy)-N-(4-chlorobenzyl)-4-oxo-1,4-dihydro-3-quinolinecarboxamide;
(123) N-(4-chlorobenzyl)-1-methoxy-4-oxo-1,4-dihydro-3-quinolinecarboxamide;
(124) N-(4-bromobenzyl)-1-(4-morpholinyl)-6-(4-morpholinylmethyl)-4-oxo-1,4-dihydro-3-quinolinecarboxamide;
(125) N-(4-fluorobenzyl)-1-(4-morpholinyl)-6-(4-morpholinylmethyl)-4-oxo-1,4-dihydro-3-quinolinecarboxamide;
(125) N-(4-chlorobenzyl)-1-{[2-(4-morpholinyl)ethoxy]methyl}-6-(4-morpholinylmethyl)-4-oxo-1,4-dihydro-3-quinolinecarboxamide;
(126) N-(4-chlorobenzyl)-1-{[2-(dimethylamino)ethoxy]methyl}-6-(4-morpholinylmethyl)-4-oxo-1,4-dihydro-3-quinolinecarboxamide;

(127) N-(4-chlorobenzyl)-1-{[2-(4-methyl-1-piperazinyl)ethoxy]methyl}-6-(4-morpholinylmethyl)-4-oxo-1,4dihydro-3-quinolinecarboxamide;
(128) N-(4-chlorobenzyl)-6-(4-morpholinylmethyl)-4-oxo-1-{[2-(1-piperidinyl)ethoxy]methyl}-1,4-dihydro-3-quinolinecarboxamide;
(129) N-(4-chlorobenzyl)-6-(4-morpholinylmethyl)-4-oxo-1-{[2-(1-pyrrolidinyl)ethoxy]methyl}-1,4-dihydro-3-quinolinecarboxamide; or a pharmaceutically acceptable salt thereof.

The following Charts A–AA describe the preparation of the compounds of the present invention. All of the starting materials are prepared by procedures described in these charts or by procedures analogous thereto, which would be well known to one of ordinary skill in organic chemistry. All of the final compounds of the present invention are prepared by procedures described in these charts or by procedures analogous thereto, which would be well known to one of ordinary skill in organic chemistry. All of the variables used in the charts are as defined below or as in the claims.

Chart A

The ethyl ester of Formula A-1, which is ethyl 4-hydroxy-6-iodo-3-quinolinecarboxylate, is prepared by heating 4-iodoaniline with diethyl ethoxymethylene malonate, first at about 150° C., then in refluxing diphenyl ether. Aminolysis of compound A-1 with 4-substituted-benzylamine at about 160° C. provides amide A-2. Palladium and copper mediated coupling of A-2 with propargyl alcohol leads to compound A-3. Alkylation of the pyridone nitrogen is accomplished with potassium carbonate and an optionally substituted alkyl halide, affording the compound of Formula A-4. Alternatively, compound A-3 is partially hydrogenated to the alkenyl derivative, compound A-5 (E or Z). Similarly, 4-quinolone structures of Formula A-4 are partially hydrogenated to afford alkenyl derivatives of Formula A-6 (E or Z). Alkylation of compound A-5 with optionally substituted alkyl halides and potassium carbonate also provides compounds of Formula A-6.

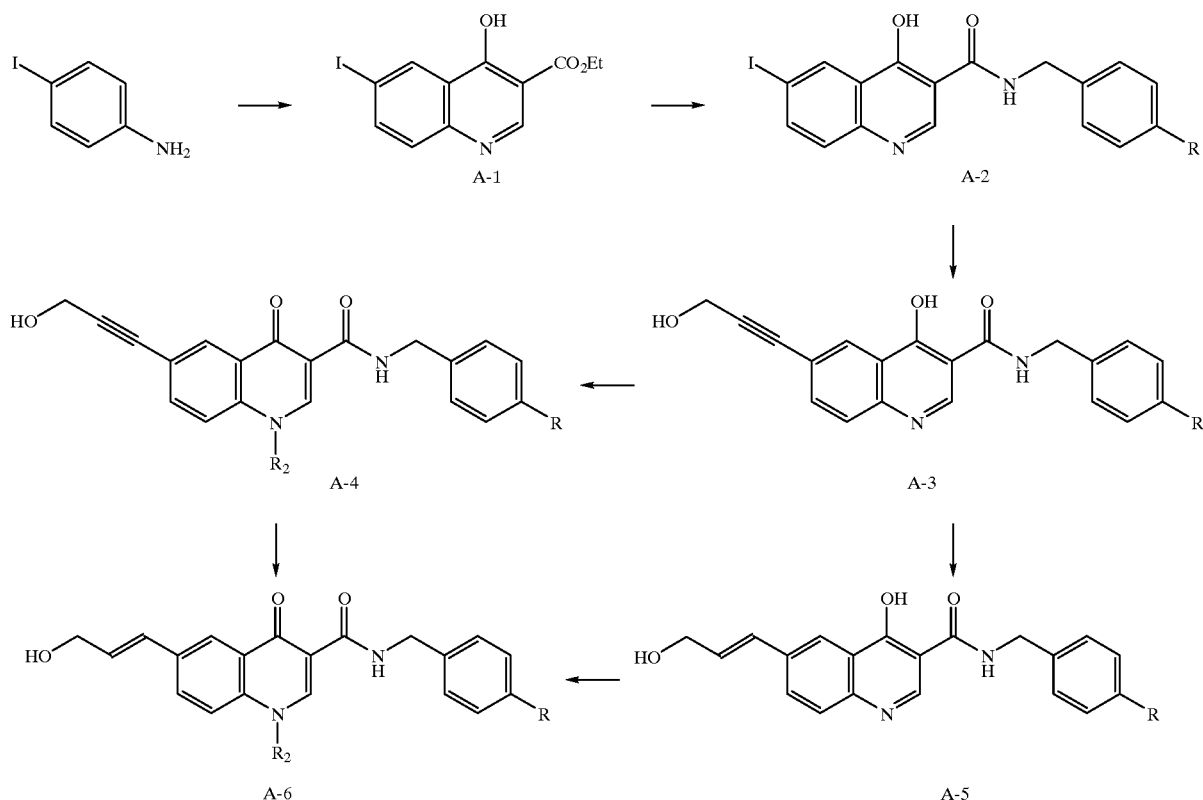

Chart B

The compound of Formula B-1, which is 2-fluoro-5-iodobenzoic acid, is prepared by carbonation of the anion of 4-fluoroiodobenzene, which is prepared by deprotonation of 4-fluoroiodobenzene with LDA. Reaction of acid B-1 with carbonyldiimidazole, followed by treatment of the resulting acyl imidazolide with ethyl trimethylsilyl malonate and subsequent decarboxylation, affords β-ketoester B-2. The ketoester is converted to quinolinones B-3 by sequential treatment with triethyl orthoformate, an amine, and potassium tert-butoxide. Aminolysis of the ester is accomplished with 4-chlorobenzylamine, giving compounds of Formula B-4. Coupling of propargyl alcohol is effected using palladium and copper catalysis, leading to compounds of Formula B-5. Hydrogenation of the triple bond using hydrogen gas and platinum catalyst provides hydroxypropyl derivatives B-6.

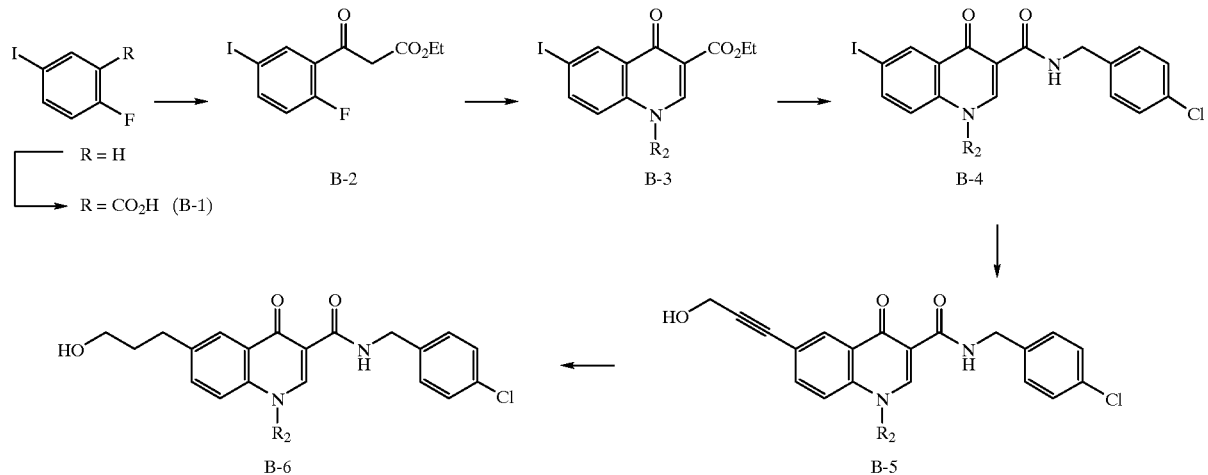

Chart C

Palladium catalyzed carbonylation of the 6-iodo-4-hydroxyquinoline-3-carboxamide A-2 affords the corresponding ester C-1 which is then reduced with LAH to afford the alcohol C-2. Alkylation of the pyridone nitrogen with an alkyl bromide, iodide, or tosylate (X=I, Br, Ts, $R^2$ is the same as defined above) in the presence of an alkali metal carbonate provides compounds of the general structure C-3. Treatment of compound C-3 with methanesulfonyl chloride followed by displacement with an amine, $HNR^7R^8$ wherein $R^7$ and $R^8$ are the same as defined above, affords compounds of the structure described by Formula C4.

Chart D

Compounds of Formula D-1 are phosphitylated with di-tert-butyl diethyl phosphoramidite to give an intermediate phosphite, which is oxidized in situ with m-chloroperbenzoic acid to provide di-tert-butyl phosphates of Formula D-2. Treatment of the phosphates with trifluoroacetic acid cleaves the tert-butyl groups, providing phosphoric acids of Formula D-3.

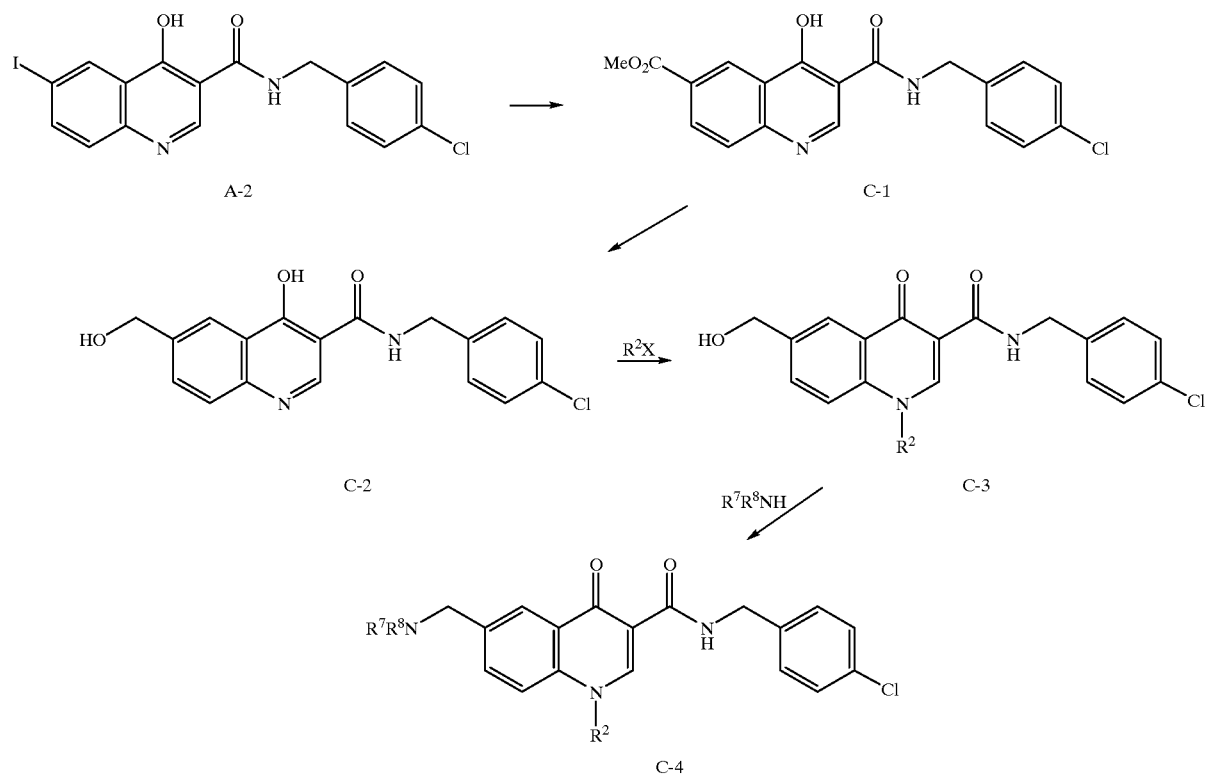

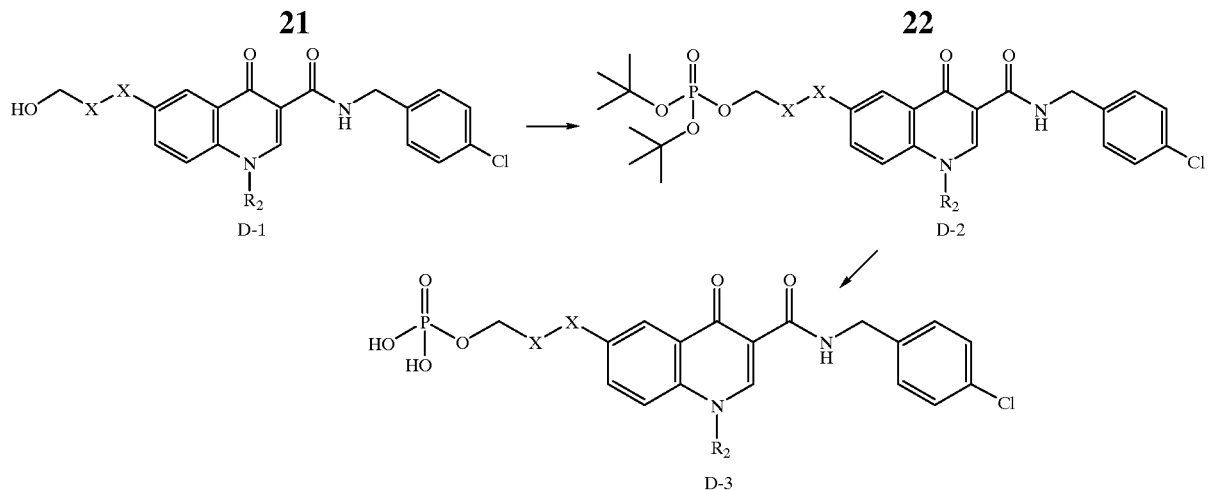

Chart E

Alcohols of Formula D-1 are coupled with suleptanic acid triethylammonium salt, which is triethylammonium 2-[(7-carboxyheptanoyl)(methyl)amino]-1-ethanesulfonate, using diisopropylcarbodiimide and 4-dimethylaminopyridine, to provide the corresponding esters. Exchange of the triethylammonium salt with sodium ion affords sodium salts E-1.

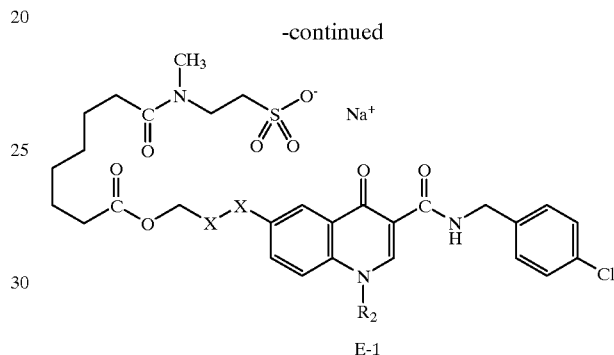

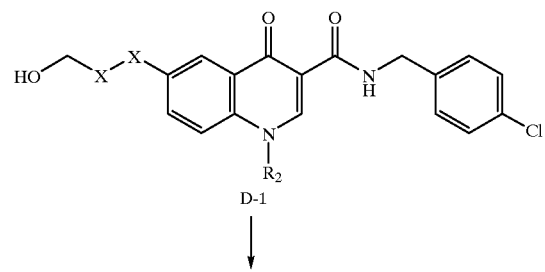

Chart F

4-Iodoaniline (F-0) is reductively alkylated with [(1-ethoxycyclopropyl)oxy]trimethylsilane and sodium cyanoborohydride to give the N-cyclopropyl aniline (F-1). Treatment with diethyl ethoxymethylenemalonate in pyridine affords the enamine (F-2) which is cyclized with polyphosphoric acid to the quinoline (F-3). Treatment with p-chlorobenzylamine at elevated temperature converts the ester to the amide (F-4). Palladium catalyzed coupling of the iodide with propargyl alcohol affords F-5. Reaction with platinum and hydrogen gas affords the saturated propyl alcohol (F-6).

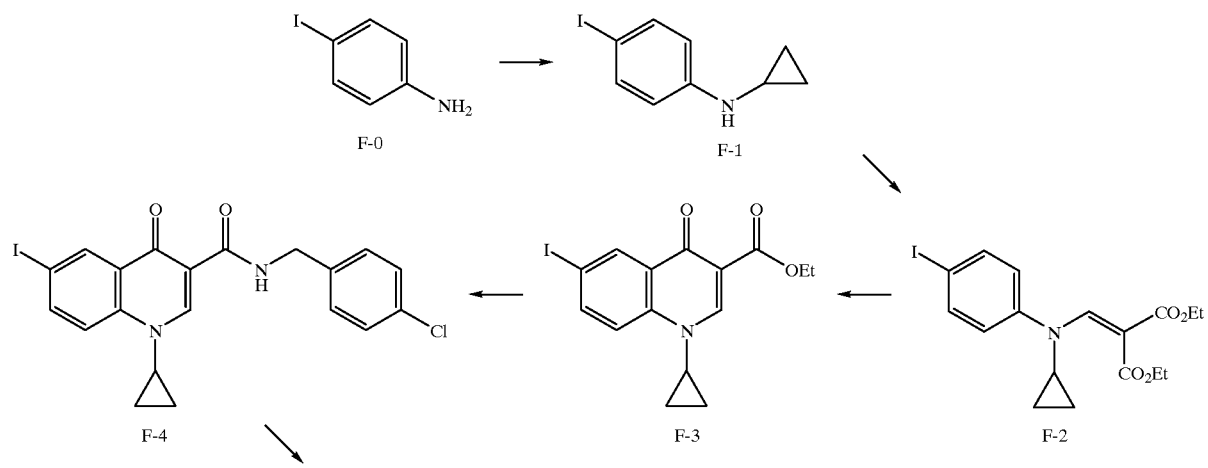

23

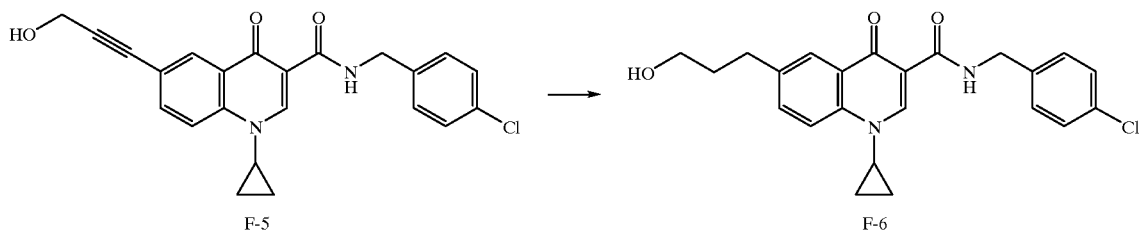

F-5 → F-6

24

Chart G

4-Nitrobenzyl bromide is treated with morpholine and potassium carbonate in acetone to give 4-(4-Nitrobenzyl) morpholine (G-1). The nitro group is reduced with platinum and hydrogen gas to afford the aniline (G-2) which is then treated with [(1-ethoxycyclopropyl)-oxy]trimethylsilane and sodium cyanoborohydride to give the N-cyclopropyl aniline (G-3). Reaction with diethyl ethoxymethylenemalonate in pyridine affords the enamine (G-4) which is cyclized with polyphosphoric acid to the quinoline (G-5). Treatment with p-chlorobenzylamine at elevated temperature converts the ester to the amide (G-6).

Chart H

Alkylation of N-(4-chlorobenzyl)-6-iodo-4-oxo-1,4-dihydro-3-quinolinecarboxamide with potassium carbonate and tert-butylbromoacetate affords H-1. Palladium catalyzed coupling of the iodide with propargyl alcohol affords H-2. Reaction with platinum and hydrogen gas affords the saturated propyl alcohol (H-3). Treatment with trifluoroactic acid affords the free acid (H4). Alternatively, H-2 is treated with trifluoroacetic acid to give H-5.

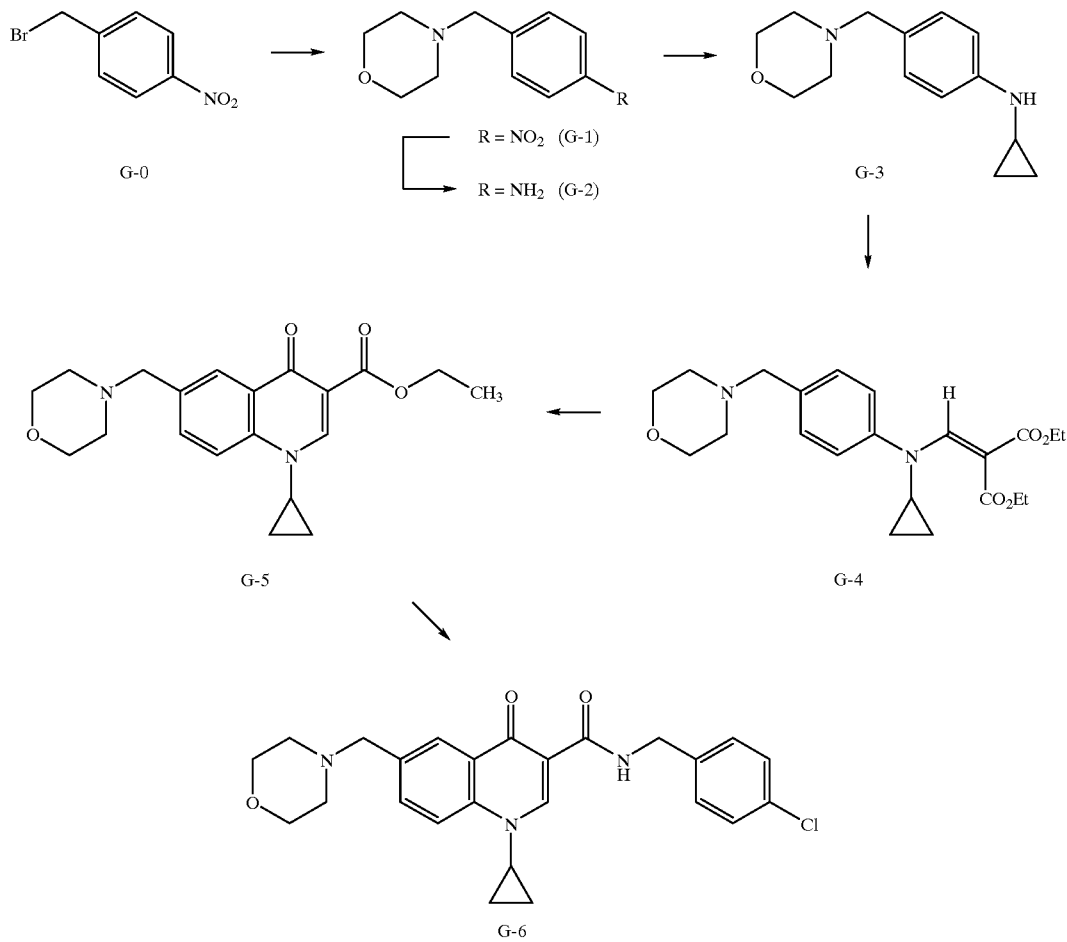

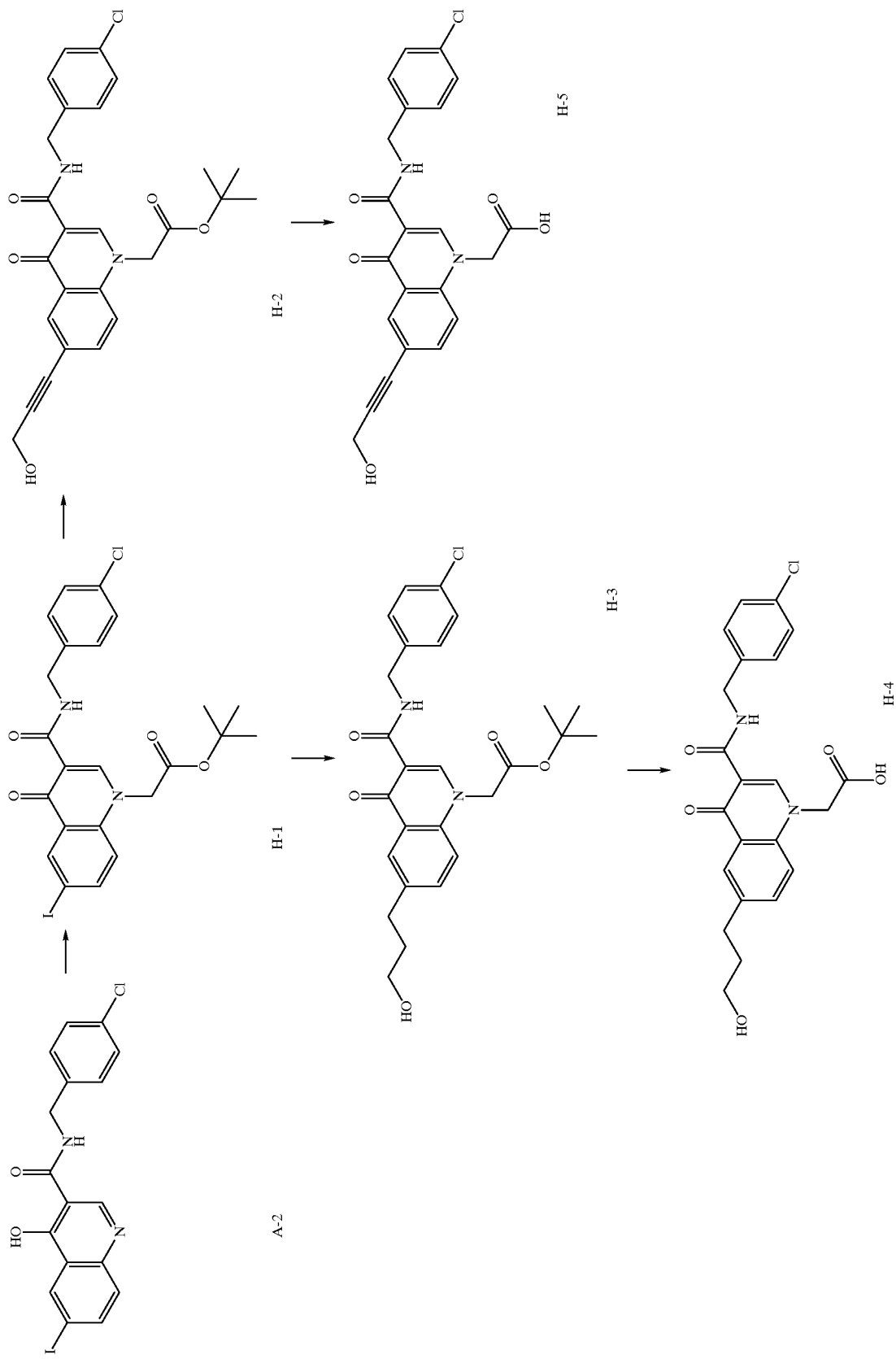

Chart I

1-Fluoro-4-nitrobenzene (I-1) is converted to 2-(4-nitroanilino-N-ethyl)-1-ethanol (I-2) by heating with the N-ethylethanolamine in ethanol. Compound I-2 is converted to the corresponding acetate (I-3) by treatment with acetyl chloride. The nitro group is reduced to the free amine with palladium on carbon and hydrogen gas. The resulting aniline is treated with diethyl ethoxymethylenemalonate to give compound I-4. The resulting enamine is cyclized by heating in diphenyl ether to give the quinoline (I-5). Compound I-5 is N-alkylated at the pyridone nitrogen by treatment with iodoalkyl and potassium carbonate to afford compound I-6. Aminolysis of the diester with 4-chlorobenzylamine affords (I-7).

Chart J

2-Fluoro-6-iodoaniline is condensed with diethyl ethoxymethylenemalonate and then heated in diphenyl ether to afford the 4-hydroxyquinoline ethyl ester (J-1). Aminolysis of compound J-1 with 4-chlorobenzylamine affords the corresponding amide (J-2). Compound J-2 is heated in the presence of an alkoxide to afford compound J-3. Palladium catalyzed coupling of the resulting quinoline with propargyl alcohol affords alkyne J-4. The pyridone nitrogen of J4 is then N-alkylated with an alkyl halide and potassium carbonate to afford 4-quinolones of Formula J-5. Hydrogenation of compound J-5 affords the hydroxypropyl derivate of Formula J-6.

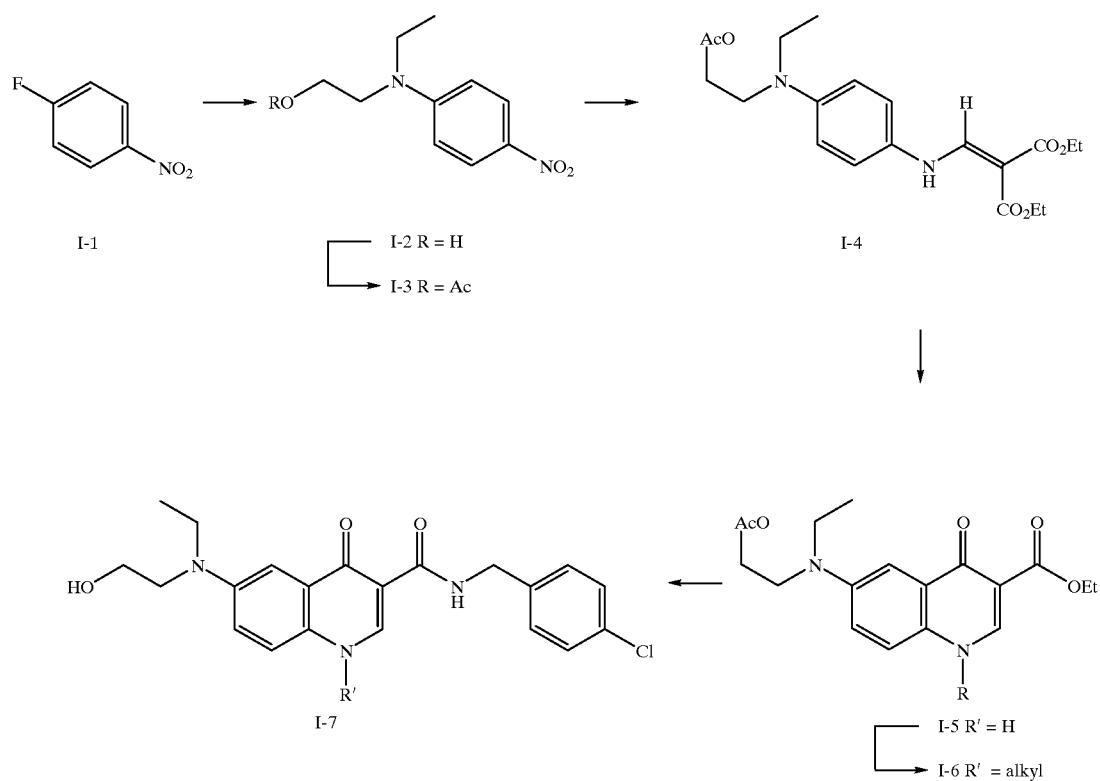

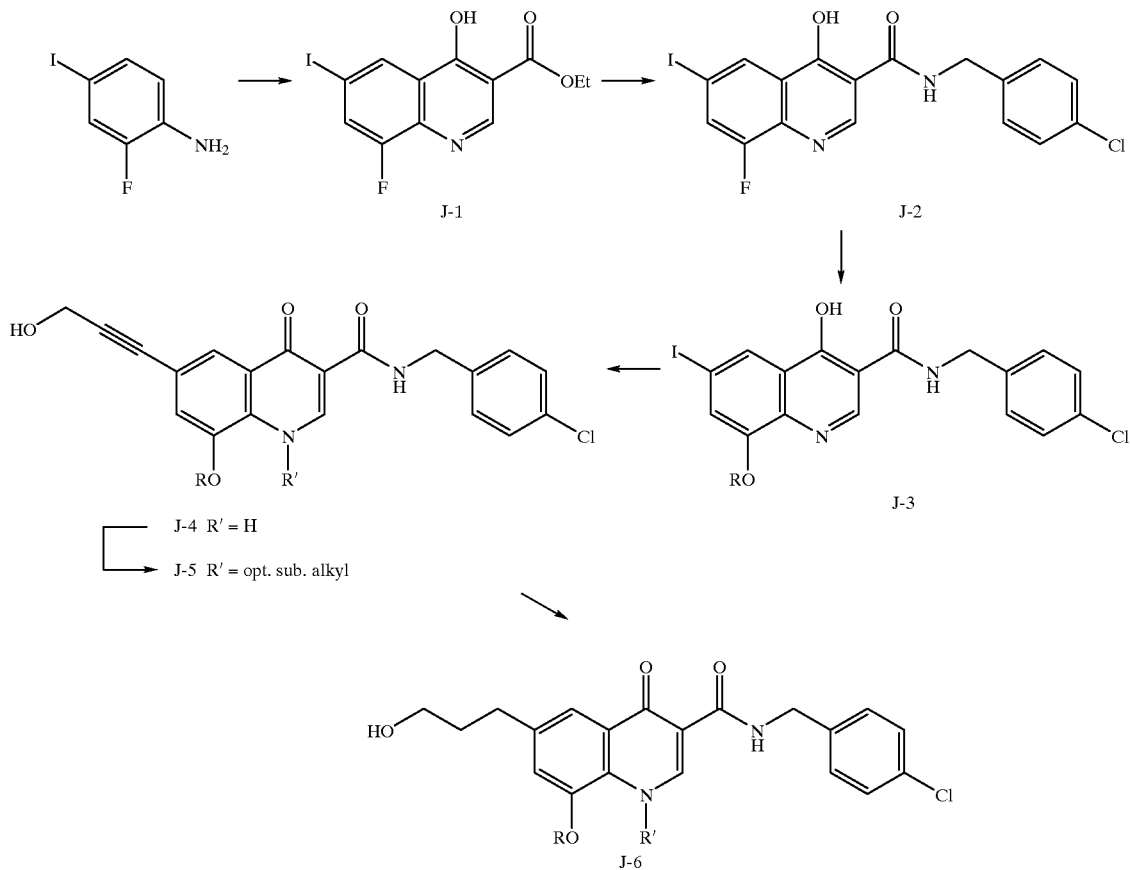
Chart K
Palladium catalyzed carbonylation of the 6-iodo-8-fluoro-4-hydroxyquinoline-3-carboxamide J-2 affords the corresponding ester K-1 which is then reduced with LAH to afford the alcohol K-2. Alkylation of the pyridone nitrogen with an alkyl halide and potassium carbonate affords compounds of Formula K-3.
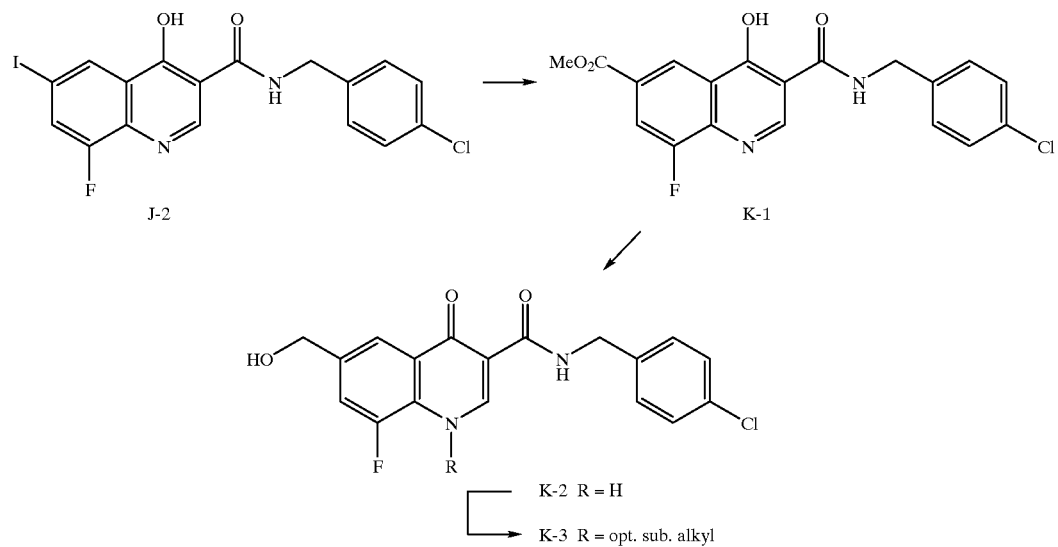

Chart L

Palladium catalyzed coupling of the 6-iodo-8-fluoro-4-hydroxyquinoline-3-carboxamide J-2 with propargyl alcohol affords alkyne L-1. The pyridone nitrogen of L-1 is then N-alkylated with an alkyl halide and potassium carbonate to afford 4-quinolones of Formula L-2. Subsequent semi-hydrogenation of compound L-2 affords hydroxyalkenyl derivatives of Formula L-3.

Chart N

Treatment of compound C-3 with methanesulfonyl chloride affords the benzylic chloride N-1. Treatment of compound N-1 with a corresponding primary or secondary amine affords compounds of Formula C-4 or the chloride atom may be displaced by other nucleophiles (e.g. azide).

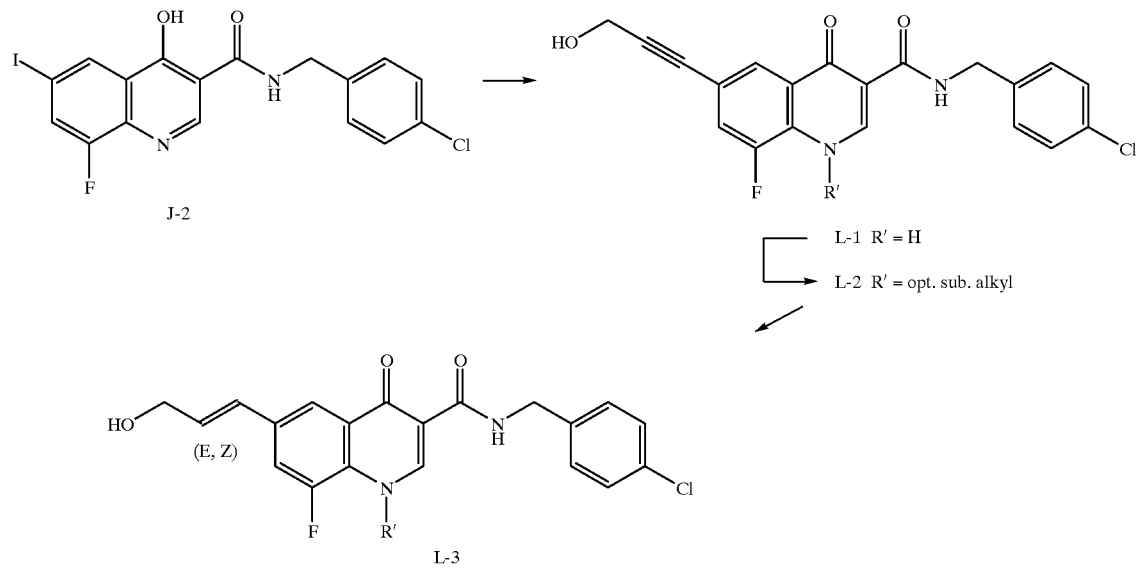

Chart M

Treatment of compound C-2 with methanesulfonyl chloride followed by reaction with morpholine affords compound M-1. Alkylation of the pyridone nitrogen with an alkyl bromide, iodide, or tosylate (X=I, Br, Ts, R is alkyl) in the presence of an alkali metal carbonate or alternatively with the corresponding alkyl alcohol under Mitsunobu conditions affords compounds of Formula M-2.

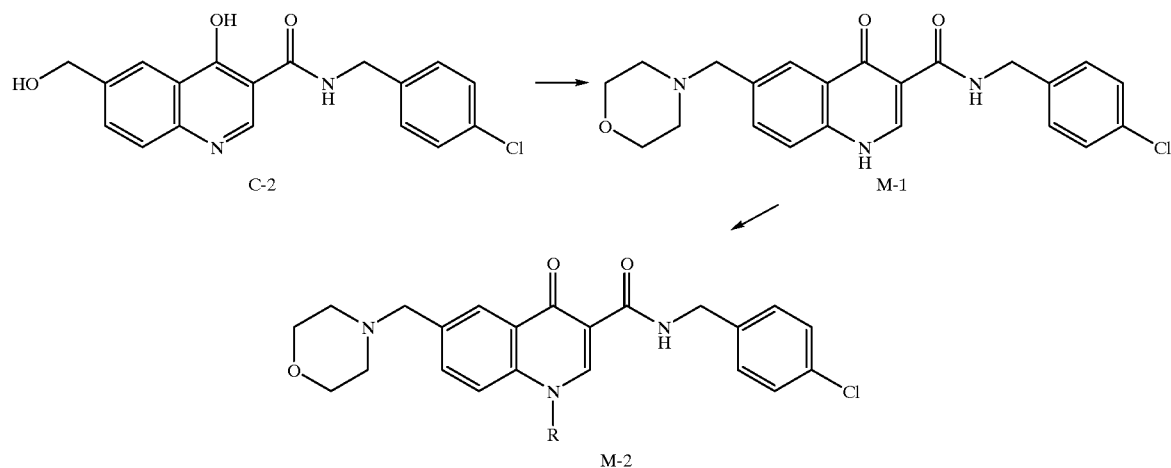

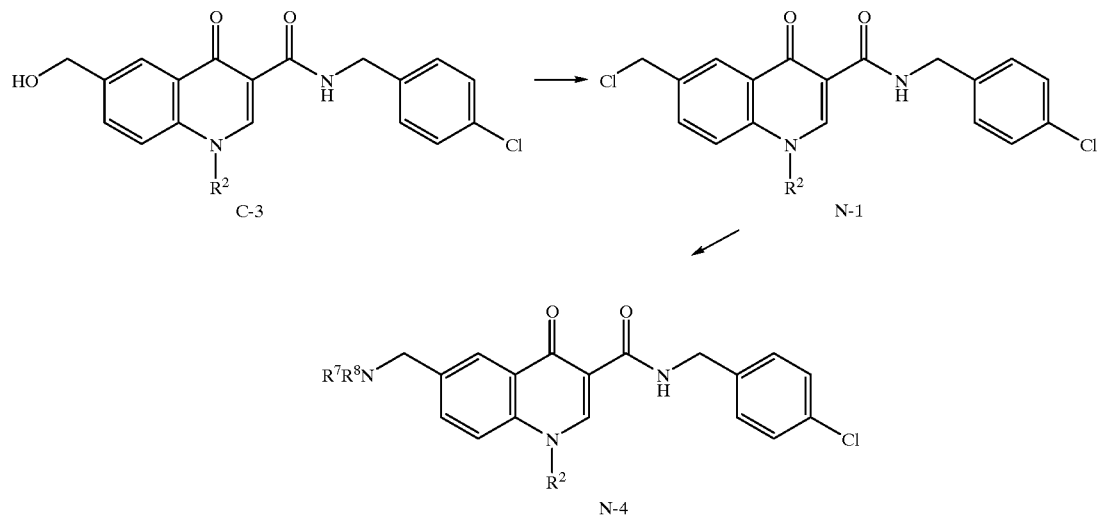

Chart O

Treatment of compound M-1 with a thiol-containing alkyl halides in the presence of an inorganic base or alternatively with the corresponding thiol-containing alkyl alcohols under Mitsunobu conditions affords compounds of Formula O-1 (wherein $R^9$ is the same as defined above). Oxidation of the sulfides of Formula O-1 with m-chloroperoxybenzoic acid in the presence of p-toluenesulfonic acid affords compounds of Formula O-2.

Chart P

Compound A-2 may be reacted with an alkyl bromide, iodide, or tosylate (X=Br, I, Ts, R is alkyl) in the presence of an alkali metal carbonate to afford compounds of the formula P-1. The resulting oiodo-4-quinolones are coupled with trialkyl alkenyl stannanes (e.g. tributyl vinyl stannane) catalyzed by $PdCl_2(PPh_3)_2$ to afford compounds such as those described by formula P-2

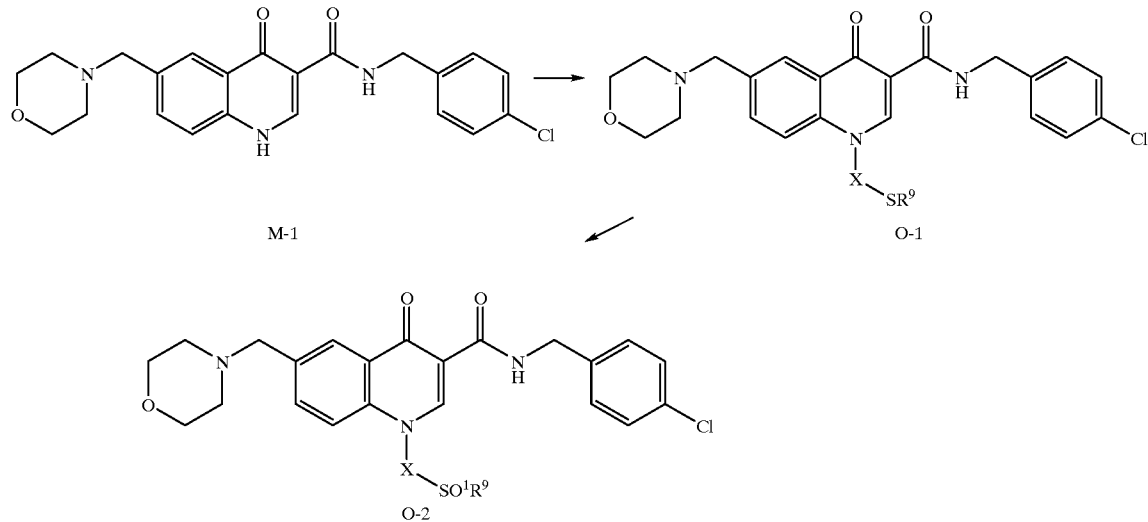

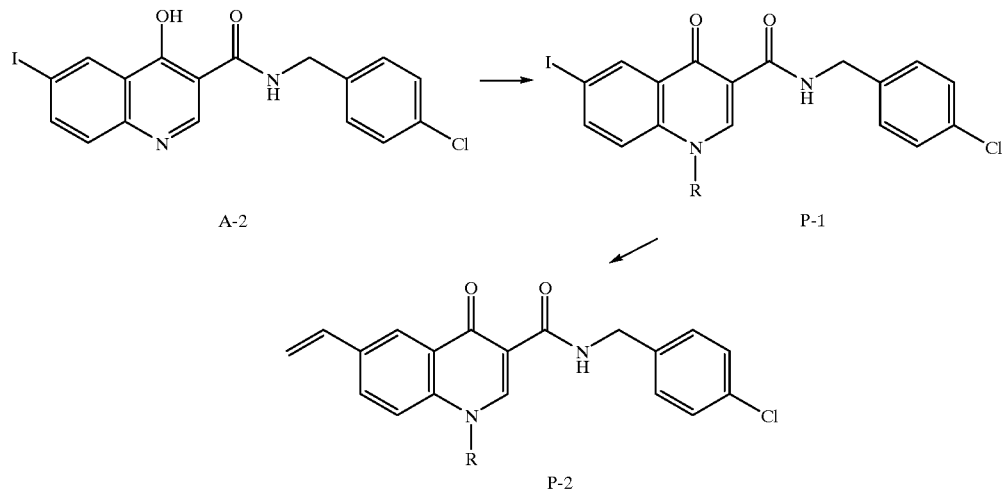

Chart Q

Alkyl chloride N-1 is treated with the sodium salt of an alkyl thiol to afford sulfides of the general formula Q-1 (wherein $R^2$ and $R^9$ is the same as defined above).

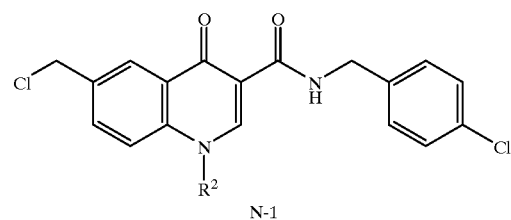

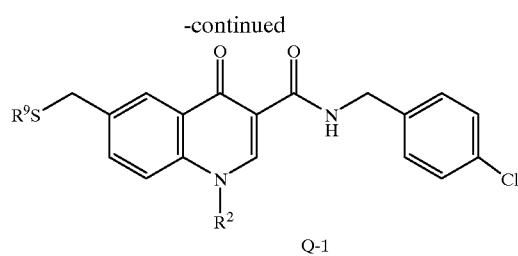

Chart R

Compounds with the 3-thioamide substitution are prepared from compound A-2 (see Chart A) by reaction with $PCl_5$ to provide the chloroimidate R-1. Subsequent treatment of chloroimidate R-1 with $H_2S$ provides the thioamide R-2 which is alkylated under Mitsunobu conditions to provide R-3. Compound R-3 may then be transformed to the desired analogs employing chemistry analogous to the carboxamide derivatives depicted in Charts A–E, N, P, or Q.

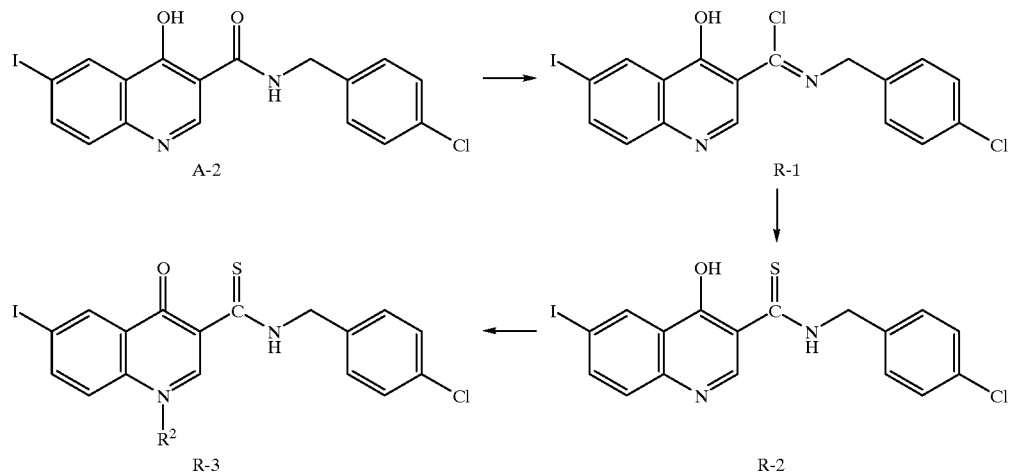

Chart S

N-(4-chlorobenzyl)-4-hydroxy-6-iodo-3-quinolinecarboxamide (Chart A-2, R=Cl) is treated with phosphorus pentachloride to form the quinolinecarboximidoyl chloride S-1. This is then treated with hydrogen sulfide to form the thioamide S-2. Alkylation under Mitsonobu conditions gives S-3 (wherein R is alkyl) which is coupled to propargyl alcohol using palladium catalysis to afford S-4.

Chart U

2-Iodoaniline is treated with diethyl ethoxyethylenemalonate at 130° C. The resulting enamine is then dissolved in $Ph_2O$ and heated to 250° C. to give the ethyl quinolinecarboxylate U-1. Condensation with neat 4-chlorobenzylamine at 180° C. gives the 4-chlorobenzylamide U-2 which is methylated with iodomethane to provide N-(4-chlorobenzyl)-8-iodo-1-methyl-4-oxo-1,4 dihydro-3-quinolinecarboxamide (U-3). Palladium catalyzed coupling to acetylenes or alkenes provides compounds of the general formula U-4.

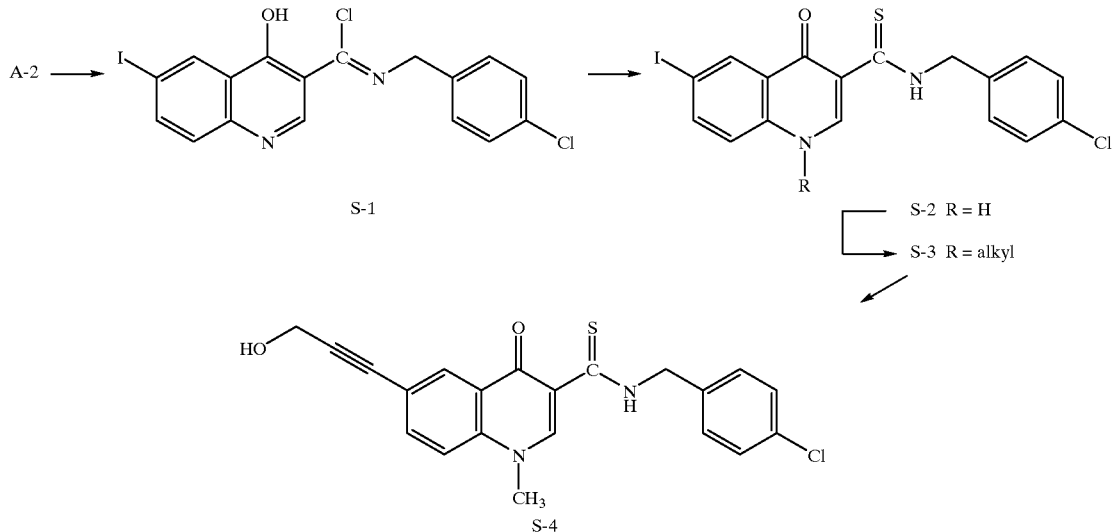

Chart T

Palladium catalyzed carbomethylation of N-(4-chlorobenzyl)-4-hydroxy-6-iodo-3-quinolinecarbothioamide (S-2) provides the quinoline 6-methyl ester T-1. Reduction to the alcohol followed by mesylation and displacement with morpholine provides the 6-morpholinylmethyl quinoline T-3. Methylation under Mitsonobu conditions gives N-(4-chlorobenzyl)-1-methyl-6-(4-morpholinylmethyl)-4-oxo-1,4-dihydro-3-quinolinecarbothioamide (T-4).

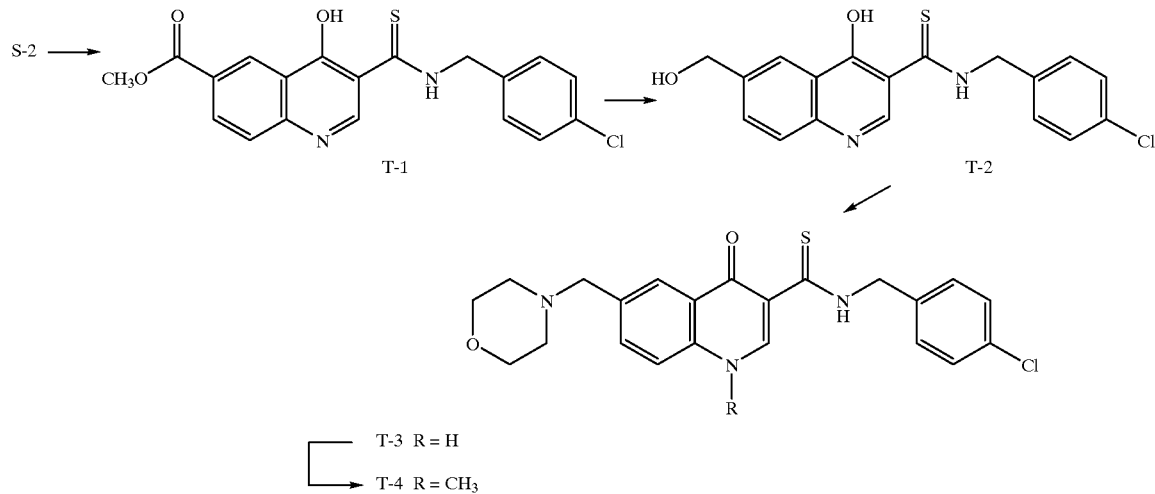

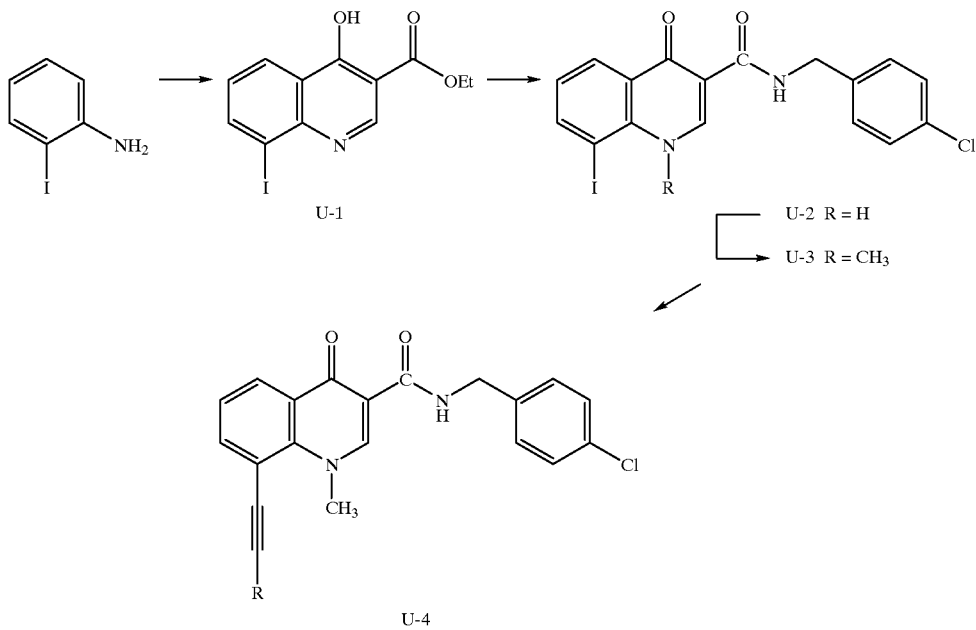

Chart V

4-Nitrobenzylbromide is treated with triphenylphosphine to form the phosphonium salt V-1. Deprotonation to form the Wittig reagent and condensation with tetrahydropyran-4-one gives the nitrobenzylidene V-2. Hydrogenation to the saturated amine and condensation with diethyl ethoxymethylenemalonate followed by thermal cyclization of the resulting enamine gives the quinolinecarboxylic ester V-3. The resulting ester is condensed with 4-chlorobenzylamine and methylated to afford V-5.

(W-3; Z=O, NMe, NBoc) which is cyclized with polyphosphoric acid to the quinoline (W-4; Z=O, NMe, NH). Treatment with 4-chlorobenzylamine at elevated temperature converts the ester to the amide (W-5; Z=O, NMe, NH). Likewise, Aniline of Formula G-2 is reductively alkylated with tetrahydrothiopyran-4-one (W-1; Z=S) to give the N-alkylated aniline (W-2; Z=S). Reaction with diethyl ethoxymethylenemalonate affords the enamine (W-3; Z=S). Oxidation with m-chloroperoxybenzoic acid affords the sul-

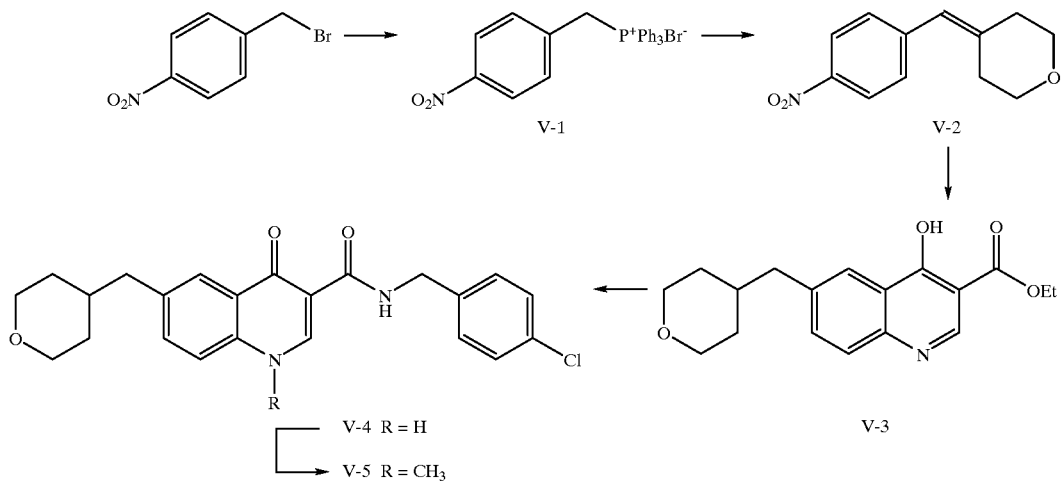

Chart W

Aniline of Formula G-2 is reductively alkylated with a substituted cyclohexanone (W-1;Z=O, NMe, NBoc) to give the N-alkylated aniline (W-2;Z=O, NMe, NBoc). Reaction with diethyl ethoxymethylenemalonate affords the enamine fone (W-2; Z=$SO_2$) which is reacted with diethyl ethoxymethylenemalonate to afford the enamine (W-3; Z=$SO_2$) then cyclized with polyphosphoric acid to the quinoline (W-4; Z=$SO_2$). Treatment with 4-chlorobenzylamine at elevated temperature converts the ester to the amide (W-5; Z=$SO_2$)

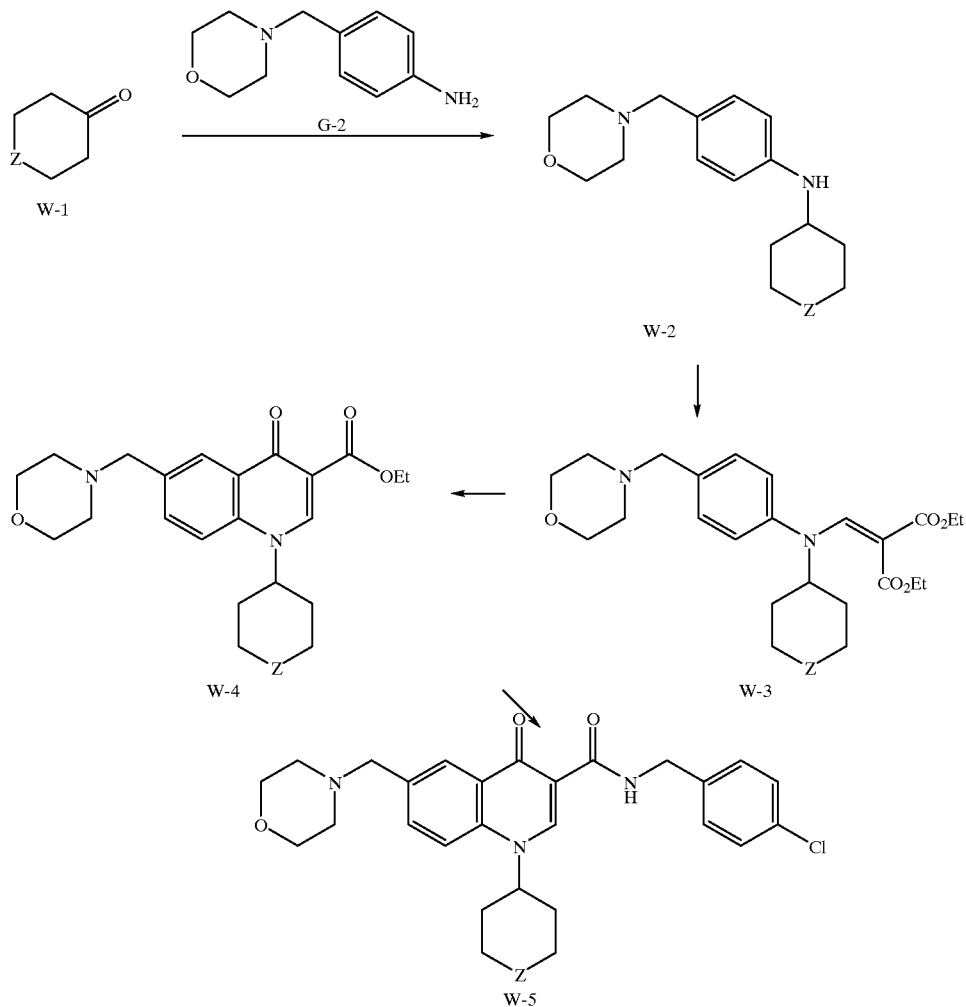

Chart X

Reductive amination of 3-bromo-4-fluorobenzaldehyde with morpholine and sodium triacetoxyborohydride affords aryl bromide X-1. Halogen-lithium exchange followed by acetylation with a N-methoxy-N-methylacetamide gives methyl ketone X-2. The resulting ketone is then converted β-keto ester X-3 with diethyl carbonate under basic conditions. Refluxing β-keto ester X-3 in triethylorthoformate and acetic anhydride produces an intermediate enol ether which is then reacted with a selected hydrazide. The resulting enamine X-4 is then cyclized by heating with sodium hydride in THF to afford the corresponding quinolone-3-ester X-5. Direct thermolysis of the ester with 4-substituted-benzylamine (X=Cl, Br, F, or CN, $R^7$ and $R^8$ are the same as defined above) at 190° C. affords amides of the general formula X-6.

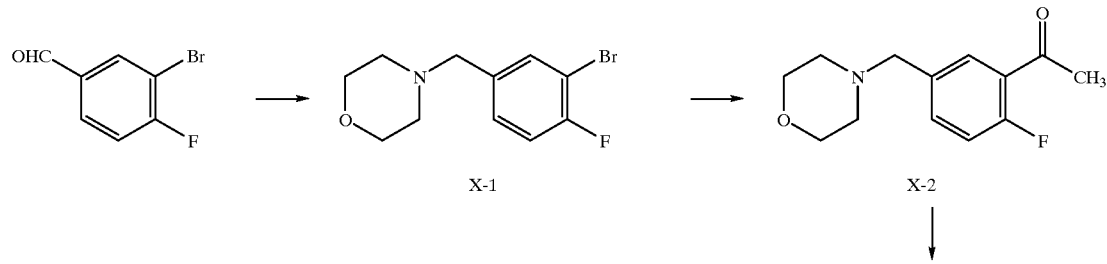

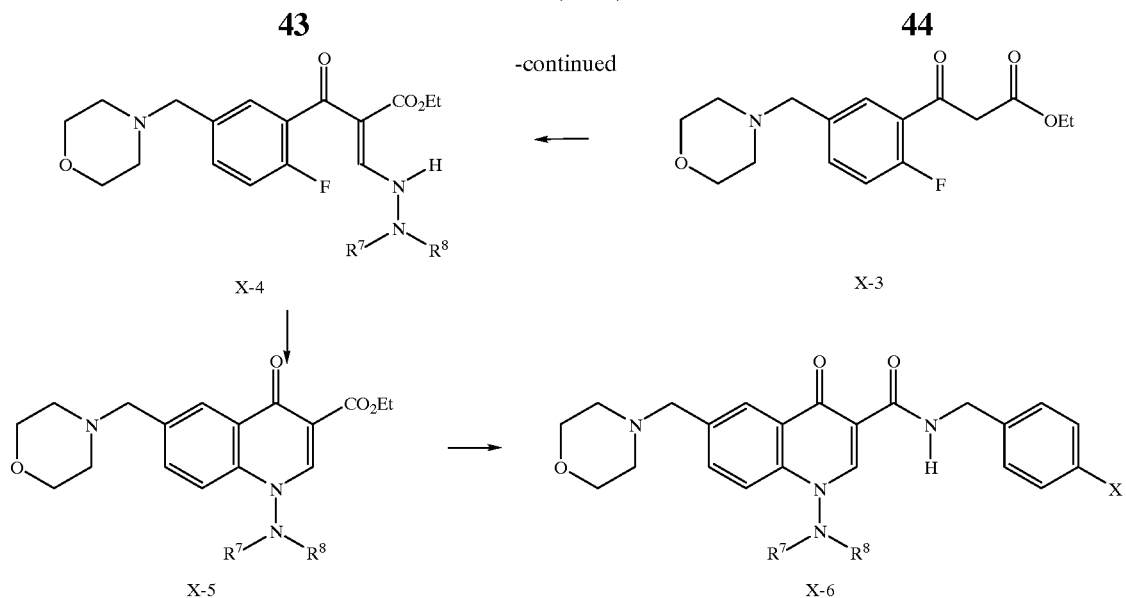

Chart Y

Butyl acetate silyl ketene acetal is reacted with 2-chloro-5-iodobenzoylchloride to afford β-ketoester Y-1. Refluxing Y-1 in triethylorthoformate and acetic anhydride produces an intermediate enol ether which is then reacted with a selected hydrazide. The resulting enamine Y-2 (wherein $R^7$ and $R^8$ are the same as defined above) is then cyclized by heating with sodium hydride to afford the corresponding quinolone-3-ester Y-3. Direct thermolysis of the ester with 4-chlorobenzylamine affords amides of the general formula Y-4. Palladium catalyzed coupling of Y-4 with propargyl alcohol affords compounds of general formula Y-5. Subsequent catalytic hydrogenation of the alkyne provides hydroxypropyl derivatives of the general formula Y-6.

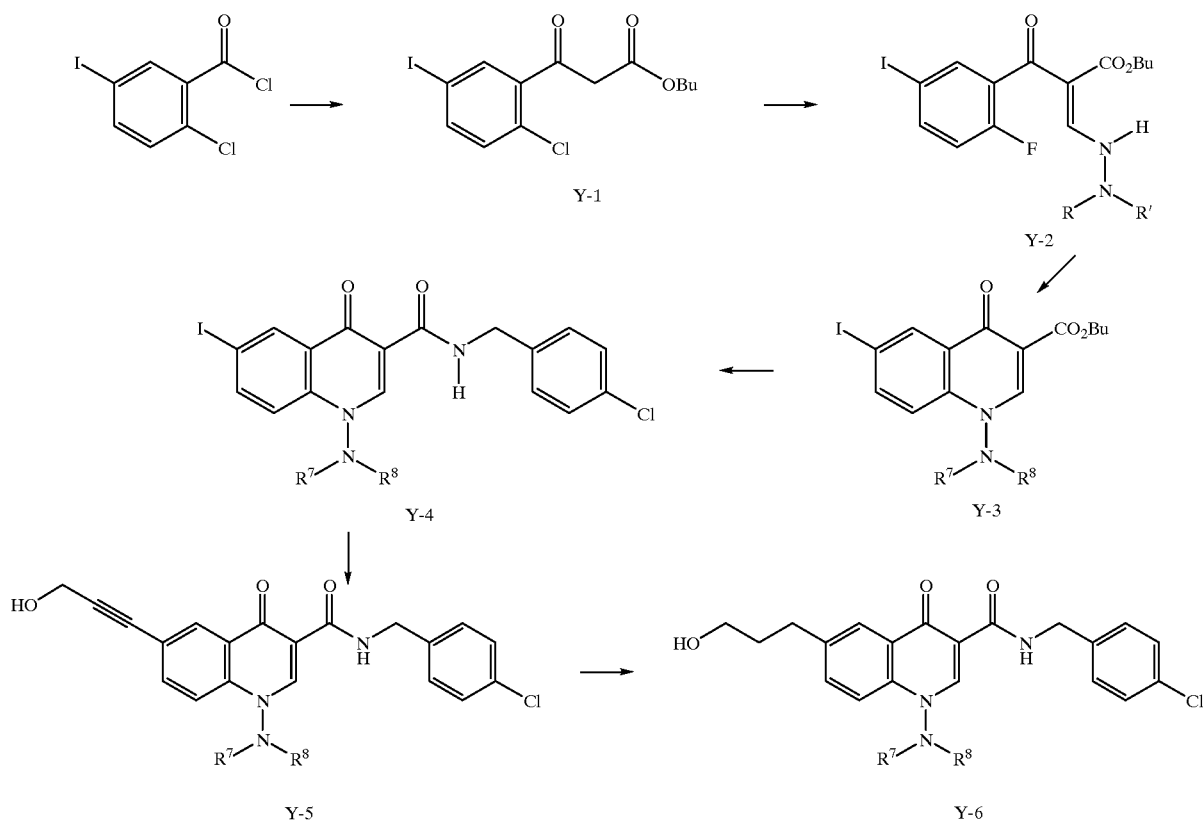

Chart Z

Alternatively where the N1-substituent is amino, N-(4-chlorobenzyl)-4-hydroxy-6-iodo-3-quinolinecarboxamide (A-2) is treated with O-(mesitylsulfonyl)hydroxylamine to afford 1-amino-quinolone Z-1. Compound Z-1 may then be transformed in a similar fashion to that described for general intermediate Y-4 above.

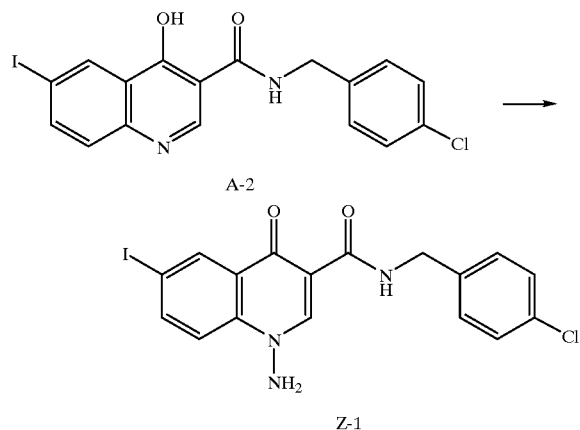

Chart AA

Ethyl 3-(2-fluorophenyl)-3-oxopropanoate (AA-1) is refluxed in triethylorthoformate and acetic anhydride to afford an intermediate enol ether which is then reacted with a selected N-alkoxyarnine. The resulting enamine AA-2 is then cyclized by heating with sodium hydride to afford the corresponding quinolone-3-ester AA-3. Direct thermolysis of the ester with 4-chlorobenzylamine affords amides of the general formula AA-4.

etoglutarate, and glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically, orally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

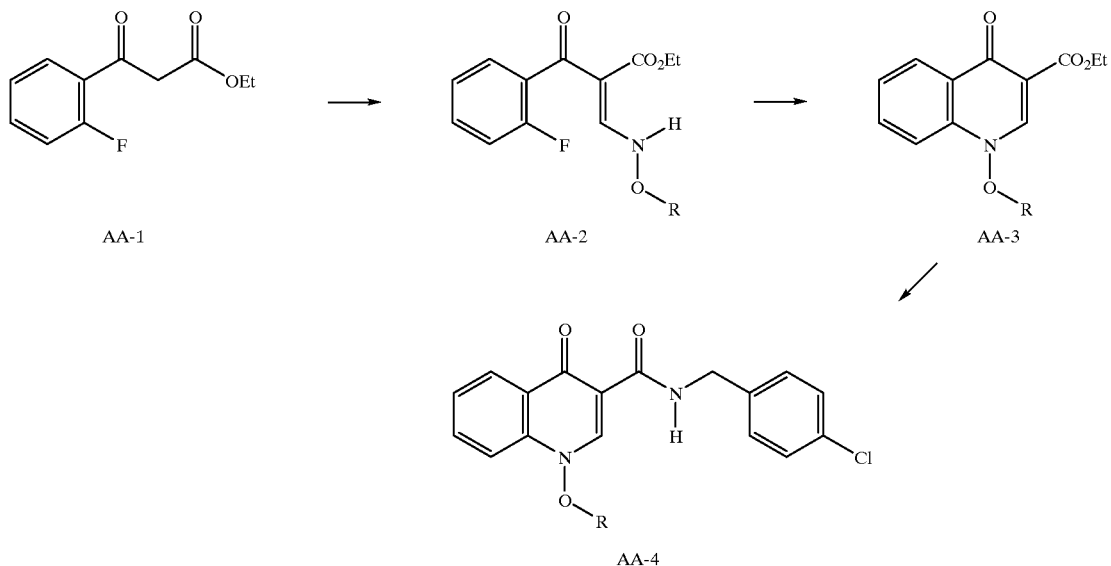

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The exact regimen for administration of the compounds and compositions disclosed herein will necessarily be dependent upon the needs of the individual subject being treated, the type of treatment and, of course, the judgment of the attending practitioner.

The antiviral activity of a compound of the invention can be determined using pharmacological models which are well known to the art, or using Test A described below.

The compounds of formula (I) and pharmaceutically acceptable salts thereof are useful as antiviral agents. Thus, they are useful to combat viral infections in animals, including man. The compounds are generally active against herpes viruses, and are particularly useful against the varicella zoster virus, the Epstein-Barr virus, the herpes simplex virus, the human herpes virus type 8 (HHV-8) and the cytomegalovirus (CMV).

While many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

Test A

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 µl volume with 5.4 mM HEPES (pH 7.5), 11.7 mM KCl, 4.5 mM MgCl$_2$, 0.36 mg/ml BSA, and 90 nM $^3$H-dTTP. Assays are run with and without CHAPS, (3-[(3-Cholamidopropyl)dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 µg/ml BSA, and 0.01% sodium azide. The HCMV polymerase, which is expressed in recombinant baculovirus-infected SF-9 cells and purified according to literature procedures, is added at 10% (or 10 µl) of the final reaction volume, i.e., 100 µl. Compounds are diluted in 50% DMSO and 10 µl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25 C. or 37 C. H$_2$O bath and terminated via the addition of 40 µl/reaction of 0.5 M EDTA (pH 8) per well. Reactions are terminated within the timeframe during which substrate incorporation is linear and varied depending upon the enzyme and conditions used, i.e., 30 min. for HCMV polymerase. Ten µl of streptavidin-SPA beads (20 mg/ml in PBS/10% glycerol) are added following termination of the reaction. Plates are incubated 10 min. at 37 C., then equilibrated to room temperature, and counted on a Packard Topcount. Linear regressions are performed and IC$_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction. Results of the testing of representative compounds of formula I in this assay are shown in Table 1 below.

TABLE 1

Biological Data

| Example | polymerase IC$_{50}$ (µM) | | |
|---|---|---|---|
| | HCMV | HSV | VZV |
| 1 | 1.7 | nd | nd |
| 2 | 1.6 | nd | nd |
| 3 | 2.3 | nd | nd |
| 4 | 0.6 | 1.0 | 1.2 |
| 5 | 1.6 | nd | nd |

TABLE 1-continued

Biological Data

| Example | polymerase IC$_{50}$ (µM) | | |
|---|---|---|---|
| | HCMV | HSV | VZV |
| 6 | 7.2 | nd | nd |
| 7 | 1.0 | 1.1 | 0.77 |
| 8 | 1.0 | nd | nd |
| 9 | <0.78 | nd | nd |
| 10 | 1.7 | nd | nd |
| 11 | 1.5 | nd | nd |
| 12 | 2 | 3.0 | 1.9 |
| 13 | 2.9 | nd | nd |
| 14 | 1.3 | 1.2 | 1.1 |
| 15 | 4.1 | nd | nd |
| 16 | 2.8 | nd | nd |
| 17 | 0.8 | 2.0 | 1.1 |
| 18 | 2.7 | nd | nd |
| 19 | 1.8 | nd | nd |
| 20 | 3.8 | nd | nd |
| 21 | 1.4 | nd | nd |
| 22 | 0.81 | nd | nd |
| 23 | 0.62 | nd | nd |
| 24 | 23.6 | nd | nd |
| 25 | 1.6 | 1.6 | 1.5 |
| 26 | 0.53 | 0.78 | 0.49 |
| 27 | 0.61 | nd | nd |
| 28 | 1.8 | nd | nd |
| 29 | 1.0 | nd | nd |
| 30 | 0.95 | nd | nd |
| 31 | 1.1 | 1.3 | 1.0 |
| 32 | 27.2 | nd | nd |
| 33 | 3.7 | nd | nd |
| 34 | >20 | nd | nd |
| 36 | >20 | nd | nd |
| 37 | >20 | nd | nd |
| 39 | 2.2 | nd | nd |
| 42 | 1.2 | nd | nd |
| 43 | 9.4 | nd | nd |
| 44 | 9.3 | nd | nd |
| 45 | 11.9 | nd | nd |
| 46 | 5.5 | nd | nd |
| 47 | 7.2 | nd | nd |
| 48 | 13.6 | nd | nd |
| 49 | 2.2 | nd | nd |
| 50 | 11.5 | nd | nd |
| 51 | 1.3 | nd | nd |
| 52 | 9.6 | nd | nd |
| 53 | 11.7 | nd | nd |
| 54 | 3.3 | nd | nd |
| 55 | 2.3 | 2.4 | 1.4 |
| 56 | 3.0 | nd | nd |
| 57 | 1.2 | nd | nd |
| 58 | 1.4 | nd | nd |
| 59 | 1.9 | nd | nd |
| 60 | 1.1 | nd | nd |
| 61 | 1.1 | 0.9 | 0.5 |
| 62 | 1.3 | 1.1 | 0.61 |
| 63 | 1.3 | nd | nd |
| 64 | 0.95 | nd | nd |
| 65 | 0.9 | 1.0 | 0.63 |
| 66 | 1.1 | nd | nd |
| 67 | 0.7 | nd | nd |
| 68 | 0.93 | nd | nd |
| 69 | 0.9 | nd | nd |
| 70 | 0.87 | nd | nd |
| 71 | 0.8 | nd | nd |
| 72 | 3.0 | nd | nd |
| 73 | 1.1 | nd | nd |
| 74 | 0.89 | 2.8 | 1.6 |
| 75 | 3.3 | 4.4 | 4.0 |
| 76 | 0.18 | <0.31 | <0.31 |
| 77 | 1.3 | 4.1 | 2.1 |
| 78 | 0.27 | nd | nd |
| 79 | 1.1 | nd | nd |
| 80 | 1.1 | nd | nd |
| 81 | 0.35 | nd | nd |
| 82 | 0.53 | nd | nd |

TABLE 1-continued

Biological Data

| Example | polymerase IC$_{50}$ ($\mu$M) | | |
|---|---|---|---|
| | HCMV | HSV | VZV |
| 83 | 0.6 | nd | nd |
| 84 | 1.2 | nd | nd |
| 85 | 6.0 | nd | nd |
| 86 | 2.5 | nd | nd |
| 87 | 4.0 | nd | nd |
| 88 | 5.9 | nd | nd |
| 89 | 6.7 | nd | nd |
| 90 | 4.4 | nd | nd |
| 91 | 2.1 | nd | nd |
| 93 | 6.2 | nd | nd |
| 94 | 0.77 | nd | nd |
| 95 | 0.3 | nd | nd |
| 96 | 1.0 | nd | nd |
| 97 | 1.5 | nd | nd |
| 98 | 0.31 | nd | nd |
| 99 | 8.0 | nd | nd |
| 100 | 2.9 | nd | nd |
| 101 | 0.3 | nd | nd |
| 102 | 0.59 | nd | nd |
| 103 | 0.83 | nd | nd |
| 104 | 1.6 | nd | nd |
| 105 | 1.3 | nd | nd |
| 106 | 3.1 | nd | nd |
| 107 | 0.84 | nd | nd |
| 108 | 0.82 | nd | nd |
| 109 | 0.48 | nd | nd |
| 110 | 0.67 | nd | nd |
| 111 | 0.73 | nd | nd |
| 112 | 0.42 | nd | nd |
| 113 | 0.64 | nd | nd |
| 114 | 0.88 | nd | nd |
| 115 | 0.62 | nd | nd |
| 116 | 14.0 | nd | nd |
| 117 | 1.5 | nd | nd |
| 118 | 1.1 | nd | nd |
| 119 | 0.5 | nd | nd |
| 120 | 2.5 | nd | nd |
| 121 | 3.9 | nd | nd |
| 122 | 2.8 | nd | nd |
| 123 | 8.2 | nd | nd |
| 124 | 1.2 | nd | nd |
| 125 | 1.1 | nd | nd |

DESCRIPTION OF PREFERRED EMBODIMENTS

Preparation 1

N-(4-Chlorobenzyl)-8-fluoro-4-hydroxy-6-iodo-3-quinolinecarboxamide

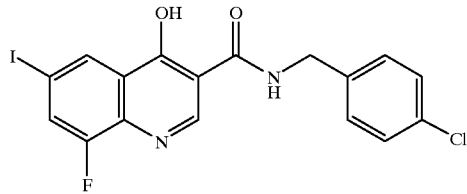

A mixture of 11.85 g of 2-fluoro-4-iodoaniline and 10.81 g of diethylethoxymethylene malonate is heated to 130° C. in a flask equipped with a Dean-Stark trap to collect formed ethanol. The mixture is then cooled to 75° C. and diluted with hexanes. The resulting solid is collected and dried. The solid is then dissolved in 60 mL diphenyl ether and heated to 250° C. for 3 h in a flask equipped with a Dean-Stark trap to collect the ethanol. The solution is allowed to cool to room temperature and the resulting solid is collected and dried to yield 11.73 g of ethyl 8-fluoro-4-hydroxy-6-iodo-3-quinolinecarboxylate. This material (0.55 g) and 3 mL of 4-chlorobenzylamine are heated at 180° C. for 1 h. The reaction is cooled and poured into 75 mL diethyl ether. The resulting solid is filtered and recrystallized from ethyl acetate/hexanes to give the title compound as an off-white solid (0.45 g).

Physical characteristics are as follows:

Mp 268–270° C.; $^1$H NMR (DMSO) δ10.17, 8.59, 8.29, 8.05, 7.37, 7.33, 4.51; IR (mull) 3180, 3078, 3059, 3004, 1647, 1607, 1551, 1524, 1489, 1344, 1297, 1285, 1240, 1183, 805 cm$^{-1}$; MS (ES-) 454.9 (M-H$^+$); HRMS (FAB) found 456.9628.

Preparation 2

N-(4-Chlorobenzyl)-4-hydroxy-6-iodo-8-methoxy-3-quinolinecarboxamide

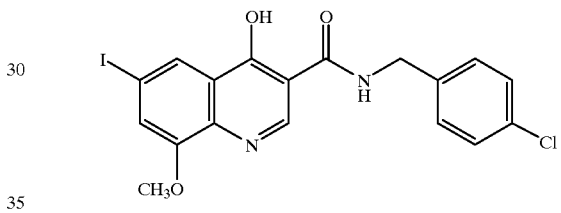

N-(4-Chlorobenzyl)-8-fluoro-4-hydroxy-6-iodo-3-quinolinecarboxamide (2.95 g) from Preparation No. 1 and sodium hydride (60% dispersion, 520 mg) is suspended in DMF (60 mL) and to the mixture is added methanol (288 μL). After being heated for 1 h at 135° C., additional sodium hydride (200 mg) is added, and the mixture is heated for an additional 1 h. The reaction mixture is allowed to cool to rt and then is poured into saturated aqueous ammonium chloride (200 mL). The resulting precipitate is filtered and washed with water (20 mL), tert-butyl methyl ether (20 mL), and heptane (20 mL). The crude product is purified by column chromatography (heptane/2-propanol, 9/1; 4/1) to afford 1.68 g (56%) of the title compound as a white solid. Recrystallization (acetic acid, water) affords a hydrate (1H$_2$O).

Physical characteristics are as follows:

Mp 241–243° C.; $^1$H NMR (DMSO-d$_6$) δ12.43, 10.28, 8.57, 8.09, 7.61, 7.41–7.34, 4.53, 4.04; $^{13}$C NMR (CF$_3$CO$_2$D) δ173.3, 167.3, 149.0, 141.4, 134.8, 133.2, 129.8, 129.2, 129.0, 124.9, 124.5, 122.5, 106.7, 94.4, 56.4, 44.0; IR (drift) 3072, 1646, 1612, 1594, 1558, 1530, 1492, 1306, 1298, 1255, 1202, 1082, 851, 846, 804 cm$^{-1}$; MS (ESI-) for m/z 467 (M-H)$^-$. Anal. Found for C$_{18}$H$_{14}$ClIN$_2$O$_3$·H$_2$O: C, 44.39; H, 3.46; N, 5.76; Cl, 7.34. Water (KF): 3.67.

Preparation 3

N-(4-Chlorobenzyl)-4-hydroxy-6-(3-hydroxy-1-propynyl)-8-methoxy-3-quinolinecarboxamide

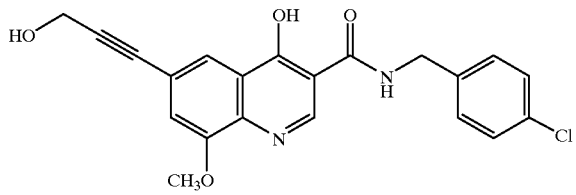

N-((4-Chlorobenzyl)-4-hydroxy-6-iodo-8-methoxy-3-quinolinecarboxamide (469 mg) from Preparation No. 2, copper (1) iodide (57 mg), and bis(triphenylphosphine)palladium (II) chloride (35 mg) are suspended in diethylarine (15 mL). Propargyl alcohol (70 µL) is added and the mixture is allowed to stir at rt for 16 h. The reaction mixture is poured into water (50 mL) and extracted with ethyl acetate (2×50 mL). The organic layer is washed with saturated aqueous ammonium chloride (3×10 mL) and brine (10 mL). The aqueous layer is back-extracted with ethyl acetate (20 mL). The combined organic layers are dried (MgSO$_4$) and concentrated. The crude product is purified by column chromatography (dichloromethane/methanol, 50/1; 33/1; 25/1; 20/1) to afford 289 mg (73%) of the title compound as a white solid.

Physical characteristics are as follows:

Mp 207–208° C.; $^1$H NMR (DMSO-d$_6$) δ12.45, 10.3, 8.58, 7.79, 7.42–7.34, 5.38, 4.53, 4.34, 4.05; $^{13}$C NMR (DMSO-d$_6$) δ178.0, 167.1, 151.8, 145.9, 141.5, 134.2, 132.6, 132.1, 131.2, 129.6, 122.5, 121.7, 117.0, 114.4, 93.3, 86.1, 59.5, 52.3, 44.3; IR (drift) 3196, 3157, 3074, 2234, 1649, 1603, 1568, 1562, 1523, 1491, 1314, 1200, 1089, 1021, 805 cm$^{-1}$; MS (ESI−) m/z 395 (M−H)$^-$. Anal. Found for C$_{21}$H$_{17}$ClN$_2$O$_4$: C, 63.26; H, 4.35; N, 7.07; Cl, 8.94.

PREPARATION 4

N-(4-Chlorobenzyl)-4-hydroxy-6-iodo-3-quinolinecarboxamide

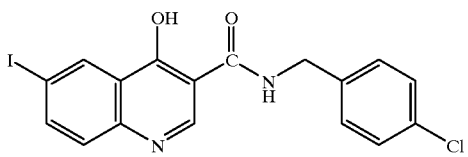

4-Iodoaniline (8.60 g) and diethyl ethoxymethylenemalonate (7.90 mL) are heated at 130° C. for 1 hour. The reaction is cooled to room temperature and 60 mL diphenyl ether is added. The solution is heated at 250° C. for 1.5 hours with removal of ethanol by a Dean-Stark trap. The reaction is cooled to room temperature and the resulting solid is filtered, washed with hexanes, and dried to yield 11.20 g of ethyl 4-hydroxy-6-iodoquinoline-3-carboxylate. A mixture of this ester (0.58 g) and 4chlorobenzylamine (4.0 mL) are heated at 180° C. for 1.5 hours. The reaction is cooled and poured into 50 mL diethyl ether. The resulting solid is filtered, triturated in ethyl acetate, and filtered again to give the desired product (0.50 g).

Physical characteristics are as follows:

Mp 297–299° C.; $^1$H NMR (300 MHz, DMSO-d$_6$) 12.71, 10.27, 8.76, 8.50, 8.02, 7.50, 7.38, 7.33, 4.52; IR (mull) 3151, 3078, 3039, 1631, 1610, 1572, 1563, 1545, 1527, 1512, 1491, 1433, 1351, 1303, 799 cm$^{-1}$; MS (ES) 438.9 (M+H), 460.9 (M+Na), 436.9 (M−H). Anal. Found: C, 46.61; H, 2.81; N, 6.34; Cl, 8.19.

Preparation 5

N-(4-Chlorobenzyl)-4-hydroxy-6-(3-hydroxy-1-propynyl)-3-quinolinecarboxamide

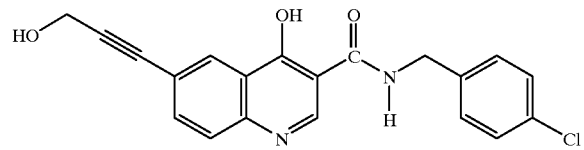

To a mixture of N-(4-chlorobenzyl)-4-hydroxy-6-iodo-3-quinolinecarboxamide from Preparation No. 4 (0.494 g) in Et$_2$NH (12.9 mL) is added CuI (10.8 mg) and (Ph$_3$P)$_2$PdCl$_2$ (39.7 mg). DMF (2 mL) is added to solubilize the reactants. To this solution is added propargyl alcohol (0.066 mL) and the reaction is stirred at room temperature for 2 days. The reaction mixture is concentrated to remove Et$_2$NH. The resulting residue is partitioned between CH$_2$Cl$_2$ (3×) and H$_2$O. A brown solid precipitated from the CH$_2$Cl$_2$ layer is filtered and collected to obtain pure product as indicated by NMR. The organic layers are combined, dried over Na$_2$SO$_4$, and concentrateed to obtain a brown residue. The residue is placed under high vac to remove residual DMF. The residue is adsorbed onto silica and chromatographed eluting with 2% MeOH in CH$_2$C$_{12}$ and 3% MeOH in CH$_2$Cl$_2$. Fractions homogenous by TLC are combined, condensed and recrystallized with EtOAc/hexanes to obtain a creme solid. The two crops yielded 325.4 mg (79%) of the desired product as a tan solid.

Physical characteristics are as follows:

MP 248–250 C.; $^1$H NMR (300 MHz, DMSO) 12.85, 10.31, 8.78, 8.22, 7.78, 7.70, 7.38, 5.39, 4.55, 4.33; IR (drift) 3161, 3073, 3003, 2960, 2914, 1656, 1614, 1557, 1517, 1487, 1299, 1014, 1006, 826, 805 cm$^{-1}$; MS (ESI) 367.0 (M+H)$^+$, 365.1 (M−H)$^-$. Anal. Found: C, 65.23; H, 4.24; N, 7.60.

Preparation 6

Methyl 3-(((4-Chlorobenzyl)amino)carbonyl)-8-fluoro-4-hydroxy-6-quinolinecarboxylate.

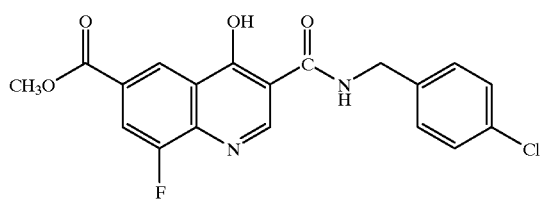

A solution of N-[(4-chlorobenzyl]-8-fluoro-4-hydroxy-6-iodo-3-quinolinecarboxamide from Preparation No. 1 (1.0 g), Et$_3$N (0.61 mL), methanol (3.55 mL), Pd(OAc)$_2$ (13.7 mg), and 1,3-bis(diphenylphosphino)propane (25.2 mg) in DMSO (12 mL) is stirred at rt until dissolution. CO(g) is slowly bubbled through the reaction for 3 h and the mixture is heated at 70° C. overnight. CO(g) is bubbled through the reaction mixture again for 4 h. The mixture is cooled to rt and diluted with water. The white solid that precipitates is collected and the filtrate partitioned against $CH_2Cl_2$. The aqueous layer is washed with $CH_2Cl_2$. The combined organic layers are dried ($Na_2SO_4$) and condensed to obtain an orange residue. The residue is placed under high vacuum to remove residual DMSO. The previously collected solid is combined with the residue, dissolved in methanol, and absorbed onto silica. The crude product is chromatagraphed eluting with 2% methanol/$CH_2Cl_2$. Fractions homogeneous by TLC are combined, condensed, and recrystallized from EtOAc/hexanes to yield 0.418 g of the title compound as a white solid.

Physical characteristics are as follows:

MP 288–290° C.; $^1$H NMR (300 MHz, DMSO) δ13.17, 10.09, 8.63, 8.58, 8.04, 7.39, 7.34, 4.54, 3.30 ppm; IR (drift) 3071, 1727, 1660, 1634, 1611, 1576, 1557, 1527, 1496, 1311, 1288, 1234, 1191, 803, 765 cm$^{-1}$; HRMS (FAB) found 389.0706. Anal. Found: C, 58.64; H13.84; N, 7.24.

Preparation 7

N-(4-Chlorobenzyl)-8-fluoro-4-hydroxy-6-(hydroxymethyl)-3-quinolinecarboxamide

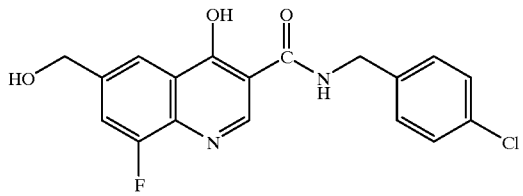

Methyl 3-{[(4-chlorobenzyl)amino]carbonyl}-8-fluoro-4-hydroxy-6-quinolinecarboxylate from Preparation No. 6 (150 mg) was dissolved in distilled THF (45 mL). The solution was heated to 35° C. to get the starting material into solution, then cooled to 18° C. for addition of LiAlH$_4$ (27.0 mg). After 2 hours additional LiAlH$_4$ (27.0 mg) was added because not much progress was seen in complete conversion to product. Complete conversion to product was achieved in 6½ hrs. The reaction was quenched by adding 0.1 mL H$_2$O, 0.1 mL 15% NaOH, and 0.1 mL to the reaction mixture. The reaction mixture was filtered to get rid of the aluminum salt that had precipitated. The filtrate was condensed to obtain a green residue. The green residue was adsorbed onto silica and chromatographed eluting with 2% MeOH in CH$_2$Cl$_2$ and 3% MeOH in CH$_2$Cl$_2$. Fractions homogenous by TLC were condensed to yield 76.8 mg (55%) of the desired product as a white solid.

Physical characteristics are as follows:

MP 263–265 C; $^1$H NMR (300 MHz, DMSO) δ12.85, 10.32, 8.62, 8.03, 7.63, 7.41, 7.36, 5.49, 4.62, 4.55; IR (drift) 3082, 2939, 1658, 1614, 1575, 1543, 1514, 1495, 1346, 1301, 1292, 1265, 891, 800, 679 cm$^{-1}$; MS (ESI) 361.1 ((M+H)$^+$, 359.1 (M–H)$^-$. Anal. Found: C, 59.76; H, 4.00; N, 7.85.

Preparation 8

Methyl 3-{[(4-chlorobenzyl)amino]carbonyl}-4-hydroxy-6-quinolinecarboxylate

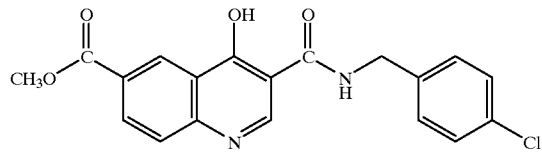

A solution of N-(4-chlorobenzyl)-4-hydroxy-6-iodo-3-quinolinecarboxamide from Preparation No. 4 (30.0 g), Et$_3$N (19.1 mL), MeOH (110.6 mL), Pd(OAc)$_2$ (431 mg), and 1,3-bis (diphenylphosphino) propane (791.9 mg) in 375 mL anhydrous DMF is stirred at room temperature until everything dissolves. CO(g) is slowly bubbled through for 2 days and the reaction is maintained at 70° C. The reaction is cooled to room temperature. The product is precipitated by adding 160 mL 1N HCl to the reaction mixture. An orange solid precipitates and is collected. The solid is triturated with EtOAc, filtered, and washed with CH$_2$Cl$_2$ to afford 23.8 g (93%) of the title compound as an off-white solid.

Physical characteristics are as follows:

Mp 290–292° C.; $^1$H NMR (300 MHz, DMSO) δ12.96, 10.26, 8.83, 8.25, 7.80, 7.39, 4.57, 3.9; IR (drift) 3222, 1724, 1646, 1619, 1574, 1544, 1512, 1489, 1404, 1359, 1288, 1277, 1242, 1210,738 cm$^{-1}$; HRMS (FAB) Found 371.0794. Anal. Found: C, 61.54; H, 3.88; N, 7.51.

Preparation 9

N-(4-Chlorobenzyl)-4-hydroxy-6-(hydroxymethyl)-3-quinolinecarboxamide

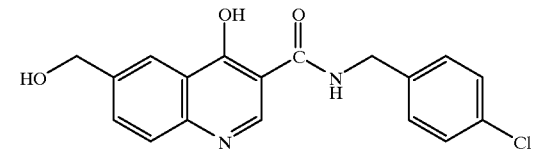

In a flame-dried 1 L 3-necked roundbottom, methyl 3-{[(4-chlorobenzyl)amino]-carbonyl}-4-hydroxy-6-quinolinecarboxylate from Preparation No. 8 (3.0 g) is dissolved in 700 mL distilled THF. The suspension is heated to 67° C. to solubilize the starting material. The reaction is allowed to cool to room temperature and then cooled in an ice bath to 10° C. Lithium aluminum hydride (552.2 mg) is added in one portion. The reaction is stirred at 25° C. and monitored by mass spectroscopy for conversion to desired product. The reaction is quenched by adding 2 mL H$_2$O, 2 mL 15% NaOH, and 2 mL H$_2$O to the reaction mixture. The reaction mixture is filtered to remove the aluminum salt that had precipitated. The filtrate is condensed to obtain a yellow-green residue. The residue is adsorbed onto silica and chromatographed eluting with 2% MeOH in CH$_2$Cl$_2$ (1 L), 3% MeOH in CH$_2$Cl$_2$ (2 L), 4% MeOH in CH$_2$Cl$_2$ (2 L), 5% MeOH in CH$_2$Cl$_2$ (1 L), 6% MeOH in CH$_2$Cl$_2$ (1 L), and 7% MeOH in CH$_2$Cl$_2$ (2 L). The desired product elutes with 4–7% MeOH in CH$_2$Cl$_2$. Fractions homogenous by TLC are condensed to yield 1.85 g (67%) of the title compound as yellow crystals.

Physical characteristics are as follows:

Mp 288–289° C.; $^1$H NMR (300 MHz, DMSO) δ12.71, 10.48, 8.74, 8.21, 7.71, 7.66, 7.39, 5.38, 4.63, 4.56; MS (ESI) 343.3 ((M+H)$^+$, 341.3 (M–H)$^-$.

Preparation 10

N-(4-Chlorobenzyl)-6-(hydroxymethyl)-1-methyl-4-oxo-1,4-dihydro-3-quinolinecarboxamide

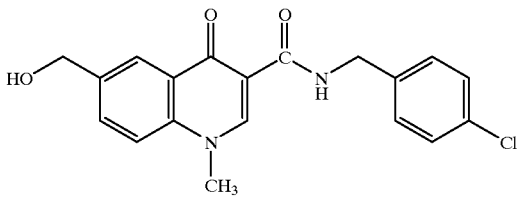

A solution of N-(4-chlorobenzyl)-4-hydroxy-6-(hydroxymethyl)-3-quinolinecarboxamide from Preparation No. 9 (300 mg,), $K_2CO_3$ (485.1 mg), and $CH_3I$ (0.11 mL) in 4 mL anhydrous DMF is heated at 90° C. for 3 h. The reaction is cooled to room temperature and diluted with $H_2O$ to dissolve any salts and precipitate the product. The crude product is adsorbed onto silica and chromatographed eluting with 3% MeOH in $CH_2Cl_2$. Fractions homogenous by TLC are combined and condensed to afford 154.2 mg (49%) of the title compound as a white solid.

Physical characteristics are as follows:

Mp 168–170° C.; $^1$H NMR (300 MHz, DMSO) δ10.45, 8.87, 8.30, 7.80, 7.38, 5.42, 4.66, 4.57, 4.02; MS (ESI) 357.2 $(M+H)^+$, 355.3 $(M-H)^-$. Anal. Found: C, 63.73; H, 4.62; N, 7.70.

Preparation 11

N-(4-Chlorobenzyl)-1,4-dihydro-6-[(1Z)-3-hydroxy-1-propenyl]-4-oxo-3-quinolinecarboxamide and

Preparation 12

N-(4-Chlorobenzyl)-1,4-dihydro-6-[(1E)-3-hydroxy-1-propenyl]4-oxo-3-quinolinecarboxamide

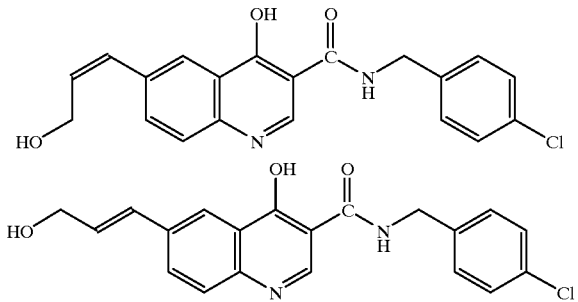

A mixture of N-(4-chlorobenzyl)-4-hydroxy -6-(3-hydroxy-1-propynyl)-3-quinolinecarboxamide from Preparation No. 5 (5.48 g) and Pd/C (10%, 0.55 g) in 3:1 $CH_2Cl_2$/MeOH (150 mL) are placed on a Parr hydrogenator under 50 psi of $H_2$ and shaken for 4 h. Another 0.30 g of Pd/C was added, and the resulting mixture was shaken for 2 h. The reaction mixture is then filtered through Celite, 0.55 g of fresh catalyst is added, and the resulting mixture is shaken under $H_2$ for 3 h. The reaction mixture is then filtered through Celite and concentrated in vacuo. Trituration from $CHCl_3$/MeOH affords a solid which is purified by HPLC chromatography on a 0.46×25 cm Chiralcel OD-H column eluting with EtOH at a rate of 0.3 mL/min to give 0.383 g of N-(4-chlorobenzyl)-1,4-dihydro-6-[(1Z)-3-hydroxy-1-propenyl]-4-oxo-3-quinolinecarboxamide (cis title compound), and 0.492 g of N-(4-chlorobenzyl)-1,4-dihydro-6-[(1E)-3-hydroxy-1-propenyl]-4-oxo-3-quinolinecarboxamide (trans title compound). Crystallization of the cis isomer from ethyl acetate gave 0.29 g of the title cis compound as a solid. Crystallization of the trans isomer from $CH_2Cl_2$/MeOH gave 0.289 g of the title trans compound as a solid.

Physical characteristics of N-(4-Chlorobenzyl)-1,4-dihydro-6-[(1Z)-3-hydroxy-1-propenyl]-4-oxo-3-quinolinecarboxamide (PREPARATION 11) are as follows:

Mp 188–191° C.; $^1$H NMR (400 MHz, DMSO-$d_6$) δ12.77, 10.47–10.41, 8.75, 8.05, 7.71–7.65, 7.42–7.36, 6.58, 5.91, 4.98, 4.56, 4.30 ppm; IR (drift) 3257, 3249, 3210, 3166, 3083, 3063, 3018, 2971, 2941, 1646, 1616, 1552, 1525, 1489, 798 cm$^{-1}$; MS (EI) m/z 368 (M+), 228, 201, 154, 142, 140, 127, 125, 115, 89, 77; HRMS (FAB) calcd for $C_{20}H_{17}ClN_2O_3$+H 369.1006, found 369.0996.

Physical characteristics of N-(4-Chlorobenzyl)-1,4-dihydro-6-[(1E)-3-hydroxy-1-propenyl]-4-oxo-3-quinolinecarboxamide (PREPARATION 12) are as follows:

Mp 212–215° C.; $^1$H NMR (400 MHz, DMSO-$d_6$) δ12.74, 10.45, 8.73, 8.16, 7.92, 7.66, 7.42–7.33, 6.72, 6.54–6.47, 4.92, 4.56, 4.17 ppm; IR (drift) 3078, 3059, 3053, 3026, 3010, 2971, 2928, 1651, 1615, 1576, 1552, 1525, 1490, 1297, 802 cm$^{-1}$; MS (EI) m/z 368 (M+), 228, 201, 198, 142, 140, 127, 125, 89, 77, 73; HRMS (FAB) calcd for $C_{20}H_{17}ClN_2O_3$+H 369.1006, found 369.0993.

Preparation 13

Ethyl 8-fluoro-6-iodo-1-methyl-4-oxo-1,4-dihydro-3-quinolinecarboxylate

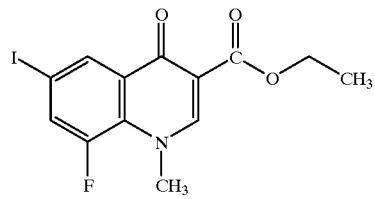

Ethyl 8-fluoro4-hydroxy-6-iodo-3-quinolinecarboxylate (18.1 g) prepared as an intermediate in Preparation No. 1 is dissolved in DMF (430 mL), and $K_2CO_3$ (36.1 g, 261 mmol) and methyl iodide (3.25 mL, 52.3 mmol) are added. The reaction mixture is heated to 95° C. for 6 h, then allowed to stir at room temperature overnight. The mixture is split into two parts. The first part is poured into $H_2O$ and extracted with five 100-mL portions of $CH_2Cl_2$. The combined organic layers are washed with five 200-mL $H_2O$, dried over $MgSO_4$, filtered, and concentrated in vacuo. The work-up is then repeated on the second portion of the reaction mixture to give a total of 15.8 g of the title compound.

Physical characteristics are as follows:

$^1$H NMR (300 MHz, CDCl$_3$) δ8.49, 8.23, 7.95–7.89, 5.73, 4.19, 4.00, 1.26 ppm.

PREPARATION 14

N-(4-Chlorobenzyl)-8-fluoro-6-iodo-1-methyl-4-oxo-1,4-dihydro-3-quinolinecarboxamide

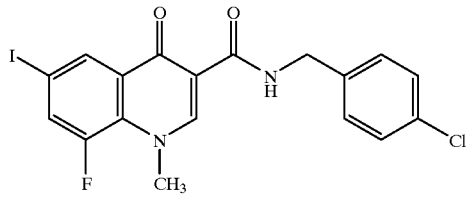

A solution of ethyl 8-fluoro-6-iodo-1-methyl-4-oxo-1,4-dihydro-3-quinolinecarboxylate from Preparation No. 13 (15.8 g) in p-chlorobenzylarnine (15.4 mL) is warmed to 190° C. The mixture is then cooled to room temperature, and hexane is added. The resulting precipitate is collected by filtration to give the title compound as a solid. An analytical sample is prepared by recrystallization from EtOH.

Physical characteristics are as follows:

Mp 243.3–244.8° C.; $^1$H NMR (400 MHz, DMSO-$d_6$) δ10.17–10.12, 8.80, 8.43, 8.12, 7.40, 7.35, 4.55, 4.15 ppm; IR (drift) 3051,3039, 1657, 1603, 1575, 1552, 1491, 1468, 1359, 1314, 1251, 1131, 880, 803, 705 cm$^{-1}$; MS (EI) mz 486 (M$^+$). Anal. found: C, 45.94; H, 2.71; N, 5.94.

Preparation 15

N-(4-Chlorobenzyl)-8-fluoro-4-hydroxy-6-(3-hydroxy-1-propynyl)-3-quinolinecarboxamide

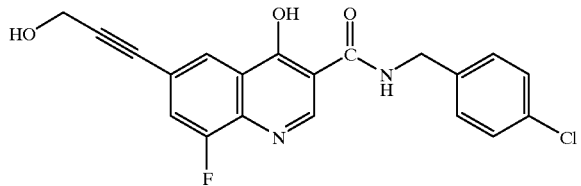

To a mixture of N-(4-chlorobenzyl)-8-fluoro4-hydroxy-6-iodo-3-quinolinecarboxamide of Preparation No. 1 (0.466 g) in 15 mL diethylamine is added CuI (0.010 g) and (Ph$_3$P)$_2$PdCl$_2$ (0.035 g). Propargyl alcohol (0.058 mL) is then added and the reaction is stirred overnight at room temperature. The diethylamine is removed in vacuo. The residue is partitioned between EtOAc and water. The insoluble material is filtered off and saved. The organic layer is washed with brine, dried and condensed. The residue is combined with the insoluble material and adsorbed onto silica and chromatographed, eluting with 3% MeOH/CH$_2$Cl$_2$. Fractions homogeneous by TLC are combined and condensed to yield 0.192 g of the desired product as a tan solid.

Physical characteristics are as follows:

Mp 277–279° C.; $^1$H NMR (300 MHz, DMSO) 13.02, 10.15, 8.59, 8.00, 7,76, 7.40, 7.33, 5.41, 4.52, 4.32; IR (mull) 3137, 3070, 3008, 1661, 1632, 1608, 1577, 1550, 1520, 1495, 1307, 1289, 1198, 1017, 802 cm$^{-1}$; MS (EI) m/z 384 (M+), 386, 384, 271, 244, 217, 142, 141, 140, 125,60; HRMS (FAB) found 385.0773.

Preparation 16

Ethyl 6-[[2-(acetyloxy)ethyl](ethyl)amino]-1-methyl-4-oxo-1,4-dihydro-3-quinolinecarboxylate

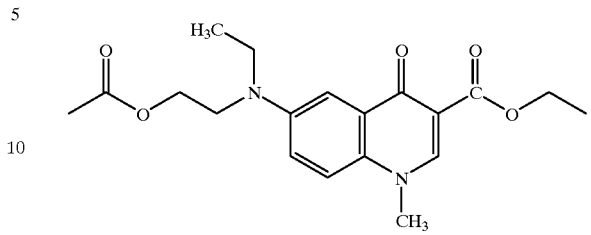

To a pressure tube containing 1-fluoro-4-nitrobenzene (5.3 mL) and is added 2-(ethylamino)-1-ethanol (10.7 g). The reaction is tightly sealed and heated to 135° C. with stirring. After 1 hour, the reaction is cooled to room temperature and concentrated under reduced pressure. The residue is dried in vacuo. The residue is chromatographed on silica eluting with ethyl acetate. The product-containing fractions are evaporated to give 10.1 g of 2-(ethyl-4-nitroanilino)-1-ethanol as an orange solid.

To a flask containing 2-(ethyl-4-nitroanilino)-1-ethanol (4.2 g) and 4-dimethylaminopyridine (0.12 g) in pyridine (20 mL) at 0° C. under a drying tube is added acetic anhydride (5.0 mL) dropwise. The reaction mixture is allowed to warm to room temperature overnight. The reaction mixture is diluted with ethyl acetate and partioned against saturated aqueous sodium carbonate. The layers are separated and the aqueous phase extracted with two additional portions of ethyl acetate. The combined organic phases are washed with brine, dried over sodium sulfate and concentrated under reduced pressure. The residue is azeotroped three times with toluene to remove residual pyridine. The residue is adsorbed onto silica and chromatographed on silica eluting with 50% ethyl acetate in heptane. The product-containing fractions are evaporated to give 4.9 g of 2-(ethyl-4-nitroanilino)ethyl acetate as a yellow oil.

To a Parr bottle containing 2-(ethyl4-nitroanilino)ethyl acetate (2.5 g) and ethyl acetate (25 mL) is added 10% palladium on carbon (0.11 g). The reaction mixture is shaken for 1 hour under 50 psi of hydrogen gas. The reaction mixture is filtered through Celite with ethyl acetate washes. The filtrate is concentrated under reduced pressure. The residue is treated with diethyl ethoxymethylenemalonate (2.4 mL) and heated to 140° C. under a flow of argon gas. After 1 hour the reaction is cooled to room temperature, adsorbed onto silica gel, and chromatographed on silica eluting with 50% ethyl acetate in heptane. The product-containing fractions are evaporated to give crude diethyl 2-({4-[[2-(acetyloxy)ethyl]-(ethyl)amino] anilino}methylene)malonate as an orange oil.

To a flask containing crude diethyl 2-({4-[[2-(acetyloxy) ethyl](ethyl)amino]-anilino}methylene)malonate (2.2 g) is added diphenyl ether (15 mL). The reaction mixture is heated from room temperature to 260° C. over 45 minutes under a flow of argon gas. After 1 hour at 260° C. the hot reaction is slowly and carefully added to stirred diethyl ether (150 mL). The resulting precipitate is filtered and washed repeatedly with heptane. The residue is adsorbed onto silica and chromatographed on silica eluting with 3% to 10% methanol in dichloromethane. The product-containing fractions are evaporated to give 0.68 g of ethyl 6-[[2-(acetyloxy) ethyl](ethyl)amino]-4-hydroxy-3-quinolinecarboxylate as a brown solid.

To a flask containing ethyl 6-[[2-(acetyloxy)ethyl](ethyl)
amino]-4-hydroxy-3-quinolinecarboxylate (0.17 g) in DMF
(5 mL) is added potassium carbonate (0.21 g) and
iodomethane (0.05 mL). The reaction is tightly capped and
heated to 90° C. After 3 hours, the reaction is cooled to room
temperature, diluted with dichloromethane, filtered and concentrated under reduced pressure. The residue is adsorbed
onto silica and chromatographed on silica eluting with 4% to
8% methanol in dichloromethane. The product-containing
fractions are evaporated to give 0.22 g of the title compound
as a orange solid.

Physical characteristics are as follows:

¹HNMR (300 MHz, CDCl₃) 8.7, 7.6, 7.3, 7.1, 4.3, 4.2,
3.8, 3.6, 3.4, 2.0, 1.4, 1.2; MS (ESI) m/z 399 (M+K⁺).

Preparation 17

N-Cyclopropyl-4-iodoaniline

To a flask containing 4-iodoaniline (2.19 g) is added
methanol (25 mL) and a few dozen dry molecular sieves
(3A). The mixture is treated with acetic acid (6 mL) followed by [(1-ethoxycyclopropyl)oxy]trimethylsilane (2.5
mL). After 1 hour, the reaction mixture is carefully treated
with sodium cyanoborohydride (2.8 g) and heated to reflux
under a nitrogen atmosphere overnight. The reaction mixture is cooled to room temperature, filtered, and concentrated under reduced pressure. The residue is diluted with
ethyl acetate and washed with aqueous sodium hydroxide
(2N). The aqueous is back-extracted once with ethyl acetate
and the combined organic layers are washed with brine,
dried over sodium sulfate, and concentarted under reduced
pressure. The residue is adsorbed onto silica and chromatographed on silica eluting with 3% to 9% ethyl acetate in
heptane. The product-containing fractions are combined and
evaporated to afford 1.85 g of the title compound as a tan oil.

Physical characteristics are as follows:

¹H NMR (300 MHz, CDCl₃) 7.5, 6.8, 2.4, 0.9, 0.7; MS
(ESI) m/z 260 (M+H⁺).

Preparation 18

Diethyl 2-[(cyclopropyl4-iodoanilino)methylene]-
malonate

To a flask containing N-yclopropyl-iodoaniline from
Preparation No. 17 (0.85 g) is added diethyl ethoxymethylenemalonate (0.9 mL) and pyridine (0.5 mL). The flask is
tightly capped and heated to 130° C. overnight. The reaction
is cooled to room temperature and azeotroped under reduced
with toluene (3×). The residue is dissolved in dichloromethane and washed with brine, dried and concentrated
under reduced pressure. The residue is adsorbed onto silica
gel and chromatographed on silica eluting with 25% to 75%
ethyl acetate in heptane. The product-containing fractions
are evaporated to give 0.78 g of the title compound as a tan
solid.

Physical characteristics are as follows:

¹H NMR (300 MHz, CDCl₃) 7.8, 7.7, 7.0, 4.2, 4.1, 3.1,
1.3, 0.9, 0.7; MS (ESI) m/z 430 (M+H⁺).

Preparation 19

Ethyl 1-cyclopropyl-6-iodo-4-oxo-1,4-dihydro-3-
quinolinecarboxylate

To a flask containing diethyl 2-[(cyclopropyl-4-
iodoanilino)methylene]malonate from Preparation No. 18

(0.22 g) is added polyphosphoric acid (1.4 g). The reaction
mixture is capped and heated to 120° C. over 1 hour. After
2 hours at 120° C. the reaction is cooled to room
temperature, treated with ice and partioned between dichloromethane and saturated aqueous bicarbonate. The basic
aqueous layer is extracted with two additional portions of
dichloromethane. The combined organic layers are washed
with brine, dried over sodium sulfate and concentrated under
reduced pressure to afford 0.19 g of the title compound as a
tan solid.

Physical characteristics are as follows:

¹H NMR (300 MHz, CDCl₃) 8.8, 8.6, 7.9, 7.7, 4.4, 3.4,
1.4, 1.3, 1.1; MS (ESI) m/z 384 (M+H⁺).

Preparation 20

N-(4-Chlorobenzyl)-1-cyclopropyl-6-iodo-4-oxo-1,
4-dihydro-3-quinolinecarboxamide

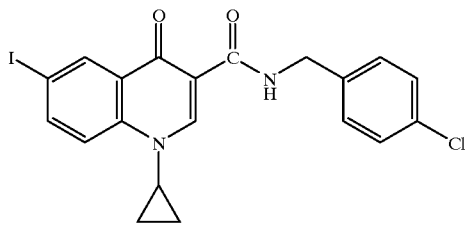

To a flask containing ethyl 1-cyclopropyl-6-iodo-4-oxo-
1,4-dihydro-3-quinolinecarboxylate from Preparation No.
19 (0.19 g) is added p-chlorobenzylamine (1.0 mL). The
reaction is tightly capped and heated to 180° C. for 1 hour.
The reaction is cooled to room temperature and partioned
between dichloromethane containing methanol and dilute
hydrochloric acid. The aqueous layer is extracted with
dichloromethane and the combined organic layers are
washed with brine, dried and concentarted under reduced
pressure. The residue is adsorbed onto silica and chromatographed on silica eluting with 2% to 6% methanol in
dichloromethane. The product containing fractions are
evaporated to give 0.10 g of the title compound as a tan
solid.

Physical characteristics are as follows:

¹H NMR (300 MHz, DMSO-d₆) 10.2, 8.7, 8.6, 8.2, 8.0,
7.4, 4.5, 3.7, 3.5, 1.3, 1.1; MS (ESI) m/z 479 (M+H⁺).

Preparation 21

4-(4-Nitrobenzyl)morpholine

To a flask containing 4-nitrobenzyl bromide (21.6 g) in
dry acetone (100 mL) is added potassium carbonate (34.5 g)
and morpholine (10 mL). The mixture is heated to reflux
overnight under a drying tube. The reaction is partioned
between ethyl acetate and water and separated. The basic
aqueous layer is extracted with two additional portions of
ethyl acetate. The combined organic layers are washed with
brine, dried, and concentrated under reduced pressure to
afford 21.3 g of the title compound as a solid.

Physical characteristics are as follows:

Mp 75–79° C.; ¹H NMR (300 MHz, CDCl₃) 8.2, 7.6, 3.7,
3.6, 2.4.

Preparation 22

4-(4-Aminobenzyl)morpholine

To a solution of 4-(4-Nitrobenzyl)morpholine from
Preparation No. 21 (0.89 g) in ethyl acetate (10 mL) is added 5% platinuim on carbon (0.04 g). The reaction is shaken under 30 psi of hydrogen gas for 1 hour. The mixture is filtered with ethyl acetate washes. The filtrate is concentrated under reduced pressure to afford 0.71 g of the title compound as a yellow solid.

Physical characteristics are as follows:

$^1$H NMR (300 MHz, CDCl$_3$) 7.1, 6.6, 3.7, 3.6, 3.4, 2.4; MS (ESI) m/z 193 (M+H$^+$).

Preparation 23

N-Cyclopropyl-4-(4-morpholinylmethyl)aniline

To a flask containing 4-(4-aminobenzyl)morpholine from Preparation No. 22 (0.96 g) is added methanol (12 mL) and a few dozen dry molecular sieves (3A). The mixture is treated with acetic acid (3 mL) followed by [(1-ethoxycyclopropyl)oxyl-trimethylsilane (1.25 mL). After 15 minutes, the reaction mixture is carefully treated with sodium cyanoborohydride (1.4 g) and heated to reflux under a nitrogen atmosphere overnight. The reaction mixture is cooled to room temperature, filtered with methanol washes, and concentrated under reduced pressure. The residue is diluted with diethyl ether and washed with aqueous sodium hydroxide (2N). The aqueous is back-extracted once with diethyl ether and once with dichloromethane. The combined organic layers are washed with brine, dried over sodium sulfate, and concentarted under reduced pressure. The residue is adsorbed onto silica and chromatographed on silica eluting with 2% to 8% methanol in dichloromethane. The product-containing fractions are combine and evaporated to afford 0.13 g of the title compound as a pink solid.

Physical characteristics are as follows:

$^1$H NMR (300 MHz, CDCl$_3$) 7.1, 6.8, 3.7, 3.4, 2.4, 0.7, 0.5; MS (ESI) m/z 233 (M+H$^+$).

Preparation 24

Diethyl 2-{[cyclopropyl-4-(4-morpholinylmethyl)anilino]methylene}malonate

To a flask containing N-cyclopropyl-4-(4-morpholinylmethyl)aniline (0.55 g) from Preparation No. 23 is added diethyl ethoxymethylenemalonate (0.45 mL) and pyridine (0.33 mL). The flask is tightly capped and heated to 145° C. for 2 hours. The reaction is cooled to room temperature and azeotroped under reduced pressure with toluene (3×). The residue is dissolved in dichloromethane and washed with brine, dried and concentrated under reduced pressure. The residue is chromatographed on silica eluting with 2% to 6% methanol in dichloromethane. The product-containing fractions are evaporated to give 0.77 g of the title compound as an oil.

Physical characteristics are as follows:

$^1$H NMR (300 MHz, CDCl$_3$) 7.8, 7.3, 7.1, 4.2, 4.1, 3.8, 3.1, 2.4, 1.3, 0.8, 0.7; MS (ESI) m/z 403 (M+H$^+$).

Preparation 25

Ethyl 1-cyclopropyl-6-(4-morpholinylmethyl-4-oxo-1,4-dihydro-3-quinolinecarboxylate

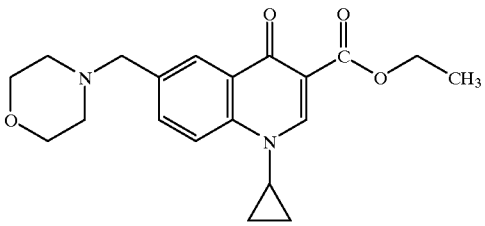

To a flask containing diethyl 2-{[cyclopropyl-4-(4-morpholinylmethyl)anilino]methylene}malonate from Preparation No. 24 (0.77 g) is added polyphosphoric acid (4.4 g). The reaction mixture is tightly capped and heated to 120° C. After 1 hour the reaction is cooled to room temperature. The reaction mixture is carefully added to a vigorously stirred mixture of dichloromethane and saturated aqueous bicarbonate. The layers are separated and the basic aqueous layer is extracted with two additional portions of dichloromethane. The combined organic layers are washed with brine, dried over sodium sulfate and concentrated under reduced pressure. The residue is chromatographed on silica eluting with 3% to 15% methanol in dichloromethane to afford 0.38 g of the title compound as a yellow solid.

Physical characteristics are as follows:

$^1$H NMR (300 MHz, CDCl$_3$) 8.6, 8.4, 7.9, 7.7, 4.4, 3.7, 3.6, 3.5, 2.5, 1.4, 1.3, 1.1; MS (ESI) m/z 357 (M+H$^+$).

Preparation 26 tert-Butyl 2-[3-{[(4-chlorobenzyl)amino]carbonyl}-6-iodo-4-oxo-1(4H)-quinolinyl]acetate

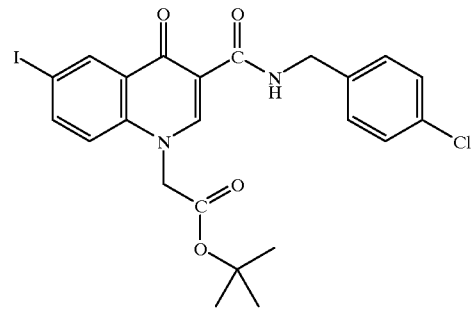

To a flask containing N-(4-chlorobenzyl)-6-iodo-4-hydoxy-3-quinolinecarboxamide (0.22 g) obtained as described in Preparation No. 4 in DMF (5 mL) is added potassium carbonate (0.21 g) and tert-butylbromoacetate (0.11 mL). After stirring overnight, the reaction is diluted with dichloromethane and partioned against water. The organic phase is washed with brine, dried over sodium sulfate, concentrated under reduced pressure, and dried in vacuo to give 0.26 g of the title compound as a white solid.

Physical characteristics are as follows:

$^1$H NMR (300 MHz, CDCl$_3$) 10.2, 8.9, 8.6, 8.1, 7.4, 7.3, 5.4, 4.5, 1.4. Anal. found: C, 49.91; H, 4.09; N, 5.08.

Example 1

N-(4-Chlorobenzyl)-6-(3-hydroxy-1-propynyl)-1-isopropyl-4-oxo-1,4-dihydro-3-quinolinecarboxamide

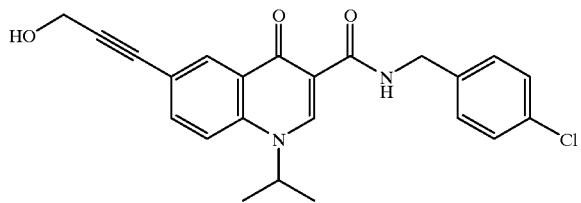

N-((4-Chlorobenzyl)-4-hydroxy-6-(3-hydroxy-1-propynyl)-3-quinolinecarboxamide (366 mg) from Preparation No. 5 and potassium carbonate (276 mg) are dissolved in DMF (5 mL). 2-Bromopropane (470 μL) is added and the mixture is heated to 100° C. for 1 h. The reaction mixture is allowed to cool to rt, poured into water (25 mL) and extracted with ethyl acetate (2×50 mL). The organic layer is washed with sat. aqueous brine (10 mL). The aqueous layer is back-extracted with ethyl acetate (20 mL). The combined organic layers are dried ($MgSO_4$) and concentrated. The crude product is purified by column chromatography (EtOAc/heptane, 1/1 to 1/0) and recrystallization (EtOH) to afford 70 mg (17%) of the title compound as a white solid.

Physical characteristics are as follows:

Mp 189–191° C. dec; $^1$H NMR (DMSO-$d_6$) δ10.28, 8.87, 8.34, 8.08, 7.85, 7.42–7.35, 5.40, 5.18, 4.55, 4.35, 1.53; IR (drift) 3314, 2227 (w), 1902 (w), 1648 (s), 1597, 1572, 1547, 1491 (s), 1342, 1321, 1214, 1037, 1025, 813, 682 cm$^{-1}$. Anal. Found for $C_{23}H_{21}ClN_2O_3$: C, 67.53; H, 5.14; N, 6.66.

Example 2

1-(sec-butyl)-N-(4-chlorobenzyl)-6-(3-hydroxy-1-propynyl)-4-oxo-1,4-dihydro-3-quinolinecarboxamide

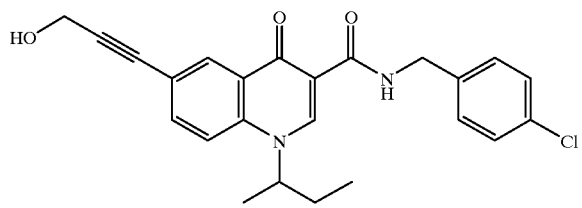

N-((4-Chlorobenzyl)-4-hydroxy-6-(3-hydroxy-1-propynyl)-3-quinolinecarboxamide (366 mg) from Preparation No. 5 and potassium carbonate (276 mg) are dissolved in DMF (5 mL). 2-Iodobutane (575 μL) is added and the mixture is heated to 100° C. for 1 h. The reaction mixture is allowed to cool to rt, poured into water (25 mL) and extracted with ethyl acetate (2×50 mL). The organic layer is washed with sat. aqueous brine (10 mL). The aqueous layer is back-extracted with ethyl acetate (20 mL). The combined organic layers are dried ($MgSO_4$) and concentrated. The crude product is purified by column chromatography (dichloromethane/methanol, 100/1; 50/1; 20/1) to afford 80 mg (19%) of the title compound as a white solid.

Physical characteristics are as follows:

Mp 200–201° C. dec; $^1$H NMR (DMSO-$d_6$) δ10.27, 8.80, 8.34, 8.12, 7.84, 7.42–7.35, 5.39, 5.02, 4.55, 4.35, 1.90, 1.51, 0.85; IR (drift) 3412, 1657, 1597, 1575, 1547, 1490, 1458, 1422, 1341, 1324, 1213, 1088, 1047, 812, 804 cm$^{-1}$. Anal. Found for $C_{24}H_{23}ClN_2O_3$: C, 68.07; H, 5.52; N, 6.45; Cl, 8.15.

Example 3

1-(sec-butyl)-N-(4-chlorobenzyl)-6-(3-hydroxy-1-propynyl)-8-methoxy-4-oxo-1,4-dihydro-3-quinolinecarboxamide

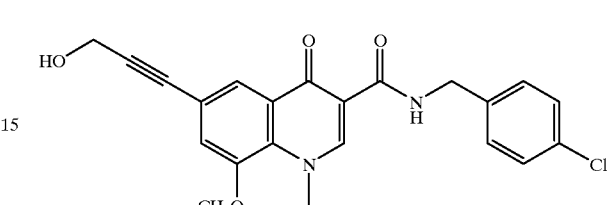

N-((4-Chlorobenzyl)-4-hydroxy-6-(3-hydroxy-1-propynyl)-8-methoxy-3-quinolinecarboxamide (300 mg) from Preparation No. 3 and potassium carbonate (310 mg) are dissolved in DMF (5 mL). 2-Iodobutane (345 μL) is added and the mixture is heated to 120° C. for 4 h. Additional 2-Iodobutane (200 μL) and potassium carbonate (100 mg) is added and the mixture is heated for 16 h. The reaction mixture is allowed to cool to rt, poured into water (75 mL) and extracted with ethyl acetate (3×50 mL). The organic layer is washed with sat. aqueous brine (10 mL). The aqueous layer is back-extracted with ethyl acetate (20 mL). The combined organic layers are dried ($MgSO_4$) and concentrated. The crude product is purified by column chromatography (EtOAc/heptane, 30/1; 10/1) to afford 60 mg (18%) of the title compound as a white solid.

Physical characteristics are as follows:

Mp 139–142° C. dec; $^1$H NMR (DMSO-$d_6$) δ10.20, 8.74, 7.95, 7.43–7.35, 5.62, 5.40, 4.54, 4.35, 4.04, 1.83, 1.50, 0.77; IR (drift) 2480, 2214, 2015, 1909, 1649, 1597, 1550, 1483, 1340, 1327, 1278, 1211, 1078, 1064, 807 cm$^{-1}$; HRMS (FAB) calcd for $C_{25}H_{25}ClN_2O_4$+H 453.1581, found 453.1593.

Example 4

N-(4-Chlorobenzyl)-8-(2-hydroxyethoxy)-6-(3-hydroxypropyl)-1-methyl-4-oxo-1,4-dihydro-3-quinolinecarboxamide]

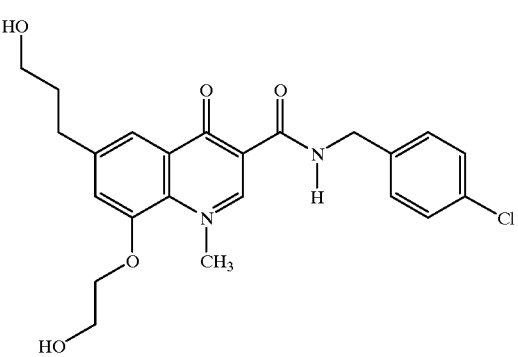

To a suspension of N-(4-chlorobenzyl)-8-fluoro-6-iodo-3-quinolinecarboxamide from Preparation No. 1 (2.28 g) in DMF (75 mL) is added sodium hydride (60% oil dispersion; 0.600 g) followed by addition of 2-benzyloxyethanol (1.42 mL). The reaction is heated to 135° C. and stirred for 1 h. The reaction mixture is cooled to room temperature and poured into saturated aqueous ammonium chloride (200 mL). The aqueous layer is extracted with dichloromethane (4×100 mL). The combined organic layers are washed with brine (50 mL), dried with $MgSO_4$, filtered, and concentrated in vacuo. The resulting yellow solid is purified by column chromatography (dichloromethane/methanol, 98/2). Fractions homogeneous by TLC are combined and concentrated in vacuo to yield a yellow solid which is recrystallized from ethanol to yield 1.568 g (53%) of the intermediate amide as an off-white solid. To a suspension of this material (1.149 g) in diethylarnine (24 mL) are added copper iodide (0.111 g) and $Pd(PPh_3)_2Cl_2$ (0.069 g) followed by addition of propargyl alcohol (0.16 mL). The reaction is stirred at room temperature for 3 d. The reaction mixture is concentrated in vacuo and partitioned between $H_2O$ (50 mL) and dichloromethane (50 mL). The aqueous layer is extracted with dichloromethane (3×50 mL). Combined organic layers are washed with saturated aqueous ammonium chloride (50 mL), dried with $MgSO_4$, filtered, and concentrated in vacuo. The resulting brown solid is purified by column chromatography (dichloromethane/methanol, 98/2). Fractions homogeneous by TLC are combined and concentrated in vacuo to yield a tan solid which is recrystallized from ethanol to yield 0.181 g (18%) of the propargyl compound as a tan, crystalline solid. To a solution of this material (0.394 g) in DMF (3 mL) is added potassium carbonate (0.317 g) followed by iodomethane (0.14 mL). The reaction is heated to 90° C. and stirred for 18 h. The reaction mixture is concentrated in vacuo and the resulting residue is purified by column chromatography (dichloromethane; dichloromethane/methanol, 98/2). Fractions homogeneous by TLC are combined and concentrated in vacuo to yield a yellow solid which is recrystallized from EtOH to yield 0.273 g (67%) of the N-methyl pyridone as a yellow solid. The pyridone (0.350 g) is dissolved in 1/1 dichloromethane/ethanol (100 mL) and hydrogenated over 10% Pd/C (53 mg) at 35 psi for 18 h. The reaction mixture is filtered through a Celite pad, and the filtrate is concentrated in vacuo. The resulting yellow oil is dissolved in methanol (60 mL) and hydrogenated over Pd Black (35 mg) for 4 h. The reaction mixture is filtered through a Celite pad, and the filtrate is concentrated in vacuo. The resulting yellow oil is purified by column chromatography (dichloromethane/methanol, 98/2; 95/5). Fractions homogeneous by TLC are combined and concentrated in vacuo to yield a pale yellow solid which is recrystallized from ethyl acetate to yield 0.104 g (35%) of the title compound as a pale yellow solid.

Physical characteristics are as follows:

Mp 175–179° C.; $^1$H NMR (300 MHz, DMSO-$d_6$) $\delta$10.43, 8.65, 7.75, 7.42–7.34, 7.29, 4.97, 4.57, 4.50, 4.27, 4.18, 3.82, 3.44, 2.73, 1.77; $^{13}$C NMR (75 MHz, DMSO-$d_6$) $\delta$175.1, 164.9, 164.8, 150.8, 150.6, 140.7, 140.0, 139.2, 131.8, 129.8, 129.6, 128.9, 128.8, 127.8, 127.3, 117.5, 117.1, 110.3, 110.2, 72.4, 60.4, 59.9, 48.2, 42.6, 41.9, 34.4, 31.9; IR (drift) 3341, 3311, 1903, 1657, 1605, 1556, 1494, 1452, 1346, 1323, 1276, 1084, 1058, 1044, 804 cm$^{-1}$; MS (ESI+) m/z 445 (M+H)$^+$. Anal. Found: C, 62.86; H, 5.87; N, 6.29; Cl, 6.26.

Example 5

N-(4-Chlorobenzyl)-8-[2-hydroxy-1-(hydroxymethyl)ethoxy]-6-(3-hydroxypropyl)1-methyl-4-oxo-1,4-dihydro-3-quinolinecarboxamide

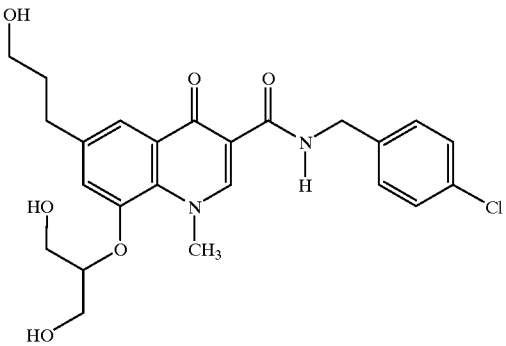

To a suspension of N-(4-chlorobenzyl)-8-fluoro-6-iodo-3-quinolinecarboxamide Preparation No. 1 (2.28 g) in DMF (75 mL) is added sodium hydride (60% oil dispersion; 0.600 g) followed by addition of 1,3-dibenzyloxy-2-propanol (2.47 mL). The reaction is heated to 135° C. and is stirred for 2 h. The reaction mixture is cooled to room temperature and poured into saturated aqueous ammonium chloride (200 mL). The aqueous layer is extracted with $CH_2Cl_2$ (4×100 mL). The combined organic layers are washed with brine (50 mL), dried with $MgSO_4$, filtered, and concentrated in vacuo. The resulting brown oil is purified by column chromatography (dichloromethane/methanol, 98/2). Mixed fractions are combined and re-purified (ethyl acetate/heptane, 1/1). Fractions homogeneous by TLC are combined and concentrated in vacuo to yield a yellow solid which is recrystallized from ethyl acetate to yield 1.701 g (48%) of the intermediate amide as a pale yellow solid. To a suspension of this material (1.330 g) in diethylamine (23 mL) are added copper iodide (0.107 g) and $Pd(PPh_3)_2Cl_2$ (0.066 g) followed by addition of propargyl alcohol (0.15 mL). The reaction is stirred at room temperature for 18 h. The reaction mixture is concentrated in vacuo. The resulting brown solid is purified by column chromatography (dichloromethane, dichloromethane/methanol, 98/2). Fractions homogeneous by TLC are combined and concentrated in vacuo to yield an orange solid which is recrystallized from diethyl ether/ethyl acetate to yield 0.727 g (61%) of the propargyl derivative as an off-white solid. To a solution of this material (0.500 g) in DMF (3 mL) is added potassium carbonate (0.325 g) followed by addition of iodomethane (0.15 mL). The reaction is heated to 90° C. and is stirred for 18 h. The reaction mixture is concentrated in vacuo, and the residue is purified by column chromatography (dichloromethane/methanol, 98/2). Fractions homogeneous by TLC are combined and concentrated in vacuo to yield a yellow solid which is recrystallized from ethyl acetate/methanol to yield 0.383 g (75%) of the N-methyl pyridone as a yellow solid. A solution of the pyridone (0.310 g) in 1/1 dichloromethane/ethanol (30 mL) is hydrogenated over 10% Pd/C (62 mg) at 35 psi for 5.5 h. The reaction mixture is filtered through a Celite pad, and the filtrate is concentrated in vacuo. The resulting yellow oil is purified by column chromatography (dichloromethane/methanol; 98/2, 95/5, 90/10). Fractions homogeneous by TLC are combined and concentrated in vacuo to yield a pale yellow solid which is recrystallized from ethyl acetate/methanol to yield 0.050 g (22%) of the title compound as a white solid.

Physical characteristics are as follows:

Mp 120–123° C.; ¹H NMR (300 MHz, DMSO-d$_6$) δ10.44, 8.64, 7.74, 7.42–7.34, 4.92, 4.56, 4.50, 4.29, 3.77–3.64, 3.44, 2.72, 1.77; ¹³C NMR (75 MHz, DMSO-d$_6$) δ175.1, 164.9, 150.8, 150.1, 140.6, 139.2, 131.8, 130.3, 130.0, 129.6, 128.9, 128.8, 127.8, 118.4, 117.0, 110.1, 82.6, 60.5, 60.2, 48.2, 41.9, 34.5, 31.9, 21.2, 14.6; IR (drift) 3388, 3343, 3326, 2350, 1970, 1902, 1651, 1601, 1552, 1499, 1268, 1118, 1077, 1052, 807 cm⁻¹; MS (ESI+) for m/z 475 (M+H)⁺. Anal. Found: C, 60.59; H, 5.72; N, 5.88.

Example 6

N-(4-Chlorobenzyl)-8-fluoro-6-(hydroxymethyl)-4-oxo-1-[3-(tetrahydro-2H-pyran-2-yloxy)propyl]-1,4-dihydro-3-quinolinecarboxamide

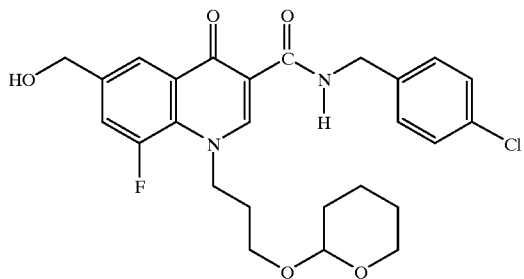

To a suspension of NaH (60% dispersion in oil, 11.1 mg) in 2.5 mL anhydrous DMF is added N-(4-chlorobenzyl)-8-fluoro-4-hydroxy-6-(hydroxymethyl)-3-quinolinecarboxamide from Preparation No. 7 (100 mg). After stirring the reaction mixture at room temperature for 15–20 min., 2-(3-bromopropoxy)tetrahydro-2H-pyran (89.4 mg) is added. The reaction is stirred at room temperature for 3 days. The reaction mixture is treated with saturated aqueous NaHCO₃, then extracted with CH₂Cl₂ (3×). The combined organic layers are washed with 15% K₂CO₃ and H₂O (2×), dried over Na₂SO₄, and condensed to obtain a yellow residue. The residue is chromatographed eluting with 2% MeOH in CH₂Cl₂. Fractions homogenous by TLC are combined and condensed to afford 34.0 mg (24%) of the title compound as a white solid.

Physical characteristics are as follows:

Mp 148–150° C.; ¹H NMR (300 MHz, DMSO) δ10.26, 8.77, 8.17, 7.65, 7.38, 5.50, 4.60, 4.46, 3.67, 3.35, 2.05, 1.61, 1.53, 1.37; IR (drift) 3333, 2940, 2918, 1651, 1603, 1563, 1490, 1352, 1281, 1120, 1069, 1036, 1018, 990, 805 cm⁻¹; MS (ESI) 503.1 ((M+H)⁺, 501.1 (M−H)⁻. Anal. Found: C, 62.03; H, 5.57; N, 5.58.

Example 7

N-(4-Chlorobenzyl)-6-(3-hydroxy-1-propenyl)-1-[2-(4-morpholinyl)ethyl]-4-oxo-1,4-dihydro 3-quinolinecarboxamide

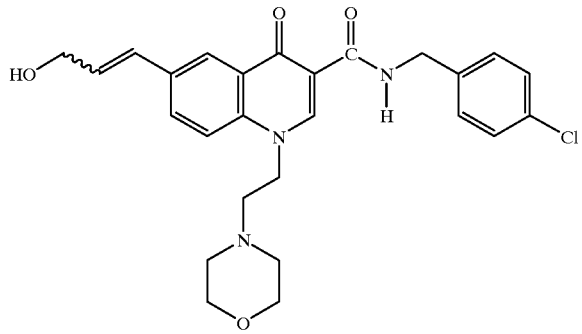

A mixture of N-(4-chlorobenzyl)-1,4-dihydro-6-[3-hydroxy-1-propenyl]-4-oxo-3-quinolinecarboxamide from Preparations No. 11 and 12 (0.52 g) is dissolved in DMF (4 mL), and potassium carbonate (0.78 g) and N-(2-chloroethyl)morpholine hydrochloride (0.52 g) are added. The mixture is heated at 90° C. for 2 h and then partitioned between water and chloroform. The organic layer is concentrated in vacuo to give a brown oil. Column chromatography (elution with 1–7% MeOH/CHCl₃) followed by crystallization from EtOAc/hexane gave the title compound as a mixture of isomers. The mixture is then purified by HPLC chromatography on a 0.46×25 cm Chiralcel OD-H column eluting with EtOH at a rate of 0.5 mL/min. This gave 0.161 g of the alkene mixture as approximately a 2:1 mixture of the trans:cis isomers, which is crystallized from ethyl acetate to give 0.13 g of the title compound as a hydrate.

Physical characteristics are as follows:

Mp 146–148.5° C.; ¹H NMR (400 MHz, DMSO-d$_6$) δ10.40, 8.79, 8.32, 7.77–7.70, 7.45, 7.34–7.28, 7.17–7.10, 6.65, 6.49, 6.53, 6.48, 4.79, 4.62, 4.35, 4.04–3.67, 3.20–2.46, 2.25, 1.87–1.80, 1.13 ppm; IR (drift) 3293, 2956, 1744, 1670, 1648, 1600, 1555, 1512, 1491, 1450, 1229, 1117, 1092, 1000, 807 cm⁻¹; HRMS (FAB) calcd for C$_{26}$H$_{28}$ClN$_3$O$_4$+H 482.1846, found 482.1849.

Example 8

N-(4-Chlorobenzyl)-8-fluoro-6-(3-hydroxy-1-propynyl)-1-methyl-4-oxo-1,4-dihydro-3-quinolinecarboxamide

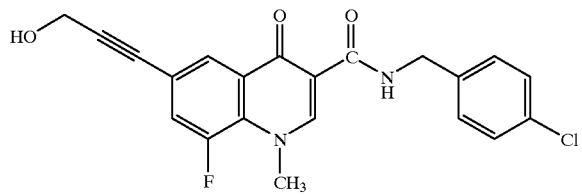

A mixture of N-(4-chlorobenzyl)-8-fluoro-6-iodo-1-methyl-4-oxo-1,4-dihydro-3-quinolinecarboxamide from Preparation No. 14 (0.600 g), propargyl alcohol (0.11 mL, 1.90 mmol), CuI (0.048 g, 0.25 mmol), and PdCl₂(PPh₃)₂ (0.178 g, 0.25 mmol) in diethylamine (42.5 mL) and CH₂Cl₂ (50 mL) are warmed to 65° C. overnight. The reaction mixture is then concentratred in vacuo. Column chromatography (elution with 5–10% MeOH/CH$_2$Cl$_2$) gave the title compound as a solid.

Physical characteristics are as follows:

Mp 186–188° C.; $^1$H NMR (400 MHz, DMSO-d$_6$) δ10.18–10.13, 8.78, 8.11, 7.77, 7.40, 7.36, 5.45, 4.56, 4.35, 4.16 ppm; $^{13}$C NMR (100 MHz, DMSO-d$_6$) δ173.8, 182.6, 151.6, 139.0, 131.8, 129.9, 129.6, 128.7, 125.2, 121.9, 119.7, 111.4, 92.4, 81.9, 49.8, 46.0, 41.8 ppm; IR (drift) 3410, 1657, 1600, 1569, 1551, 1541, 1493, 1472, 1362, 1342, 1284, 1127, 806, 799, 726 cm$^{-1}$; MS (EI) m/z 398 (M$^+$); HRMS (EI) calcd for C$_{21}$H$_{16}$ClFN$_2$O$_3$ 398.0833, found 398.0838.

Example 9

N-(4-Chlorobenzyl)-8-fluoro-6-[(Z)-3-hydroxy-1-propenyl)-1-methyl-4-oxo-1,4-dihydro-3-quinolinecarboxamide

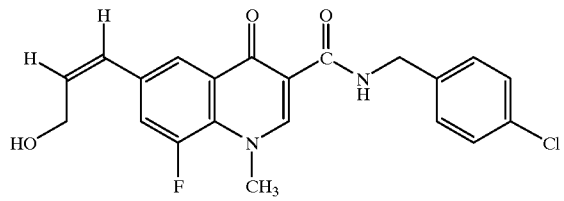

A mixture of N-(4-chlorobenzyl)-8-fluoro-1,4-dihydro-6-(3-hydroxy-1-propynyl)-1-methyl-4-oxo-3-quinolinecarboxamide from Example No. 8 (0.200 g) and Pd/C (10%, 0.040 g) in MeOH (10 mL) and CH$_2$Cl$_2$ (10 mL) is placed on a Parr shaker under 50 psi of H$_2$ for 6 h. The reaction mixture is filtered through Celite and concentrated in vacuo. Recrystallization from EtOAc gave the title compound as a solid.

Physical characteristics are as follows:

Mp 182–184° C.; $^1$H NMR (400 MHz, DMSO-d$_6$) δ10.28–10.21, 8.76, 7.98, 7.64, 7.40, 7.36, 6.55, 6.00–5.93, 5.04–5.02, 4.56, 4.30–4.28, 4.18–4.16 ppm; IR (drift) 3048, 1658, 1626, 1601, 1579, 1552, 1493, 1361, 1284, 1271, 1122, 1039, 1016, 806, 798 cm$^{-1}$; MS (EI) m/z 400 (M$^+$). Anal. found: C, 62.76; H, 4.61; N, 6.86.

Example 10

N-(4-Chlorobenzyl)-1-[2-(diethylamino)ethyl]-8-fluoro-6-(3-hydroxy-1-propynyl)-4-oxo-1,4-dihydro-3-quinolinecarboxamide

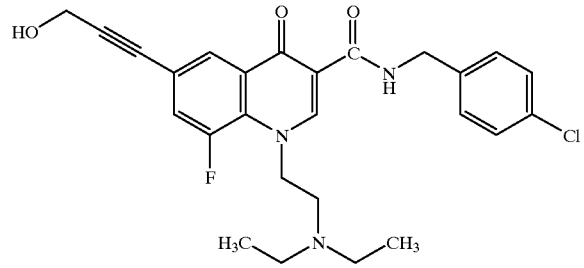

A solution of N-(4-chlorobenzyl)-8-fluoro-4-hydroxy-6-(3-hydroxy-1-propynyl)-3-quinolinecarboxamide from Preparation No. 15 (0.96 g) is dissolved in DMF (7 mL), and K$_2$CO$_3$ (1.38 g) and 2-bromo-N,N-diethylethylamine hydrobromide (1.30 g) are added. The reaction mixture is heated to 95° C. for 16. Water is added and an oily solid formed, which is isolated by decanting the liquid. Column chromatography (elution with 1–3% MeOH/CHCl$_3$) gave 0.373 g of the title compound which is crystallized from ethyl acetate to give 0.163 g of a solid.

Physical characteristics are as follows:

Mp 148–150° C.; $^1$H NMR (400 MHz, DMSO-d$_6$) δ10.1, 8.7, 8.2, 7.82, 7.4–7.3, 5.4, 4.5, 4.3, 2.7, 2.4, 0.7 ppm; IR (drift) 2967, 1650, 1625, 1596, 1580, 1555, 1485, 1369, 1282, 1232, 1083, 1065, 1018, 1009, 806 cm$^{-1}$; MS (EI) m/z 483 (M+). Anal. found: C, 64.23; H, 5.69; N, 8.49.

Example 11

N-(4-Chlorobenzyl)-6-(3-hydroxy-1-propynyl)-4-oxo-1-propyl-1,4-dihydro-3-quinolinecarboxamide

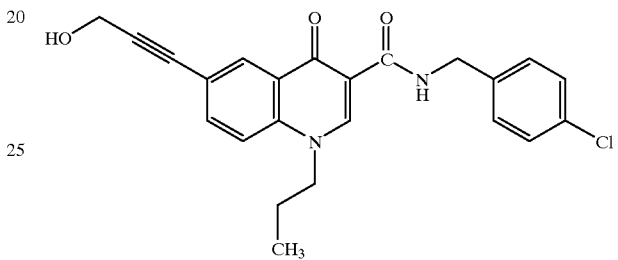

A suspension of 0.50 g of N-(4-chlorobenzyl)-4-hydroxy-6-(3-hydroxy-1-propynyl)-3-quinolinecarboxamide from Preparation No. 5, potassium carbonate (0.76 g), and 1-iodopropane (0.47 g) in DMF is heated to 100° C. for 6 hrs and stirred at room temperature overnight. The reaction mixture is filtered, and the solvent is evaporated at reduced pressure leaving a light brown solid. The solid is stirred with ethyl acetate for an hour and filtered. The solvent is evaporated from the filtrate under reduced pressure, leaving 0.12 g of the title compound as a yellowish-white solid.

Physical characteristics are as follows:

Mp 183–184° C.; $^1$H NMR (DMSO-d$_6$) δ10.3, 8.9, 8.3, 7.9, 7.8, 7.4, 5.4, 4.5, 4.4, 4.3, 1.8, 0.9; MS (ESI+) for m/z 431.2 (M+Na)$^+$.

Example 12

N-(4-Chlorobenzyl)-1-[2-(diethylamino)ethyl]-6-(3-hydroxy-1-propynyl)-4-oxo-1,4-dihydro-3-quinolinecarboxamide

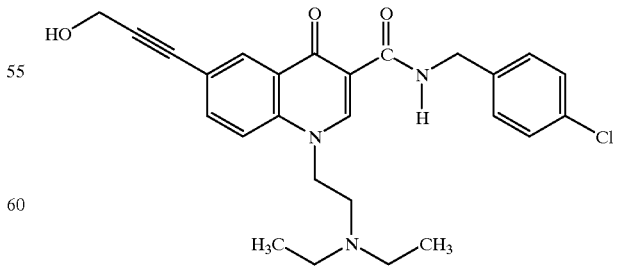

A solution of N-(4-chlorobenzyl)-4-hydroxy-6-(3-hydroxy-1-propynyl)-3-quinolinecarboxamide from Preparation No. 5 (0.616 g) is dissolved in DMF (4 mL), and K₂CO₃ (0.93 g, 6.72 mmol) and 2-bromo-N,N-diethylethylamine hydrobromide (0.88 g, 3.35 mmol) are added. The reaction mixture is heated to 90° C. for 16. The mixture is partitioned between CHCl₃ and water. The organic layer is concentrated in vacuo to give an oil. Column chromatography (elution with 1–5% MeOH/CHCl₃) gave 0.10 g of a brown oil. Crystallization from ethyl acetate/hexane gave 0.013 g of the title compound as a solid.

Physical characteristics are as follows:

Mp 145–148° C.; ¹H NMR (400 MHz, CDCl₃) δ8.7, 8.5, 7.7, 7.4, 7.3, 4.6, 4.5, 4.2, 2.8, 2.5, 0.9 ppm; MS (EI) m/z 465 (M+); HRMS (FAB) calcd for C₂₆H₂₈ClN₃O₃+H 466.1897, found 466.1898.

Example 13

N-(4-Chlorobenzyl)-1-[2-(dimethylamino)ethyl]-6-(3-hydroxy-1-propynyl)-4-oxo-1,4-dihydro-3-quinolinecarboxamide, hydrochloride salt

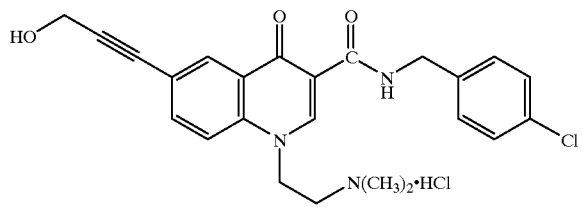

A solution of N-(4-chlorobenzyl-4-hydroxy-6-(3-hydroxy-1-propynyl)-3-quinolinecarboxamide from Preparation No. 5 (0.515 g) is dissolved in DMF (10 mL), and K₂CO₃ (0.778 g) and diisoproplyaminoethyl chloride-hydrochloride (0.56 g) are added. The reaction mixture is heated to 95° C. for 14 h, then allowed to stir at room temperature overnight. The mixture is then poured into H₂O and an oil formed, which is isolated by decanting the liquid. The oil is dissolved in MeOH/CH₂Cl₂, and etheral HCl is added to adjust the pH to 2. The mixture is concentrated in vacuo to give the title compound as the hydrochloride salt.

Physical characteristics are as follows:

Mp 187–188° C.; ¹H NMR (400 MHz, DMSO-d₆) δ11.21, 10.25–10.21, 8.97, 8.31, 8.11, 7.84, 7.40, 7.36, 5.44, 4.93–4.90, 4.57, 4.36, 3.51–3.49, 2.84 ppm; ¹³C NMR (100 MHz, DMSO-d₆) δ174.8, 163.7, 149.2, 138.5, 138.4, 135.2, 131.3, 129.2, 128.8, 128.2, 127.1, 119.2, 118.1, 111.6, 91.2, 82.3, 53.6, 49.4, 47.6, 42.6 ppm; IR (drift)3332,3281, 3252, 3044, 2591, 2451, 1663, 1599, 1579, 1551, 1489, 1373, 1228, 813, 808 cm⁻¹; MS (EI) m/z 437 (M⁺); HRMS (FAB) calcd for C₂₄H₂₄ClN₃O₃+H 438.1584, found 438.1580.

EXAMPLE 14

N-(4-Chlorobenzyl)-6-(3-hydroxy-1-propynyl)-1-[2-(1-piperidinyl)ethyl]-4-oxo-1,4-dihydro-3-quinolinecarboxamide

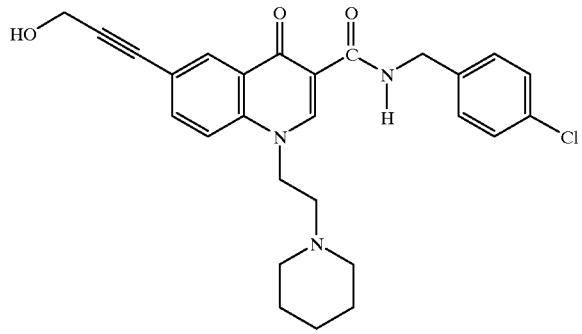

A solution of N-(4-chlorobenzyl)-4-hydroxy-6-(3-hydroxy-1-propynyl)-3-quinolinecarboxamide from Preparation No. 5 (0.367 g) is dissolved in DMF (10 mL), and K₂CO₃ (0.55 g, 4.0 mmol) and 1-(2-chloroethyl)piperidine hydrochloride (0.375 g, 2.0 mmol) are added. The reaction mixture is heated to 90° C. for 3 h, and then allowed to stir at room temperature for 48 h. Water is added and a precipitate formed. The precipitate is filtered and allowed to dry at room temperature and then under reduced pressure to give 0.171 g of a solid. The solid is dissolved in CHCl₃ and filtered. The filtrate is concentrated in vacuo and crystallized from ethyl acetate to give 0.066 g of the title compound as a solid.

Physical characteristics are as follows:

Mp 176–180° C.; ¹H NMR (400 MHz, DMSO-d₆) δ10.3, 8.8, 8.3, 7.9, 7.8, 7.4, 5.4, 4.6–4.5, 4.3, 2.6, 2.4, 1.4, 1.3 ppm; IR (drift) 2934, 2919, 1655, 1598, 1579, 1552, 1489, 1452, 1368, 1316, 1227, 1026, 1016, 816, 806 cm⁻¹; MS (EI) m/z 477 (M+); MS (FAB) m/z 478 (MH+); HRMS (FAB) calcd for C₂₇H₂₈ClN₃O₃+H 478.1897, found 478.1907.

Example 15

N-(4-Chlorobenzyl)-6-(3-hydroxy-1-propynyl)-1-[3-(1-piperidinyl)propyl]-4-oxo-1,4-dihydro-3-quinolinecarboxamide

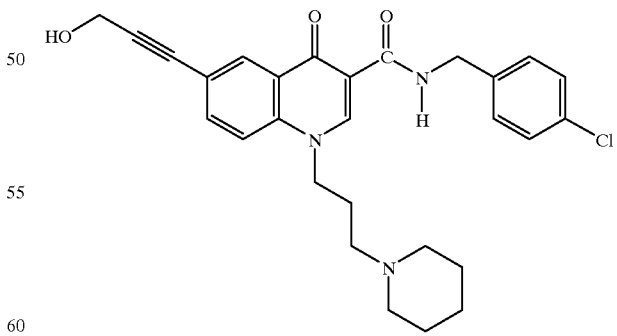

A solution of N-(4-chlorobenzyl)-4-hydroxy-6-(3-hydroxy-1-propynyl)-3-quinolinecarboxamide from Preparation No. 5 (0.367 g) is dissolved in DMF (10 mL), and K₂CO₃ (0.55 g) and N-(3chloropropyl)piperidine hydrochloride (0.408 g) are added. The reaction mixture is heated to 90° C. for 10 h, and then allowed to stir at room temperature for 38 h. Water is added and a precipitate formed. The precipitate is filtered and allowed to dry at room temperature and then under reduced pressure to give 0.187 g of a solid. The solid is dissolved in CHCl$_3$ and filtered to remove 0.045 g of a precipitate. The filtrate is concentrated in vacuo and crystallized from ethyl acetate to give 0.065 g of the title compound as a solid.

Physical characteristics are as follows:

Mp 160–163° C.; $^1$H NMR (400 MHz, DMSO-d$_6$) δ10.3, 8.9, 8.3, 7.9, 7.8, 7.4, 5.4, 4.6, 4.5, 4.4, 2.2–2.1, 1.9, 1.4, 1.3 ppm; IR (drift) 3371, 2938, 2918, 1655, 1599, 1569, 1551, 1489, 1374, 1228, 1089, 1042, 1037, 816, 806 cm$^{-1}$; MS (EI) m/z 491 (M+); MS (FAB) m/z 492 (MH+), 494, 493, 492, 491, 490, 126, 124, 98, 96, 45; HRMS (FAB) calcd for C$_{28}$H$_{30}$ClN$_3$O$_3$+H 492.2054, found 492.2061.

Example 16

N-(4-Chlorobenzyl)-1,4-dihydro-6-(3-hydroxy-1-propynyl)-1-[2-(1-methyl-2-pyrrolindinyl)ethyl]-4-oxo3-quinolinecarboxamide

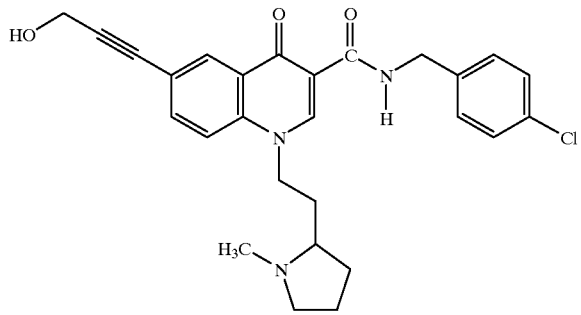

A solution of N-(4-chlorobenzyl)-4-hydroxy-6-(3-hydroxy-1-propynyl)-3-quinolinecarboxamide from Preparation No. 5 (0.458 g) is dissolved in DMF (10 mL), and K$_2$CO$_3$ (0.69 g, 5.0 mmol) and 3-chloromethyl-1-methylpiperidine hydrochloride (0.47 g, 2.5 mmol) are added. The reaction mixture is heated to 90° C. for 2.5 h. Water is added and a precipitate formed. The precipitate is filtered and allowed to dry at room temperature to give 0.41 g of a solid. The solid is triturated with CHCl$_3$ and filtered to give 0.33 g of the title compound as a solid.

Physical characteristics are as follows:

Mp 154–158° C.; $^1$H NMR (400 MHz, DMSO-d$_6$) δ10.3, 8.9, 8.3, 7.9, 7.4–7.3, 5.4, 4.6, 4.5, 4.3, 2.9, 2.2, 2.1–2.0, 1.9, 1.8, 1.6, 1.5 ppm; IR (drift) 2963, 2941, 2784, 1656, 1620, 1599, 1551, 1490, 1457, 1359, 1316, 1222, 1032, 815, 807 cm$^{-1}$; HRMS (FAB) calcd for C$_{27}$H$_{28}$ClN$_3$O$_3$+H 478.1897, found 478.1907. % Water (KF): 4.69. Anal. found: C, 64.67; H, 6.03; N, 8.32.

Example 17

N-(4-Chlorobenzyl)-1-[2-(diisopropylamino)ethyl]-6-(3-hydroxy-1-propynyl)-4-oxo-1,4-dihydro-3-quinolinecarboxamide

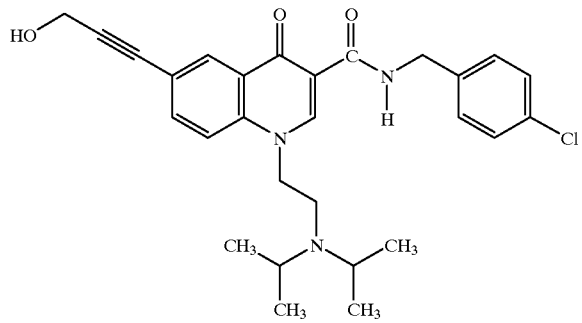

A solution of N-(4-chlorobenzyl)-4-hydroxy-6-(3-hydroxy-1-propynyl)-3-quinolinecarboxamide from Preparation No. 5 (0.458 g) is dissolved in DMF (10 mL), and K$_2$CO$_3$ (0.69 g) and 2-(diisoproplyamino)ethyl chloride hydrochloride (0.50 g) are added. The reaction mixture is heated to 90° C. for 2 h, then allowed to stir at room temperature overnight. A drop of water is added and the mixture is heated for 20 h. An additional equivalent of 2-(diisoproplyamino)ethyl chloride hydrochloride (0.25 g, 1.25 mmol) is added and the mixture is heated at 100° C. for 5 h, and then stirred at room temperature overnight. Water is added and an oily solid formed, which is isolated by decanting the liquid. Column chromatography (elution with 1–2% MeOH/CHCl$_3$) gave 0.45 g of a solid. Crystallization by dissolving in CH$_2$Cl$_2$ with a few drops of MeOH and adding to a 1:1 solution of pentane/Et$_2$O gave 0.22 g of the title compound as a solid.

Physical characteristics are as follows:

Mp 188–191° C.; $^1$H NMR (300 MHz, CDCl$_3$) δ10.4, 8.7, 8.4, 7.6, 7.4, 7.3, 4.6, 4.5, 4.2, 3.0, 2.8, 0.9 ppm; IR (drift) 2967, 1650, 1597, 1575, 1551, 1490, 1366, 1225, 1178, 1165, 1040, 1028, 1019, 816, 807 cm$^{-1}$; MS (EI) m/z 493 (M+). Anal. found: C, 67.96; H, 6.59; N, 8.33.

Example 18

N-(4-Chlorobenzyl)-6-(3-hydroxy-1-propynyl)-1-[2-(1-pyrolidinyl)ethyl]-4-oxo-1,4-dihydro-3-quinolinecarboxamide

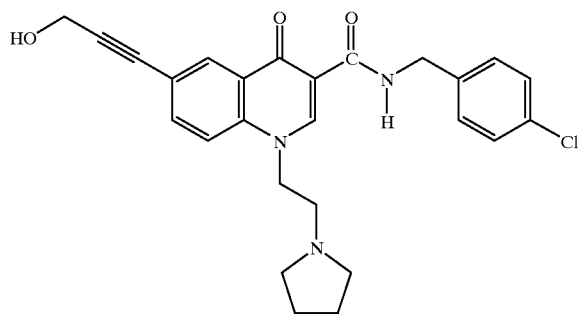

A solution of N-(4-chlorobenzyl-4-hydroxy-6-(3-hydroxy-1-propynyl)-3-quinolinecarboxamide from Preparation No. 5 (0.458 g) is dissolved in DMF (10 mL), and K₂CO₃ (0.69 g) and 1-(2-chloroethyl)pyrrolidine hydrochloride (0.425 g) are added. The reaction mixture is heated to 90° C. for 3 h. Water is added and a dark solid formed, which is isolated by decanting the liquid. Column chromatography (elution with 1–5% MeOH/CHCl₃) gave 0.17 g of a solid. Crystallization by dissolving in CH₂Cl₂ with a few drops of MeOH and adding to a 1:1 solution of pentane/Et₂O gave 0.153 g of the title compound as a solid.

Physical characteristics are as follows:

Mp 189–192° C.; ¹H NMR (400 MHz, DMSO-d₆) δ10.2, 8.8, 8.3, 7.9, 7.8, 7.4, 5.4, 4.6–4.5, 4.3, 2.8, 2.5, 1.6 ppm; IR (drift) 3358, 2965, 1656, 1598, 1580, 1555, 1489, 1371, 1357, 1229, 1143, 1025, 819, 806, 746 cm⁻¹.

Example 19

N-(4-Chlorobenzyl)-6-(3-hydroxy-1-propynyl)-1-[2-(4-morpholinyl)ethyl]-4-oxo-1,4-dihydro-3-quinolinecarboxamide

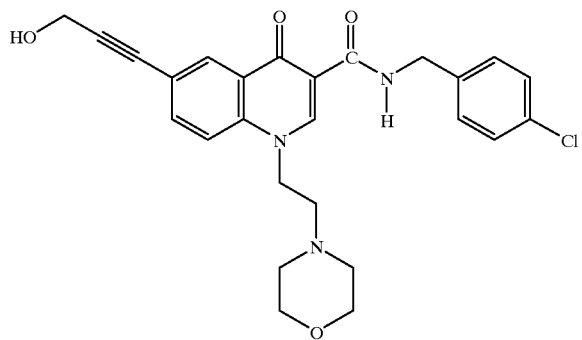

A solution of N-(4-chlorobenzyl-4-hydroxy-6-(3-hydroxy-1-propynyl)-3-quinolinecarboxamide from Preparation No. 5 (0.458 g) is dissolved in DMF (10 mL), and K₂CO₃ (0.69 g) and 4-(2-chloroethyl)morpholine hydrochloride (0.47 g) are added. The reaction mixture is heated to 90° C. for 2 h. Water is added and a dark solid formed, which is isolated by decanting the liquid. Column chromatography (elution with 1–5% MeOH/CHCl₃) gave 0.183 g of a solid. Crystallization by dissolving in CH₂Cl₂ with a few drops of MeOH and adding to a 1:1 solution of pentane/Et₂O gave 0.13 g of the title compound as a solid.

Physical characteristics are as follows:

Mp 215–218° C.; ¹H NMR (300 MHz, CDCl₃) δ10.4, 8.7, 8.4, 7.6, 7.4, 7.3, 4.6, 4.5, 4.3, 3.7, 2.8, 2.5 ppm; IR (drift) 1650, 1597, 1559, 1491, 1454, 1361, 1353, 1318, 1302, 1231, 1116, 1026, 1016, 820, 807 cm⁻¹; MS (EI) m/z 479 (M+).

Example 20

N-(4-Chlorobenzyl)-1-[3-(dimethylamino)propyl]-6-(3-hydroxy-1-propynyl)-4-oxo-1,4-dihydro-3-quinolinecarboxamide

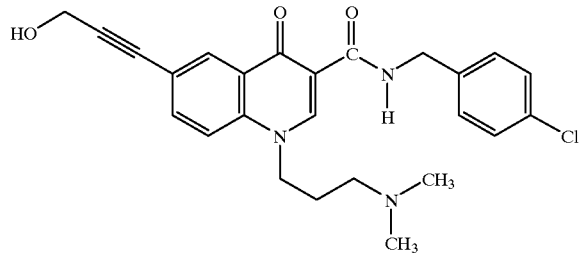

A solution of N-(4-chlorobenzyl)-4-hydroxy-6-(3-hydroxy-1-propynyl)-3-quinolinecarboxamide from Preparation No. 5 (0.458 g) is dissolved in DMF (10 mL), and K₂CO₃ (0.69 g) and 3-dimethylaminopropyl chloride hydrochloride (0.42 g) are added. The reaction mixture is heated to 90° C. for 6 h. Water is added and a dark solid formed, which is isolated by decanting the liquid. Column chromatography (elution with 1–20% MeOH/CHCl₃) gave 0.103 g of a solid. Crystallization by dissolving in CH₂Cl₂ with a few drops of MeOH and adding to a 1:1 solution of pentane/Et₂O gave 0.072 g of the title compound as a solid.

Physical characteristics are as follows:

Mp 172–175° C.; ¹H NMR (400 MHz, CDCl₃) δ10.5, 8.8, 8.2, 7.6, 7.5, 7.4–7.3, 4.6, 4.4, 4.3, 2.8, 2.5, 2.2 ppm; IR (drift) 1655, 1597, 1580, 1556, 1489, 1455, 1379, 1315, 1228, 1092, 1035, 1026, 818, 805, 747 cm⁻¹; MS (EI) m/z 451 (M⁺).

Example 21

N-(4-Chlorobenzyl)-6-(3-hydroxy-1-propynyl)-4-oxo-1-vinyl-1,4-dihydro-3-quinolinecarboxamide

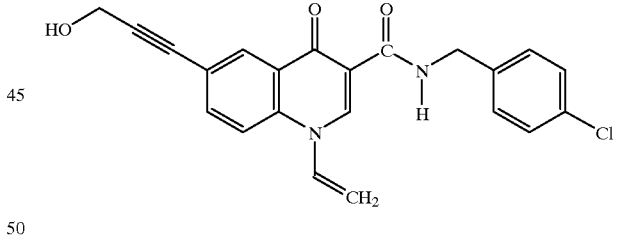

A solution of N-(4-chlorobenzyl)-4-hydroxy-6-(3-hydroxy-1-propynyl)-3-quinolinecarboxamide from Preparation No. 5 (1.83 g) is dissolved in DMF (25 mL), and K₂CO₃ (1.38 g) and 1,2-dibromoethane (4.3 mL) are added. The reaction mixture is heated to 90° C. for 2 h. Water is added and the mixture is extracted with ethyl acetate and then chloroform. The combined organic layers are concentrated in vacuo to give 2.5 g of a dark oil. Column chromatography (elution with 1–3% MeOH/CHCl₃) gave 0.378 g of 1-(1-bromoethyl)-N-(4-chlorobenzyl)-6-(3-hydroxy-1-propynyl)-4-oxo-1,4-dihydro-3-quinolinecarboxamide as a solid which is used without further purification. 1-(1-bromoethyl)-N-(4-chlorobenzyl)-6-(3-hydroxy-1-propynyl)-4-oxo-1,4-dihydro-3-quinolinecarboxamide (0.347 g) is suspended in 1:1 THF/CH₃CN (15 mL) and sodium carbonate (0.16 g) and ethylamine (0.4 mL) are added and the mixture is refluxed for 16 h. An additional amount of ethylamine (0.80 mL) is added and the mixture is refluxed for 16 h. An additional amount of ethylamine (0.80 mL) and DMF (5 mL) is added and the mixture is heated at 100° C. for 6 h, and then held at room temperature for 48 h. Potassium carbonate (0.193 g) is added and the mixture is heated at 100° C. for 3 h. The mixture is concentrated in vacuo and partitioned between ethyl acetate and water. The organic layer is concentrated in vacuo to give 0.60 g of an oil. Column chromatography (elution with 1–5% MeOH/ CHCl$_3$) gave 0.118 g of the title compound as a solid.

Physical characteristics are as follows:

Mp 171–174° C.; $^1$H NMR (400 MHz, DMSO-d$_6$) δ10.2, 8.8, 8.3, 7.9–7.8, 7.6, 7.4–7.3, 5.8, 5.6, 5.4, 4.5, 4.3 ppm; IR (drift) 3299, 1650, 1594, 1578, 1550, 1487, 1355, 1338, 1320, 1227, 1087, 1025, 821, 807, 688 cm$^{-1}$. Anal. found: C, 66.95; H, 4.20; N, 7.05.

Example 22

N-(4-chlorobenzyl)-6-[(E)-3-hydroxy-1-propenyl]-1-methyl-4-oxo-1,4-dihydro-3-quinolinecarboxamide

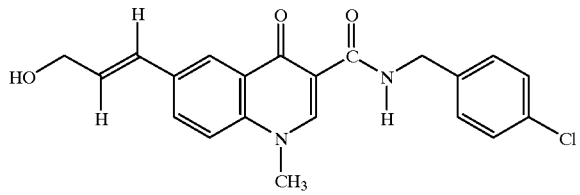

A mixture of N-(4-Chlorobenzyl)-6-[(1E)-3-hydroxy-1-propenyl]-4-hydroxy-3-quinolinecarboxamide from Preparation No. 12 (0.184 g), K$_2$CO$_3$ (0.276 g) and iodomethane (0.062 mL) in DMF (2 mL) is heated in a stoppered flask at 90° C. for 1 h. Water is added and the mixture is allowed to cool and stir at room temperature for 16 h during which a precipitate formed. The precipitate is filtered and dried in vacuo at 60° C. for 48 h to give 0.164 g of the title compound as a solid.

Physical characteristics are as follows:

Mp 103–106° C.; $^1$H NMR (400 MHz, DMSO-d$_6$) δ10.4, 8.8, 8.2, 8.0, 7.8, 7.4–7.3, 6.7, 6.6–6.5, 4.9, 4.6, 4.2, 4.0 ppm; IR (drift) 3044, 1656, 1603, 1552, 1497, 1423, 1362, 1319, 1238, 1128, 1093, 1017,967,827,807 cm$^{-1}$; HRMS (FAB) calcd for C$_{21}$H$_{19}$ClN$_2$O$_3$+H 383.1162, found 383.1170.

Example 23

N-(4-chlorobenzyl)-6-[(Z)-3-hydroxy-1-propenyl]-1-methyl-4-oxo-1,4-dihydro-3-quinolinecarboxamide

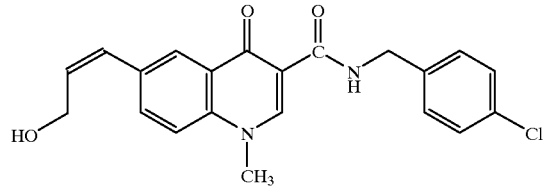

A mixture of N-(4-chlorobenzyl)-6-[(1Z)-3-hydroxy-1-propenyl]-4-hydroxy-3-quinolinecarboxamide from Preparation No. 11 (0.184 g), K$_2$CO$_3$ (0.276 g) and iodomethane (0.062 mL) in DMF (2 mL) is heated in a stoppered flask at 90° C. for 1 h. Water is added and the mixture is allowed to cool and stir at room temperature for 16 h during which a precipitate formed. The precipitate is filtered and dried in vacuo at 60° C. for 48 h to give a solid. Crystallization by dissolving in CH$_2$Cl$_2$ with a few drops of MeOH and adding to a 1:1 solution of pentane/Et$_2$O gave 0.085 g of the title compound as a solid.

Physical characteristics are as follows:

Mp 137–141° C.; $^1$H NMR (400 MHz, DMSO-d$_6$) δ10.4, 8.8, 8.1, 7.8, 7.7, 7.4–7.3, 6.6, 5.9, 5.0, 4.5, 4.3, 4.0 ppm; IR (drift) 1656, 1603, 1550, 1497, 1363, 1317, 1242, 1124, 1089, 1037, 1017, 822, 808, 799, 723 cm$^{-1}$; HRMS (FAB) calcd for C$_{21}$H$_{19}$ClN$_2$O$_3$+H$_1$ 383.1162, found 383.1154.

Example 24

N-(4-Chlorobenzyl)-6-[ethyl(2-hydroxyethyl)amino]-1-methyl-4-oxo-1,4-dihydro-3-quinolinecarboxamide

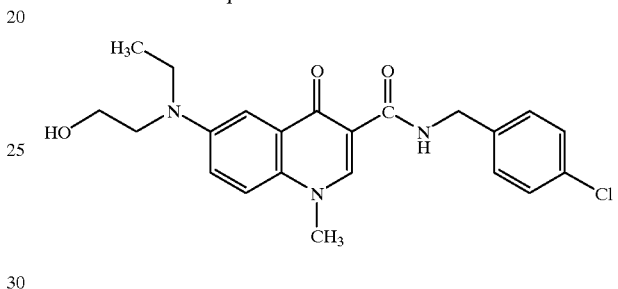

To a flask containing ethyl 6-[[2-(acetyloxy)ethyl](ethyl)amino]-1-methyl-4-oxo-1,4-dihydro-3-quinolinecarboxylate from Preparation No. 16 (0.22 g) is added p-chlorobenzylamine (1.0 mL). The reaction is tightly capped and heated to 190° C. overnight. The reaction is cooled to room temperature. The residue is adsorbed onto silica and chromatographed on silica eluting with 4% to 8% methanol in dichloromethane. The product-containing fractions are evaporated to give 0.12 g of the title compound as a off-white solid.

Physical characteristics are as follows:

$^1$H NMR (300 MHz, DMSO-d$_6$) 10.6, 8.7, 7.6, 7.4, 4.8, 4.5, 4.0, 3.6, 3.5, 1.1; HRMS (FAB) found 414.1573.

Example 25

N-(4-Chlorobenzyl)-1-cyclopropyl-6-(3-hydroxy-1-propynyl)-4-oxo-1,4-dihydro-3-quinolinecarboxamide

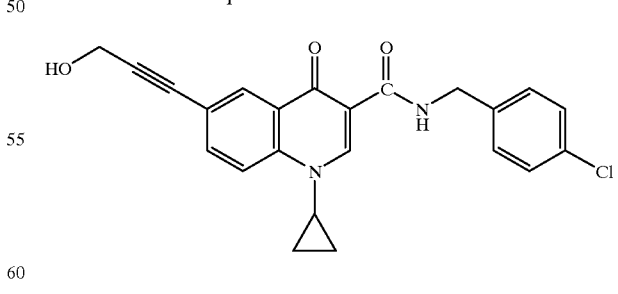

To a dry flask under an atmosphere of argon gas containing 0.24 g of N-(4-chlorobenzyl)-1-cyclopropyl-6-iodo-4-oxo-1,4-dihydro-3-quinolinecarboxamide from Preparation No. 20, 0.01 g of copper (I) iodide and 0.04 g of dichlorobis(triphenylphosphine)palladium (II) is added diethylamine (1.5 mL) and propargyl alcohol (0.04 mL). After 3 hours reaction is diluted with DMF (0.5 mL) and left to stir overnight. The reaction is concentrated under reduced pressure, diluted with dichloromethane containing a small amount of methanol, and partioned against water. The organic layer is washed with brine, dried and concentrated under reduced pressure. The residue is adsorbed onto silica and chromatographed on silica eluting with 2% to 6% methanol in dichloromethane . The product-containing fractions are combined and concentrated under reduced pressure to afford 0.17 g of the title compound as a solid.

Physical characteristics are as follows:

$^1$H NMR (300 MHz, DMSO-d$_6$) 10.2, 8.7, 8.3, 8.2, 7.9, 7.4, 5.4, 4.5, 4.4, 3.7, 1.3, 1.1; HRMS (FAB) 407.1170 (M+H$^+$).

Example 26

N-(4-Chlorobenzyl)-1-cyclopropyl-6-(3-hydroxypropyl)-4-oxo-1,4-dihydro-3-quinolinecarboxamide

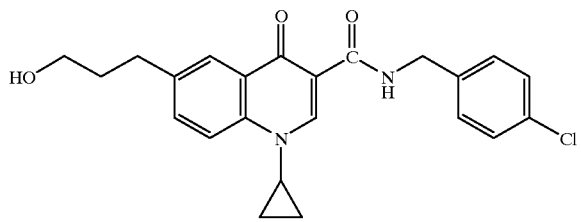

To a solution of N-(4-chlorobenzyl)-1-cyclopropyl-6-(3-hydroxy-1-propynyl)-4-oxo-1,4-dihydro-3-quinolinecarboxamide (0.17 g) from Example No. 25 in THF (3 mL) and methanol (3 mL) is added platinuim oxide (0.01 g). The mixture is placed under an atmosphere of hydrogen gas. After 1 hour, the mixture is filtered through Celite with THF:methanol washes. The filtrate is concentrated under reduced pressure. The residue is adsorbed onto silica and chromatographed on silica eluting with 2% to 4% methanol in dichloromethane. The product-containing fractions are concentrated under reduced pressure to afford 0.13 g of the title compound as a white solid.

Physical characteristics are as follows:

$^1$H NMR (300 MHz, DMSO-d$_6$) 10.4, 8.7, 8.1, 7.7, 7.4, 4.5, 3.7, 3.4, 2.8, 1.7, 1.3, 1.1. Anal. Found: C, 67.05; H, 5.46; N, 6.68.

Example 27

N-(4-Chlorobenzyl)-1-cyclopropyl-6-(4-morpholinylmethyl)-4-oxo-1,4-dihydro-3-quinolinecarboxamide

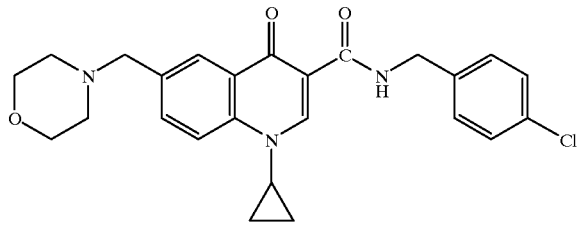

To a flask containing ethyl 1-cyclopropyl-6-(4-morpholinylmethyl)-4-oxo-1,4-dihydro-3-quinolinecarboxylate (0.38 g) from Preparation No. 25 is added 4-chlorobenzylamine (2.0 mL). The reaction is tightly capped and heated to 165° C. overnight. The reaction is cooled to room temperature, adsorbed onto silica and chromatographed on silica eluting with 1% to 6% methanol in dichloromethane. The product-containing fractions are evaporated to give a solid which is dissolved in a minimal amount of dichloromethane. The solution is added to 1:1 diethyl ether:pentane to precipitate the title compound as a white solid. This solid is collected by filtration and dried in vacuo to afford 0.36 g of the title compound.

Physical characteristics are as follows:

$^1$H NMR (300 MHz, CDCl$_3$) 10.4, 8.9, 8.4, 8.0, 7.8, 7.3, 4.6, 3.7, 3.5, 2.5, 1.3, 1.2. Anal. found C, 66.30; H, 6.07; N, 8.97.

Example 28 tert-Butyl 2-[3-{[(4-chlorobenzyl)amino]carbonyl}-6-(3-hydroxy-1-propynyl)-4-oxo-1(4H)-quinolinyl]acetate

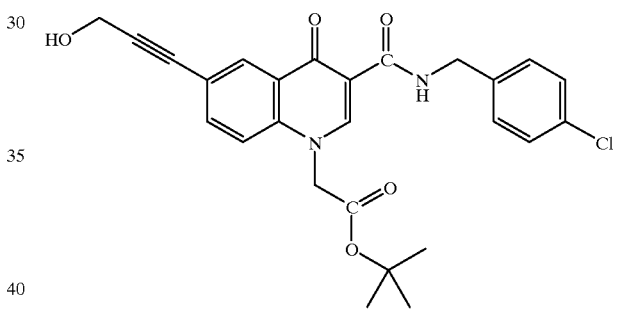

To a dry flask under an atmosphere of argon gas containing 0.23 g of tert-butyl 2-[3-{[(4-chlorobenzyl)amino]carbonyl}-6-iodo-4-oxo-1(4H)-quinolinyl]acetate from Preparation No. 26, 0.01 g of copper (I) iodide and 0.03 g of dichlorobis(triphenylphosphine)palladium (II) is added diethylamine (2.0 mL) and propargyl alcohol (0.03 mL). After 1 hour the reaction is diluted with DMF (1.0 mL) and left to stir overnight. The reaction is concentrated under reduced pressure, diluted with dichloromethane containing a small amount of methanol, and partioned against water. The organic layer is washed with brine, dried and concentrated under reduced pressure. The residue is adsorbed onto silica and chromatographed on silica eluting with 2% to 4% methanol in dichloromethane . The product-containing fractions are combined and concentrated under reduced pressure to afford 0.13 g of the title compound as a solid.

Physical characteristics are as follows:

$^1$H NMR (300 MHz, DMSO-d$_6$) 10.2, 8.9, 8.3, 7.8, 7.6, 7.4, 5.4, 4.5, 4.3, 3.7, 1.4; MS (ESI) m/z 481 (M+H$^+$).

Example 29

2-[3-{[(4-Chlorobenzyl)amino]carbonyl}-6-(3-hydroxy-1-propynyl)-4-oxo-1(4H)-quinolinyl]acetic acid

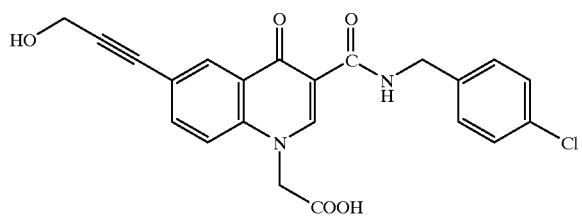

To a suspension of tert-butyl 2-[3-{[(4-chlorobenzyl)amino]carbonyl}-6-(3-hydroxy-1-propynyl)-4-oxo-1(4H) quinolinyl]acetate (0.07 g) from Example No. 28 in dichloromethane (1 mL) is added trifluoroacetic acid (1 mL). After 3 hours, the resulting solution is concentrated under reduced pressure. The residue is dissolved in a small amount of dichloromethane:methanol:DMF and slowly added to vigorously stirring 1:1 diethyl ether:pentane. The resulting precipitate is collected filtration to afford 0.05 g of the title compound as a solid.

Physical characteristics are as follows:

$^1$H NMR (300 MHz, DMSO-$d_6$) 10.2, 8.9, 8.3, 7.9, 7.8, 7.7, 7.3, 5.4, 4.5, 4.3 ppm; MS (ESI) m/z 425 (M+H$^+$).

Example 30

N-(4-Chlorobenzyl)-1-(2-hydroxyethyl)-6-(3-hydroxy-1-propynyl)-4-oxo-1,4-dihydro-3-quinolinecarboxamide

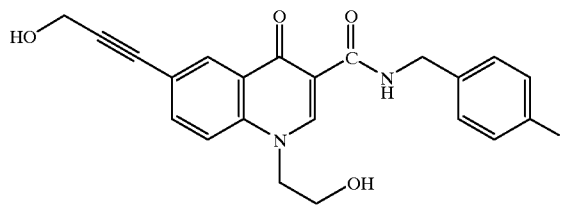

To a flask containing N-(4-chlorobenzyl)-4-hydroxy-6-(3-hydroxy-1-propynyl)-3-quinolinecarboxamide from Preparation No. 5 (0.37 g) is added potassium carbonate (2.75 g) and bromoethanol (0.71 mL). The flask is tightly capped and heated to 100° C. After 4 hours the reaction is cooled to room temperature and partioned between dichloromethane containing methanol and water. The organic layer is washed with two additional portions of water, brine, dried and concentrated under reduced pressure. The residue is adsorbed onto silica and chromatographed on silica eluting with 2% to 10% methanol in dichloromethane to afford 0.09 g of the title compound as a white solid.

Physical characteristics are as follows:

$^1$H NMR (300 MHz, DMSO-$d_6$) 10.2, 8.8, 8.3, 7.9, 7.8, 7.4, 5.4, 5.0, 4.5, 4.3, 3.7 ppm; MS (ESI) m/z 433 (M+Na$^+$).

Example 31

N-(4-Chlorobenzyl)-6-(3-hydroxy-1-propynyl)-1-methyl-4-oxo-1,4-dihydro-3-quinolinecarboxamide

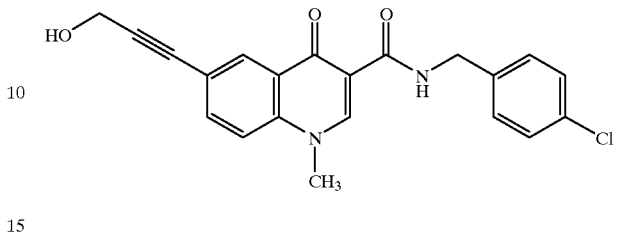

A suspension of 6.90 g of N-(4-chlorobenzyl-4-hydroxy-6-(3-hydroxy-1-propynyl)-3-quinolinecarboxamide from Preparation No. 5, 10.4 g of potassium carbonate, and 2.3 mL of methyl iodide in 40 mL of DMF is stirred at 90° C. for 4 h, then cooled and diluted with 350 mL of water. The resulting solid is filtered, washed well with water, and dried under vacuum. Flash chromatography of the solid on silica using 3–5% methanol in dichloromethane provides 6.02 g of the title compound as a yellow solid.

Physical properties as follows:

$^1$H NMR (CDCl$_3$+CD$_3$OD) δ4.03, 4.45, 4.6, 7.3, 7.6, 7.8, 8.5, 8.8 ppm; HRMS 381.1006

Preparation 27

N-(4-Chlorobenzyl)-6-(3-hydroxypropyl)-1-methyl-4-oxo-1,4-dihydro-3-quinolinecarboxamide

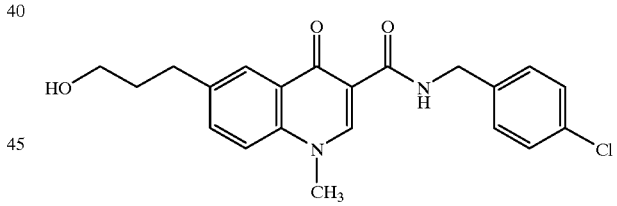

A mixture of 0.50 g of N-(4-chlorobenzyl)-6-(3-hydroxy-1-propynyl)-1-methyl-4-oxo-1,4-dihydro-3-quinolinecarboxamide from Example No. 31 and 50 mg of 5% platinum on carbon catalyst in 20 mL of 1:1 THF-methanol is stirred under 1 atm hydrogen for 3 h, then filtered through diatomaceous earth. The filtrate is concentrated under reduced pressure and the residual solid flash chromatographed on silica gel using 4–5% methanol in dichloromethane to afford 0.45 g of the title compound as a yellow solid. Further purification is achieved by recrystallization of the solid from 15 mL of acetonitrile.

Physical properties as follows:

$^1$H NMR (CDCl$_3$+CD$_3$OD) δ1.9, 2.9, 3.6, 4.0, 4.6, 7.3, 7.5, 7.7, 8.3, 8.8 ppm; HRMS 385.13 10.

Example 32

Di(tert-butyl) 3-(3-{[(4-chlorobenzyl)amino]carbonyl}-1-methyl-4-oxo-1,4-dihydro-6-quinolinyl)propyl phosphate

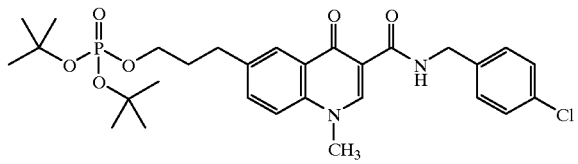

To a suspension of 77 mg of N-(4-chlorobenzyl)-6-(3-hydroxypropyl)-1-methyl-4-oxo-1,4-dihydro-3-quinolinecarboxamide from Preparation No. 27 and 25 mg of 1H-tetrazole in 2 mL of 1:1 chloroform-TBF, stirred under argon, is added 90 μL of di-tert-butyl diethyl phosphoramidite. After 18 h the solution is cooled to 0° C., and a slight excess of m-CPBA (ca 110 mg) is added. After 10 min, the mixture is partitioned between ethyl acetate and aqeuous NaHSO₃. The organic phase is washed with dilute aqueous HCl, water, and aqueous NaHCO₃, dried (Na₂SO₄), and concentrated under reduced pressure. Flash chromatography of the residue on silica using 2% methanol in dichloromethane provides 111 mg of the title compound as a white crystalline solid.

Physical properties as follows:

$^1$H NMR (CDCl$_3$) δ1.49, 2.0, 2.9, 3.94, 4.0, 4.6, 7.3, 7.5, 7.6, 8.3, 8.8 ppm; IR 2981, 1662, 1609, 1551, 1500, 1369, 1266, 1000, 810 cm⁻; HRMS 577.2241.

Example 33

3-(3-{[(4-Chlorobenzyl)amino]carbonyl}-1-methyl-4-oxo-1,4-dihydro-6-quinolinyl)propyl dihydrogen phosphate

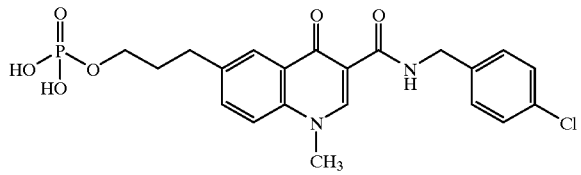

A solution of 77.8 mg of di(tert-butyl) 3-(3-{[(4-chlorobenzyl)amino]carbonyl}-1-methyl-4-oxo-1,4-dihydro-6-quinolinyl)propyl phosphate from Example No. 32 in 1 mL of 1:1 TFA-dichloromethane is stirred for 1 h, then added slowly to 20 mL of rapidly stirred 1:1 ether-hexane. The precipitated solid is filtered, washed with hexane, and dried under vacuum to afford 67 mg of the title compound as a white solid.

Physical properties as follows:

$^1$H NMR (CDCl$_3$+CD$_3$OD+TFA) δ2.1, 3.0, 4.0, 4.11, 4.7, 7.3, 7.7, 8.3, 9.0 ppm; HRMS 465.0981

Example 34

Di(tert-butyl) 3-(3-{[(4-chlorobenzyl)amino]carbonyl}-1-cyclopropyl-4-oxo-1,4-dihydro-6-quinolinyl)propyl phosphate

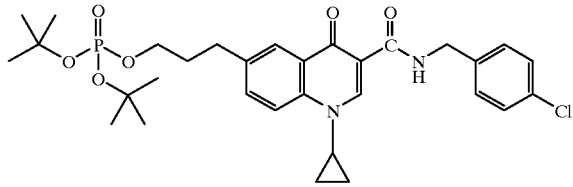

The title compound was prepared from N-(4-chlorobenzyl)-1-cyclopropyl-6-(3-hydroxypropyl)-4-oxo-1,4-dihydro-3-quinolinecarboxamide (Example No. 26) following procedures analogous to those described in Example No. 32.

Physical properties as follows:

$^1$H NMR (CDCl$_3$) 1.2, 1.3, 1.52, 2.1, 2.9, 3.5, 4.0, 4.6, 7.3, 7.6, 8.0, 8.3, 8.91, 10.5 ppm; IR 1666, 1606, 1547, 1490, 1266, 1039, 996 cm⁻¹; HRMS 603.2382.

Example 35

Sodium 2-[{8-[3-(3-{[(4-chlorobenzyl)amino]carbonyl}-1methyl-4-oxo-1,4-dihydro-6-quinolinyl)propoxyl-8-oxooctanoyl}(methyl)amino]-1-ethanesulfonate

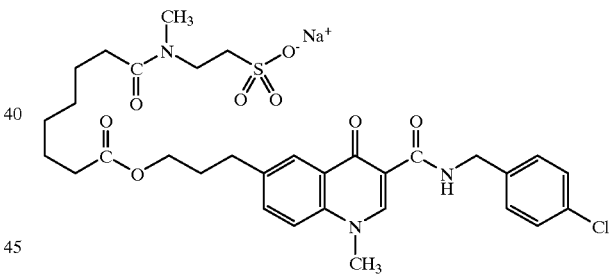

A solution of 77 mg of N-(4-chlorobenzyl)-6-(3-hydroxypropyl)-1-methyl-4-oxo-1,4-dihydro-3-quinolinecarboxamide from Preparation No. 27, 0.46 mL of a 0.65 M solution of suleptanic acid triethylammonium salt in acetonitrile, 27 mg of DMAP, and 38 μL of DIC in 1 mL of DMF is stirred at room temperature for 18 h, then concentrated under reduced pressure. Flash chromatography of the residue on silica using 5–20% methanol in dichloromethane affords a solid, which is dissolved in chloroform and butanol. This solution is stirred with 25 mL of saturated aqueous sodium sulfate, then filtered through anhydrous sodium sulfate and concentrated under reduced pressure to afford 113 mg of the title compound as a white solid.

Physical properties as follows:

$^1$H NMR (CDCl$_3$) δ1.3, 1.6, 2.0, 2.3, 2.8–3.2, 3.7, 3.9, 4.1, 4.6, 7.1–7.3, 7.5, 7.6, 8.3, 8.8 ppm; MS ES– 660; HRMS 662.2289

Example 36

Sodium 2-[{8-[3-(3-{[(4-chlorobenzyl)amino]carbonyl}-1-cyclopropyl-4-oxo-1,4-dihydro-6-quinolinyl)propoxy]-8-oxooctanoyl}(methyl)amino]-1-ethanesulfonate

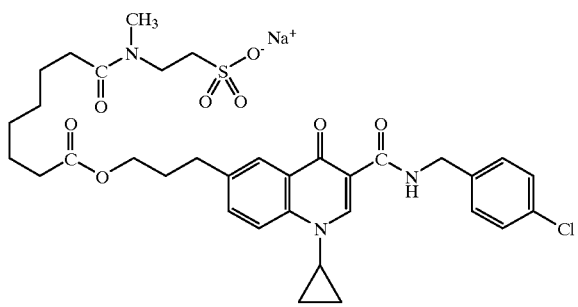

The title compound was prepared from N-(4-chlorobenzyl)-1-cyclopropyl-6-(3-hydroxypropyl)-4-oxo-1,4dihydro-3-quinolinecarboxamide (Example No. 26) following procedures analogous to those described in Example 35.

Physical properties as follows:

$^1$H NMR (CDCl$_3$) δ1.3, 1.4, 1.6, 2.0, 2.3, 2.7–3.3, 3.5, 3.7, 4.1, 4.6, 7.1–7.3, 7.5, 7.9, 8.3, 8.9, 10.5 ppm; IR 2936, 1732, 1664, 1606, 1547, 1490, 1348, 1192, 1060, 1036, 809, 732 cm$^{-1}$; MS ES– 686; HRMS 688.2447

Example 37

Sodium 2-[(8-{[3-(3-{[(4-chlorobenzyl)amino]carbonyl}-1-methyl-4-oxo-1,4-dihydro-6-quinolinyl)-2-propynyl]oxy}-8-oxooctanoyl)(methyl)amino]-1-ethanesulfonate

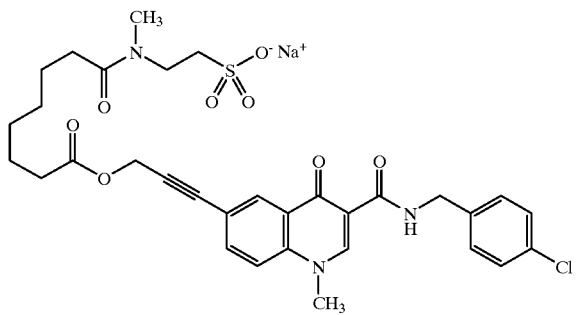

The title compound was prepared from N-(4-chlorobenzyl)-6-(3-hydroxy-1-propynyl)-1-methyl-4-oxo-1,4-dihydro-3-quinolinecarboxamide (Example No.31) following procedures analogous to those described in Example 35.

Physical properties as follows:

$^1$H NMR (CDCl$_3$+CD$_3$OD) δ1.3, 1.6, 2.3, 3.0–3.4, 3.7, 4.0, 4.1, 4.6, 4.9, 6.8, 7.3, 7.6, 7.8, 8.1, 8.5, 8.8 ppm; HRMS 680.1797.

Example 38

Sodium 2-[(8-{[3-(3-{[(4-chlorobenzyl)amino]carbonyl}-1-cyclopropyl-4-oxo-1,4-dihydro-6-quinolinyl)-2-propynyl]oxy)-8-oxooctanoyl)(methyl)amino]-1-ethanesulfonate

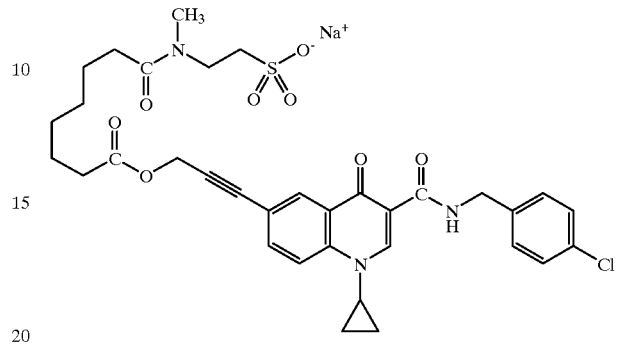

The title compound was prepared from N-(4-chlorobenzyl)-1-cyclopropyl-6-(3-hydroxy-1-propynyl)-4-oxo-1,4-dihydro-3-quinolinecarboxamide (Example No. 25) following procedures analogous to those described in Example 35.

Physical properties as follows:

$^1$H NMR (CDCl$_3$) δ1.1, 1.2–1.4, 1.6, 2.2–2.4, 2.9–3.2, 3.5, 3.8, 4.6, 4.9, 7.3, 7.8, 7.9, 8.4, 8.9, 10.3 ppm; MS ES– 682; HRMS 684.2159.

Preparation 28

2-Fluoro-5-iodobenzoic acid

To an argon-covered, stirred solution of 16.8 mL of diisopropylethylamine in 200 mL of THF, cooled at –78° C., is added dropwise 67 mL of a 1.6 M solution of butyllithium in hexane. The solution is allowed to warm to 0C and then recooled to –78° C. To this solution is added dropwise 11.5 mL of 4-fluoroiodobenzene in 10 mL of THF. The solution is stirred for 90 min at –78° C., then cannulated rapidly onto a Dry Ice-ether slurry. The mixture is allowed to warm to room temperature, then extracted with 300 mL of 0.3 M NaOH. The aqueous phase is chilled in ice and acidified with 40 mL of 6N HCl. The precipitate is extracted with two portions of ether, and the organic phase dried (MgSO$_4$) and concentrated under reduced pressure. Recrystallization of the residue with ethyl acetate-hexane provides 19.57 g of the title compound as white needles. A second crop of 3.78 g is obtained by recrystallization of the mother liquor residue.

Physical properties as follows:

$^1$H NMR (CDCl$_3$) δ6.97, 7.88, 8.33 ppm. Anal found: C, 31.57; H, 1.59.

Preparation 29

Ethyl 3-(2-fluoro-5-iodophenyl)-3-oxopropanoate

To a stirred solution of 5.32 g of 2-fluoro-5-iodobenzoic acid from Preparation No. 28 in 20 mL of THF, under argon, is added 3.9 g of carbonyldiimidazole. In a separate flask, 2.8 mL of chlorotrimethylsilane is added to a mixture of 3.74 g of potassium ethyl malonate in 20 mL of acetonitrile. The mixture is stirred under argon for 18 h, then cooled to 0° C. for the dropwise addition of 6.6 mL of DBU. The mixture is stirred for 3 h at 0° C., then the solution of acyl imidazolide prepared above is added via cannula. After 2 h, the mixture is partitioned between ether and excess dilute HCl, and the organic phase is washed with dilute HCl and brine and dried (MgSO$_4$). Removal of the solvent under reduced pressure left a colorless oil, which is flash chromatographed on silica using 10% ethyl acetate in hexane to provide 5.07 g of the title compound as dense pinkish prisms.

Physical properties as follows:

$^1$H NMR (CDCl$_3$) δ1.34, 4.27, 5.82, 6.89, 7.7, 8.2 ppm; IR 1624, 1485, 1419, 1245, 1193, 1070, 1028, 813 cm$^{-1}$.

Preparation 30

Ethyl 1-(tert-butyl)-6-iodo4-oxo-1,4-dihydro-3-quinolinecarboxylate

A solution of 2.36 g of ethyl 3-(2-fluoro-5-iodophenyl)-3-oxopropanoate from Preparation No. 29, 2.0 mL of triethyl orthoformate, and 15 mL of acetic anhydride is refluxed under argon for 2 h, then the solvents are distilled off under reduced pressure. To the residual oil is added 10 mL of dry tert-butanol and 0.74 mL of tert-butylamine, and the solution is stirred at 80° C. for 2 h. Potassium tert-butoxide (0.87 g) is then added, and stirring continued at 80° C. under argon for 18 h. The mixture is then cooled and partitioned between dilute HCl and chloroform-methanol. The organic phase is dried (MgSO$_4$) and concentrated under reduced pressure. Flash chromatography of the residue on silica using 2–4% methanol in dichloromethane provides 1.32 g of the title compound as an off-white solid.

Physical properties as follows:

$^1$H NMR (CDCl$_3$) δ1.42, 1.87, 4.4, 7.7, 7.9, 8.9 ppm; HRMS 400.0414. Anal. Found: C, 48.05; H, 4.50; N, 3.52.

Preparation 31

1-(tert-Butyl)-N-(4-chlorobenzyl)-6-iodo-4-oxo-1,4-dihydro-3-quinolinecarboxamide

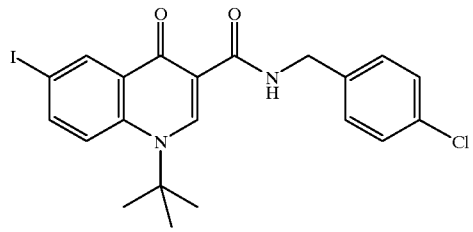

A slurry of 1.11 g of ethyl 1-(tert-butyl)-6-iodo4oxo-1,4-dihydro-3-quinolinecarboxylate from Preparation No. 30 in 2.0 g of 4-chlorobenzylamine is heated under argon at 160° C. for 18 h, then cooled to room temperature and triturated with 1N HCl. The solid is filtered, washed well with water, and dried under vacuum. Flash chromatography using 20% ethyl acetate in dichloromethane provides 1.22 g of the title compound as a white solid.

Physical properties as follows:

$^1$H NMR (CDCl$_3$) δ1.89, 4.6, 7.3, 7.7, 7.9, 8.9, 9.22, 10.4 ppm; IR 1664, 1536, 1468, 1342, 1180 cm$^{-1}$. Anal. Found: C, 51.27; H, 4.19; N, 5.62.

Example 39

1-(tert-Butyl)-N-(4-chlorobenzyl)-6-(3-hydroxy-1-propynyl-4-oxo-1,4-dihydro-3-quinolinecarboxamide

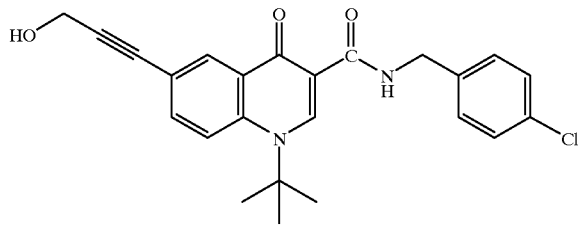

To a stirred slurry of 1.15 g of 1-(tert-butyl)-N-(4-chlorobenzyl)-6-iodo4-oxo-1,4-dihydro-3-quinolinecarboxamide from Preparation No. 31, 156 mg of copper (I) iodide, and 66 mg of dichlorobis(triphenylphosphine)palladium (II) in 23 mL of diethylamine, under argon, is added 0.16 mL of propargyl alcohol. The mixture is stirred for 18 h at room temperature, then concentrated under reduced pressure. The residue is partitioned between water and chloroform-methanol, and the organic phase dried (MgSO$_4$) and concentrated under reduced pressure. Flash chromatography of the residue on silica using 2–4% methanol in dichloromethane affords 977 mg of tan solid. Recrystallization from ethanol provides 850 mg of the title compound as a beige solid.

Physical properties as follows:

$^1$H NMR (CDCl$_3$) δ1.92, 4.47, 4.6, 7.3, 7.7, 8.0, 8.5, 9.19, 10.5 ppm; HRMS 423.1466. Anal. Found: C, 67.74; H, 5.53; N, 6.61.

Preparation 32

1-(tert-Butyl)-N-(4-chlorobenzyl)-6-(3-hydroxypropyl-4-oxo-1,4-dihydro-3-quinolinecarboxamide

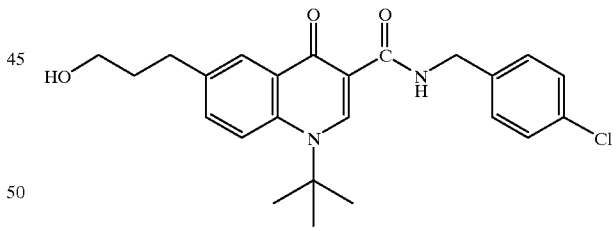

A mixture of 303 mg of i-(tert-butyl)-N-(4-chlorobenzyl)-6-(3-hydroxy-1-propynyl-4-oxo-1,4-dihydro-3-quinolinecarboxamide from Example No. 39 and 15 mg of platinum oxide in 10 mL of 1:1 THF-methanol is stirred under 1 atm of hydrogen gas for 3 h, then filtered through diatomaceous earth and concentrated under reduced pressure. The mixture was purified by flash chromatography on silica using 2–3% methanol in dichloromethane to afford 294 mg of the title compound.

Physical properties as follows:

$^1$H NMR (CDCl$_3$) δ1.89, 1.9, 2.9, 3.7, 4.6, 7.3, 7.5, 7.9, 8.4, 9.21, 10.6 ppm; IR 1658, 1596, 1548, 1484, 1349, 1184, 810, 731 cm$^{-1}$; HRMS 427.1762

Example 40

Sodium 2-[{8-[3-(1-(tert-butyl)-3-{[(4-chlorobenzyl)amino]-carbonyl}-4-oxo-1,4-dihydro-6-quinolinyl)propoxy]-8-oxooctanoyl}(methyl)amino]-1-ethanesulfonate

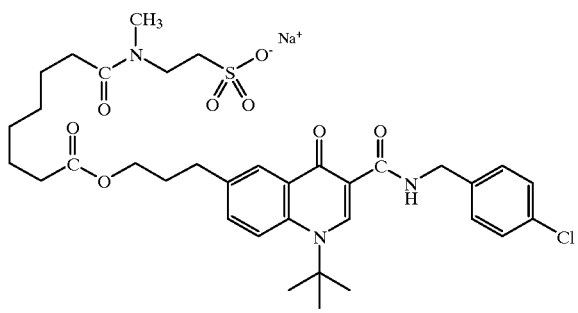

The title compound was prepared from 1-(tert-butyl)-N-(4-chlorobenzyl)-6-(3-hydroxypropyl)-4-oxo-1,4-dihydro-3-quinolinecarboxamide (Preparation No. 32) following procedures analogous to those described in Example 35.

Physical properties as follows:

$^1$H NMR (CDCl$_3$) δ1.2–1.4, 1.6, 1.9, 2.0, 2.2–2.4, 2.8–3.2, 3.7, 4.1, 4.6, 7.1–7.3, 7.5, 7.9, 8.4, 9.2, 10.5 ppm; IR 2937, 1732, 1663, 1596, 1546, 1484, 1184 cm$^{-1}$; HRMS 748.2394.

Example 41

Sodium 2-[(8-{[3-(1-(tert-butyl)-3-([(4-chlorobenzyl)amino]-carbonyl}-4-oxo-1,4-dihydro-6-quinolinyl)-2-propynyl]oxy}-8-oxooctanoyl)(methyl)amino]-1-ethanesulfonate

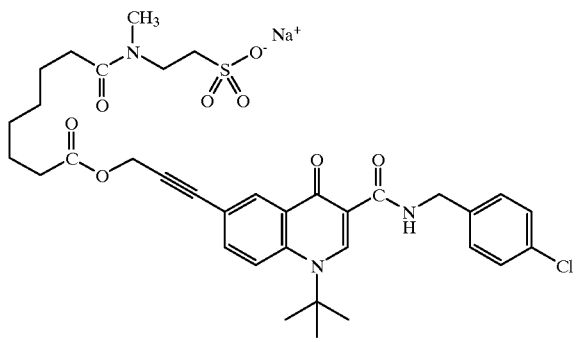

The title compound was prepared from 1-(tert-butyl)-N-(4-chlorobenzyl)-6-(3-hydroxy-1-propynyl)-4-oxo-1,4-dihydro-3-quinolinecarboxamide (Example No. 39) following procedures analogous to those described in Example 35.

Physical properties as follows:

$^1$H NMR (CDCl$_3$) δ1.3, 1.6, 1.9, 2.2–2.4, 2.6, 2.8–3.2, 3.7, 4.6, 4.9, 7.1–7.3, 7.7, 7.9, 8.6, 9.2, 10.4 ppm; IR 2936, 1741, 1666, 1592, 1544, 1482, 1341, 1182 cm$^{-1}$ MS ES– 698; HRMS 700.2496

Example 42

N-(4-Chlorobenzyl)-6-(3-hydroxy-1-propynyl)-1-[2-(2-methoxyethoxy)ethyl]-4-oxo-1,4-dihydro-3-quinolinecarboxamide

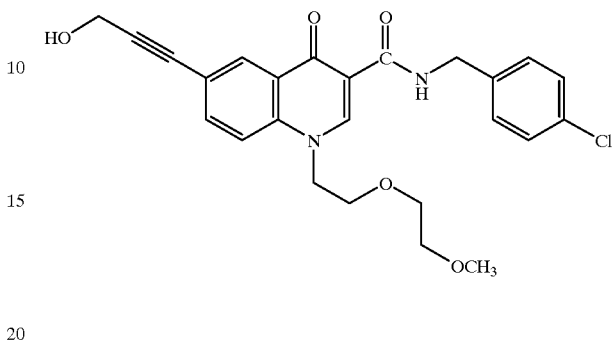

The title compound is prepared according to procedures analogous to those described in Preparation No 30–31 and Example No. 39 from ethyl 1-(tert-butyl)-6-iodo-4-oxo-1,4-dihydro-3-quinolinecarboxylate.

Physical properties as follows:

$^1$H NMR (CDCl$_3$) δ3.29, 3.5, 3.6, 3.8–4.0, 4.34.–4.5, 4.7, 7.3, 7.5, 8.2, 8.76, 10.4 ppm; MS ES+ 469; HRMS 469.1508. Anal. Found: C, 63.98; H, 5.42; N, 6.04.

Preparation 32

4-(Aminomethyl)benzonitrile

A mixture of 4-(boromomethyl)benzonitrile (7.1 g) and sodium azide (2.6 g) in DMF (40 mL) is stirred for 19 hrs. The reaction mixture is then diluted with water (150 mL) and extracted with ether (2×50 mL). The organic phases are combined, washed with water (50 mL) and brine (50 mL), and dried with MgSO$_4$. Filtration and evaporation of the solvent leaves 5.5 g of 4-(azidomethyl)benzonitrile as a clear, colorless oil.

Triphenylphosphine (7.67 g) is added to a solution of 4-(azidomethyl)-benzonitrile (4.19 g) in THF (30 mL) and stirred for 1 hr. Water (10 mL) is added, and the solution is stiffed for 16 hrs. The reaction mixture is diluted with ether (50 mL) and extracted with HCl (3 N, 3×25 mL) and water (1×25 mL). The aqueous phases are combined and washed with ether (50 mL). Sodium hydroxide is added until the pH=12. After extracting with ether (2×50 mL), the solution is dried with MgSO$_4$ and filtered. The solvent is evaporated under reduced pressure. The resulting crude mixture is then purified via bulb to bulb distillation at 150° C. and 1 torr to afford 1.74 g (50%) of the title compound as a clear, colorless oil.

Physical characteristics are as follows:

$^1$H NMR (DMSO-d$_6$) δ7.7, 7.5, 3.8, 1.9

Example 43

N-(4-Cyanobenzyl)-6-(3-hydroxy-1-propynyl)-1-methyl-4-oxo-1,4-dihydro-3-quinolinecarboxamide

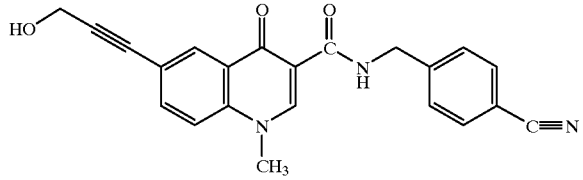

Ethyl 4-hydroxy-6-iodo-3-quinolinecarboxylate prepared as an intermediate in Preparation No. 4 (5.0 g), potassium carbonate (10.4 g) and methyl iodide (0.94 mL) are suspended in DMF (100 mL) and heated to 95° C. under a nitrogen atmosphere for 6.5 hrs. After the mixture is brought to room temperature potassium carbonate is filtered off, and the solvent is evaporated under reduced pressure until a white solid precipitates out of solution. This white solid is filtered, washed with water and dried in a stream of air. A sample of this solid (2.0 g) is suspended in ethanol (12 mL) and sodium hydroxide (8 mL, 3 N) is added. The mixture is stirred overnight. The mixture is then acidified with 3 N HCl. The resulting solid is filtered, washed with 3×30 mL water and dried in a stream of air. A sample of this solid (1.0 g) and 1,1'-carbonyldiimidazole (1.0 g) are suspended in DMF (20 mL) and heated to 70° C. for 2 hrs. The mixture is brought to room temperature and treated with water (0.054 mL). A solution of 0.42 g of 4-(aminomethyl)benzonitrile from Preparation No. 32b in 10 mL DMF is added to the mixture and allowed to stir at room temperature for 24 hrs. Dilution with 30 mL H$_2$O causes a white solid to precipitate out of solution. The solid is filtered and washed with 3×20 mL 1:1 DMF: water. A sample of this white solid (0.5 g) is suspended in diethylamine (17 mL) and treated with copper iodide (0.06 g), bis-triphenylphosphine palladium chloride (0.04 g), and propargyl alcohol (0.08 mL). The reaction is stirred at room temperature overnight, and the volume is reduced by evaporation under reduced pressure to a brown, viscous oil. The oil is diluted with CH$_2$Cl$_2$ producing an off-white solid. This solid is filtered and then dissolved in hot acetic acid. The insoluble impurities are filtered from the solution while still hot, and the product precipitates as the solution cools. The solid is filtered, washed with 3×25 mL water and dried in a stream of air on a fritted funnel. The procedure affords 0.31 g of the title compound as an off-white solid.

Physical characteristics are as follows:

Mp 230–232° C.; $^1$H NMR (DMSO-d$_6$) δ10.3, 8.8, 8.3, 7.8, 7.7, 7.5, 5.4, 4.6, 4.3, 4.0.

Example 44

6-((Bis(2-hydroxyethyl)amino)methyl)-N-(4-chlorobenzyl)-1-1-methyl-4-oxo-1,4-dihydro-3-quinolinecarboxamide.

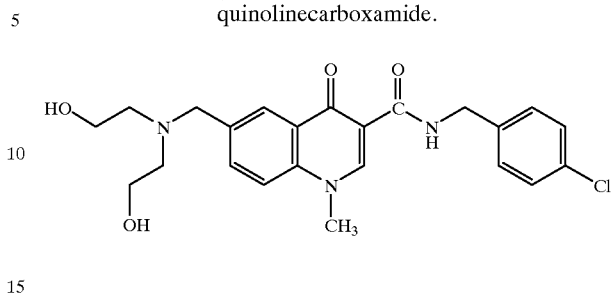

Methanesulfonyl chloride (0.048 1L) is added to a cold (0° C.) solution of N-(4-chlorobenzyl)-6-(hydroxymethyl)-1-methyl-4-oxo-1,4-dihydro-3-quinolinecarboxamide (200 mg) from Preparation No. 10, DMAP (11.5 mg), and 2,4,6-collidine (0.087 mL) in anhydrous DMF (9.5 mL). The mixture is stirred at room temperature until starting material is consumed and diethanolamine (0.54 mL) is added. The reaction mixture is heated to 56° C. for 1.5 h. The reaction mixture is cooled to room temperature and partitioned between CH$_2$Cl$_2$ and water. The aqueous layer is extracted with CH$_2$Cl$_2$ three times. The combined organic layers are washed with brine, dried (Na$_2$SO$_4$), and concentrated to afford a yellow residue. The resulting solid was adsorbed onto silica and purified by chromatography (eluent 1% MeOH in CH$_2$Cl$_2$ (1 L), 2% MeOH in CH$_2$Cl$_2$ (1 L), 3% MeOH in CH$_2$Cl$_2$ (1 L), 4% MeOH in CH$_2$Cl$_2$ (2L)). Fractions homogenous by TLC were combined and concentrated to afford 69.3 mg (28%) of the title compound as a white solid.

Physical characteristics are as follows:

Mp 165–166° C.; $^1$H NMR (300 MHz, DMSO-d$_6$) δ10.45, 8.86, 8.24, 7.86, 7.79, 7.38, 4.56, 4.38, 4.02, 3.81, 3.46, 2.56; IR (drift) 3324, 2935, 2923, 2820, 1667, 1611, 1551, 1491, 1362, 1235, 1087, 1080, 814, 808, 796 cm$^{-1}$; Anal. found for C$_{23}$H$_{26}$ClN$_3$O$_4$: C, 61.90; H, 5.94; N, 9.35.

Example 45

N-(4-Chlorobenzyl)-6-(((2-hydroxyethyl)(methyl)amino)-methyl)-1-methyl-4-oxo-1,4-dihydro-3-quinolinecarboxamide

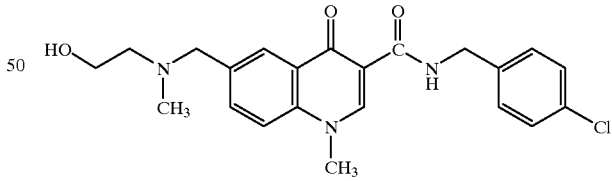

Methanesulfonyl chloride (0.065 mL) is added to a cold (0° C.) solution of N-(4-chlorobenzyl)-6-(hydroxymethyl)-1-methyl-4-oxo-1,4-dihydro-3-quinolinecarboxamide (0.27 g) from Preparation No. 10, DMAP (0.017 g), and 2,4,6-collidine (0.12 mL) in anhydrous DMF (14 mL). The mixture is stirred at room temperature overnight and 2-(methylamino)ethanol (0.61 mL) is added. The reaction mixture is stirred at room temperature for 2 h, poured into water, and extracted with CH$_2$Cl$_2$ (3×). The organic layers are combined, dried (Na$_2$SO$_4$), filtered, and concentrated in vacuo. The residue is dissolved in CH$_2$Cl$_2$/MeOH and adsorbed onto silica. Purification by chromatography (eluent $CH_2Cl_2$ (1 L), 1.5% $MeOH/CH_2Cl_2$ (1 L), 2.5% $MeOH/CH_2Cl_2$ (1 L), 3.5% $MeOH/CH_2Cl_2$ (1 L), 5% $MeOH/CH_2Cl_2$ (1 L), 6% $MeOH/CH_2Cl_2$ (1 L)) affords the product as a clear residue. The residue is crystallized by addition of $CH_2Cl_2$/hexanes followed by removal of the solvents in vacuo to give 0.21 g (69%) of the title compound as a white solid.

Physical characteristics are as follows:

Mp 130–131° C.; $^1H$ NMR (DMSO-$d_6$) δ10.44, 8.86, 8.23, 7.80, 7.40, 7.36, 4.56, 4.42, 4.02, 3.67, 3.52, 2.46, 2.17; IR (drift) 3435, 1665, 1610, 1549, 1497, 1367, 1352, 1316, 1233, 1123, 1090, 1020, 819, 808, 662 $cm^{-1}$; Anal. Found for $C_{22}H_{24}ClN_3O_3$: C, 63.70; H, 5.98; N, 9.85.

Preparation 33

1,4-Oxazepane

To a stirred solution of tetrahydro4H-pyran-4-one (4.19 mL) in conc. HCl (23 mL) cooled to 0° C. is added portion-wise sodium azide (4.42 mL). After addition was complete, the reaction is stirred at room temperature for 4 h. Solid sodium carbonate is added portion-wise until the solution was slightly alkaline (pH=9). Water is added during addition of sodium carbonate to dissolve the salt. The alkaline solution is diluted with $CHCl_3$ (125 mL) and the phases are separated. The aqueous layer are extracted with $CHCl_3$ (2×75 mL). The combined organic layers are dried ($Na_2SO_4$), filtered, and concentrated to afford 2.5 g (48%) of 1,4-oxazepan-5-one as an orange-brown residue. $^1H$ NMR (300 MHz, $CDCl_3$) δ6.66, 3.80, 3.35, 2.72.

To a solution of 1,4-oxazepan-5-one (2.5 g) in distilled THF (86 mL) cooled to 0° C. is added dropwise a solution of $LiAlH_4$ in TPF (1M, 21.9 mL). The reaction mixture is stirred at room temperature for 2.5 h during which additional $LiAlH_4$ (11 mL) is added. The reaction is quenched by successive addition of water (4 mL), 15% NaOH (4 mL), and water (4 mL). The reaction mixture is filtered, and the filtrate is dried ($Na_2SO_4$), filtered, and concentrated to obtain 963 mg (44%) of 1,4-oxazepane as a residue.

Physical characteristics are as follows:

$^1H$ NMR (300 MHz, $CDCl_3$) δ3.82, 3.73, 2.96, 1.88

Example 46

N-(4-Chlorobenzyl)-1-methyl-6-(1,4-oxazepan-4-ylmethyl)-4-oxo-1,4-dihydro-3-quinolinecarboxamide

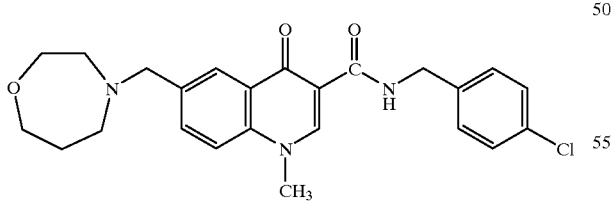

Methanesulfonyl chloride (0.080 mL) is added to a cold (0° C.) solution of N-(4-chlorobenzyl)-6-(hydroxymethyl)-1-methyl-4-oxo-1,4-dihydro-3-quinolinecarboxamide (330 mg) from Preparation No. 10, DMAP (19.1 mg), and 2,4,6-collidine (0.14 mL) in anhydrous DMF (15.7 mL). The mixture is stirred at room temperature until the starting material is consumed and a solution of 1,4-oxepane (0.963 g) from Preparation No. 33 in anhydrous DMF (3 mL) is added. The reaction mixture is heated to 56° C. for 1.5 h. The mixture is cooled to room temperature and the product is precipitated by addition of water (125 mL). The solid was adsorbed onto silica and purified by column chromatography (eluent 100% $CH_2Cl_2$ (1 L), 1% MeOH in $CH_2Cl_2$ (2 L), 1.5% MeOH in $CH_2Cl_2$ (1 L), 2% MeOH in $CH_2Cl_2$ (3 L)). Fractions homogenous by TLC are combined and concentrated to afford 124.5 mg (31%) of the title compound as a white solid.

Physical characteristics are as follows:

Mp 178–179° C.; $^1H$ NMR (300 MHz, DMSO-$d_6$) δ10.43, 8.87, 8.27, 7.81, 7.38, 4.56, 4.02, 3.79, 3.70, 3.61, 2.64, 1.81; IR (drift) 2939, 1655, 1606, 1573, 1551, 1502, 1363, 1351, 1344, 1132, 1091, 1080, 828, 816, 808 $cm^{-1}$; Anal. found for $C_{24}H_{26}ClN_3O_3$: C, 65.14; H, 6.01; N, 9.39.

Preparation 34

1,4-Thiazepane

To a stirred solution of tetrahydrothiopyran-4-one (4.74 g) in conc. HCl (20.7 mL) cooled to 0° C. is added portion-wise sodium azide (3.98 g, 61.2 mmol). After addition is complete, the reaction is stirred at room temperature for 4 h. Solid sodium carbonate is then added portion-wise until the solution was slightly alkaline (pH=9). Water is added during addition of sodium carbonate to dissolve the salt. The alkaline solution is diluted with $CHCl_3$ (125 mL), and the phases are separated. The aqueous layer is extracted with $CHCl_3$ (2×75 mL). The combined organic layers are dried ($Na_2SO_4$), filtered, and concentrated. The crude product is recrystallized from $CH_2Cl_2$/hexanes to afford 4.30 g (81%) of 1,4-thiazepan-5-one as a white solid.

Physical characteristics are as follows:

Mp 114–116° C.; $^1H$ NMR (300 MHz, $CDCl_3$) δ6.41, 3.66, 2.96, 2.76.

To a solution of 1,4-thiazepan-5-one (3.0 g) in distilled THF (90 mL) cooled to 0° C. is added dropwise a solution of $LiAlH_4$ in THF (1M solution, 22.9 mL). The mixture is stirred at room temperature for 2 h. The reaction is quenched by successive addition of water (2 mL), 15% NaOH (2 mL) and water (2 mL). The reaction mixture is filtered to remove the aluminum salt that had precipitated. The filtrate was dried ($Na_2SO_4$), filtered, and concentrated to obtain 2.63 g (98%) of 1,4-thiazepane as a yellow residue.

Physical characteristics are as follows:

$^1H$ NMR (300 MHz, $CDCl_3$) δ3.07, 2.96, 2.75, 1.92.

Example 47

N-(4-Chlorobenzyl)-1-methyl-4-oxo-6-(1,4-thiazepan-4-ylmethyl)-1,4-dihydro-3-quinolinecarboxamide

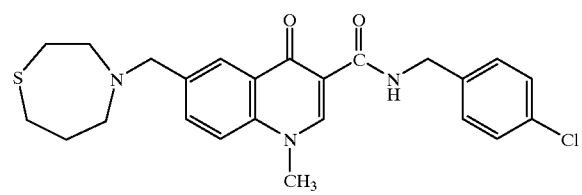

Methanesulfonyl chloride (0.096 mL) is added to a cold (0° C.) solution of N-(4-chlorobenzyl)-6-(hydroxymethyl)-1-methyl-4-oxo-1,44dihydro-3-quinolinecarboxamide (400 mg) from Preparation No. 10, DMAP (23 mg), and 2,4,6-collidine (0.17 mL) in anhydrous DMF (19 mL). The mixture is stirred at room temperature until the starting material is consumed and 1,4 thiazepane (1.13 g) from Preparation No. 34 is added. The reaction mixture is heated to 65° C. for 1.5 h. The mixture is cooled to room temperature and the product is precipitated by addition of water (125 mL). The solid is adsorbed onto silica and purified by column chromatography (eluent 100% $CH_2Cl_2$ (1 L), 0.5% MeOH in $CH_2Cl_2$ (1 L), 1% MeOH in $CH_2Cl_2$ (2.5 L), 1.5% MeOH in $CH_2Cl_2$ (2.5 L)). Fractions homogenous by TLC are combined and concentrated to afford 338.7 mg (66%) of the title compound as a white solid.

Physical characteristics are as follows:

Mp 166–167° C.; $^1$H NMR (300 MHz, DMSO-$d_6$) δ10.44, 8.86, 8.28, 7.84, 7.80, 7.38, 4.56, 4.02, 3.88, 2.91, 2.83, 2.76, 2.68, 1.80; IR (drift) 2919, 1656, 1605, 1573, 1551, 1501, 1420, 1363, 1317, 1240, 1131, 1109, 819, 808, 661 cm$^{-1}$; Anal. found for $C_{24}H_{26}ClN_3O_2S$: C, 63.13; H, 5.73; N, 9.15.

Example 48

N-(4-Chlorobenzyl)-1-methyl-6-(2-oxa-5-azabicyclo [2.2.1]-hept-5-ylmethyl)-4-oxo-1,4-dihydro-3-quinolinecarboxamide

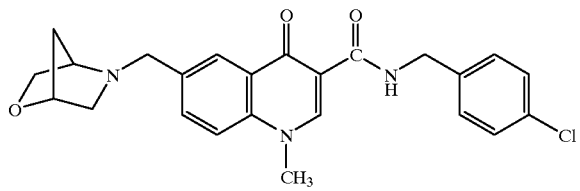

Methanesulfonyl chloride (0.06 mL) is added to a cold (0° C.) solution of N-(4-chlorobenzyl)-6-(hydroxymethyl)-1-methyl-4-oxo-1,4-dihydro-3-quinolinecarboxamide (250 mg) from Preparation No. 10, DMAP (14.4 mg), and 2,4, 6-collidine (0.11 mL) in anhydrous DMF (12 mL). The mixture is stirred at room temperature until the starting material is consumed. (1S, 4S)-(+)-2-Aza-5-oxabicyclo [2.2.1]heptane hydrochloride (475.9 mg) and $Et_3N$ (0.49 mL) are added to the solution. The reaction mixture is heated to 65° C. overnight. The mixture is cooled to room temperature and filtered to remove the salt that had precipitated out of solution. The filtrate is diluted with water (125 mL) to precipitate the product. The solid is adsorbed onto silica and purified by column chromatography (eluent 1% MeOH in $CH_2Cl_2$ (1 L), 2% MeOH in $CH_2Cl_2$ (1 L), 3% MeOH in $CH_2Cl_2$ (2.5 L)). Fractions homogenous by TLC are combined, concentrated, and recrystallized from $CH_2Cl_2$/hexanes to afford 164.0 mg (53%) of the title compound as a white solid.

Physical characteristics are as follows:

Mp 162–163° C.; $^1$H NMR (300 MHz, DMSO-$d_6$) δ10.44, 8.86, 8.28, 7.84, 7.79, 7.38, 4.56, 4.36, 4.02, 3.94, 3.88, 3.54, 3.46, 2.73, 2.43, 1.84, 1.61; IR (drift) 1655, 1605, 1573, 1550, 1500, 1364, 1316, 1222, 1131, 1091, 844, 822, 810, 721, 662 cm$^{-1}$; $[\alpha]_D^{25}$=+35 (c=0.89, methanol); Anal. found for $C_{24}H_{24}ClN_3O_3$: C, 65.86; H, 5.58; N, 9.58.

Example 49

N-(4-Chlorobenzyl)-6-(2,3-dihydro-4H-1,4-benzoxazin-4-ylmethyl)-1-methyl-4-oxo-1,4-dihydro-3-quinolinecarboxamide

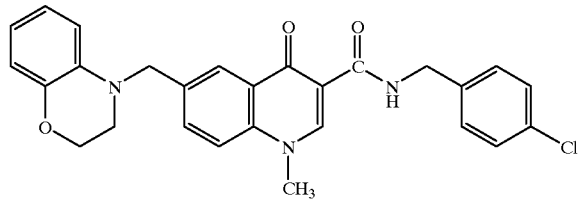

A solution of $LiAlH_4$ (34 mL, 1M in THF) is added dropwise via addition funnel to a cold (0° C.) solution of (2H)1,4-benzoxazin-3(4H)-one (5.04 g) in freshly distilled THF (110 mL). The $LiAlH_4$ is added at such a rate to keep the reaction temperature below 10° C. The mixture is stirred at room temperature for 2 h and then is quenched successively with water (5 mL), 15% NaOH (5 mL), and water (5 mL) again. The resulting precipitate is filtered and the filtrate is concentrated in vacuo. The residue is dissolved in $CH_2Cl_2$ and dried ($Na_2SO_4$), filtered, and concentrated to afford the product benzomorpholine as a yellow oil which was used without further purification in the next step.

Methanesulfonyl chloride (0.10 mL) is added to a cold (0° C.) solution of N-(4-chlorobenzyl)-6-(hydroxymethyl)-1-methyl-4-oxo-1,4-dihydro-3-quinolinecarboxamide (0.41 g) from Preparation No. 10, DMAP (0.030 g), and 2,4,6-collidine (0.19 mL) in anhydrous DMF (15 mL). The mixture is stirred at room temperature for 12 h and then benzomorpholine (1.60 g) from above is added. The reaction mixture is stirred at room temperature for 2 h and is then heated to 65° C. overnight. The mixture is cooled to room temperature and poured water. The solid is dissolved in $CH_2Cl_2$/MeOH and adsorbed onto silica. Purification by column chromatography (eluent $CH_2Cl_2$ (1 L), 1% MeOH/ $CH_2Cl_2$ (2 L)) and then recrystallization from $CH_2Cl_2$/ hexanes affords 0.56 g (100%) of the title compound as a pale gold solid.

Physical characteristics are as follows:

Mp 193–194° C.; $^1$H NMR (DMSO-$d_6$) δ10.40, 8.86, 8.24, 7.82, 7.39, 7.35, 6.68, 6.53, 4.65, 4.54, 4.24, 4.01, 3.44; IR (drift) 1653, 1604, 1576, 1551, 1502, 1365, 1347, 1329, 1307, 1254, 1235, 1214, 818, 811, 733 cm$^{-1}$; Anal. Found for $C_{27}H_{24}ClN_3O_3$: C, 68.06; H, 5.09; N, 8.80.

Example 50

6-((Benzyl(2-hydroxyethyl)amino)methyl)-N-(4-chlorobenzyl)-1-methyl-4-oxo-1,4-dihydro-3-quinolinecarboxamide

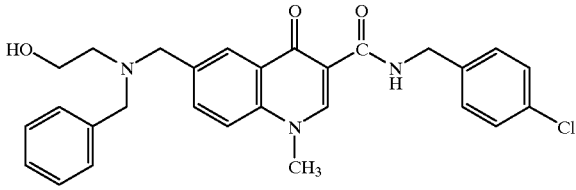

Methanesulfonyl chloride (0.193 mL) is added to a solution of N-(4-chlorobenzyl)-6-(hydroxymethyl)-1-methyl-4- oxo-1,4-dihydro-3uinolinecarboxamide (357 mg) from Preparation No. 10, DMAP (20 mg), and 2,4,6-collidine (0.33 mL) in DMF (20 mL). The mixture is stirred at room temperature for 3 h and then N-benzylethanolamine (1.42 mL) is added. The reaction mixture is stirred at room temperature for 20 h, poured into water (60 mL), and extracted with ethyl acetate (3×50 mL). The organic layers are washed with sat. aq. sodium bicarbonate (10 mL) and brine (10 mL), dried ($Na_2SO_4$), and concentrated. The crude product was purified by column chromatography ($CH_2Cl_2$/ methanol, 100/1; 50/1) to afford 0.35 g (71 %) of the title compound as a white solid.

Physical characteristics are as follows:

Mp 133–135° C.; $^1$H NMR (DMSO-$d_6$) δ10.44, 8.86, 8.29, 7.89–7.79, 7.42–7.21, 4.56, 4.42, 4.02, 3.76, 3.62, 3.5; $^{13}$C NMR (DMSO-$d_6$) δ175.4, 164.4, 148.6, 139.4, 138.9, 138.7, 136.9, 133.5, 131.4, 129.1, 128.5, 128.3, 128.2, 126.8, 126.7, 125.2, 117.5, 110.4, 59.2, 58.1, 57.5, 55.2, 41.4, 41.2; IR (drift) 1653, 1606, 1549, 1499, 1456, 1362, 1318, 1234, 1224, 1128, 1062, 817, 810, 799, 739 cm$^{-1}$; HRMS (FAB) calcd for $C_{28}H_{28}ClN_3O_3$+H m/z 490.1897, found 490.1900. Anal. Found for $C_{28}H_{28}ClN_3O_3$68.62; H, 5.89; N, 8.54; Cl, 7.17.

Preparation 35

N-(4-Chlorobenzyl)-6-(chloromethyl)-1-methyl-4-oxo-1,4-dihydro-3-quinolinecarboxamide

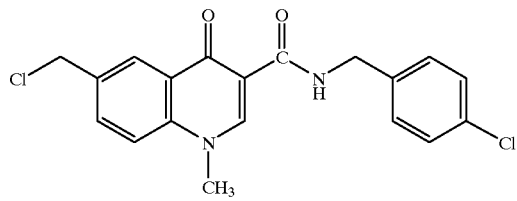

A solution of N-(4-chlorobenzyl)-6-(hydroxymethyl)-1-methyl-4-oxo-1,4-dihydro-3-quinolinecarboxamide from Preparation No. 10 (1.0 g), collidine (0.44 mL), and DMAP (57.9 mg) in anhydrous DMF (48 mL) is cooled to 0° C. Methanesulfonyl chloride (0.24 mL) is added dropwise. The reaction is stirred at room temperature. The crude product is precipitated by addition of water and is filtered. The resulting solid is adsorbed onto silica and purified by chromatography (eluent 100% $CH_2Cl_2$ (1 L), 1% MeOH in $CH_2Cl_2$ (1 L)). Product-containing fractions were combined and concentrated to afford 948.8 mg (90%) of the title compound as a white solid.

Physical characteristics are as follows:

Mp 241–242° C.; $^1$H NMR (300 MHz, DMSO-$d_6$) δ10.36, 8.89, 8.39, 7.92, 7.86, 7.36, 4.98, 4.57, 4.03; IR (drift) 1658, 1605, 1578, 1550, 1544, 1503, 1364, 1348, 1275, 1222, 820, 808, 798, 694, 656 cm$^{-1}$; Anal. found for $C_{19}H_{16}Cl_2N_2O_2$: C, 60.81; H, 4.16; N, 7.49.

Example 51

6-(Azidomethyl)-N-(4-chlorobenzyl)-1-methyl-4-oxo-1,4-dihydro-3-quinolinecarboxamide

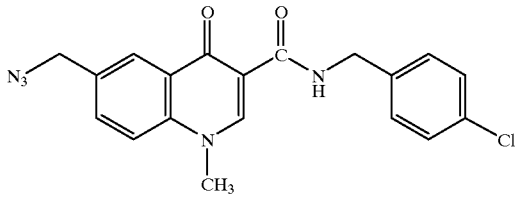

A solution of N-(4-chlorobenzyl)-6-(chloromethyl)-1-methyl-4-oxo-1,4-dihydro-3-quinolinecarboxamide from Preparation No. 35 (200 mg) and sodium azide (176.8 mg) in anhydrous DMF (7 mL) is heated at 60° C. overnight. The reaction is cooled to room temperature and poured into water to precipitate the product. The solid is adsorbed onto silica and purified by chromatography (eluent 100% $CH_2Cl_2$ (1 L), 0.5% MeOH in $CH_2Cl_2$ (1 L), and 1% MeOH in $CH_2Cl_2$ (1 L)). Fractions homogenous by TLC were combined and concentrated to afford 182.7 mg (90%) of the title compound as a white solid.

Physical characteristics are as follows:
Mp 219–220° C.; $^1$H NMR (300 MHz, DMSO-$d_6$) δ10.38, 8.90, 8.33, 7.88, 7.38, 4.67, 4.57, 4.04; IR (drift) 2107, 2075, 1656, 1603, 1580, 1550, 1543, 1501, 1362, 1241, 1221, 822, 808, 798, 722 cm$^{-1}$; Anal. found for $C_{19}H_{16}ClN_5O_2$: C, 59.62; H, 4.15; N, 18.08.

Preparation 36 t-Butyl 4,4-difluoro-1-piperidinecarboxylate and t-butyl 4-fluoro-3,6-dihydro-1 [2H]-pyridinecarboxylate Diethylaminosulfur trifluoride (4.39 mL) is added to a solution of 1-(t-butoxycarbonyl) 4-piperidone in distilled THF (41 mL). The reaction is heated at 60° C. for 6 hrs, then allowed to cool to room temperature overnight. The reaction mixture is poured into 120 mL ice water. The phases are separated, and the aqueous layer is extracted with EtOAc three times. The combined organic layers are dried over $Na_2SO_4$, filtered, and concentrated to afford yellow crystals. The crude product is adsorbed onto silica and purified by chromatography (eluent 1% EtOAc in hexanes (1 L), 2% EtOAc in hexanes (1 L), 3% EtOAc in hexanes (1 L)). Fractions homogenous by TLC are combined and concentrated to yield a mixture of two products. The products are separated by HPLC to afford 543.8 mg (16%) of t-butyl 4,4-difluoro-1-piperidine-carboxylate [$^1$H NMR (300 MHz, CDCl$_3$) δ3.56, 1.94, 1.48] as a white solid and 196 mg (7%) of t-butyl 4-fluoro-3,6-dihydro-1[2H]-pyridinecarboxylate [$^1$H NMR (300 MHz, CDCl$_3$) δ5.21, 3.93, 3.62, 2.31, 1.48] as a yellow residue.

Preparation 37

4,4-Difluoropiperidine

To a solution of t-butyl 4,4-difluoro-1-piperidinecarboxylate from Preparation No. 36 (510 mg) in $CH_2Cl_2$ (2 mL) is added trifluoroacetic acid (0.71 mL). The reaction is stirred at room temperature for 2.5 hours, and is then partitioned between saturated $NaHCO_3$ and $CH_2Cl_2$. The aqueous layer is extracted with $CH_2Cl_2$ (3×). The combined organic layers are dried (Na$_2$SO$_4$), filtered, and concentrated until product began to evaporate (vigorous bubbling seen). At least 50 mg (18%) of 4,4-difluoropiperidine was obtained as a clear liquid.

Physical characteristics are as follows:

$^1$H NMR (300 MHz, CDCl$_3$) δ2.98, 1.94, 1.84.

Example 52

N-(4-chlorobenzyl)-6-((4,4-difluoro-1-piperidinyl)methyl)-1-methyl-4-oxo-1,4-dihydro-3-quinolinecarboxamide

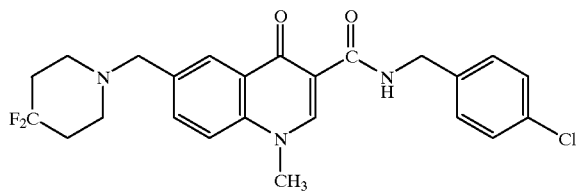

To a solution of N-(4-chlorobenzyl)-6-(chloromethyl)-1-methyl-4-oxo-1,4-dihydro-3-quinolinecarboxamide from Preparation No. 35 (50 mg) in 1-methyl-2-pyrrolidinone (3 mL) is added N,N-diisopropylethylamine (0.03 mL) and 4,4-difluoropiperidine from Preparation No. 37 (50 mg). The reaction mixture is stirred at room temperature overnight and then heated at 50° C. for 4 hrs. The mixture is cooled to room temperature and poured into water to precipitate the product. The crude solid is recrystallized from CH$_2$Cl$_2$/hexanes to afford 51.5 mg (84%) of the title compound as a white solid.

Physical characteristics are as follows:

Mp 214–215° C.; $^1$H NMR (300 MHz, DMSO-d$_6$) δ10.43, 8.88, 8.25, 7.81, 7.38, 4.56, 4.02, 3.72, 2.51, 1.96; IR (drift) 2823, 1655, 1606, 1574, 1551, 1502, 1490, 1362, 1132, 1085, 1017, 949, 830, 808, 802 cm$^{-1}$; HRMS (FAB) calcd for C$_{24}$H$_{24}$ClF$_2$N$_3$O$_2$+H 460.1603, found 460.1598; Anal. found for C$_{2424}$ClF$_2$N$_3$O$_2$: C, 62.12; H, 5.26; N, 8.99.

Preparation 38

4-Fluoro-1,2,3,6-tetrahydropyridine hydrochloride

Dry HCl is passed over the surface of a cold (0° C.) solution of t-butyl 4-fluoro-3,6-dihydro-1[2H]-pyridinecarboxylate from Preparation No 36 (196 mg) in MeOH (3 mL) for 1 min. The reaction mixture is stoppered and stirred at 0° C. for 15 min., then at room temperature for 15 min. The mixture is concentrated to afford 119 mg (100%) of 4-fluoro-1,2,3,6-tetrahydropyridine hydrochloride as an orange-brown residue.

Example 53

N-(4-Chlorobenzyl)-6-((4-fluoro-3,6-dihydro-1(2H)-pyridinyl)methyl)-1-methyl-4-oxo-1,4-dihydro-3-quinolinecarboxamide

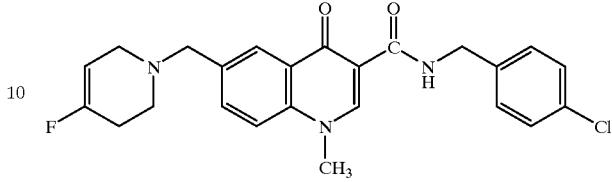

To a solution of N-(4-chlorobenzyl)-6-(chloromethyl)-1-methyl-4-oxo-1,4-dihydro-3-quinolinecarboxamide from Preparation No. 35 (60 mg) in 1-methyl-2-pyrrolidinone (3 mL) is added N,N-diisopropylethylamine (0.075 mL) and 4-fluoro-1,2,3,6-tetrahydropyridine hydrochloride from Preparation No. 38 (119 mg). The reaction mixture is stirred at room temperature overnight and then heated at 60° C. for 4 hrs. The mixture is cooled to room temperature and poured into water to precipitate the product. The crude solid is adsorbed onto silica and purified by chromatography (eluent 100% CH$_2$Cl$_2$ (1 L), 0.25% MeOH in CH$_2$Cl$_2$ (1 L), 0.5% MeOH in CH$_2$Cl$_2$ (1 L), 0.75% MeOH in CH$_2$Cl$_2$ (1 L), 1% MeOH in CH$_2$Cl$_2$ (1 L), 1.25% MeOH in CH$_2$Cl$_2$ (1 L), 1.5% MeOH in CH$_2$Cl$_2$ (2 L)). Fractions homogenous by TLC are combined and concentrated to afford 32.2 mg (46%) of the desired product as a white solid.

Physical characteristics are as follows:

Mp 221–223° C.; $^1$H NMR (300 MHz, DMSO-d$_6$) δ10.43, 8.88, 8.25, 7.82, 7.38, 5.24, 4.57, 4.03, 3.75, 2.94, 2.66, 2.26; IR (drift) 1656, 1607, 1574, 1553, 1501, 1364, 1131, 1119, 1109, 832,819,808,781,730,661 cm$^{-1}$; Anal. found for C$_{24}$H$_{23}$ClFN$_3$O$_2$: C, 65.29; H, 5.27; N, 9.44.

Preparation 39

N-(4-Chlorobenzyl)-6-iodo-1-methyl-4-oxo-1,4-dihydro-3-quinolinecarboxamide

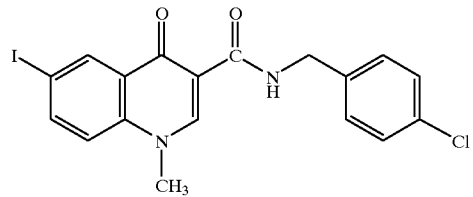

N-(4-Chlorobenzyl)-4-hydroxy-6-iodo-3-quinolinecarboxamide (12.07 g) from Preparation No. 4 and potassium carbonate (5.70 g) are disolved in DMF (90 mL). Iodomethane (2.1 mL) is added and the mixture is stirred at room temperature for 1 h. The resulting suspension is poured into water (500 mL) and filtered. The crude solid is washed with water (50 mL) and diethyl ether (100 mL) and then is recrystallized from ethanol to afford 10.6 g (85%) of the title compound as a white solid.

Physical characteristics are as follows:

Mp 205–208° C.; $^1$H NMR (DMSO-d$_6$) δ10.25, 8.89, 8.59, 8.14, 7.66, 7.42–7.33, 4.55, 4.00; $^{13}$C NMR (CF$_3$CO$_2$D) δ173.3, 167.6, 147.9, 147.3, 140.1, 135.5, 135.4, 133.9, 129.6, 123.3, 119.1, 106.7, 95.3, 44.5, 44.2; IR

Example 54

N-(4-Chlorobenzyl)-1-methyl-4-oxo-6-vinyl-1,4-dihydro-3-quinolinecarboxamide [32112-mes-57B]

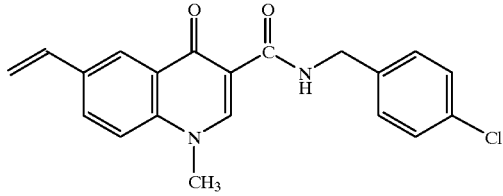

Tributylvinylstannane (0.32 mL) is added to a solution of N-(4-chlorobenzyl)-6-iodo-1-methyl-4-oxo-1,4-dihydro-3-quinolinecarboxamide (0.45 g) from Preparation No. 39 and PdCl$_2$(PPh$_3$)$_2$ (70 mg). The mixture is stirred at room temperature for 1 h and then is heated to 60° C. for 30 min. After cooling to room temperature, the reaction mixture is poured into water (60 mL), filtered, and washed with water (20 mL) and diethyl ether (20 mL). The crude product is purified by recrystallization from acetonitrile to afford 0.20 g (57%) of the title compound as a white solid.

Physical characteristics are as follows:

Mp 193–196° C.; $^1$H NMR (DMSO-d$_6$) δ10.40, 8.86, 8.31, 8.04, 7.82, 7.42–7.35, 6.93, 5.99, 5.39, 4.56, 4.03; $^{13}$C NMR (CF$_3$CO$_2$D) δ173.9, 167.7, 146.7, 141.1, 140.0, 135.9, 135.4, 133.4, 129.6, 129.5, 123.1, 122.4, 119.8, 118.2, 106.2, 44.4, 44.2; IR (drift) 1654, 1618, 1602, 1550, 1541, 1498, 1362, 1318, 1238, 1225, 911, 822, 806, 798, 717 cm$^{-1}$; MS (EI) m/z 352 (M$^+$, 26). Anal. Found for C$_{20}$H$_{17}$ClN$_2$O$_2$: Found: C, 68.08; H, 4.92; N, 7.91; Cl, 10.01.

Preparation 40

N-(4-Chlorobenzyl-4-hydroxy-6-(4-morpholinylmethyl)-3-quinolinecarboxamide

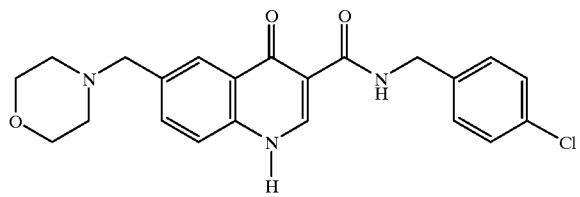

A solution of N-(4-chlorobenzyl)-4-hydroxy-6-(hydroxymethyl)-3-quinolinecarboxamide (1.71 gm) from Preparation No. 9 in DMF (50 mL) at 0° C. under a drying tube is treated with 4-dimethylaminopyridine (0.12 gm), 2,4,6-collidine (1.05 mL) and methanesulfonylchloride (0.60 mL). The mixture is allowed to slowly warm to room temperature overnight. The reaction mixture is then treated with morpholine (8.0 mL) and stirred for 4 hrs. The reaction mixture is poured into water (250 mL) and extracted with dichloromethane (5×50 mL). The combined organic layers are washed with water, brine, dried (Na$_2$SO$_4$) and concentrated under reduced pressure. The crude product is purified by recrystallization from methanol-acetonitrile (1/1, 150 mL) to afford 1.7 gm of the title compound as a white solid.

Physical characteristics are as follows:

$^1$H NMR (DMSO-d$_6$) δ12.7, 10.4, 8.7, 8.1, 7.8–7.6, 7.4–7.3, 4.5, 3.6, 2.3; MS (ESI+) m/z 412, MS (ESI−) m/z 410.

Example 55

N-(4-Chlorobenzyl)-1-[2-(2-hydroxyethoxy)ethyl]-6-(3-hydroxy-1-propynyl)-4-oxo-1,4-dihydro-3-quinolinecarboxamide

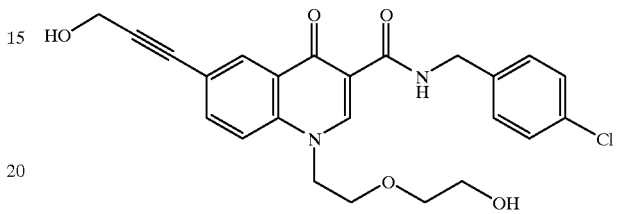

A solution of N-(4-chlorobenzyl)-4-hydroxy-6-(3-hydroxy-1-propynyl)-3-quinolinecarboxamide (0.37 gm) from Preparation No. 5 in DMF (10 mL) is treated with potassium carbonate (2.75 gm), potassium iodide (1.66 gm) and 2-(2-chloroethoxy)ethanol (1.0 mL). The mixture is tightly capped and heated to 100° C. for 48 hrs. The reaction mixture is allowed to cool to room temperature, poured into water and extracted with dichloromethane. The layers are separated and the aqueous layer is re-extracted with dichloromethane containing a small amount of methanol and finally again with dichloromethane. The combined organic layers are washed with brine, dried (Na$_2$SO$_4$) and concentrated under reduced pressure. The crude product is purified by flash column chromatography eluting with 3% to 15% methanol in dichloromethane and then by recrystallization from methanol to afford 82 mg of the title compound as a light yellow solid.

Physical characteristics are as follows:

$^1$H NMR (DMSO-d$_6$) δ10.2, 8.8, 8.3, 7.9, 7.8, 7.4–7.3, 5.4, 4.6, 4.5, 3.8, 3.4; MS (ESI+) m/z 455.

Example 56

N-(4-Chlorobenzyl)-1-{2-[2-(2-methoxyethoxy)ethoxy]ethyl}-6-(4-morpholinylmethyl)-4-oxo-1,4-dihydro-3-quinolinecarboxamide

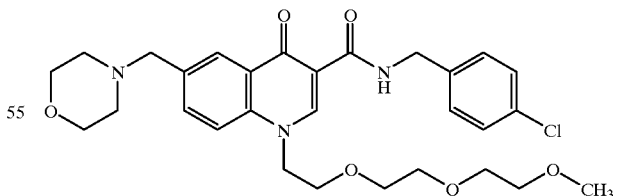

A dry flask containing N-(4-chlorobenzyl-4-hydroxy-6-(4-morpholinylmethyl)-3-quinolinecarboxamide (0.20 gm) from Preparation No. 40 in dry THF (5 mL) under an argon atmosphere is added triphenylphosphine (165 mg), triethyleneglycol monomethyl ether (0.10 mL) and diethyl azodicarboxylate (0.10 mL). The mixture is stirred at room temperature for 2 hrs. The reaction mixture is concentrated under reduced pressure. The crude product is purified by flash column chromatography eluting with 2% to 8% methanol in dichloromethane and then by recrystallization from ethyl acetate-heptane to afford 164 mg of the title compound as a white solid.

Physical characteristics are as follows:

$^1$H NMR (CDCl$_3$) δ10.5, 8.8, 8.4, 7.8, 7.5, 7.3–7.2, 4.6, 4.4, 3.9, 3.7–3.3, 2.4; MS (ESI+) m/z 558. Anal. found for C$_{29}$H$_{36}$ClN$_3$O$_6$: C, 62.17; H, 6.64; N, 7.63.

Example 57

N-(4-Chlorobenzyl)-1-[2-(2-hydroxyethoxy)ethyl]-6-(4-morpholinylmethyl)-4-oxo-1,4-dihydro-3-quinolinecarboxamide

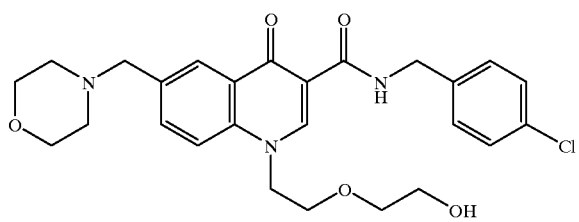

A dry flask containing N-(4-chlorobenzyl)-4-hydroxy-6-(4-morpholinylmethyl)-3-quinolinecarboxamide (0.20 gm) from Preparation No. 40 in dry THF (5 mL) under an argon atmosphere is added triphenylphosphine (165 mg), diethyleneglycol (0.20 mL) and diethyl azodicarboxylate (0.10 mL). The mixture is stirred at room temperature for 2 hrs. The reaction mixture is concentrated under reduced pressure. The crude product is purified by flash column chromatography eluting with 10% to 40% methanol in ethyl acetate and then by recrystallization from ethyl acetate to afford 68 mg of the title compound as a white solid.

Physical characteristics are as follows:

$^1$H NMR (CDCl$_3$) δ10.5, 8.9, 8.4, 7.8, 7.5, 7.3–7.2, 4.6, 4.4, 3.9, 3.7–3.5, 2.4; MS ESI+) m/z 500; Anal. found for C$_{26}$H$_{30}$ClN$_3$O$_5$: C, 62.23; H, 6.12; N, 8.29.

Example 58

N-(4-Chlorobenzyl)-1-[2-(2-ethoxyethoxy)ethyl]-6-(4-morpholinylmethyl)-4-oxo-1,4-dihydro-3-quinolinecarboxamide

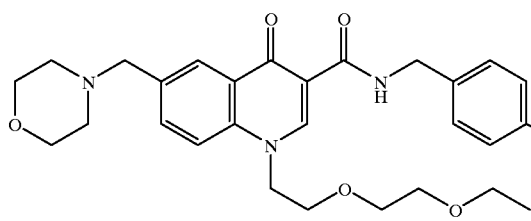

A dry flask containing N-(4-chlorobenzyl)-4-hydroxy-6-(4-morpholinylmethyl)-3-quinolinecarboxamide (0.20 gm) from Preparation No. 40 in dry THF (5 mL) under an argon atmosphere is added triphenylphosphine (164 mg), 2-ethoxy-(2-ethoxy)ethanol (0.09 mL) and diethyl azodicarboxylate (0.10 mL). The mixture is stirred at room temperature overnight. The reaction mixture is again treated with triphenylphosphine (164 mg), 2-ethoxy-(2-ethoxy)ethanol (0.09 mL) and diethyl azodicarboxylate (0.10 mL). After 4 hours, the reaction mixture is concentrated under reduced pressure. The crude product is purified by flash column chromatography eluting with acetone and then by recrystallization from ethyl acetate-heptane to afford 0.18 gm of the title compound as a white solid.

Physical characteristics are as follows:

$^1$H NMR (CDCl$_3$) δ10.5, 8.8, 8.4, 7.8, 7.5, 7.3–7.2, 4.6, 4.4, 3.9, 3.7–3.4, 2.5, 1.1; MS (ESI+) m/z 528. Anal. found for C$_{28}$H$_{34}$ClN$_3$O$_5$: C, 63.67; H, 6.55; N, 7.90.

Example 59

N-(4-Chlorobenzyl)-6-(4-morpholinylmethyl)-4-oxo-1-(2-propynyl)-1,4-dihydro-3-quinolinecarboxamide

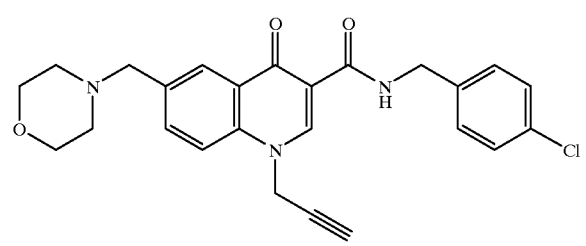

A dry flask containing N-(4-chlorobenzyl-4-hydroxy-6-(4-morpholinylmethyl)-3-quinolinecarboxamide (0.20 gm) from Preparation No. 40 in dry THF (5 mL) under an argon atmosphere is added triphenylphosphine (393 mg), propargyl alcohol (0.09 mL) and diethyl azodicarboxylate (0.18 mL). The mixture is stirred at room temperature overnight. The reaction mixture is concentrated under reduced pressure and adsorbed onto silica gel. The crude product is purified by flash column chromatography eluting with 2% to 6% methanol in dichloromethane and then by recrystallization from acetonitrile to afford 0.20 gm of the title compound as a white solid.

Physical characteristics are as follows:

Mp 221–224° C. (dec); $^1$H NMR (CDCl$_3$) δ10.4, 8.9, 8.4, 7.8, 7.6, 7.3, 5.0, 4.6, 3.7, 3.6, 2.4; MS (ESI+) m/z 450. Anal. found for C$_{25}$H$_{24}$ClN$_3$O$_3$: C, 66.57; H, 5.41; N, 9.28.

Example 60

N-(4-Chlorobenzyl)-1-[2-(ethylsulfanyl)ethyl]-6-(4-morpholinylmethyl)-4-oxo-1,4-dihydro-3-quinolinecarboxamide

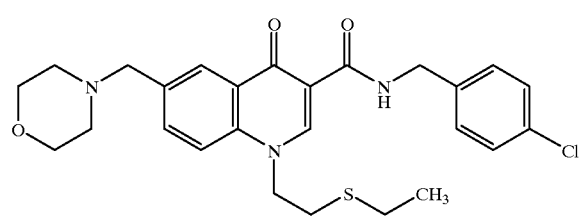

A dry flask containing N-(4-chlorobenzyl-4-hydroxy-6-(4-morpholinylmethyl)-3-quinolinecarboxamide (0.20 gm) from Preparation No. 40 in dry THF (5 mL) under an argon atmosphere is added triphenylphosphine (393 mg), ethyl 2-hydroxyethylsulfide (0.16 mL) and diethyl azodicarboxylate (0.18 mL). The mixture is stirred at room temperature overnight then concentrated under reduced pressure. The crude product is purified by flash column chromatography eluting with 2% to 6% methanol in dichloromethane and then by recrystallization from ethanolcyclohexane to afford 0.21 gm of the title compound as a white solid.

Physical characteristics are as follows:

Mp 140–142° C.; $^1$H NMR (CDCl$_3$) δ10.4, 8.8, 8.4, 7.8, 7.5, 7.3, 4.6, 4.4, 3.7, 3.6, 3.0, 2.6, 2.4, 1.3; MS (ESI+) m/z 500. Anal. found for C$_{26}$H$_{30}$ClN$_3$O$_3$S: C, 62.36; H, 6.16; N, 8.37.

Example 61

N-(4-Chlorobenzyl)-1-[3-(methylsulfanyl)propyl]-6-(4-morpholinylmethyl)-4-oxo-1,4-dihydro-3-quinolinecarboxamide

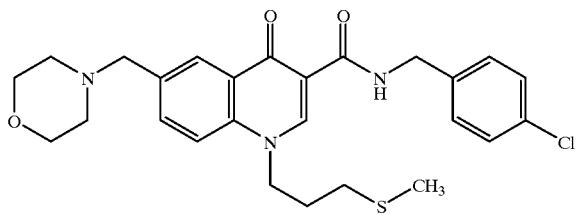

A dry flask containing N-(4-chlorobenzyl)-4-hydroxy-6-(4-morpholinylmethyl)-3-quinolinecarboxamide (0.20 gm) from Preparation No. 40 in dry THF (5 mL) under an argon atmosphere is added triphenylphosphine (396 mg), 3-methylthiolpropanol (0.16 mL) and diethyl azodicarboxylate (0.18 mL). The mixture is stirred at room temperature 48 hours and then concentrated under reduced pressure. The crude product is purified by flash column chromatography eluting with 2% to 6% methanol in dichloromethane and then by recrystallization from toluene-cyclohexane to afford 0.14 gm of the title compound as a white solid.

Physical characteristics are as follows:

Mp 102–104° C.; $^1$H NMR (CDCl$_3$) δ10.5, 8.8, 8.4, 7.8, 7.6, 7.3–7.2, 4.6, 4.4, 3.7, 3.6, 3.0, 2.6, 2.5, 2.2; MS (ESI+) m/z 500; HRMS (FAB) found 500.1779 for C$_{26}$H$_{30}$ClN$_3$O$_3$S+H.

Example 62

N-(4-Chlorobenzyl)-1-(4-hydroxy-2-butynyl)-6-(4-morpholinylmethyl)-4-oxo-1,4-dihydro-3-quinolinecarboxamide

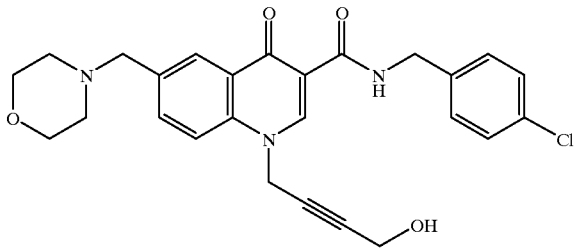

A dry flask containing N-(4-chlorobenzyl)-4-hydroxy-6-(4-morpholinylmethyl)-3-quinolinecarboxamide (0.20 gm) from Preparation No. 40 in dry THF (5 mL) under an argon atmosphere is added triphenylphosphine (393 mg), 1,4-butyne diol (0.45 gm) and diethyl azodicarboxylate (0.18 mL). The mixture is stirred at room temperature overnight, concentrated under reduced pressure and adsorbed onto silica gel. The crude product is purified by flash column chromatography eluting with 2% to 6% methanol in dichloromethane and then by recrystallization from methanol-acetonitrile to afford 0.16 gm of the title compound as a white solid.

Physical characteristics are as follows:

Mp 215–217° C. (dec); $^1$H NMR (CDCl$_3$) δ10.4, 8.9, 8.4, 7.8, 7.6, 7.3, 5.0, 4.6, 4.3, 3.7, 3.6, 2.5; MS (ESI+) m/z 480; Anal. found for C$_{26}$H$_{26}$ClN$_3$O$_4$: C, 64.68; H, 5.52; N, 8.62.

Example 63

N-(4-Chlorobenzyl)-6-{[(2-hydroxy-2-phenylethyl)(methyl)-amino]methyl}-1-methyl-4-oxo-1,4-dihydro-3quinolinecarboxamide

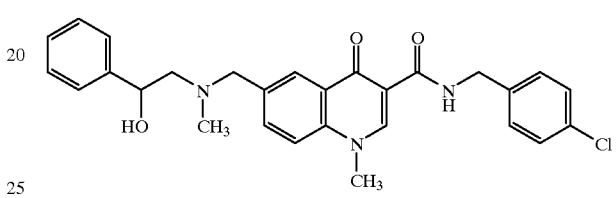

A solution of N-(4-chlorobenzyl)-6-(chloromethyl)-1-methyl-4-oxo-1,4-dihydro-3-quinolinecarboxamide (0.06 gm) from Preparation No. 35 in dry NMP (2 mL) containing diisopropylethylarnine (0.04 mL) is treated with α-(methylaminomethyl)-benzyl alcohol (0.04 gm). The reaction mixture is shaken at room temperature for 3 days then concentrated under reduced pressure. The residue is partioned between dichloromethane and water. The separated organic layer is washed with two additional portions of water, brine, dried (Na$_2$SO$_4$) and concentrated under reduced pressure. The residue is adsorbed onto silica and purified by flash column chromatography eluting with 2% to 6% methanol in dichloromethane and then by recrystallization from ethyl acetate-hexanes to afford 0.05 gm of the title compound as a white solid.

Physical characteristics are as follows:

$^1$H NMR (CDCl$_3$) δ10.4, 8.8, 8.4, 7.8, 7.5, 7.3, 5.0, 4.8, 4.6, 4.0, 3.9–3.6, 2.6, 2.3; MS (ESI+) m/z 490; HRMS (FAB) found for C$_{28}$H$_{28}$ClN$_3$O$_3$+H: 490.1895.

Example 64

1-{2-[Bis(2-hydroxyethyl)amino]ethyl}-N-(4-chlorobenzyl)-6-(4-morpholinylmethyl-4-oxo-1,4-dihydro-3-quinolinecarboxamide

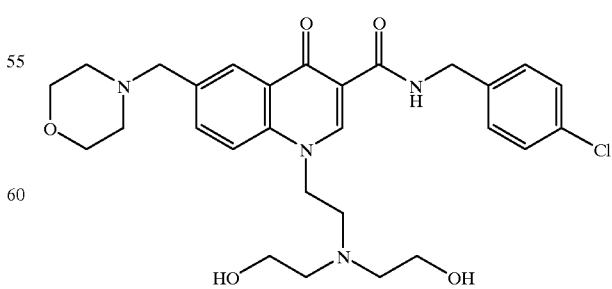

A dry flask containing N-(4-chlorobenzyl-4-hydroxy-6-(4-morpholinylmethyl)-3-quinolinecarboxamide (0.20 gm)

from Preparation No.40 in dry THF (5 mL) under an argon atmosphere is added triphenylphosphine (363 mg), triethanolamine (1.3 mL) and diethyl azodicarboxylate (0.18 mL). The mixture is stirred at room temperature for 4 days. The reaction mixture is concentrated under reduced pressure and the crude product is purified by flash column chromatography eluting with 3% to 9% methanol in dichloromethane. The product fractions are concentrated under reduced pressure, dissolved in a small volume of ethyl acetate-diethyl ether and added dropwise to a large volume of hexanes. The resulting precipitant is collected by filtration, washed with diethyl ether followed by hexanes to afford 0.04 gm of the title compound as a white solid.

Physical characteristics are as follows:

$^1$H NMR (CDCl$_3$) δ10.5, 9.0, 8.4, 7.8, 7.5, 7.3, 4.6, 4.3, 3.7–3.4, 3.0, 2.7, 2.4; MS (ESI+) m/z 543; HRMS (FAB) found 543.2369 for $C_{28}H_{35}ClN_4O_5$+H.

Example 65

N-(4-Chlorobenzyl)-1-[3-(methylsulfinyl)propyl]-6-(4-morpholinylmethyl)-4-oxo-1,4-dihydro-3-quinolinecarboxamide

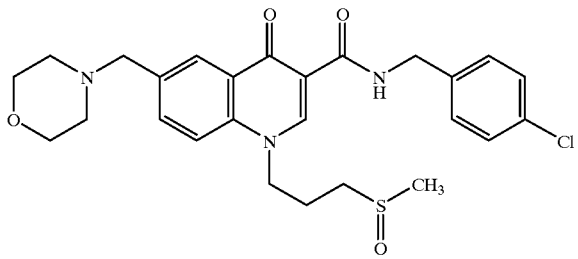

A solution of N-(4-chlorobenzyl)-1-[3-(methylsulfanyl) propyl]-6-(4-morpholinylmethyl)-4-oxo-1,4-dihydro-3-quinolinecarboxamide (0.10 gm) from Example No. 61 in dichloromethane (2 mL) at 0° C. is added p-toluenesulfonic acid hydrate (0.04 gm) followed by m-chloroperoxybenzoic acid (~85%)(0.045 gm). The mixture is stirred for 0.5 hrs. The reaction mixture is diluted with dichloromethane, washed with saturated aqueous sodium sulfite, saturated aqueous sodium bicarbonate, brine, dried (Na$_2$SO$_4$) and concentrated under reduced pressure. The crude product is purified by flash column chromatography eluting with 3% to 9% methanol in dichloromethane. The product fractions are combined and recrystallized from ethyl acetate-methanol-hexanes to afford 0.07 gm of the title compound as a white solid.

Physical characteristics are as follows:

$^1$H NMR (DMSO-d$_6$) δ10.4, 8.9, 8.2, 7.9, 7.8, 7.4, 4.6, 3.6, 2.9–2.7, 2.5, 2.4, 2.0; MS (ESI+) m/z 516; HRMS (FAB) found 516.1729 for $C_{26}H_{30}ClN_3O_4S$+H.

Example 66

N-(4-Chlorobenzyl)-1-{3-[(3-hydroxypropyl) sulfanyl]propyl}-6-(4-morpholinylmethyl)-4-oxo-1,4-dihydro-3-quinolinecarboxamide

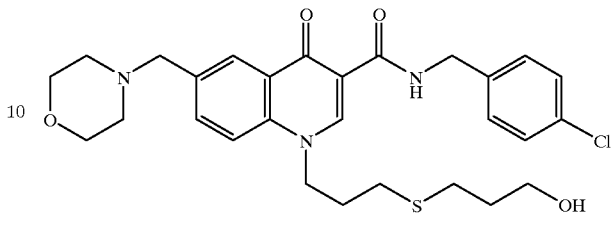

A dry flask containing N-(4-chlorobenzyl-4-hydroxy-6-(4-morpholinylmethyl)-3-quinolinecarboxamide (0.20 gm) from Preparation No. 40 in dry THF (5 mL) under an argon atmosphere is added triphenylphosphine (314 mg), 3,3'-thiodipropanol (0.7 mL) and diethyl azodicarboxylate (0.18 mL). The mixture is stirred at room temperature overnight. The reaction mixture is concentrated under reduced pressure and the crude product is purified by flash column chromatography eluting with 5% to 15% methanol in dichloromethane. The product fractions are concentrated under reduced pressure and recrystallized from ethyl acetate-hexanes to afford 0.20 gm of the title compound as a white solid.

Physical characteristics are as follows:

$^1$H NMR (DMSO-d$_6$) δ10.4, 8.9, 8.2, 7.9, 7.8, 7.3, 4.5, 4.3, 3.6, 3.4, 2.5–2.3, 2.0, 1.6; MS (ESI+) m/z 544; Anal. found for $C_{28}H_{34}ClN_3O_4S$: C, 61.69; H, 6.30; N, 7.67.

Example 67

N-(4-Chlorobenzyl)-1-[3-(methylsulfonyl)propyl]-6-(4-morpholinylmethyl)-4-oxo-1,4dihydro-3-quinolinecarboxamide

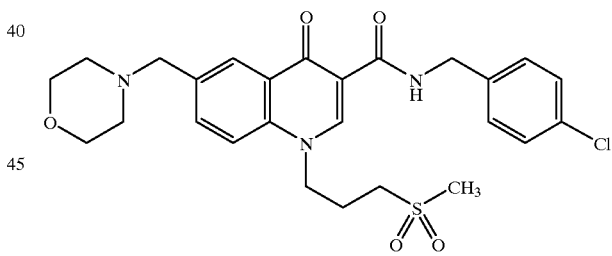

A solution of N-(4-chlorobenzyl)-1-[3-(methylsulfanyl) propyl]-6-(4-morpholinylmethyl)-4-oxo-1,4-dihydro-3-quinolinecarboxamide (0.10 gm) from Example No. 61 in dichloromethane (2 mL) at 0° C. is added p-toluenesulfonic acid hydrate (0.04 gm) followed by m-chloroperoxybenzoic acid (~85%) (0.09 gm). The mixture is stirred for 0.5 hrs. The reaction mixture is diluted with dichloromethane, washed with saturated aqueous sodium sulfite, saturated aqueous sodium bicarbonate, brine, dried (Na$_2$SO$_4$) and concentrated under reduced pressure. The crude product is purified by flash column chromatography eluting with 3% to 6% methanol in dichloromethane to afford 0.07 gm of the title compound as a white solid.

Physical characteristics are as follows:

$^1$H NMR (CDCl$_3$) δ10.4, 8.8, 8.4, 7.8, 7.6, 7.3, 4.6, 4.5, 3.7, 3.6, 3.1, 2.5; MS (ESI+) m/z 532; Anal. found for $C_{26}H_{30}ClN_3O_5S$: C, 58.29; H, 5.72; N, 7.77.

Example 68

N-(4-Chlorobenzyl)-1-[2-(ethylsulfinyl)ethyl]-6-(4-morpholinylmethyl)-4-oxo-1,4-dihydro-3-quinolinecarboxamide

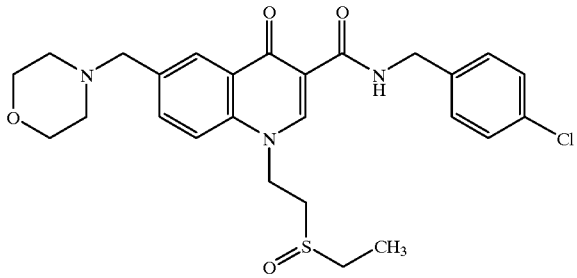

A solution of N-(4-chlorobenzyl)-1-[2-(ethylsulfanyl)ethyl]-6-(4-morpholinylmethyl)-4-oxo-1,4-dihydro-3-quinolinecarboxamide (0.10 gm) from Example No. 60 in dichloromethane (2 mL) at 0° C. is added p-toluenesulfonic acid hydrate (0.04 gm) followed by m-chloroperoxybenzoic acid (~85%) (0.045 gm). The mixture is stirred for 0.5 hrs. The reaction mixture is diluted with dichloromethane, washed with saturated aqueous sodium sulfite, saturated aqueous sodium bicarbonate, brine, dried ($Na_2SO_4$) and concentrated under reduced pressure. The crude product is purified by flash column chromatography eluting with 3% to 9% methanol in dichloromethane and then by recrystallization from acetonitrile to afford 0.05 gm of the title compound as a white solid.

Physical characteristics are as follows:

$^1$H NMR (DMSO-$d_6$) δ10.4, 8.9, 8.3, 7.9, 7.8, 7.4–7.3, 4.9, 4.6, 3.6, 3.3, 3.1, 2.8–2.7, 2.4, 1.2; MS (ESI+) m/z 516; HRMS (FAB) found 516.1729 for $C_{26}H_{30}ClN_3O_4S$+H; Anal. found for $C_{26}H_{30}ClN_3O_4S$: C, 60.55; H, 5.95; N, 8.04.

Example 69

N-(4-Chlorobenzyl)-1-[2-(ethylsulfonyl)ethyl]-6-(4-morpholinylmethyl)-4-oxo-1,4-dihydro-3-quinolinecarboxamide

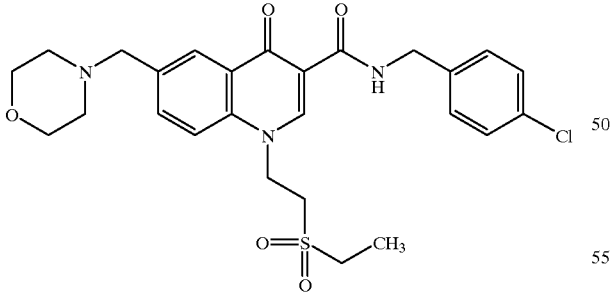

A solution of N-(4-chlorobenzyl)-1-[2-(ethylsulfanyl)ethyl]-6-(4-morpholinylmethyl)-4-oxo-1,4-dihydro-3-quinolinecarboxamide (0.10 gm) from Example No. 60 in dichloromethane (2 mL) at 0° C. is added p-toluenesulfonic acid hydrate (0.04 gm) followed by m-chloroperoxybenzoic acid (~85%) (0.085 gm). The mixture is stirred for 0.5 hrs. The reaction mixture is diluted with dichloromethane, washed with saturated aqueous sodium sulfite, saturated aqueous sodium bicarbonate, brine, dried ($Na_2SO_4$) and concentrated under reduced pressure. The crude product is purified by recrystallization from acetonitrile to afford 0.08 gm of the title compound as a white solid.

Physical characteristics are as follows:

$^1$H NMR (DMSO-$d_6$) δ10.4, 8.9, 8.3, 7.8, 7.4–7.3, 4.9, 4.6, 3.7, 3.6, 3.2, 2.4, 1.2; MS (ESI+) m/z 532; HRMS (FAB) found 532.1677 for $C_{26}H_{30}ClN_3O_5S$+H.

Example 70

N-(4-Chlorobenzyl)-1-(3-[(3-hydroxypropyl)sulfinyl]propyl)-6-(4-morpholinylmethyl-4-oxo-1,4-dihydro-3-quinolinecarboxamide

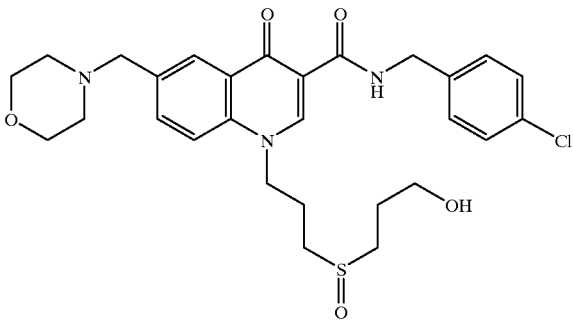

A solution of N-(4-chlorobenzyl)-1-(3-[(3-hydroxypropyl)sulfanyl]propyl)-6-(4-morpholinylmethyl-4-oxo-1,4-dihydro-3-quinolinecarboxamide (0.27 gm) from Example No. 66 in dichloromethane (5 mL) at 0° C. is added p-toluenesulfonic acid hydrate (0.10 gm) followed by m-chloroperoxybenzoic acid (~85%) (0.10 gm). The mixture is stirred for 0.5 hrs. The reaction mixture is diluted with dichloromethane, washed with saturated aqueous sodium sulfite, saturated aqueous sodium bicarbonate, brine, dried ($Na_2SO_4$) and concentrated under reduced pressure. The crude product is purified by flash column chromatography eluting with 3% to 25% methanol in dichloromethane to afford 0.17 gm of the title compound as a white solid.

Physical characteristics are as follows:

$^1$H NMR (CDCl$_3$) δ10.5, 8.8, 8.4, 7.8, 7.6, 7.3, 4.6, 4.5, 3.8–3.5, 3.0–2.7, 2.5, 2.0; MS (ESI+) mnz 560; HRMS (FAB) found 560.1988 for $C_{28}H_{34}ClN_3O_5S$+H.

Example 71

N-(4-Chlorobenzyl)-1-(3-[(3-hydroxypropyl)sulfonyl]propyl)-6-(4-morpholinylmethyl)-4-oxo-1,4-dihydro-3-quinolinecarboxamide

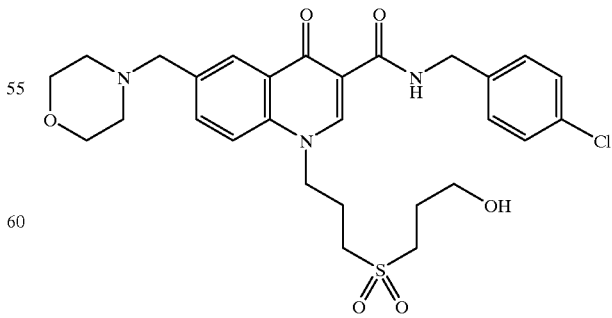

A solution of N-(4-chlorobenzyl)-1-(3-[(3-hydroxypropyl)sulfanyl]propyl)-6-(4-morpholinylmethyl)-

4-oxo-1,4-dihydro-3-quinolinecarboxamide (0.27 gm) from Example No. 66 in dichloromethane (5 mL) at 0° C. is added p-toluenesulfonic acid hydrate (0.10 gm) followed by m-chloroperoxybenzoic acid (~85%) (0.20 gm). The mixture is stirred for 0.5 hrs. The reaction mixture is diluted with dichloromethane, washed with saturated aqueous sodium sulfite, saturated aqueous sodium bicarbonate, brine, dried (Na$_2$SO$_4$) and concentrated under reduced pressure. The crude product is purified by flash column chromatography eluting with 3% to 9% methanol in dichloromethane and then by recrystallization from acetonitrile to afford 0.08 gm of the title compound as a white solid.

Physical characteristics are as follows:

$^1$H NMR (CDCl$_3$) δ10.5, 8.8, 8.4, 7.8, 7.6, 7.3, 4.9, 4.6, 4.5, 3.8–3.6, 3.2–3.1, 2.5, 2.1; MS (ESI+) m/z 576; Anal. found for C$_{28}$H$_{34}$ClN$_3$O$_6$S: C, 58.12; H, 6.06; N, 7.33.

Example 72

N-(4-Chlorobenzyl)-6-(4-morpholinylmethyl)-4-oxo-1-[2-phenylsulfanyl)ethyl]-1,4-dihydro-3-quinolinecarboxamide

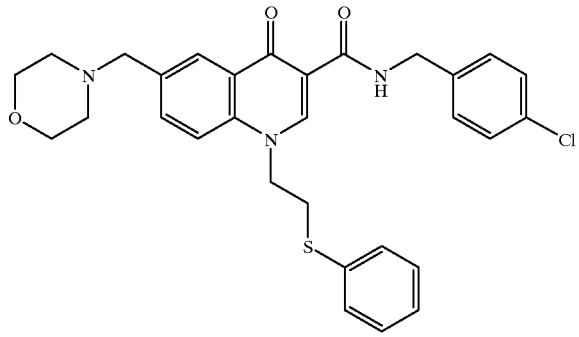

A dry flask containing N-(4-chlorobenzyl)-4-hydroxy-6-(4-morpholinylmethyl)-3-quinolinecarboxamide (0.20 gm) from Preparation No. 40 in dry THF (5 mL) under an argon atmosphere is added triphenylphosphine (284 mg), 2-hydroxyethyl phenyl sulfide (0.27 mL) and diethyl azodicarboxylate (0.17 mL). The mixture is stirred at room temperature overnight. The reaction mixture is concentrated under reduced pressure and the crude product is purified by flash column chromatography eluting with 5% to 15% methanol in dichloromethane. The product fractions are concentrated under reduced pressure and recrystallized from acetonitrile to afford 0.21 gm of the title compound as a white solid.

Physical characteristics are as follows:

Mp 166–167° C.; $^1$H NMR (DMSO-d$_6$), 10.4, 8.9, 8.2, 7.9, 7.8, 7.3, 4.5, 4.3, 3.6, 3.4, 2.5–2.3, 2.0, 1.6; MS (ESI+) m/z 544; Anal. found for C$_{28}$H$_{34}$ClN$_3$O$_4$S: C, 61.69; H, 6.30; N, 7.67.

Example 73

N-(4-Chlorobenzyl)-1-[(methylsulfanyl)methyl]-6-(morpholinylmethyl-4-oxo-1,4-dihydro-3-quinolinecarboxamide

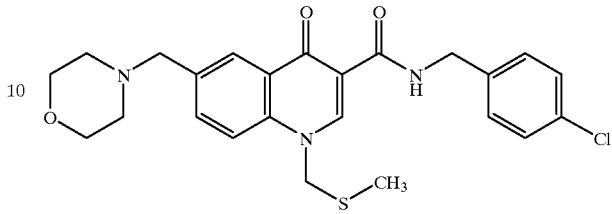

A solution of N-(4-chlorobenzyl)-4-hydroxy-6-(4-morpholinylmethyl)-3-quinolinecarboxamide (0.21 gm) from Preparation No. 40 in DMF (4 mL) is treated with cesium carbonate (0.33 gm) and chlormethyl methyl sulfide (0.05 mL). The mixture is tightly capped, stirred at room temperature for 3 hrs and then heated to 90° C. for 1 hr. The reaction mixture is allowed to cool to room temperature, diluted with dichloromethane (50 mL) and washed with water (2x), brine, dried (Na$_2$SO$_4$) and concentrated under reduced pressure. The crude product is purified by flash column chromatography eluting with 2% to 4% methanol in dichloromethane and then by recrystallization from acetonitrile to afford 0.1 gm of the title compound as a white solid.

Physical characteristics are as follows:

Mp 199–201° C.; $^1$H NMR (DMSO-d$_6$) δ10.3, 9.0, 8.2, 7.9, 7.8, 7.4–7.3, 5.7, 4.5, 3.6, 2.4, 2.1; MS (ESI+) m/z 472; Anal. found for C$_{24}$H$_{26}$ClN$_3$O$_3$S: C, 61.00; H, 5.62; N, 8.92.

Example 74

N-(4-Chlorobenzyl)-6-([(2-hydroxy-2-[4-hydroxyphenyl]-ethyl) [methyl]amino]methyl)-1-methyl-4-oxo-1,4-dihydro-3-quinolinecarboxamide

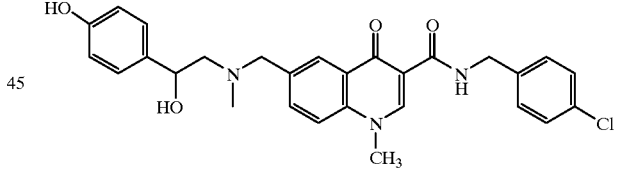

A solution of N-(4-chlorobenzyl)-6-(chloromethyl)-1-methyl-4-oxo-1,4-dihydro-3-quinolinecarboxamide (0.09 gm) from Preparation No. 35 in dry DMF (2 mL) containing diisopropylethylamine (0.07 mL) is treated with synephrine (0.05 gm). The reaction mixture is stirred overnight. The reaction mixture is diluted with dichloromethane (50 mL) and washed with water (2x10 mL), brine (10 mL), dried (Na$_2$SO$_4$) and concentrated under reduced pressure. The residue is purified by flash column chromatography eluting with 3% to 6% methanol in dichloromethane and then by recrystallization from toluene to afford 0.09 gm of the title compound as a tan solid.

Physical characteristics are as follows:

$^1$H NMR (CDCl$_3$) δ10.5, 8.8, 8.4, 7.8, 7.5, 7.3, 7.1, 6.7, 4.6, 3.9, 3.8, 3.6, 2.6–2.4, 2.3; MS (ESI+) m/z 506; HRMS (FAB) found 506.1848 for C$_{28}$H$_{28}$ClN$_3$O$_4$+H.

Example 75

N-(4-Chlorobenzyl)-6-[(3-hydroxy-1-azetidinyl)methyl]-1-methyl-4-oxo-1,4-dihydro-3-quinolinecarboxamide

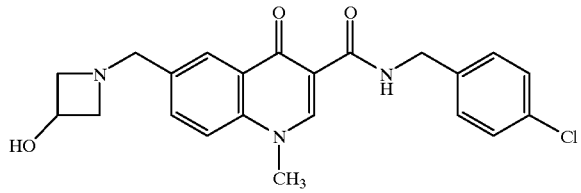

A solution of N-(4-chlorobenzyl)-6-(chloromethyl)-1-methyl-1,4-dihydro-3-quinolinecarboxamide (0.09 gm) from Preparation No. 35 in dry NMP (2 mL) containing diisopropylethylamine (0.14 mL) is treated with 3-azetidinol hydrochloride (0.04 gm) (prepared as described in Helv. Chim. Acta 1988, 1035). The reaction mixture is stirred overnight. The reaction mixture is diluted with dichloromethane (50 mL) and washed with water (2×10 mL), brine (10 mL), dried ($Na_2SO_4$) and concentrated under reduced pressure. The residue is purified by flash column chromatography eluting with 5% to 20% methanol in dichloromethane and then by recrystallization from methanol-acetonitrile to afford 0.08 gm of the title compound as an off-white solid.

Physical characteristics are as follows:
$^1$H NMR (DMSO-$d_6$) δ10.4, 8.8, 8.2, 7.8, 7.4, 5.3, 4.5, 4.2, 4.0, 3.7, 3.5, 2.8; MS (ESI+) m/z 412; HRMS (FAB) found 412.1412 for $C_{22}H_{22}ClN_3O_3$+H.

Example 76

N-(4-Chlorobenzyl)-6-(morpholinylmethyl)-4-oxo-1-[(phenylsulfanyl)methyl]-1,4-dihydro-3-quinolinecarboxamide

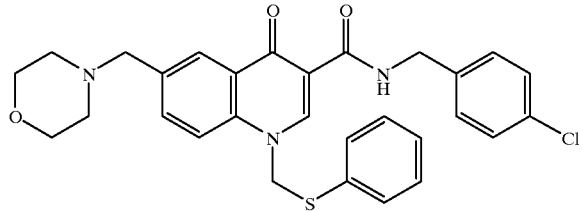

A solution of N-(4-chlorobenzyl)-4-hydroxy-6-(4-morpholinylmethyl)-3-quinolinecarboxamide (0.21 gm) from Preparation No. 40 in DMF (4 mL) is treated with cesium carbonate (0.30 gm) and chloromethyl phenyl sulfide (0.08 mL). The mixture is tightly capped and heated to 75° C. for 8 hrs. The reaction mixture is allowed to cool to room temperature, diluted with dichloromethane (50 mL) and washed with water (2×10 mL), brine, dried ($Na_2SO_4$) and concentrated under reduced pressure. The crude product is purified by flash column chromatography eluting with 2% to 4% methanol in dichloromethane and then by recrystallization from ethyl acetate-hexanes to afford 0.19 gm of the title compound as a white solid.

Physical characteristics are as follows:
$^1$H NMR (DMSO-$d_6$) δ10.2, 8.4, 8.2, 7.9, 7.8, 7.4–7.3, 6.0, 4.5, 3.6, 2.4; MS (ESI+) m/z 534; Anal. found for $C_{29}H_{28}ClN_3O_3S$: C, 64.88; H, 5.27; N, 7.75.

Example 77

N-(4-Chlorobenzyl)-6-([(2-hydroxy-2-[4-hydroxy-3-methoxyphenyl]ethyl)[methyl]amino]methyl)-1-methyl-4-oxo-1,4-dihydro-3-quinolinecarboxamide

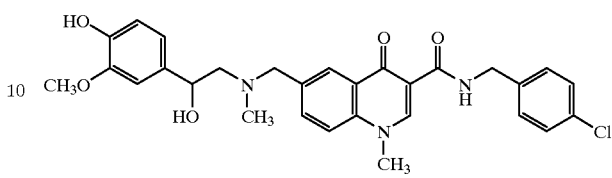

A solution of N-(4-chlorobenzyl)-6-(chloromethyl)-1-methyl-4-oxo-1,4-dihydro-3-quinolinecarboxamide (0.09 gm) from Preparation No. 35 in dry DMF (2 mL) containing diisopropylethylamine (0.18 mL) is treated with dl-metanephrine hydrochloride (0.12 gm). The reaction mixture is stirred at room temperature for 3 days. The reaction mixture is diluted with dichloromethane (50 mL) and washed with water (2×10 mL), brine (10 mL), dried ($Na_2SO_4$) and concentrated under reduced pressure. The residue is purified by flash column chromatography eluting with 2% to 5% methanol in dichloromethane and then by recrystallization from methanol-toluene to afford 0.08 gm of the title compound as an off-white solid.

Physical characteristics are as follows:
$^1$H NMR (DMSO-$d_6$) δ10.4, 8.9, 8.7, 8.2, 7.7, 7.4, 6.8, 6.7, 4.9, 4.6, 4.0, 3.7, 2.5, 2.2; MS (ESI+) m/z 536; HRMS (FAB) found 536.1949 for $C_{29}H_{30}ClN_3O_5$+H.

Example 78

N-(4-Chlorobenzyl)-6-[(3,3-dihydroxy-1-azetidinyl)methyl]-1-methyl-4-oxo-1,4-dihydro-3-quinolinecarboxamide

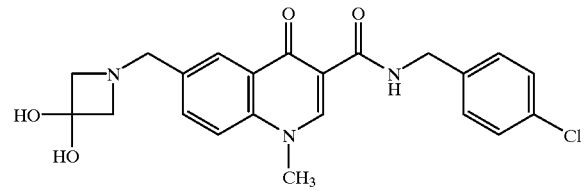

A solution of N-(4-chlorobenzyl)-6-[(3-hydroxy-1-azetidinyl)methyl]-1-methyl-4-oxo-1,4-dihydro-3-quinolinecarboxamide (0.10 gm) from Example No. 75 in dry DMSO (3 mL) containing triethylamine (0.35 mL) is treated with pyridine-sulfar trioxide complex (0.25 gm). The reaction mixture is stirred at room temperature for 2 hrs. The reaction mixture is diluted with ethyl acetate and washed with water (2×), brine, dried ($Na_2SO_4$) and concentrated under reduced pressure. The residue is purified by recrysrallization from acetonitrile to afford 0.06 gm of the title compound as a tan solid.

Physical characteristics are as follows:
$^1$H NMR (DMSO-$d_6$) δ10.4, 8.9, 8.3, 7.8, 7.4, 4.6, 4.2, 4.0; MS (ESI+) m/z 442 (MeOH adduct); HRMS (FAB) found 428.1381 for $C_{22}H_{22}ClN_3O_4$+H.

Example 79

N-(4-Chlorobenzyl)-1-[(methylsulfinyl)methyl]-6-(4-morpholinylmethyl)-4-oxo-1,4-dihydro-3-quinolinecarboxamide

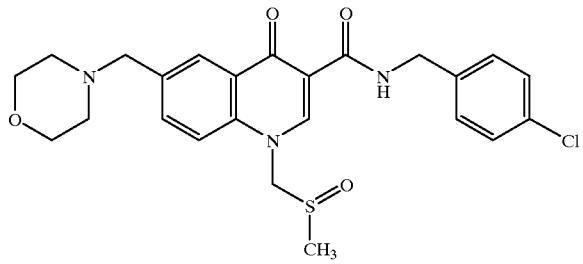

A solution of N-(4-chlorobenzyl)-1-[(methylsulfanyl)methyl]-6-(4-morpholinylmethyl)-4-oxo-1,4-dihydro-3-quinolinecarboxamide (0.14 gm) from Example No. 73 in dichloromethane (4 mL) at 0° C. is added p-toluenesulfonic acid hydrate (0.06 gm) followed by m-chloroperoxybenzoic acid (~85%) (0.06 gm). The mixture is stirred for 1 hr. The reaction mixture is diluted with dichloromethane, washed with saturated aqueous sodium sulfite, saturated aqueous sodium bicarbonate, brine, dried ($Na_2SO_4$) and concentrated under reduced pressure. The crude product is purified by recrystallization from methanol-acetonitrile to afford 0.11 gm of the title compound as a white solid.

Physical characteristics are as follows:
$^1$H NMR ($CDCl_3$) δ10.3, 8.9, 8.4, 7.8, 7.6, 7.3, 5.3, 4.6, 3.7, 3.6, 2.8, 2.5; MS (ESI+) m/z 488; Anal. found for $C_{24}H_{26}ClN_3O_4S$: C, 58.71; H, 5.38; N, 8.57.

Example 80

N-(4-Chlorobenzyl)-1-[(methylsulfonyl)methyl]-6-(4-morpholinylmethyl)-4-oxo-1,4-dihydro-3-quinolinecarboxamide

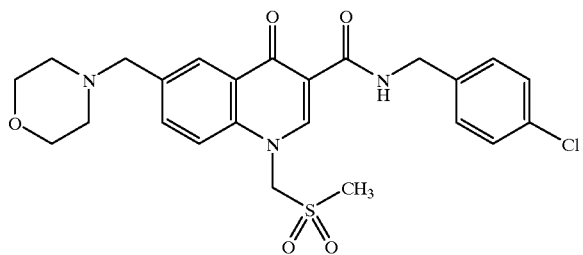

A solution of N-(4-chlorobenzyl)-1-[(methylsulfanyl)methyl]-6-(4-morpholinylmethyl)-4-oxo-1,4-dihydro-3-quinolinecarboxamide (0.14 gm) from Example No. 73 in dichloromethane (4 mL) at 0° C. is added p-toluenesulfonic acid hydrate (0.06 gm) followed by m-chloroperoxybenzoic acid (~85%) (0.13 gm). The mixture is stirred for 1 hr. The reaction mixture is diluted with dichloromethane, washed with saturated aqueous sodium sulfite, saturated aqueous sodium bicarbonate, brine, dried ($Na_2SO_4$) and concentrated under reduced pressure. The crude product is purified by flash column chromatography eluting with 3% to 9% methanol in dichloromethane and then by recrystallization from ethyl acetate-hexanes to afford 0.08 gm of the title compound as a white solid.

Physical characteristics are as follows:
$^1$H NMR ($CDCl_3$) δ10.4, 9.1, 8.4, 7.8, 7.7, 7.3, 5.6, 4.7, 3.7, 3.6, 3.0, 2.5; MS (ESI+) m/z 504. Anal. found for $C_{24}H_{26}ClN_3O_5S$: C, 56.85; H, 5.20; N, 8.20.

Example 81

N-(4-Chlorobenzyl)-6-(4-morpholinylmethyl)-4-oxo-1-[(phenylsulfinyl)methyl]-1,4-dihydro-3-quinolinecarboxamide

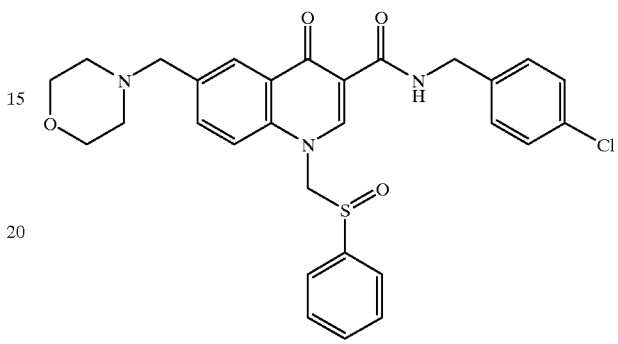

A solution of N-(4-chlorobenzyl)-6-(4-morpholinylmethyl)-4-oxo-1-[(phenylsulfanyl)methyl]-1,4-dihydro-3-quinolinecarboxamide (0.08 gm) from Example No. 76 in dichloromethane (2 mL) at 0° C. is added p-toluenesulfonic acid hydrate (0.03 gm) followed by m-chloroperoxybenzoic acid (~85%) (0.03 gm). The mixture is stirred for 1 hr. The reaction mixture is diluted with dichloromethane, washed with saturated aqueous sodium sulfite, saturated aqueous sodium bicarbonate, brine, dried ($Na_2SO_4$) and concentrated under reduced pressure. The crude product is purified by recrystallization from acetonitrile to afford 0.06 gm of the title compound as a white solid.

Physical characteristics are as follows:
$^1$H NMR ($CDCl_3$) δ10.2, 8.4, 7.8, 7.6, 7.3, 5.2, 4.6, 3.7, 3.6, 2.4; MS (ESI+) m/z 550; HRMS (FAB) found 550.1569 for $C_{29}H_{28}ClN_3O_4S+H$.

Example 82

N-(4-Chlorobenzyl)-6-(4-morpholinylmethyl)-4-oxo-1-[(phenylsulfonyl)methyl]-1,4-dihydro-3-quinolinecarboxamide

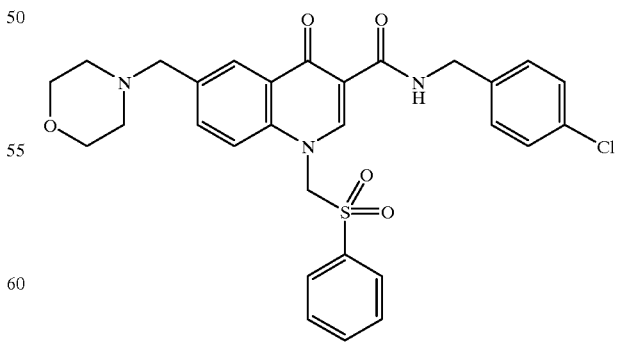

A solution of N-(4-chlorobenzyl)-6-(4-morpholinylmethyl)-4-oxo-1-[(phenylsulfanyl)methyl]-1,4-dihydro-3-quinolinecarboxamide (0.08 gm) from Example No. 76 in dichloromethane (4 mL) at 0° C. is added p-toluenesulfonic acid hydrate (0.03 gm) followed by m-chloroperoxybenzoic acid (~85%) (0.06 gm). The mixture is stirred for 1 hr. The reaction mixture is diluted with dichloromethane, washed with saturated aqueous sodium sulfite, saturated aqueous sodium bicarbonate, brine, dried (Na$_2$SO$_4$) and concentrated under reduced pressure. The crude product is purified by recrystallization from acetonitrile to afford 0.07 gm of the title compound as a white solid.

Physical characteristics are as follows:

$^1$H NMR (CDCl$_3$) δ10.1, 8.3, 7.8–7.5, 7.3, 5.5, 4.6, 3.7, 3.6, 2.5; MS (ESI+) m/z 566; HRMS (FAB) found 566.1516 for C$_{29}$H$_{28}$ClN$_3$O$_5$S+H.

Example 83

N-(4-chlorobenzyl)-6-(3-hydroxypropyl)-1-[2-(2-methoxyethoxy)ethyl]-4-oxo-1,4-dihydro-3-quinolinecarboxamide

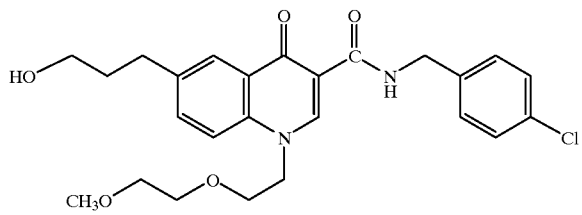

The title compound is prepared from N-(4-chlorobenzyl)-6-(3-hydroxy-1-propynyl)-1-[2-(2-methoxyethoxy)ethyl]-4-oxo-1,4-dihydro-3-quinolinecarboxamide, which is the product of Example No. 42, according to the procedure described in Preparation No. 27.

Preparation 41

N-(4Chlorobenzyl)-6-(hydroxymethyl)-1-[2-(2-methoxyethoxy)-ethyl]-4-oxo-1,4-dihydro-3-quinolinecarboxamide

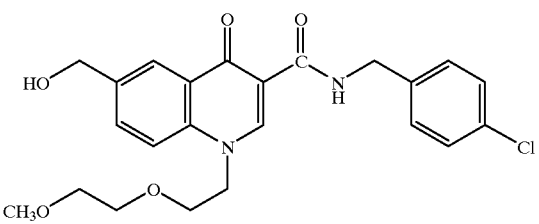

A stirred mixture of N-(4-chlorobenzyl-4-hydroxy-6-(hydroxymethyl)-3-quinolinecarboxamide (3.3 g) from Preparation No. 9, cesium carbonate (6.33 g), and 2-(2-methoxyethoxy)ethyl p-toluenesulfonate (4.0 g) in of DMF (10 mL) is heated at 50° C. for 18 h, then cooled and partitioned between ethyl acetate and dilute HCl. The organic phase is washed with water and brine, dried over MgSO$_4$, and concentrated under reduced pressure. Flash chromatography of the residue on silica using 4–5% methanol in dichloromethane provides 3.0 g of the title compound.

Physical characteristics are as follows:

Mp 161–162.5° C.; $^1$H NMR (CDCl$_3$) δ3.29, 3.45, 3.57, 3.88, 4.39, 4.61, 4.77, 7.2–7.4, 7.58, 8.30, 8.55, 10.4 ppm; IR 3381, 2876, 1655, 1605, 1551, 1495, 1226, 1106 cm$^{-1}$.

HRMS (m+H) 445.1525; Anal. Found for C$_{23}$H$_{25}$N$_2$O$_5$Cl$_1$: C, 62.06; H, 5.72; N, 6.42.

Example 84

N-(4-Chlorobenzyl)-1-[2-(2-methoxyethoxy)ethyl]-6-(4-morpholinylmethyl-4-oxo-1,4-dihydro-3-quinolinecarboxamide

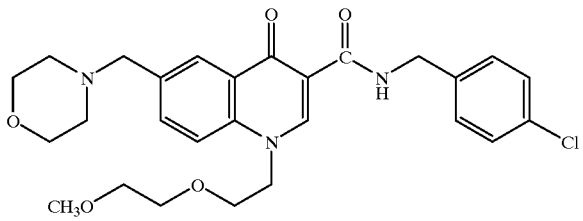

To a stirred solution of N-(4-chlorobenzyl)-6-(hydroxymethyl)-1-[2-(2-methoxyethoxy)ethyl]4-oxo-1,4-dihydro-3-quinolinecarboxamide (197 mg) from Preparation No. 41 in DMF (1 mL) is added 2,4,6-collidine (0.14 mL) and DMAP (8 mg). The solution is cooled to 0° C., and methanesulfonyl choride (69 μL) is added. After 18 h, the mixture is added to 20 mL of rapidly stirred water containing 0.75 mL of 1N HCl. The resulting precipitate is filtered, washed well with water, and dried in vacuo to afford 183 mg of N-(4-chlorobenzyl)-6-(chloromethyl)-1-[2-(2-methoxyethoxy)ethyl]4-oxo-1,4-dihydro-3-quinolinecarboxamide.

To a solution of the above chloride (93 mg) in DMF (1 mL) is added morpholine (53 μL). The solution is stirred for 18 h, then concentrated under reduced pressure. Flash chromatography of the residue on silica using 3–4% methanol in dichloromethane provides 98.7 mg of the title compound as a white crystalline solid. An analytical sample may be prepared by recrystallization from ethyl acetate in hexane.

Physical characteristics are as follows:

Mp 116–118° C.; $^1$H NMR δ2.46, 3.46, 3.58, 3.63, 3.70, 3.91, 4.45, 4.64, 7.3, 7.54, 7.77, 8.41, 8.82, 10.5 ppm; IR 2815, 1662, 1606, 1549, 1494, 1224, 1116 cm$^{-1}$. HRMS (M+H) 514.2114; Anal. Found for C$_{27}$H$_{32}$N$_3$O$_5$Cl: C, 63.00; H, 6.28; N, 8.09.

Example 85

N-(4-Chlorobenzyl)-1-[2-(2-methoxyethoxy)ethyl]-4-oxo-6-[(4-oxo-1-piperidinyl)methyl]-1,4-dihydro-3-quinolinecarboxamide

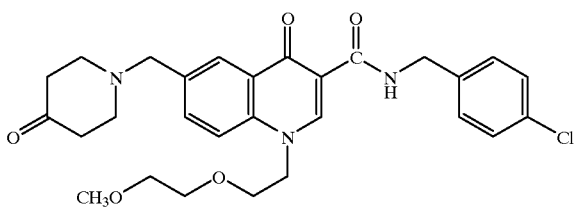

The title compound is prepared in a manner analogous to that described in Example No. 84.

Physical characteristics are as follows:

$^1$H NMR (CDCl$_3$) δ2.45, 2.77, 3.30, 3.46, 3.58, 3.76, 3.92, 4.47, 4.64, 7.3, 7.59, 7.80, 8.01, 8.45, 8.83, 10.5 ppm;

IR 3060, 2912, 1717, 1663, 1606, 1550, 1494, 1224, 1091 cm$^{-1}$. HRMS (M+H) 526.2107.

Example 86

N-(4-Chlorobenzyl)-6-{[(cyanomethyl)(methyl) amino]methyl}-1-[2-(2-methoxyethoxy)ethyl]-4-oxo-1,4-dihydro-3-quinolinecarboxamide

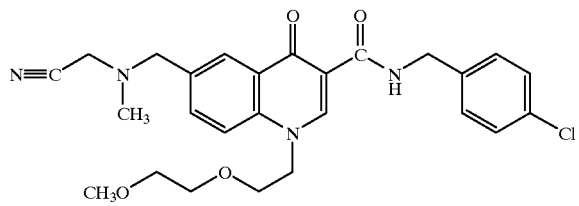

The title compound is prepared in a manner analogous to that described in Example No. 84.

Physical characteristics are as follows:

Mp 118–120° C.; $^1$H NMR (CDCl$_3$) δ2.43, 3.29, 3.4–3.5, 3.58, 3.75, 3.91, 4.46, 4.64, 7.3, 7.58, 7.71, 8.45, 8.83, 10.5 ppm. IR 3062, 2877, 1662, 1606, 1550, 1495, 1224, 1107, 811 cm$^{-1}$. HRMS (M+H) 497.1950; Anal. Found for $C_{26}H_{29}N_4O_4Cl_1$: C, 62.71; H, 5.96; N, 11.24.

Example 87

N-(4-Chlorobenzyl)-6-{[(3R)-3-hydroxypyrrolidinyl]methyl}-1-[2-(2-methoxyethoxy)ethyl]-4-oxo-1,4-dihydro-3-quinolinecarboxamide

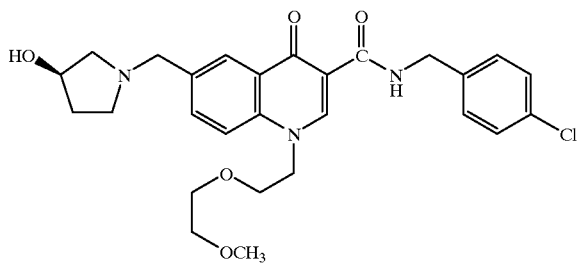

The title compound is prepared in a manner analogous to that described in Example No. 84.

Physical characteristics are as follows:

Mp 106–109° C.; $^1$H NMR (CDCl$_3$) δ1.74, 2.20, 2.35, 2.56, 2.66, 2.87, 3.29, 3.45, 3.58, 3.76, 3.90, 4.33, 4.45, 4.63, 7.3, 7.54, 7.77, 8.39, 8.81, 10.5 ppm; IR 3239, 2915, 1659, 1605, 1550, 1494, 1225, 1093, 810 cm$^{-1}$; HRS (M+H) 514.2114; Anal Found for $C_{27}H_{32}N_3O_5Cl_1$: C, 62.89; H, 6.34; N. 8.10.

Example 88

N-(4-Chlorobenzyl)-6-{[[(1R,2S)-2-hydroxy-1-methyl-2-phenylethyl](methyl)amino]methyl}-1-[2-(2-methoxyethoxy)ethyl]-4-oxo-1,4-dihydro-3-quinolinecarboxamide

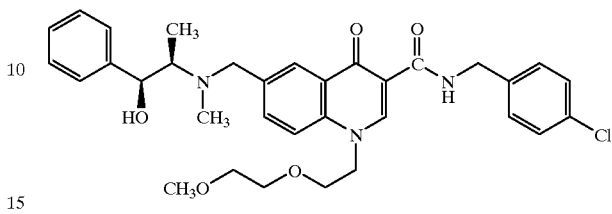

The title compound is prepared in a manner analogous to that described in Example No. 84.

Physical characteristics are as follows:

Mp 106–109° C.; $^1$H NMR (CDCl$_3$) δ1.05, 2.20, 2.94, 3.29, 3.46, 3.57, 3.74, 3.89, 4.43, 4.63, 4.87, 7.3, 7.46, 7.54, 8.33, 8.80, 10.5 ppm; IR 3404, 2876, 1658, 1605, 1549, 1494, 1106, 810 cm$^{-1}$; HRMS (M+H) 592.2576.

Example 89

N-(4-Chlorobenzyl)-6-{[(2-hydroxy-2-phenylethyl) (methyl)amino]methyl}-1-[2-(2-methoxyethoxy) ethyl]-4-oxo-1,4-dihydro-3-quinoline-carboxamide

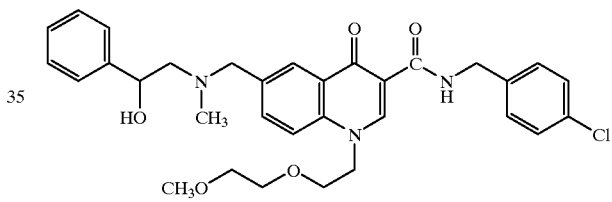

The title compound is prepared in a manner analogous to that described in Example No. 84.

Physical characteristics are as follows:

$^1$H NMR (CDCl$_3$) δ2.33, 2.6, 3.29, 3.46, 3.58, 3.67, 3.89, 4.45, 4.63, 4.78, 7.3, 7.57, 7.76, 8.38, 8.83, 10.5 ppm; IR 3240, 2878, 1661, 1606, 1550, 1494, 1225, 1093, 810 cm$^{-1}$; HRMS (M+H) 578.2410.

Example 90

N-(4-Chlorobenzyl)-6-{[[2-hydroxy-2-(4-hydroxyphenyl)ethyl](methyl)amino]methyl}-1-[2-(2-methoxyethoxy)ethyl]-4-oxo-1,4-dihydro-3-quinolinecarboxamide

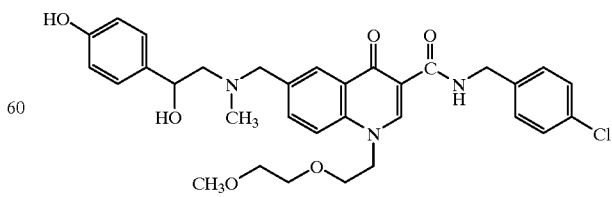

The title compound is prepared in a manner analogous to that described in Example No. 84.

Physical characteristics are as follows:

¹H NMR (CDCl₃) δ2.30, 2.4–2.7, 3.28, 3.45, 3.55, 3.63, 3.84, 4.40, 4.65, 6.74, 7.11, 7.3, 7.53, 7.73, 8.36, 8.80, 10.55 ppm; IR 3240, 2879, 1654, 1605, 1550, 1495, 1226, 811, 731 cm⁻¹; HRMS (M+H) 594.2363.

Example 91

1-{2-[2-(tert-Butoxy)ethoxy]ethyl}-N-(4-chlorobenzyl)-6-(4-morpholinylmethyl)-4-oxo-1,4-dihydro-3-quinolinecarboxamide

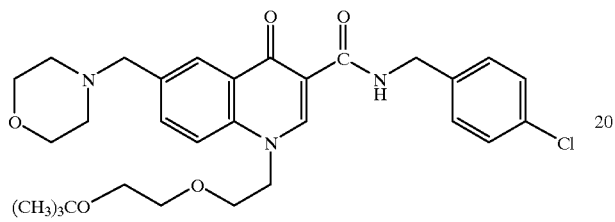

The title compound is prepared in a manner analogous to that described in Example No. 84.

Physical characteristics are as follows:

Mp 130–132.5° C.; ¹H NMR (CDCl₃) δ1.10, 2.46, 3.41, 3.53, 3.63, 3.70, 3.92, 4.44, 4.64, 7.3, 7.56, 7.77, 8.41, 8.81, 10.50 ppm; IR 2972, 1663, 1506, 1550, 1494, 1364, 1224, 1117, 1092, 809 cm⁻¹; HRMS (M+H) 556.2578; Anal. Found for $C_{30}H_{38}N_3O_5Cl$: C, 64.79; H, 6.87; N, 7.51.

Example 92

1-{2-[2-(tert-Butoxy)ethoxy]ethyl}-N-(4-chlorobenzyl)-6-{[[2-hydroxy-2-(4-hydroxyphenyl)ethyl](methyl)amino]methyl}-4-oxo-1,4-dihydro-3-quinolinecarboxamide

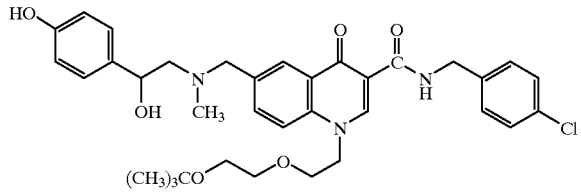

The title compound is prepared in a manner analogous to that described in Example No. 84.

Physical characteristics are as follows:

¹H NMR (CDCl₃) δ1.12, 2.32, 2.5–2.7, 3.43, 3.54, 3.6, 3.8, 4.41, 4.64, 4.70, 6.77, 7.13, 7.3, 7.52, 7.75, 8.36, 8.80, 10.51 ppm; IR 3238, 2974, 1654, 1605, 1550, 1494, 1365, 1226, 1092, 811,731 cm⁻¹.

Example 93

N-(4-Chlorobenzyl)-1-[2-(2-methoxyethoxy)ethyl]-6-[(methylsulfanyl)methyl]-4-oxo-1,4-dihydro-3-quinolinecarboxamide

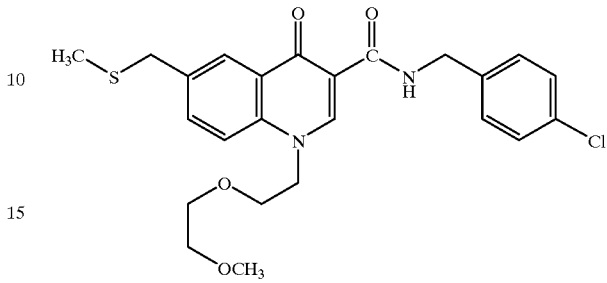

To a suspension of N-(4-chlorobenzyl)-6-(chloromethyl)-1-[2-(2-methoxyethoxy)ethyl]-4-oxo-1,4-dihydro-3-quinolinecarboxamide (175 mg) prepared as described in Example No. 84, in DMF (1.5 11) is added sodium thiomethoxide (40 mg). The mixture is stirred for 18 h, then added to 25 ml of rapidly stirred water. The solid is filtered, washed well with water, dried in vacuo, and recrystallized from acetonitrile to afford 139 mg of the title compound as pale yellow crystals.

Physical characteristics are as follows:

Mp 154–155° C.; HRMS m/z 475.1457; Anal. Found for $C_{24}H_{27}N_2O_4ClS$: C, 60.63; H, 5.75; N, 5.91.

Preparation 42

N-(4-Chlorobenzyl-4-hydroxy-6-iodo-3-quinolinecarboximidoyl chloride.

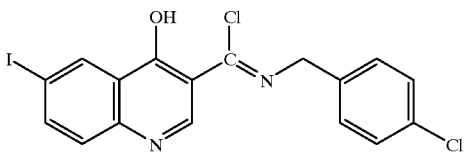

A suspension of N-(4-chlorobenzyl)-4-hydroxy-6-iodo-3-quinolinecarboxamide (0.75 g) from Preparation No. 4 in dichloroethane (15 mL) is heated to 65° C. Phosphorus pentachloride (0.57 g) is added in one portion. After 1.25 h, the reaction mixture is cooled to room temperature and the solvent is evaporated in a stream of nitrogen. Dichloromethane (20 mL) is added followed by toluene (6 mL) and the resulting solid is filtered and dried to give N-(4-chlorobenzyl-4-hydroxy-6-iodo-3-quinolinecarboximidoyl chloride (0.77 g).

Physical characteristics are as follows:

Mp 172–174° C.; ¹H NMR (300 MHz, DMSO-d₆) δ14.44, 13.13, 10.29, 8.76, 8.52, 8.05, 7.57, 7.40, 7.35, 4.55 ppm; IR (drift) 3025, 2410, 1660, 1615, 1573, 1556, 1529, 1494, 1462, 1398, 1367, 1324, 1316, 1302, 928 cm⁻¹; MS (FAB) m/z 439, 577, 576, 575, 442, 441, 440, 439, 298, 127, 125.

Preparation 43

N-(4-Chlorobenzyl)-4-hydroxy-6-iodo-3-quinolinecarbothioamide.

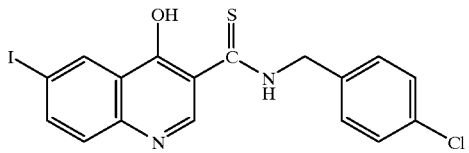

Hydrogen sulfide is bubbled for 30 minutes into a solution of anhydrous pyridine (40 mL) cooled to 0° C. N-(4-Chlorobenzyl)-4hydroxy-6-iodo-3-quinolinecarboximidoyl chloride (1.14 g) from Preparation No. 42 is added in one portion. After 15 minutes, the ice bath is removed and the reaction is stirred at room temperature for 18 h with continuous bubbling of $H_2S$. The reaction mixture is poured into ice water and the resulting solid is filtered and dried. The solid is dissolved in $CH_2Cl_2$/MeOH, adsorbed onto silica, and purified by chromatography (eluent $CH_2Cl_2$ (1 L), 0.5% MeOH:$CH_2Cl_2$ (1 L), 0.75% MeOH:$CH_2Cl_2$ (6 L)) to give N-(4-chlorobenzyl)-4-hydroxy-6-iodo-3-quinolinecarbothioamide (0.90 g) as a yellow solid.

Physical characteristics are as follows:

Mp 275–276° C.; $^1H$ NMR (300 MHz, DMSO-$d_6$) δ13.09, 9.44, 8.55, 8.09, 7.56, 7.44, 5.02 ppm; IR (drift) 3069, 3061, 1620, 1607, 1557, 1534, 1518, 1493, 1381, 1352, 1344, 1288, 1194, 813, 745 cm$^{-1}$; MS (FAB) m/z 455 (MH$^+$), 531, 457, 455, 454, 417, 262, 247, 125, 124, 107.

Preparation 44

N-(4-Chlorobenzyl)-6-iodo-1-methyl-4-oxo-1,4-dihydro-3-quinolinecarbothioamide

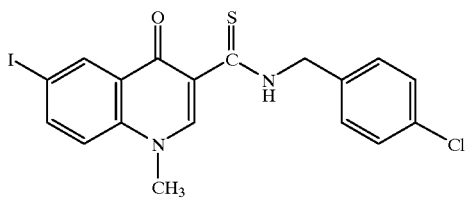

To a suspension of N-(4-chlorobenzyl)-4-hydroxy-6-iodo-3-quinolinecarbothioamide (0.20 g) from Preparation No. 43 and triphenylphosphine (0.15 g) in freshly distilled tetrahydrofuran (5 mL) is added MeOH (0.027 mL) followed by diethyl azodicarboxylate. After an initial exotherm, the reaction is stirred at room temperature for 3 h. To drive the reaction to completion, additional triphenylphosphine (0.030 g), methanol (0.010 mL), and diethyl azodicarboxylate (0.020 mL) are added. The reaction is stirred at room temperature overnight. The reaction is concentrated in vacuo. The residue is dissolved in $CH_2Cl_2$ and adsorbed onto silica. Purification by chromatography (eluent $CH_2Cl_2$ (1 L), 1% MeOH:$CH_2Cl_2$ (1 L)) affords N-(4-chlorobenzyl)-6-iodo-1-methyl-4-oxo-1,4-dihydro-3-quinolinecarbothioamide (0.065 g) as a yellow solid.

Physical characteristics are as follows:

Mp 153–155° C.; $^1H$ NMR (300 MHz, DMSO-$d_6$) δ13.04, 9.50, 8.61, 8.18, 7.71, 7.44, 5.02, 4.06 ppm; IR (drift) 1619, 1597, 1576, 1528, 1489, 1385, 1365, 1352, 1332, 1307, 1220, 1180, 1117, 812, 650 cm$^{-1}$; MS (FAB) m/z 469 (MH$^+$), 547, 545, 471, 470, 469, 468, 371, 328, 125, 123.

Example 94

N-(4-chlorobenzyl)-6-(3-hydroxy-1-propynyl)-1-methyl4-oxo-1,4-dihydro-3-quinolinecarbothioamide

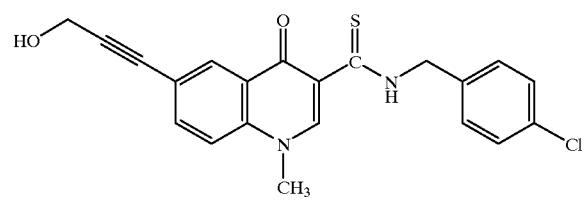

A suspension of N-(4-chlorobenzyl)-6-iodo-1-methyl-4-oxo-1,4-dihydro-3-quinolinecarbothioamide (0.20 g) from Preparation No. 44, propargyl alcohol (0.030 mL), copper iodide (0.028 g), and bis(triphenylphosphine)palladium(II) chloride (0.0095 g) in diethylamine (10 mL) is stirred at room temperature for 18 h. The solid in the reaction mixture is filtered, then dissolved in $CH_2Cl_2$/MeOH, and adsorbed onto silica. Purification by chromatography (eluent 1% MeOH:$CH_2Cl_2$ (1 L), 2% MeOH:$CH_2Cl_2$ (1 L)) affords the title compound as a yellow solid (0.12 g).

Physical characteristics are as follows:

Mp 200–201° C.; $^1H$ NMR (300 MHz, DMSO-$d_6$) δ13.04, 9.47, 8.30, 7.89, 7.44, 5.42, 5.04, 4.35, 4.08 ppm; IR (drift) 3311, 1625, 1602, 1572, 1535, 1490, 1392, 1368, 1352, 1337, 1312, 1030, 1015, 831, 801 cm$^{-1}$; MS (ESI) m/z 397.0 (M+H)$^+$

Preparation 45

Methyl 3-{[(4-Chlorobenzyl)amino]carbothioyl}-4-hydroxy-6-quinolinecarboxylate.

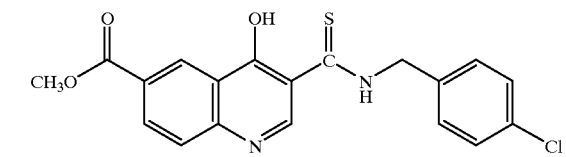

Dimethylformamide (anhydrous, 5 mL) is added to a flame-dried flask. The solution is purged with nitrogen for 15 minutes. To this solution is added N-(4-chlorobenzyl)-4-hydroxy-6-iodo-3-quinolinecarbothioamide (0.25 g) from Preparation No. 44, methanol (0.90 mL), triethylamine (0.16 mL), and dichlorobis(triphenylphosphine)palladium (0.068 g). The reaction is placed under a CO balloon and stirred at 70° C. for 3 h. The reaction is cooled to room temperature and poured into 1N HCl (40 mL). The resulting solid is filtered and dried. The solid is dissolved in $CH_2Cl_2$/MeOH and adsorbed onto silica. Purification by chromatography (eluent $CH_2Cl_2$ (1 L), 1% MeOH:$CH_2Cl_2$ (2 L), 3% MeOH:$CH_2Cl_2$ (1 L)) affords methyl 3-{[(4-chlorobenzyl)amino]carbothioyl}-4-hydroxy-6-quinolinecarboxylate (0.090 g) as a yellow solid.

Physical characteristics are as follows:

Mp 259–261° C.; $^1H$ NMR (300 MHz, DMSO-$d_6$) δ13.24, 13.03, 9.46, 8.85, 8.28, 7.84, 7.45, 5.04, 3.91 ppm;

IR (drift) 1713, 1630, 1572, 1564, 1539, 1519, 1494, 1483, 1436, 1296, 1275, 1237, 1201, 799, 769 cm$^{-1}$; MS (FAB) m/z 387 (MH$^+$), 389, 388, 387, 386, 371, 246, 127, 125, 92, 45.

Preparation 46

N-(4-chlorobenzyl)-4-hydroxy-6-(hydroxymethyl)-3-quinolinecarbothioamide.

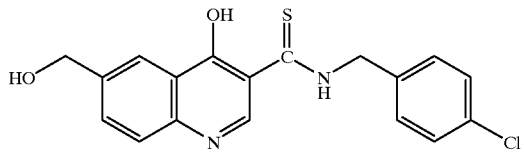

To a suspension of methyl 3-{[(4-chlorobenzyl)amino]carbothioyl})-4-hydroxy-6-quinolinecarboxylate (0.062 g) from Preparation No. 45 in freshly distilled THF (8 mL) at room temperature is added lithium aluminum hydride (1M in THF, 0.34 mL) dropwise. After 45 minutes, the reaction is quenched sequentially with 1 mL water, 1 mL 15% NaOH, and 1 mL water. The reaction mixture is concentrated in vacuo. The residue is adsorbed onto silica. Purification by chromatography (eluent 1% MeOH:CH$_2$Cl$_2$ (1 L), 2% MeOH:CH$_2$Cl$_2$ (1 L), 3% MeOH:CH$_2$Cl$_2$ (1 L)) affords N-(4-chlorobenzyl)-4-hydroxy-6-(hydroxymethyl)-3-quinolinecarbothioamide (0.038 g).

Physical characteristics are as follows:

Mp 240–242° C.; $^1$H NMR (300 MHz, DMSO-d$_6$) δ13.35, 13.01, 9.41, 8.23, 7.75, 7.70, 7.45, 5.42, 5.04, 4.64 ppm; IR (drift) 2962, 2943, 2907, 2889, 1631, 1588, 1530, 1493, 1439, 1414, 1217, 1003, 883, 822, 812 cm$^{-1}$; HRMS (FAB) calcd for C$_{18}$H$_{15}$ClN$_2$O$_2$S+H$_1$ 359.0621, found 359.0638.

Preparation 47

N-(4-chlorobenzyl)-4-hydroxy-6-(4-morpholinylmethyl)-3-quinolinecarbothioamide.

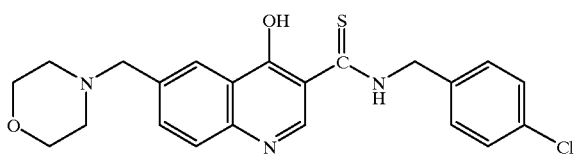

To a solution of N-(4-chlorobenzyl-4-hydroxy-6-(hydroxymethyl)-3-quinolinecarbothioamide (0.082 g) from Preparation No. 46 in anhydrous dimethylformamide (4 mL) in a flame-dried flask is added dimethylaminopyridine (0.011 g), 2,4,6-collidine (0.035 mL), and methanesulfonyl chloride (0.017 mL). The reaction mixture is stirred at room temperature for 1 h after which time thin layer chromatography indicates starting material is nearly consumed. Morpholine (0.20 mL) is added in one portion. The reaction is stirred for 1.5 h and then poured into water. The aqueous solution is extracted 2× with CH$_2$Cl$_2$ and 2× with 3% MeOH:CH$_2$Cl$_2$. The organics are combined, dried over Na$_2$SO$_4$, filtered, and concentrated. Residual DMF is removed on the vacuum pump. The residue is dissolved in CH$_2$Cl$_2$ and hexanes was added to give a solid (starting material) which is filtered and dried. Upon allowing this filtrate to evaporate overnight, a second solid is obtained. This solid is dissolved in CH$_2$Cl$_2$ and adsorbed onto silica. Purification by chromatography (eluent CH$_2$Cl$_2$ (1 L), 1% MeOH:CH$_2$Cl$_2$ (1 L), 2% MeOH:CH$_2$Cl$_2$ (1 L) 2.5% MeOH:CH$_2$Cl$_2$ (1 L), 3% MeOH:CH$_2$Cl$_2$ (2 L)) affords N-(4-chlorobenzyl)-4-hydroxy-6-(4-morpholinylmethyl)-3-quinolinecarbothioamide (0.028 g) as a yellow solid.

Physical characteristics are as follows:

Mp 215–216° C.; $^1$H NMR (300 MHz, DMSO-d$_6$) δ13.35, 13.04, 9.41, 8.18, 7.75, 7.70, 7.45, 5.03, 3.60, 3.57, 2.37 ppm; IR (drift) 1621, 1591, 1575, 1540, 1524, 1490, 1352, 1297, 1287, 1115, 1107, 923, 855, 831, 798 cm$^-$; HRMS (FAB) calcd for C$_{22}$H$_{22}$ClN$_3$O$_2$S+H$_1$ 428.1199, found 428.1198.

Example 95

N-(4-Chlorobenzyl)-1-methyl-6-(4-morpholinylmethyl)-4-oxo-1,4-dihydro-3-quinolinecarbothioamide

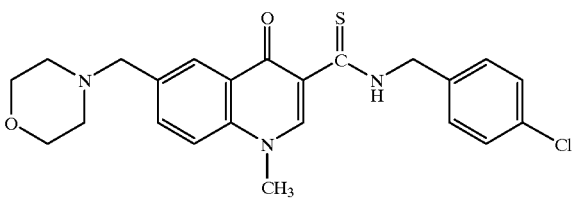

A flame-dried flask is charged with N-(4-chlorobenzyl)-4-hydroxy-6-(4-morpholinylmethyl)-3-quinolinecarbothioamide (0.060 g) from Preparation No. 47, triphenylphosphine (0.045 g), and freshly distilled THF (1.5 mL). To this solution is added methanol (8.00 μL) and diethyl azodicarboxylate (28.00 μL). The reaction is stirred at room temperature for 18 h. Monitoring of the reaction still shows a significant amount of starting material left. Additional PPh$_3$ (0.025 g), methanol (5.00 μL), and diethyl azodicarboxylate (14.00 μL) are added and the reaction is stirred for 18 h. Since monitoring of the reaction still shows some starting material, 10 equivalents each of PPh$_3$, methanol, and diethyl azodicarboxylate are added. A reasonable exotherm is seen after adding diethyl azodicarboxylate. The reaction is immediately monitored by TLC and starting material is consumed. The solvents are removed and the residue is dissolved in CH$_2$Cl$_2$/MeOH and adsorbed onto silica. Purification by column chromatography (eluent CH$_2$Cl$_2$ (1 L), 1% MeOH:CH$_2$Cl$_2$ (1 L), 2% MeOH:CH$_2$Cl$_2$ (2 L), 4% MeOH:CH$_2$Cl$_2$ (1 L), 7% MeOH:CH$_2$Cl$_2$ (1 L)) affords the title compound contaminated with triphenylphosphine oxide. These fractions are combined and concentrated and the residue is again adsorbed onto silica. Purification by a second chromatography (eluent 1:1 hexanes:ethyl acetate (1 L), 45:55 hexanes:ethyl acetate (1 L), 4:6 hexanes:ethyl acetate (1 L), 35:65 hexanes:ethyl acetate (1 L), 1:3 hexanes:ethyl acetate (1 L), 2:8 hexanes:ethyl acetate (1 L), 1:9 hexanes:ethyl acetate (1 L), 100% ethyl acetate (1 L), 2% MeOH:CH$_2$Cl$_2$ (1 L), 4% MeOH:CH$_2$Cl$_2$ (1 L)) affords the title compound as a light yellow residue. The residue is dissolved in CH$_2$Cl$_2$ and hexanes are added until cloudy. The solution is placed in the freezer overnight and the title compound as a solid is subsequently filtered and dried (0.020 g).

Physical characteristics are as follows:

Mp 167–169° C.; $^1$H NMR (300 MHz, DMSO-d$_6$) δ13.24, 9.45, 8.25, 7.84, 7.42, 5.01, 4.07, 3.62, 3.55, 2.35 ppm; HRMS (FAB) calcd for $C_{23}H_{24}ClN_3O_2S+H$, 442.1356, found 442.1357.

Preparation 48

N-(4-Corobenzyl)-8-iodo-1-methyl-4-oxo-1,4-dihydro-3-quinolinecarboxamride

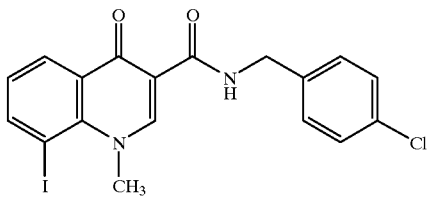

A solution of 2-iodoaniline (8.22 g) and diethyl ethoxymethylenemalonate (8.00 mL) is heated at 130° C. for 1 h. The reaction is cooled to room temperature. Diphenyl ether (100 mL) is added and the reaction is heated at 250° C. for 1.25 h. The reaction is cooled to room temperature and the resulting solid is filtered, washed thoroughly with hexanes, and dried to give ethyl 4-hydroxy-8-iodo-3-quinolinecarboxylate (6.84 g).

A portion of the resulting ethyl 4-hydroxy-8-iodo-3-quinolinecarboxylate (4.01 g) and 4-chlorobenzylamine (20.00 mL) are heated at 180° C. for 1.5 h. The reaction is cooled to room temperature. Ethyl acetate is added, followed by hexanes, and the solid is filtered, washed with hexanes, and dried to give N-(4-chlorobenzyl)-4-hydroxy-8-iodo-3-quinolinecarboxamide (3.98 g).

A suspension of the above N-(4-chlorobenzyl)-4-hydroxy-8-iodo-3-quinolinecarboxamide (0.88 g), $K_2CO_3$ (1.12 g), and iodomethane (0.14 mL) in anhydrous dimethylformamide (25 mL) is heated at 90° C. until the reaction is complete by TLC. The reaction mixture is cooled to room temperature and poured into water (150 mL). The resulting solid is filtered and dried. The solid is dissolved in $CH_2Cl_2$/MeOH and adsorbed onto silica. Purification by chromatography (eluent $CH_2Cl_2$ (1 L), 0.5% MeOH:$CH_2Cl_2$ (1 L), 1% MeOH:$CH_2Cl_2$ (1 L), 1.5% MeOH:$CH_2Cl_2$ (1 L), 2% MeOH:$CH_2Cl_2$ (1 L)) affords the title compound as a white solid (0.50 g).

Physical characteristics are as follows:

Mp 222–223° C.; $^1$H NMR (300 MHz, DMSO-$d_6$) δ10.16, 8.77, 8.51, 8.36, 7.38, 7.34, 7.21, 4.53, 4.38 ppm; IR (drift) 1662, 1600, 1574, 1551, 1536, 1489, 1436, 1418, 1358, 1116, 1105, 798, 779, 750, 724 cm$^{-1}$; MS (EI) m/z 452, 285, 159, 156, 140, 130, 128, 103, 102, 77, 76.

Example 96

N-(4-Chlorobenzyl)-8-(3-hydroxy-1-propynyl)-1-methyl-4-oxo-1,4-dihydro-3-quinolinecarboxamide

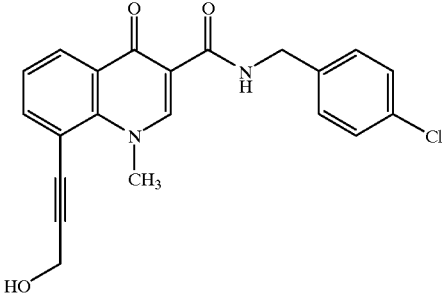

A solution of N-(4-chlorobenzyl)-8-iodo-1-methyl-4-oxo-1,4-dihydro-3-quinolinecarboxamide (0.21 g) from Preparation No. 48, copper iodide (0.029 g), bis(triphenylphosphine)palladium(II) chloride (0.012 g), and propargyl alcohol (0.035 mL) in diethylamine (15 mL) is stirred at room temperature for 18 h. Dichloromethane followed by hexanes is added to the reaction mixture. The resulting solid is filtered, washed thoroughly with hexanes, and dried. The solid is dissolved in $CH_2Cl_2$/MeOH and adsorbed onto silica. Purification by chromatography (eluent $CH_2Cl_2$ (1 L), 0.5% MeOH:$CH_2Cl_2$ (1 L), 1% MeOH:$CH_2Cl_2$ (1 L), 1.5% MeOH:$CH_2Cl_2$ (1 L), 2% MeOH:$CH_2Cl_2$ (1 L), 3% MeOH:$CH_2Cl_2$ (1 L)) affords the title compound as a yellow solid (0.13 g).

Physical characteristics are as follows:

Mp 228–230° C.; $^1$H NMR (300 MHz, DMSO-$d_6$) δ10.26, 8.78, 8.38, 7.92, 7.51, 7.40, 7.36, 5.44, 4.56, 4.44, 4.39 ppm; IR (drift) 3358, 1660, 1606, 1551, 1492, 1431, 1360, 1243, 1123, 1042, 801, 784, 758, 750, 695 cm$^{-1}$; MS (ESI) for m/z 381.0 ((M+H)$^+$, 379.0 (M–H)$^-$.

Example 97

N-(4-Chlorobenzyl)-8-(4-hydroxy-1-butynyl)-1-methyl-4-oxo-1,4-dihydro-3-quinolinecarboxamide

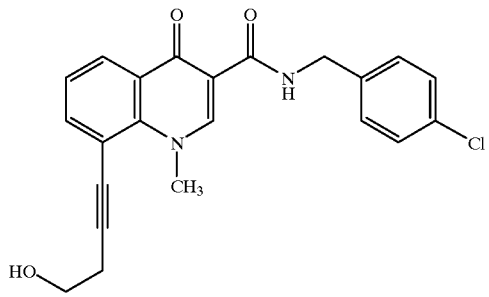

A solution of N-(4-chlorobenzyl)-8-iodo-1-methyl-4-oxo-1,4-dihydro-3-quinolinecarboxamide (0.22 g) from Preparation No. 48, copper iodide (0.029 g), bis(triphenylphosphine)palladium(II) chloride (0.013 g), and 3-butyn-1-ol (0.040 mL) in diethylamine (15 mL) is stirred at room temperature for 18 h. Hexanes are added to the reaction mixture and the resulting solid is filtered and dried. The solid is dissolved in $CH_2Cl_2$/MeOH and adsorbed onto silica. Purification by chromatography (eluent $CH_2Cl_2$ (1 L), 1.5% MeOH:CH₂Cl₂ (1 L), 2% MeOH:CH₂Cl₂ (2 L), 3% MeOH:CH₂Cl₂ (1 L)) affords the title compound as a light yellow solid (0.16 g).

Physical characteristics are as follows:

Mp 195–197° C.; $^1$H NMR (300 MHz, DMSO-$d_6$) δ 10.27, 8.77, 8.35, 7.91, 7.48, 7.41, 7.36, 4.97, 4.55, 4.45, 3.64, 2.65 ppm; IR (drift) 1661, 1604, 1555, 1489, 1427, 1359, 1242, 1118, 1090, 1073, 839, 803, 782, 753, 695 cm$^{-1}$; MS (ESI) for m/z 395.0 (M+H)$^+$.

Preparation 49

(4-Nitrobenzyl)triphenylphosphonium bromide.

To a solution of triphenylphosphine (15.34 g) in Et₂O (150 mL) is added 4-nitrobenzylbromide (12.96 g). The solution is allowed to stir overnight and the resulting solid is filtered and dried to yield 10.95 g of (4-nitrobenzyl)(triphenyl)phosphonium bromide as a white solid.

Physical characteristics are as follows:

$^1$H NMR (300 MHz, CDCl₃) δ 7.79, 7.63, 7.48, 5.99 ppm.

Preparation 50

4-(4-Nitrobenzylidene)tetrahydro-2H-pyran.

To a 100 mL flask under N₂ is added NaH (0.40 g of a 60% solution in mineral oil) and anhydrous DMSO (7 mL). The resulting solution is heated at 80° C. for 1 h and then cooled in an ice-water bath. To this is added a suspension of the phosphonium bromide (4.78 g) from Preparation No. 49 in warm DMSO (40 mL). The mixture is stirred at room temperature for 10 min. Tetrahydro4H-pyran-4-one (0.92 mL) is then added dropwise. The mixture is allowed to stir at room temperature overnight and then at 80° C. for 8 h. The mixture is poured over ice and extracted with Et₂O. The combined extracts are combined and concentrated. The crude product is chromatographed (Biotage flash 40 M, eluent gradient from hexane to 60/40 CH₂Cl₂/hexanes) to yield 0.464 g of 4-(4-nitrobenzylidene)tetrahydro-2H-pyran as a yellow solid.

Physical characteristics are as follows:

$^1$H NMR (300 MHz, CDCl₃) δ 8.20, 7.36, 6.39, 3.83, 3.70, 2.55, 2.46 ppm.

Preparation 51

Ethyl 4-Hydroxy-6-(tetrahydro-2H-pyran-4-ylmethyl)-3-quinolinecarboxylate.

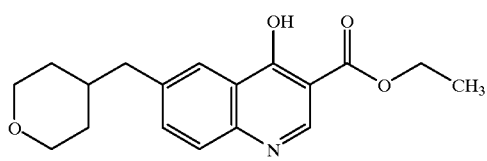

A mixture of 4-(4-nitrobenzylidene)tetrahydro-2H-pyran (400 mg) from Preparation No. 50 and platinum (IV) oxide (40 mg) in MeOH (40 ml) is hydrogenated at 40 psi H₂ for 4 h. The reaction mixture is filtered through Celite and concentrated. CH₂Cl₂ (50 mL) and diethyl ethoxymethylenemalonate (0.37 mL) are then added to the residue and the mixture was concentrated at 40° C. To this residue is then added diphenyl ether (20 mL). The mixture is heated to 250° C. for 1 h. The mixture is then cooled and diluted with hexanes. The resulting product is collected, washed with hexanes and dried to yield 0.453 g of ethyl 4-hydroxy-6-(tetrahydro-2H-pyran-4-ylmethyl)-3-quinolinecarboxylate.

Physical characteristics are as follows:

Mp 275–280° C.; $^1$H NMR (300 MHz, DMSO-$d_6$) δ 12.30, 8.49, 7.90, 7.52, 4.18, 3.78, 3.20, 2.61, 1,73, 1,43, 1.25 ppm; IR (drift) 2952, 2928, 1699, 1615, 1581, 1562, 1524, 1377, 1296, 1208, 1175, 1103, 1096, 808, 610 cm$^{-1}$; MS (ESI+) for C₁₈H₂₁NO₄ m/z 316.2 (M+H)$^+$.

Preparation 52

N-(4-Chlorobenzyl)-4-hydroxy-6-(tetrahydro-2H-pyran-4-ylmethyl)-3-quinolinecarboxamide.

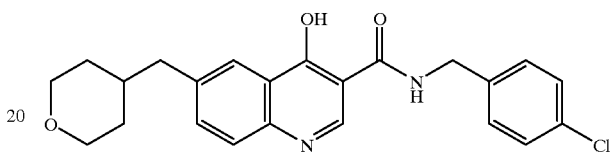

A solution of ethyl 4-hydroxy-6-(tetrahydro-2H-pyran-4-ylmethyl)-3-quinolinecarboxylate (0.315 g) from Preparation No. 51 and 4-chlorobenzylamine (0.61 nL) is heated to 180° C. for 1 h. The reaction mixture is cooled to 65° C. and diluted with CH₂Cl₂. Hexanes are added to initiate precipitation of the product. The resulting solid is collected and dried to yield 0.33 g of N-(4-chlorobenzyl)-4-hydroxy-6-(tetrahydro-2H-pyran-4-ylmethyl)-3-quinolinecarboxamide as an off-white solid.

Physical characteristics are as follows:

Mp 184–185° C.; $^1$H NMR (300 MHz, DMSO-$d_6$) δ 12.71, 10.50, 8.71, 7.99, 7.60, 7.36, 4.53, 3.78, 3.19, 2.64, 1.74, 1.43, 1.21 ppm; IR (drift) 2968, 2959, 2924, 2916, 2842, 1660, 1620, 1538, 1489, 1365, 1094, 851, 833, 806, 797 cm$^{-1}$; MS (ESI+) for C₂₃H₂₃ClN₂O₃ m/z 411.1 (M+H)$^+$.

Example 98

N-(4-Chlorobenzyl)-1-methyl-4-oxo-6-(tetrahydro-2H-pyran-4-ylmethyl)-1,4-dihydro-3-quinolinecarboxamide

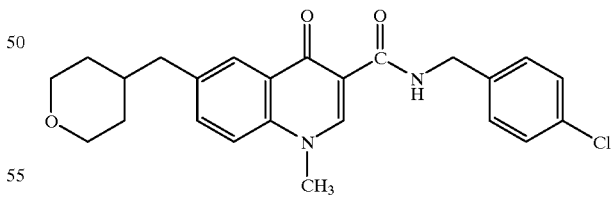

To a solution of N-(4-chlorobenzyl-4-hydroxy-6-(tetrahydro-2H-pyran4-ylmethyl)-3-quinolinecarboxamide (0.200 g) from Preparation No. 52 in anhydrous DMF (10 mL) is added K₂CO₃ (0.269 g) and CH₃I (0.04, mL). The mixture is stirred for 15 min. Water (10 mL) is then added and the resulting solid is collected and dried. The crude product is chromatographed (Biotage flash 40 S, gradient CH₂Cl₂, then 1% MeOH/CH₂Cl₂ then 2% MeOH/CH₂Cl₂) to yield 0.161 g of the title compound as a white solid.

Physical characteristics are as follows:

Mp 219–221° C.; $^1$H NMR (300 MHz, DMSO-$d_6$) δ10.45, 8.83, 8.08, 7.75, 7.68, 7.36, 4.54, 3.99, 3.78, 3.19, 2.67, 1.76, 1.43, 1.22 ppm; IR (drift) 2929, 2914, 2850, 1655, 1606, 1572, 1551, 1501, 1487, 1364, 1133, 1088, 847, 826, 808 cm$^{-1}$.

Example 99

N-(4-Chlorobenzyl)-6-{[3-(ydroxyimino)-1-azetidinyl]methyl}-1-methyl-4-oxo-1,4-dihydro-3-quinolinecarboxamide

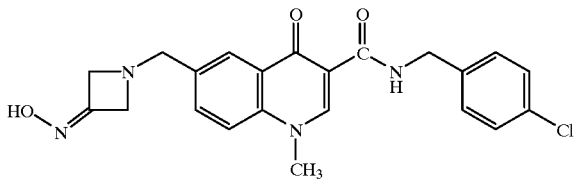

A suspension of N-(4-chlorobenzyl)-6-[(3-hydroxy-1-azetidinyl)methyl]-1-methyl-4-oxo-1,4-dihydro-3-quinolinecarboxamide (0.09 gm) of Example No. 75 in methyl sulfoxide (3 mL) is treated with triethylamine (0.35 mL) and cooled in a water bath. The mixture is treated with sulfur trioxide pyridine complex (0.25 gm) and allowed to stir for 2 hours. The mixture is diluted with diethyl ether containing a small amount of methanol and dichloromethane. The organic phase is washed with three portions of water, brine, dried over sodium sulfate, filtered, and concentrated under reduced pressure. The residue is suspended in ethanol (95%, 2 mL) and treated with hydroxylamine hydrochloride (0.03 gm) and sodium hydroxide (0.02 gm). The flask is tightly capped and heated at 65° C. overnight. The reaction mixture is cooled to room temperature and partitioned between dichloromethane containing methanol and water. The aqueous phase is extracted with dichloromethane containing methanol and dichloromethane. The combined organic phase is washed with water, brine, dried over sodium sulfate, and concentrated under reduced pressure. The residue is purified by flash column chromatography on silica gel eluting with a small amount of methanol in dichloromethane and then by recrystallization from acetonitrile-methanol to afford 14 mg of the title compound as a tan solid.

Physical characteristics are as follows:

$^1$H NMR (DMSO-$d_6$) δ10.7, 10.4, 8.9, 8.2, 7.8, 7.4, 4.6, 4.0, 3.9, 3.3; MS (ESI+) m/z 425; HRMS (FAB) found 425.1379 for $C_{22}H_{21}ClN_4O_3$+H.

Example 100

N-(4-Chlorobenzyl)-1-{2-[2-(4-morpholinyl)ethoxy]ethyl}-6-(4-morpholinylmethyl-4-oxo-1,4-dihydro-3-quinolinecarboxamide

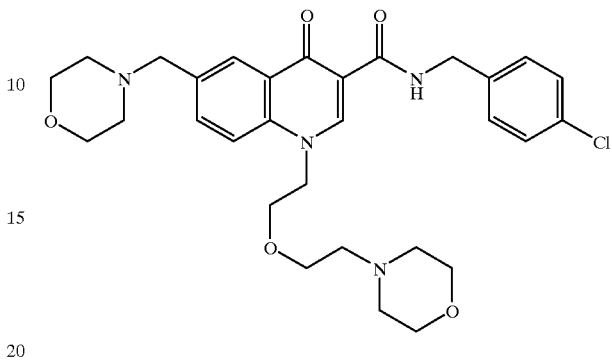

A solution of N-(4-chlorobenzyl)-1-[2-(2-hydroxyethoxy)ethyl]-6-(4-morpholinylmethyl)-4-oxo-1,4-dihydro-3-quinolinecarboxamide (0.10 gm) of Example No. 57 and 4-dimethylaminopyridine (0.002 gm) in pyridine (2 mL) at 0° C. is treated with tosyl chloride (0.05 gm). The mixture is allowed to warm to room temperature overnight. The mixture is treated with an additional portion of tosyl chloride (0.05 gm), stirred 4 hours, then treated with morpholine (0.20 mL) and allowed to stir overnight. The mixture is concentrated under reduced pressure and the residual pyridine azeotropically removed with toluene. The residue is purified by flash column chromatography on silica gel eluting with 2% to 10% methanol containing ammonia in dichloromethane and then by recrystallization from ethyl acetate-hexanes to afford 29 mg of the title compound as a white solid.

Physical characteristics are as follows:

$^1$H NMR (DMSO-$d_6$) δ10.4, 8.8, 8.2, 7.9, 7.7, 7.4, 4.6, 4,5, 3.7, 3.6, 3.5, 3.4, 3.3, 2.4, 2.3, 2.2; MS (ESI+) m/z 569; HRMS (FAB) found 569.2531 for $C_{30}H_{37}ClN_4O_5$+H.

Example 101

N-(4-Chlorobenzyl)-1-([(4-chlorophenyl)sulfanyl]methyl)-6-(4-morpholinylmethyl)-4-oxo-1,4-dihydro-3-quinolinecarboxamide

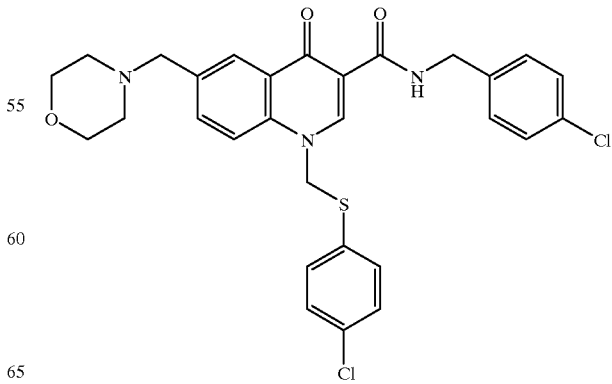

A suspension of N-(4-chlorobenzyl-4-hydroxy-6-(4-morpholinylmethyl)-3-quinolinecarboxamide (0.25 gm) from Preparation No. 40 and cesium carbonate (0.39 gm) in DMF (3 mL) is treated with chloromethyl 4-chlorophenyl sulfide (0.13 mL). The mixture is tightly capped and heated to 105° C. for 2 hrs. The reaction mixture is allowed to cool to room temperature, diluted with dichloromethane (50 mL), washed with water (2×10 mL), brine, dried ($Na_2SO_4$) and concentrated under reduced pressure. The crude product is purified by flash column chromatography eluting with 1% to 3% methanol in dichloromethane and then by trituration with ethyl acetate to afford 0.26 gm of the title compound as a white solid.

Physical characteristics are as follows:

$^1$H NMR (DMSO-$d_6$) δ10.2, 8.5, 8.2, 7.9, 7.8, 7.4–7.3, 6.0, 4.5, 3.6, 3.5, 2.4; MS (ESI+) m/z 568; Anal. Found: C, 61.14; H, 4.77; N, 7.30.

Example 102

N-(4-Chlorobenzyl)-1-([(4-chlorophenyl)sulfinyl]methyl)-6-(4-morpholinylmethyl-4-oxo-1,4-dihydro-3-quinolinecarboxamide

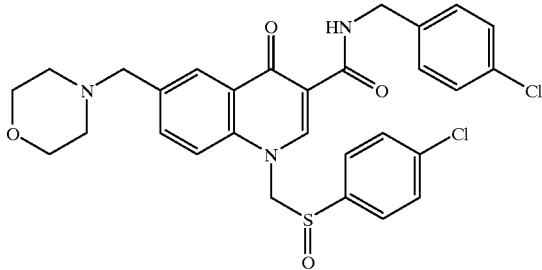

A solution of N-(4-chlorobenzyl)-1-([(4-chlorophenyl)sulfanyl]methyl)-6-(4-morpholinylmethyl)-4-oxo-1,4-dihydro-3-quinolinecarboxamide (0.11 gm) from Example No. 101 in dichloromethane (2 mL) at 0° C. is treated with p-toluenesulfonic acid hydrate (0.04 gm) followed by m-chloroperoxybenzoic acid (~85%) (0.04 gm). The mixture is stirred for 0.75 hr. The reaction mixture is diluted with dichloromethane, washed with saturated aqueous sodium sulfite, saturated aqueous sodium bicarbonate, brine, dried ($Na_2SO_4$) and concentrated under reduced pressure. The crude product is purified by recrystallization from acetonitrile to afford 0.10 gm of the title compound as a white solid.

Physical characteristics are as follows:

$^1$H NMR (DMSO-$d_6$) δ10.2, 8.7, 8.2, 7.8, 7.7, 7.5, 7.4, 6.0, 4.5, 3.6, 2.3; MS (ESI+) m/z 584; HRMS (FAB) found 584.1171 for $C_{29}H_{27}Cl_2N_3O_4S$+H.

Example 103

N-(4-Chlorobenzyl)-1-([(4-chlorophenyl)sulfonyl]methyl)-6-(4-morpholinylmethyl)-4-oxo-1,4-dihydro-3-quinolinecarboxamide

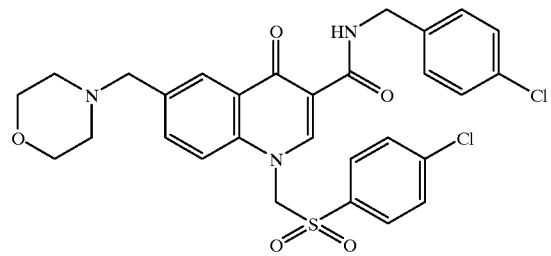

A solution of N-(4-chlorobenzyl)-1-([(4-chlorophenyl)sulfanyl]methyl)-6-(4-morpholinylmethyl)-4-oxo-1,4-dihydro-3-quinolinecarboxamide (0.11 gm) from Example No. 101 in dichloromethane (2 mL) at 0° C. is treated with p-toluenesulfonic acid hydrate (0.04 gm) followed by m-chloroperoxybenzoic acid (~85%) (0.09 gm). The mixture is stirred for 0.75 hr. The reaction mixture is diluted with dichloromethane, washed with saturated aqueous sodium sulfite, saturated aqueous sodium bicarbonate, brine, dried ($Na_2SO_4$) and concentrated under reduced pressure. The crude product is purified by recrystallization from acetonitrile to afford 0.09 gm of the title compound as a white solid.

Physical characteristics are as follows:

$^1$H NMR (DMSO-$d_6$) δ10.1, 8.7, 8.2, 7.7, 7.6, 7.5, 7.4, 6.4, 4.5, 3.5, 2.3; MS (ESI+) nzz 600; HRMS (FAB) found 600.1121 for $C_{29}H_{27}Cl_2N_3O_5S$+H.

Example 104

N-(4-Chlorobenzyl)-1-[(4-chlorophenoxy)methyl]-6-(4-morpholinylmethyl)-4-oxo-1,4-dihydro-3-quinolinecarboxamide A suspension of N-(4-chlorobenzyl)-4-hydroxy-6-(4-morpholinylmethyl)-3-quinolinecarboxamide (0.21 gm) from Preparation No. 40 and cesium carbonate (0.33 gm) in DMF (2 mL) is treated with α,4-dichloroanisole (0.13 gm). The mixture is tightly capped and heated to 100° C. for 3 hrs. The reaction mixture is allowed to cool to room temperature, diluted with dichloromethane (50 mL) and washed with water. The aqueous phase is extracted with two additional portions of dichloromethane. The combined organic phase is washed with brine, dried ($Na_2SO_4$) and concentrated under

Example 105

N-(4-Chlorobenzyl)-1-[(2-methoxyethoxy)methyl]-6-(4-morpholinylmethyl)-4-oxo-1,4-dihydro-3-quinolinecarboxamide

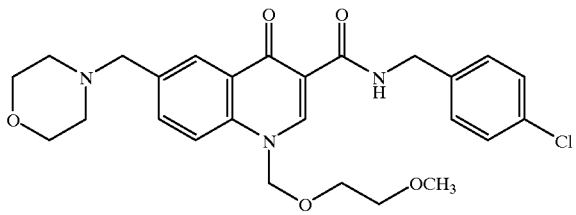

A suspension of N-(4-chlorobenzyl-4-hydroxy-6-(4-morpholinylmethyl)-3-quinolinecarboxamide (0.21 gm) from Preparation No. 40 and cesium carbonate (0.34 gm) in DMF (2 mL) is treated with 2-methoxyethoxymethyl chloride (0.07 mL). The mixture is tightly capped and heated to 100° C. for 3 hrs. The reaction mixture is allowed to cool to room temperature, diluted with dichloromethane and washed with water. The aqueous phase is extracted with two additional portions of dichloromethane. The combined organic phase is washed with brine, dried ($Na_2SO_4$) and concentrated under reduced pressure. The crude product is purified by flash column chromatography eluting with 1% to 5% methanol in dichloromethane and then by recrystallization with acetonitrile to afford 0.08 gm of the title compound as a white solid.

Physical characteristics are as follows:

Mp 150–152° C.; $^1$H NMR (DMSO-$d_6$) δ10.3, 9.0, 8.2, 7.9, 7.8, 7.4, 5.8, 4.5, 3.6, 3.4, 3.1, 2.4; MS (ESI+) m/z 500; Anal. Found: C, 62.49; H, 6.03; N, 8.50.

Example 106

2-{3-{[(4-Chlorobenzyl)amino]carbonyl}-6-(4-morpholinylmethyl)-4-oxo -1(4H)-quinolinyl]methoxy}ethyl benzoate

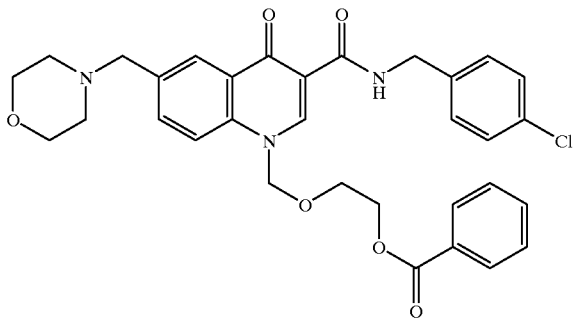

A suspension of N-(4-chlorobenzyl)-4-hydroxy-6-(4-morpholinylmethyl)-3-quinolinecarboxamide (0.41 gm) from Preparation No. 40 and cesium carbonate (0.65 gm) in DMF (5 mL) is treated with benzoyloxyethylchloromethylether (~85%, 0.31 mL). The mixture is tightly capped and heated to 110° C. for 3 hrs. The reaction mixture is allowed to cool to room temperature, diluted with dichloromethane and washed with water (3×). The organic phase is washed with brine, dried ($Na_2SO_4$) and concentrated under reduced pressure. The crude product is purified by flash column chromatography eluting with 2% to 6% methanol in dichloromethane and then by recrystallization with acetonitrile to afford 0.08 gm of the title compound as a white solid.

Physical characteristics are as follows:

$^1$H NMR (DMSO-$d_6$) δ10.3, 9.0, 8.2, 7.9, 7.7, 7.6, 7.4, 5.9, 4.6, 4.3, 3.9, 3.5, 3.3, 2.3; MS (ESI+) m/z 590; HRMS (FAB) found 590.2046 for $C_{32}H_{32}ClN_3O_6$+H.

Example 107

N-(4-Chlorobenzyl)-1-[(2-hydroxyethoxy)methyl]-6-(4-morpholinylmethyl-4-oxo-1,4-dihydro-3-quinolinecarboxamide

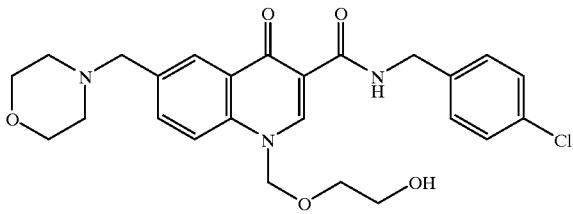

A flask containing 2-{[3-{[(4-chlorobenzyl)amino]carbonyl}-6-(4-morpholinylmethyl)-4-oxo-1(4H)-quinolinyl]methoxy}ethyl benzoate (0.12 gm) from Example No. 106 is treated with methanol saturated with ammonia (5 mL). The mixture is tightly capped and stirred at room temperature for 3 days. The reaction mixture is concentrated under reduced pressure. The crude product is purified by flash column chromatography eluting with 2% to 10% methanol in dichloromethane and then by recrystallization with acetonitrile to afford 0.07 gm of the title compound as a white solid.

Physical characteristics are as follows:

$^1$H NMR (DMSO-$d_6$) δ10.3, 9.0, 8.2, 7.9, 7.8, 7.4, 5.8, 4.7, 4.5, 3.6, 3.5, 3.3, 2.4; MS (ESI+) m/z 486; Anal. Found: C, 61.69; H, 5.85; N, 8.61.

Example 108

N-(4-Chlorobenzyl)-6-(4-morpholinylmethyl)-4-oxo-1-tetrahydro-2H-pyran-4-yl-1,4-dihydro-3-quinolinecarboxamide (formula W-5; Z=O)

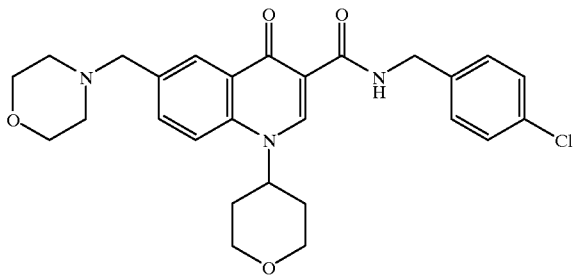

A flask containing 4-(4-aminobenzyl)morpholine from Preparation No. 22 (0.48 g) is treated with methanol (5 mL) and a few dozen dry molecular sieves (3 Å). The mixture is treated with acetic acid (1 mL) and terahydro-4H-pyran-4-one (0.24 mL). After 1 hour, the mixture is carefully treated with sodium cyanoborohydride (0.6 g) and heated to reflux under an argon atmosphere. After 1 hour, the mixture is cooled to room temperature and filtered with methanol washes. The filtrate is diluted with diethyl ether and washed with aqueous sodium hydroxide (2N). The aqueous is back-extracted with dichloromethane. The combined organic layers are washed with brine, dried over sodium sulfate, and concentrated under reduced pressure. The residue is flash column chromatographed on silica eluting with 2% to 5% methanol in dichloromethane. The product-containing fractions are combined and evaporated to afford 0.34 g of N-[4-(4-morpholinylmethyl)phenyl]tetrahydro-2H-pyran-4-amine as a white solid.

A flask containing N-[4-(4-morpholinylmethyl)phenyl] tetrahydro-2H-pyran-4-amine (0.34 g) is treated with diethyl ethoxymethylenemalonate (0.30 mL) and pyridine (0.20 mL). The flask is tightly capped and heated to 140° C. for 2 hours. The reaction is cooled to room temperature and azeotroped under reduced pressure with toluene (3×). The residue is dissolved in dichloromethane and washed with water, brine, dried and concentrated under reduced pressure. The residue is chromatographed on silica eluting with 2% to 6% methanol in dichloromethane. The product-containing fractions are evaporated to give 0.41 g of diethyl 2-{[4-(4-morpholinylmethyl)(tetrahydro-2H-pyran-4-yl)anilino]methylene}malonate as a tan oil.

A flask containing diethyl 2-{[4-(4-morpholinylmethyl)(tetrahydro-2H-pyran-4-yl)anilino]methylene}malonate (0.41 g) is treated with polyphosphoric acid (1.5 g). The reaction mixture is heated to 100° C. under a flow of nitrogen gas. After 1 hour the reaction is cooled to room temperature. The reaction mixture is carefully added to a vigorously stirred mixture of dichloromethane and saturated aqueous bicarbonate. The layers are separated and the basic aqueous layer is extracted with three additional portions of dichloromethane. The combined organic layers are washed with water, brine, dried over sodium sulfate and concentrated under reduced pressure. The residue is chromatographed on silica eluting with 2% to 6% methanol in dichloromethane to afford 0.24 g of ethyl 6-(4-morpholinylmethyl)-4-oxo-1-tetrahydro-2H-pyran4-yl-1,4-dihydro-3-quinolinecarboxylate as a tan solid.

A flask containing ethyl 6-(4-morpholinylmethyl)-4-oxo-1-tetrahydro-2H-pyran-4-yl-1,4-dihydro-3-quinolinecarboxylate (0.21 g) is treated with 4-chlorobenzylamine (2.0 mL). The reaction is tightly capped and heated to 190° C. for 1 hour. The reaction is cooled to room temperature, adsorbed onto silica and chromatographed on silica eluting with 2% to 6% methanol in dichloromethane and then by recrystallization from ethyl acetate to afford 0.14 g of the title compound.

Physical characteristics are as follows:

$^1$H NMR (DMSO-$d_6$) δ10.4, 8.8, 8.3, 8.1, 7.8, 7.4, 5.0, 4.5, 4.0, 3.7, 3.6, 3.5, 2.4, 2.0; MS (ESI+) m/z 496; Anal. Found: C, 65.20; H, 6.17; N, 8.23.

Example 109

N-(4-Chlorobenzyl)-1-(1-methyl-4-piperidinyl)-6-(4-morpholinylmethyl)-4-oxo-1,4-dihydro-3-quinolinecarboxamide (formula W-5; Z=NMe)

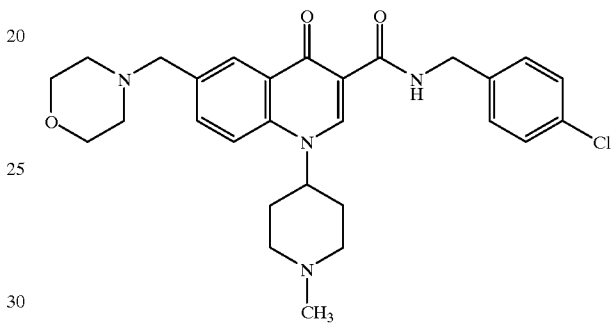

A flask containing 4-(4-aminobenzyl)morpholine from Preparation No. 22 (0.48 g) is treated with tetrhydrofuran (10 mL) and N-methyl-4-piperidone (0.37 mL) under an argon atmosphere. The solution is treated with acetic acid (0.20 mL) followed by sodium triacetoxyborohydride (0.80 g). After stirring overnight, the mixture is partitioned between diethyl ether and saturated aqueous sodium bicarbonate containing sodium hyroxide. The aqueous is back-extracted with additional portions of dichloromethane. The combined organic layer is washed with brine, dried over sodium sulfate, and concentrated under reduced pressure. The residue is purified by flash column chromatography on silica gel eluting with 2% to 5% methanol saturated with ammonia in dichloromethane to afford 0.52 g of 1-methyl-N-[4-(4-morpholinylmethyl)phenyl]-4-piperidinamine as a tan solid.

A flask containing 1-methyl-N-[4-(4morpholinylmethyl)phenyl]-4-piperidinamine (0.52 g) is treated with diethyl ethoxymethylenemalonate (0.55 mL). The flask is tightly capped and heated to 150° C. for 1 hour. The reaction is cooled to room temperature, treated with diethyl ethoxymethylenemalonate (0.55 mL) and heated to 180° C. for 2 hours. The reaction is cooled to room temperature and flash column chromatographed on silica eluting with 5% to 20% methanol in dichloromethane. The product-containing fractions are evaporated to give 0.75 g of diethyl 2-{[(1-methyl-4-piperidinyl)-4-(4-morpholinylmethyl)anilino]methylene}malonate as tan solid.

A flask containing diethyl 2-{[(1-methyl-4-piperidinyl)-4-(4-morpholinylmethyl)anilino]methylene}malonate (0.36 g) is treated with polyphosphoric acid (1.8 g). The reaction mixture is heated to 130° C. under a flow of nitrogen gas. After 4 hours the reaction is cooled to room temperature. The reaction mixture is carefully added to a vigorously stirred mixture of dichloromethane and saturated aqueous bicarbonate. The layers are separated and the basic aqueous layer is extracted with three additional portions of dichloromethane. The combined organic layers are washed with brine, dried over sodium sulfate and concentrated under reduced pressure to afford 0.32 g of crude ethyl 1-(1-methyl-4-piperidinyl)-6-(4-morpholinylmethyl)-4-oxo-1,4-dihydro-3-quinolinecarboxylate as a tan solid.

A flask containing crude ethyl 1-(1-methyl-4-piperidinyl)-6-(4-morpholinylmethyl)-4-oxo-1,4-dihydro-3-quinolinecarboxylate (0.31 g) is treated with 4-chlorobenzylarnine (2.0 mL). The reaction is tightly capped and heated to 165° C. overnight. The reaction is cooled to room temperature, adsorbed onto silica and chromatographed on silica eluting with 2% to 10% methanol saturated with ammonia in dichloromethane and then by recrystallization from ethyl acetate-hexanes to afford 0.11 g of the title compound.

Physical characteristics are as follows:
$^1$H NMR (DMSO-$d_6$) δ10.4, 8.8, 8.3, 8.0, 7.8, 7.4, 4.8, 4.5, 3.6, 3.5, 2.9, 2.4, 2.2, 2.0; MS (ESI+) m/z 509; Anal. Found: C, 65.71; H, 6.56; N, 10.85.

Example 110

N-(4-Chlorobenzyl)-6-(4-morpholinylmethyl)-4-oxo-1-(4-piperidinyl)-1,4-dihydro-3-quinolinecarboxamide (formula W-5; Z=NH)

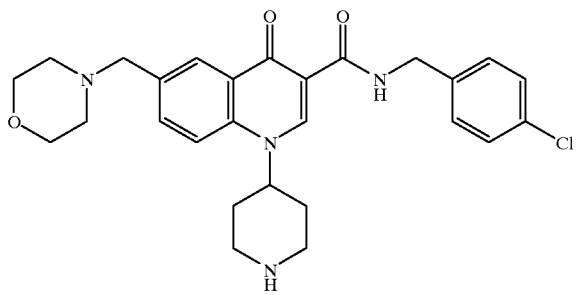

A flask containing 4-(4-aminobenzyl)morpholine from Preparation No. 22 (0.48 g) is treated with tetrahydrofuran (10 mL) and tert-butyl 4-oxo-1-piperidinecarboxylate (0.60 gm) under an argon atmosphere. The solution is treated with acetic acid (0.20 mL) followed by sodium triacetoxyborohydride (0.80 g). After stirring 3 days, the mixture is concentrated under reduced pressure. The residue is partitioned between dichloromethane and dilute aqueous sodium hydroxide. The aqueous is back-extracted with additional portions of dichloromethane. The combined organic layer is washed with brine, dried over sodium sulfate, and concentrated under reduced pressure. The residue is flash column chromatographed on silica gel eluting with 2% to 6% methanol in dichloromethane to afford 0.96 g of tert-butyl 4-[4-(4-morpholinylmethyl)anilino]-1-piperidinecarboxylate as a tan solid.

A flask containing tert-butyl 4-[4-(4-morpholinylmethyl)anilino]-1-piperidinecarboxylate (0.94 g) is treated with diethyl ethoxymethylenemalonate (1.0 mL). The flask is tightly capped and heated to 150° C. for 2 hours. The reaction is then heated to 175° C. for 2 hours. The reaction is cooled to room temperature and flash column chromatographed on silica eluting with 2% to 5% methanol in dichloromethane. The product-containing fractions are evaporated to give 0.78 g of diethyl 2-{[1-(tert-butoxycarbonyl)-4-piperidinyl]-4-(4-morpholinylmethyl)anilino]methylene}malonate as tan solid.

A flask containing a solution of diethyl 2-{[[1-(tert-butoxycarbonyl-4-piperidinyl]-4-(4-morpholinylmethyl)anilino]methylene}malonate (0.36 g) in toluene (2 mL) is treated with polyphosphoric acid (2.1 g). The reaction mixture is heated to 120° C. under a flow of nitrogen gas. After 1 hour the reaction is cooled to room temperature. The reaction mixture is carefully added to a vigorously stirred mixture of dichloromethane and saturated aqueous bicarbonate. The layers are separated and the basic aqueous layer is extracted with three additional portions of dichloromethane. The combined organic layers are washed with brine, dried over sodium sulfate and concentrated under reduced pressure to afford 0.14 g of crude ethyl 6-(4-morpholinylmethyl)-4-oxo-1-(4-piperidinyl)-1,4-dihydro-3-quinolinecarboxylate as a tan oil.

A flask containing crude ethyl 6-(4-morpholinylmethyl)-4-oxo-1-(4-piperidinyl)-1,4-dihydro-3-quinolinecarboxylate (0.14 g) is treated with 4-chlorobenzylamine (1.0 mL). The reaction is tightly capped and heated to 180° C. for 2 hours. The reaction is cooled to room temperature and flash column chromatographed on silica eluting with 2% to 10% methanol saturated with ammonia in dichloromethane and then by recrystallization from acetonitrile to afford 0.10 g of the title compound as a white solid.

Physical characteristics are as follows:
$^1$H NMR (DMSO-$d_6$) δ10.4, 8.8, 8.3, 8.1, 7.8, 7.4, 4.9, 4.5, 3.6, 3.5, 3.1, 2.8, 2.4, 2.0, 1.8; MS (ESI+) m/z 495; Anal. Found: C, 65.11; H, 6.38; N, 11.23.

Example 111

N-(4-Chlorobenzyl)-1-(1,1-dioxohexahydro-thiopyran-4-yl)-6-(4-morpholinylmethyl)-4-oxo-1,4-dihydro-3-quinolinecarboxamide (formula W-5; Z=SO$_2$)

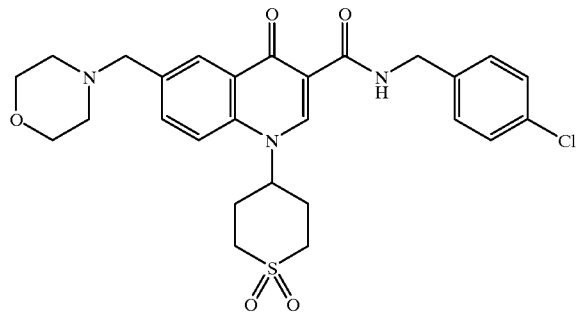

A flask containing 4-(4-aminobenzyl)morpholine from Preparation No. 22 (0.48 g) is treated with tetrahydrofuran (10 mL) and terahydrothiopyran-4-one (0.35 gm) under an argon atmosphere. The solution is treated with acetic acid (0.20 mL) followed by sodium triacetoxyborohydride (0.80 g). After stirring overnight, the mixture is concentrated under reduced pressure. The residue is partitioned between dichloromethane and dilute aqueous sodium hydroxide. The aqueous is back-extracted with dichloromethane. The combined organic layers are washed with brine, dried over sodium sulfate, and concentrated under reduced pressure. The residue is purified by flash column chromatography on silica eluting with 2% to 6% methanol in dichloromethane and then by recrystallization from cyclohexane to afford 0.53 g of N-[4-(4-morpholinylmethyl)phenyl]tetrahydro-2H-thiopyran-4-amine as a tan solid.

A flask containing N-[4-(4-morpholinylmethyl)phenyl]tetrahydro-2H-thiopyran-4-amine (0.44 g) is treated with diethyl ethoxymethylenemalonate (0.35 mL). The flask is tightly capped and heated to 160° C. for 2 hours. The reaction is cooled to room temperature, treated with diethyl ethoxymethylenemalonate (0.35 mL) and pyridine (0.35 mL) and heated to 150° C. for 1 hour in a tightly sealed flask. The reaction is cooled to room temperature and azeotroped under reduced pressure with toluene (3×). The residue is flash column chromatographed on silica gel eluting with ethyl acetate. The product-containing fractions are evaporated to give 0.59 g of diethyl 2-{[4-(4-morpholinylmethyl)(tetrahydro-2H-thiopyran-4-yl)anilino]methylene}malonate as a tan solid.

A solution of diethyl 2-{[4-(4-morpholinylmethyl)(tetrahydro-2H-thiopyran-4-yl)anilino]methylene}malonate (0.30 gm) in dichloromethane (5 mL) at 0° C. is treated with p-toluenesulfonic acid hydrate (0.57 gm) followed by m-chloroperoxybenzoic acid (~85 %) (0.32 gm). The mixture is stirred for 3 hr. The reaction mixture is diluted with dichloromethane, washed with saturated aqueous sodium sulfite, saturated aqueous sodium bicarbonate, brine, dried ($Na_2SO_4$) and concentrated under reduced pressure. The crude product is purified by flash column chromatography on silica gel eluting with 2% to 6% methanol in dichloromethane to afford 0.12 gm of 4-[4-(4-morpholinylmethyl)anilino]tetrahydrothiopyran-1,1(2H)-dione as a white solid.

A flask containing 4-[4-(4-morpholinylmethyl)anilino]tetrahydro-thiopyran-1,1(2H)-dione (0.11 g) is treated with diethyl ethoxymethylenemalonate (0.15 mL). The flask is tightly capped and heated to 155° C. for 2 hours. The reaction is cooled to room temperature, treated with diethyl ethoxymethylenemalonate (0.15 mL) and pyridine (0.15 mL) and heated to 120° C. for 2 hour in a tightly sealed flask. The reaction is cooled to room temperature and azeotroped under reduced pressure with toluene (3×). The residue is treated with diethyl ethoxymethylenemalonate (0.5 mL) and heated to 190° C. After 2 hours, the reaction is cooled to room temperature and flash column chromatographed on silica gel eluting with 2% to 6% methanol in dichloromethane. The product-containing fractions are evaporated to give 0.11 g of diethyl 2-{[(1,1-dioxohexahydrothiopyran-4-yl)-4-(4-morpholinylmethyl)anilino]methylene}malonate as a tan solid.

A flask containing a solution of diethyl 2-{[(1,1-dioxohexahydro-thiopyran-4-yl)-4-(4-morpholinylmethyl)anilino]methylene}malonate (0.11 g) in toluene (2 mL) is treated with polyphosphoric acid (1.5 g). The reaction mixture is heated to 120° C. under a flow of nitrogen gas. After 2 hours the reaction is cooled to room temperature. The reaction mixture is carefully added to a vigorously stirred mixture of dichloromethane and saturated aqueous bicarbonate. The layers are separated and the basic aqueous layer is extracted with two additional portions of dichloromethane. The combined organic layers are washed with brine, dried over sodium sulfate and concentrated under reduced pressure. The residue is purified by flash column chromatography on silica gel eluting with 2% to 10% methanol in dichloromethane to afford 0.06 g of crude ethyl 1-(1,1-dioxohexahydro-thiopyran-4-yl)-6-(4-morpholinylmethyl)-4-oxo-1,4-dihydro-3-quinolinecarboxylate as an off-white solid.

A flask containing ethyl 1-(1,1-dioxohexahydro-thiopyran-4-yl)-6-(4-morpholinylmethyl)-4-oxo-1,4-dihydro-3-quinolinecarboxylate (0.06 g) is treated with 4-chlorobenzylamine (0.6 mL). The reaction is tightly capped and heated to 190° C. for 2 hours. The reaction is cooled to room temperature, adsorbed onto silica gel, flash column chromatographed on silica eluting with 2% to 10% methanol in dichloromethane. The product-containing fractions are concentrated under reduced pressure and triturated with diethyl ether. The resulting residue is dissolved in a small amount of dichloromethane and added dropwise to stirring diethyl ether (40 mL). The resulting precipitant is collected by suction filtration to afford 0.05 g of the title compound as an off-white solid.

Physical characteristics are as follows:
$^1$H NMR (DMSO-$d_6$) δ10.3, 8.7, 8.3, 8.0, 7.8, 7.4, 5.3, 4.5, 3.6, 3.5, 3.3, 2.4; MS (ESI+) m/z 544; HRMS (FAB) found 544.1665 for $C_{27}H_{30}ClN_3O_5S$+H.

Preparation 53

4-(3-bromo-4-fluorobenzyl)morpholine

Morpholine (0.96 mL) and acetic acid (0.57 mL) are added to a solution of 3-bromo-4-fluorobenzaldehyde (2.03 g) in dichloroethane (40 mL). Sodium triacetoxyborohydride (3.18 g) is added in portions over an hour, and the reaction is stirred at room temperature for 18 hours. The reaction is quenched with a 1 N solution of NaOH (10 mL) and diluted with $CH_2Cl_2$ (100 mL). The organic layer is washed with 1 N NaOH (3×35 mL). The aqueous layers are back-extracted with $CH_2Cl_2$ (20 mL). The combined organic layers are extracted with 0.1 N HCl (6×25 mL). The combined aqueous layers are basified (pH=12) with 2 N NaOH, and the product is extracted with $CH_2Cl_2$ (6×25 mL). The combined organic layers are washed with brine (20 mL) and dried ($MgSO_4$). The solution is concentrated in vacuo to afford 2.23 g (82%) of the title compound as a clear, colorless oil.

Physical characteristics are as follows:
$^1$H NMR (DMSO-$d_6$) δ 7.62, 7.35, 7.32, 3.57, 3.45, 2.34; HRMS (FAB) calcd for $C_{11}H_{13}BrFNO$+H 274.0243, found 274.0243. Anal. Found for $C_{11}H_{13}BrFNO$: C, 48.15; H, 4.83; N, 5.10.

Preparation 54

1-[2-Fluoro-5-(4-morpholinylmethyl)phenyl]-1-ethanone

A solution of 4-(3-bromo-4-fluorobenzyl)morpholine (35.5 g) of Preparation No. 53 in THF (400 mL) is cooled to −75° C., and n-butyllithium is added via addition funnel maintaining the temperature below −65° C. A solution of N-methyl-N-methoxyacetamide (16.0 g, prepared as described in *Tetrahedron Lett.* 1983, 24, 1857) in THF (50 mL) is added via addition funnel, again maintaining temperature below −65° C. The reaction is stirred at −75° C. for 1 hour and then is allowed to warm to room temperature overnight. The reaction mixture is quenched with 1 N HCl (150 mL) and diluted with ethyl acetate (400 mL). The layers are separated, and the aqueous layer is basified with sat. sodium bicarbonate solution. The aqueous layer is extracted with ethyl acetate (2×100 mL). The combined organic layers are washed with sat. sodium bicarbonate (2×100 mL) and brine (50 mL). The aqueous layers are back-extracted with ethyl acetate (100 mL). The combined organic layers are dried ($Na_2SO_4$) and concentrated in vacuo to a yellow oil. The oil is purified by fractional distillation at 135–140° C./0.3 torr to afford 19.7 g (64%) of the title compound as a clear, colorless oil.

Physical characteristics are as follows:

$^1$H NMR (DMSO-$d_6$) δ7.72, 7.58, 7.31, 3.56, 3.48, 2.58, 2.34; IR (liq.) 2421, 2259, 1996, 1979, 1919, 1688, 1612, 1492, 1417, 1361, 1291, 1281, 1212, 1118, 865 cm$^{-1}$; MS (ESI+) m/z 238 (M+H)$^+$. Anal. Found for $C_{13}H_{16}FNO_2$: C, 65.43; H, 6.75; N, 5.84.

Preparation 55

Ethyl 3-[2-Fluoro-5-(4-morpholinylmethyl)phenyl]-3-oxopropanoate

A solution of 1-[2-fluoro-5-(4-morpholinylmethyl) phenyl]-1-ethanone (19.6 g) of Preparation No. 54 in diethyl carbonate (150 mL) is cooled to 0° C., and sodium hydride (60% dispersion, 6.6 g) is added slowly to the reaction mixture. The reaction is stirred at 0° C. for 3 hours, and then is allowed to warm to room temperature overnight. The reaction mixture is quenched with acetic acid (10 mL), diluted with water (200 mL) and then basified with sat. sodium carbonate. The solution is then extracted with ether (3×200 mL). The combined organic layers are washed with sat. sodium bicarbonate (100 mL) and brine (50 mL). The combined aqueous layers are back-extracted with ether (50 mL). The combined organic layers are then dried (Na$_2$SO$_4$) and concentrated in vacuo to an orange oil. The crude product is purified in 2 batches by column chromatography (heptane/IPA, 8/1; 4/1) to afford 20.2 g (79%) of the title compound as a yellow oil.

Physical characteristics are as follows:

$^1$H NMR (DMSO-$d_6$) δ7.78, 7.62, 7.32, 4.21, 4.05, 3.57, 3.50, 2.34, 1.16; IR (liq.) 2419, 2261, 1996, 1979, 1744, 1689, 1626, 1611, 1493, 1331, 1260, 1215, 1147, 1117, 865, cm$^{-1}$; MS (ESI+) m/z 310 (M+H)$^+$; Anal. Calcd for $C_{16}H_{20}FNO_4$: C, 62.12; H, 6.52; N, 4.53. Found: C, 61.96; H, 6.67; N, 4.44.

Preparation 56

Ethyl 1-(4-Morpholinyl)-6-(4-morpholinylmethyl)-4-oxo-1,4-dihydro-3-quinolinecarboxylate

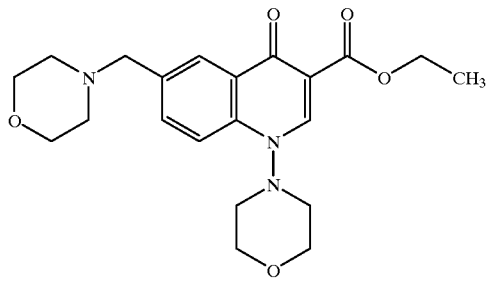

Ethyl 3-[2-fluoro-5-(4-morpholinylmethyl)phenyl]-3-oxopropanoate (10.0 g) of Preparation No. 55, triethylorthoformate (10.8 mL) and acetic anhydride (10.7 mL) are combined in a flask equipped with a Dean-Stark trap and condenser. The reaction is heated to 150° C. for 3.5 hours. The excess acetic anhydride and triethylorthoformate are distilled off at 100° C. and 0.2 torr leaving a burgundy oil containing a mixture of E- and Z-isomers of ethyl-3-ethoxy-2-[2-fluoro-5-(4-morpholinylmethyl)benzoyl]-2-propenoate.

This crude mixture is dissolved in ethanol (50 mL), and 4-aminomorpholine (4.7 mL) is added. The reaction mixture is stirred at room temperature for 2.5 hours and concentrated in vacuo. The resulting burgundy oil is purified in two batches by column chromatography (MeOH/CH$_2$Cl$_2$: 1%, 2%; 5%) to give ethyl (E)- and (Z)-2-[2-fluoro-5-(4-morpholinylmethyl)benzoyl]-3-(4-morpholinylamino)-2-propenoate as a yellow oil.

The crude enamine is dissolved in THF, and sodium hydride is slowly added to the solution. After heating the mixture to 70° C. for 2 hours, the reaction is quenched with water (5 mL) and concentrated in vacuo to a burgundy slurry. More water (100 mL) is added, and the remaining THF removed in vacuo. The resulting yellow precipitate suspended in an aqueous solution is filtered on a fritted funnel and washed twice with water and once with ether to afford 5.9 g (55%) of the title compound as a powdery, yellow solid.

Physical characteristics are as follows:

Mp 209–211° C.; $^1$H NMR (DMSO-$d_6$) δ8.87, 8.20, 8.11, 7.74, 4.23, 3.97, 3.78, 3.59, 3.57, 3.03, 2.37, 1.30; MS (ESI+) m/z 402 (M+H)$^+$; Anal. Found for $C_{21}H_{27}N_3O_5$: C, 62.83; H, 6.75; N, 10.44.

Example 112

N-(4-Chlorobenzyl)-1-(4-morpholinyl)-6-(4-morpholinylmethyl)-4-oxo-1,4-dihydro-3-quinolinecarboxamide

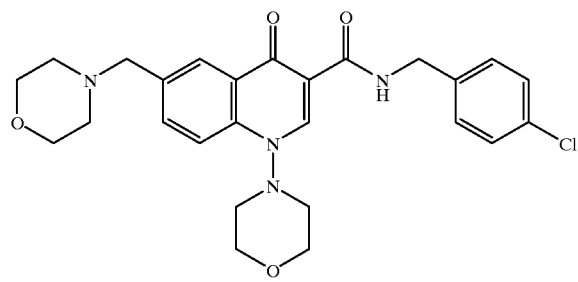

Ethyl 1-(4-morpholinyl)-6-(4-morpholinylmethyl)-4-oxo-1,4-dihydro-3-quinolinecarboxylate (5.0 g) from Preparation No. 56 and 4-chlorobenzylamine (7.6 mL) are combined and heated to 190° C. for 7 hours. After cooling to room temperature, the mixture solidifies. The solid is triturated with a 10:1 mixture of EtOAc/MTBE (30 mL) and filtered on a frit. The crude solid is triturated again, this time with a hot mixture of 10:1 EtOAc/MTBE (110 mL). The suspension is cooled to room temperature and filtered on a frit to afford 4.9 g (79%) of the title compound as a white solid.

Physical characteristics are as follows:

Mp 195–196° C.; $^1$H NMR (DMSO-$d_6$) δ10.30, 9.14, 8.28, 8.20, 7.81, 7.40, 4.56, 3.98, 3.80, 3.62, 3.57, 3.28, 3.08, 2.37; IR (mull) 2286, 1969, 1952, 1926, 1652, 1599, 1585, 1524, 1489, 1352, 1283, 1111, 862, 808, 724 cm$^{-1}$; MS (ESI+) for m/z 497 (M+H)$^+$. Anal. Found for $C_{26}H_{29}ClN_4O_4$: C, 62.69; H, 5.94; N, 11.22; Cl, 7.11.

Example 113

N-(4Chlorobenzyl)-1-(4methyl-1-piperazinyl)-6-(4-morpholinylmethyl)-4-oxo-1,4-dihydro-3-quinolinecarboxamide

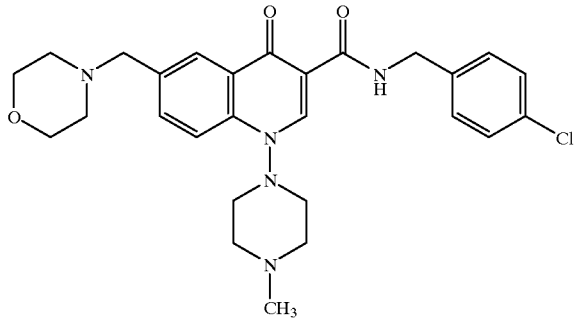

The title compound is prepared according to procedures analogous to those described in Preparation No. 56 employing 1-amino-4-methylpiperazine and Example No. 112. The crude product is purified by recrystallization in EtOH to afford 0.87g of the title compound as a white solid.

Physical characteristics are as follows:

Mp 135–139° C.; $^1$H NMR (DMSO-$d_6$) δ10.32, 8.97, 8.18, 7.80, 7.36, 4.54, 3.59, 3.55, 3.21, 3.05, 2.88, 2.36, 2.27; IR (drift) 2796, 2309, 1934, 1659, 1597, 1568, 1544, 1489, 1352, 1323, 1289, 1115, 1008, 865, 809 cm$^{-1}$; MS (ESI+) m/z 510 (M+H)$^+$. HRMS (FAB) calcd for $C_{27}H_{32}ClN_5O_3$+H 510.2272, found 510.2290. Anal. Found for $C_{27}H_{32}ClN_5O_3$: C, 63.59; H, 6.40; N, 13.33; Cl, 6.86.

Example 114

N-(4-Chlorobenzyl)-6-(4-morpholinylmethyl)-4-oxo-1-(1-piperidinyl)-1,4-dihydro-3-quinolinecarboxamide

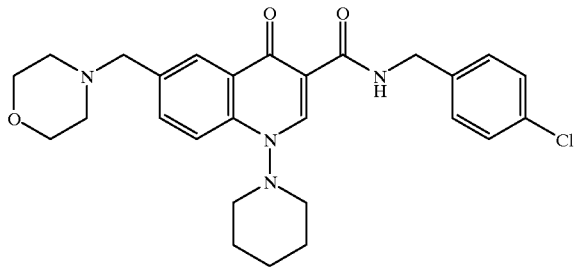

The title compound is prepared according to procedures analogous to those described in Preparation No. 56 employing 1-aminopiperadine and Example No. 112. The crude product is purified by recrystallization in acetonitrile to afford 0.73 g of the title compound as a white solid.

Physical characteristics are as follows:

Mp 161–164° C.; $^1$H NMR (DMSO-$d_6$) δ10.38, 9.07, 8.22, 8.20, 7.81, 7.40, 4.56, 3.61, 3.57, 3.10, 2.37, 1.81, 1.40; IR (drift) 2942, 2853, 1657, 1597, 1574, 1549, 1531, 1488, 1354, 1326, 1291, 1115, 807, 796, 680 cm$^{-1}$; MS (ESI+) for m/z 495 (M+H)$^+$; Anal. Calcd for $C_{27}H_{31}ClN_4O_3$: C, 65.51; H, 6.31; N, 11.32; Cl, 7.16. Found: C, 65.50; H, 6.23; N, 11.40; Cl,7.19.

Example 115

N-(4-Chlorobenzyl)-6-(4-morpholinylmethyl)-4-oxo-1-(1-pyrrolidinyl)-1,4-dihydro-3-quinolinecarboxamide

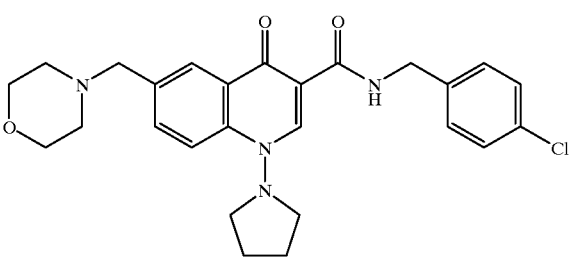

The title compound is prepared according to procedures analogous to those described in Preparation No. 56 employing 1-amiinopyrrolidine and Example No. 112. The crude product is purified by recrystallization in methanol to afford 0.39 g of the title compound as a white solid.

Physical characteristics are as follows:

Mp 211–214° C.; $^1$H NMR (DMSO-$d_6$) δ) 10.35, 9.08, 8.16, 8.13, 7.78, 7.36, 4.54, 3.59, 3.55, 3.14, 2.35, 2.05, 1.93; IR (drift) 2857, 2805, 1966, 1944, 1655, 1600, 1576, 1545, 1488, 1361, 1324, 1134, 1113, 863, 809 cm$^{-1}$; MS (ESI+) for m/z 481 (M+H)$^+$; Anal. Found for $C_{26}H_{29}ClN_4O_3$: C, 64.57; H, 6.13; N, 11.53; Cl, 7.19.

Example 116

N-(4-Chlorobenzyl)-1-[(2R)-2-(methoxymethyl)pyrrolidinyl]-6-(4-morpholinylmethyl)-4-oxo-1,4-dihydro-3-quinolinecarboxamide

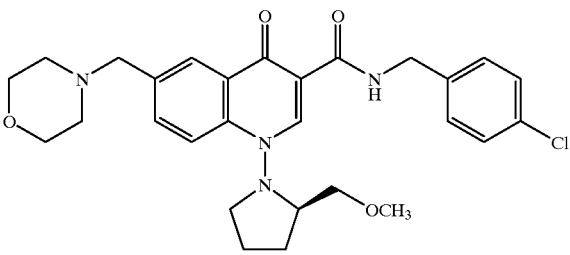

The title compound is prepared according to procedures analogous to those described in Preparation No. 56 employing (R)-(+)-1-amino-2-(methoxymethyl)pyrrolidine and Example No. 112. The crude product is purified by column chromatography (MeOH/$CH_2Cl_2$: 0.5%, 1.5%, 2.5%) and trituration with ether to afford 0.79 g of the title compound as a white solid.

Physical characteristics are as follows:

MP 98–100° C.; $^1$H NMR (DMSO-$d_6$) δ) 10.35, 9.15, 8.22, 8.18, 7.77, 7.39, 4.56, 3.61, 3.57, 3.39, 3.25, 2.89, 2.37, 2.16, 2.01, 1.70; IR (drift) 2350, 1663, 1597, 1580, 1549, 1488, 1351, 1325, 1203, 1116, 1093, 867, 831, 807, 800 cm$^{-1}$; HRMS (FAB) calcd for $C_{28}H_{33}ClN_4O_4$+H 525.2268, found 525.2275.

Example 117

N-(4-Chlorobenzyl)-1-(dimethylamino)-6-(4-morpholinylmethyl)-4-oxo-1,4-dihydro-3-quinolinecarboxamide

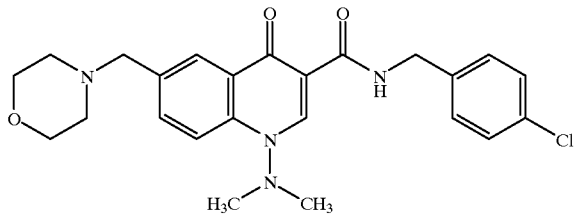

The title compound is prepared according to procedures analogous to those described in Preparation No. 56 employing 1,1-dimethylhydrazine and Example No. 112. The crude product is purified by recrystallization in methanol to afford 0.2 g of the title compound as a white solid.

Physical characteristics are as follows:

Mp 170–171° C.; $^1$H NMR (DMSO-$d_6$) δ10.38, 9.10, 8.20, 8.14, 7.82, 7.39, 4.57, 3.61, 3.57, 2.92, 2.37; IR (drift) 1962, 1932, 1661, 1597, 1551, 1489, 1462, 1360, 1352, 1323, 1113, 913, 866, 811, 804 cm$^{-1}$; MS (ESI+) for m/z 455 (M+H)$^+$; HRMS (FAB) calcd for $C_{24}H_{27}ClN_4O_3$+H 455.1850, found 455.1857.

Preparation 57

1-Amino-N-(4-chlorobenzyl)-6-iodo-4-oxo-1,4-dihydro-3-quinolinecarboxamide

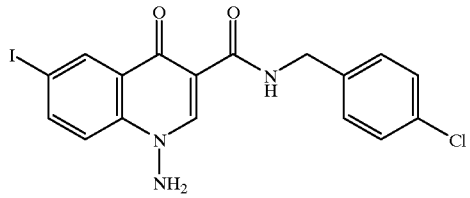

A suspension of N-(4-chlorobenzyl)-4-hydroxy-6-iodo-3-quinolinecarboxamide (2.0 g) of Preparation No. 4 and of potassium carbonate (2.0 g) in DMF (40 mL) is stirred at room temperature for 5 hrs and then treated with of O-(mesitylsulfonyl)hydroxylamine (1.5 g). After 24 hrs, the solvent is evaporated under reduced pressure and the residue is diluted with water(150 mL). The resulting solid is filtered and washed with water (3x) and ether (2x). Recrystallization from hot acetic acid/water affords 1.35 g of the title compound as a tan solid.

Physical characteristics are as follows:

Mp 230–235° C. (dec). $^1$H NMR (DMSO-$d_6$) δ8.81, 8.54, 8.13, 7.89, 7.40–7.32, 6.69, 4.54.

Example 118

1-Amino-N-(4-chlorobenzyl)-6(3-hydroxy-1-propynyl)-4-oxo-1,4-dihydro-3-quinolinecarboxamide

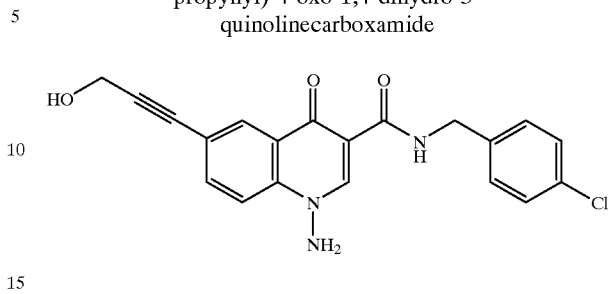

1-Amino-N-(4-chlorobenzyl)-6-iodo-4-oxo-1,4-dihydro-3-quinolinecarboxamide (0.25 g) from Preparation No. 57, copper (I) iodide (32 mg), and bis(triphenylphosphine) palladium (II) chloride (19 mg) are suspended in diethylamine (8 mL). Propargyl alcohol (39 μL) is added and the mixture is allowed to stir at room temperature for 16 h. The mixture is diluted with ethanol and then concentrated in vacuo. The crude solid is triturated with dichloromethane and recrystallized in acetic acid to affording 76 mg of the title compound as a beige solid.

Physical properties are as follows:

Mp 230–235° C. (dec); $^1$H NMR (DMSO-$d_6$) δ10.25, 8.79, 8.22, 8.07, 7.85, 7.35, 6.70, 5.39, 4.52, 4.32; HRMS (FAB) calcd for $C_{20}H_{16}ClN_3O_3$+H 382.0958, found 382.0952;

Example 119

1-Amino-N-(4-chlorobenzyl)-6-(3-hydroxypropyl)-4-oxo-1,4-dihydro-3-quinolinecarboxamide

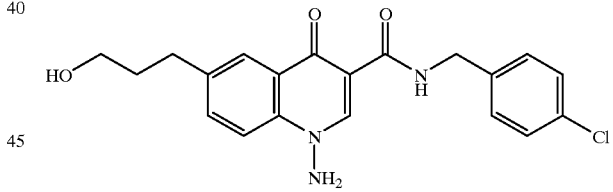

1-Amino-N-(4-chlorobenzyl)-6-(3-hydroxy-1-propynyl)-4-oxo-1,4-dihydro-3-quinolinecarboxamide (0.21 g) from Example No. 118 is dissolved in a 1:1 mixture of methanol/DMF. To the solution is added 5% platinum on carbon (0.11 g) and acetic acid (0.5 mL). The reaction is shaken under a hydrogen atmosphere (35 psi) for 4.5 hours. The catalyst is removed by filtration through Celite. The filtrate is concentrated in vacuo, and the resulting white solid is triturated with dichloromethane. The crude product is then purified by column chromatography (MeOH/CH$_2$Cl$_2$: 3%, 5%) yielding 0.10 g of the title compound as a white solid.

Physical properties are as follows:

Mp 187–188° C.; $^1$H NMR (DMSO-$d_6$) δ10.44, 8.77, 8.06, 7.98, 7.71, 7.36, 6.67, 4.54, 4.50, 3.40, 2.77, 1.74; IR (drift) 3272, 3183, 2941, 1916, 1644, 1598, 1559, 1491, 1433, 1242, 1093, 842, 805, 740, 724 cm$^{-1}$; HRMS (FAB) calcd for $C_{20}H_{20}ClN_3O_3$+H 386.1271, found 386.1282.

151

Preparation 58

Butyl 1-(Dimethylamino)-6-iodo-4-oxo-1,4-dihydro-3-quinolinecarboxylate

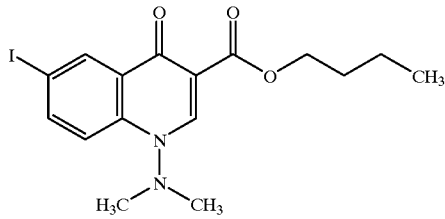

A solution of of the TBDMS ketene acetal of butyl acetate (8.1 g) and triethylamine (5.6 mL) in THF (20 mL) is added in one portion to a solution of 2-chloro-5-iodobenzoyl chloride in THF (40 mL). The mixture is stirred 24 h and then the solvent was evaporated in a stream of nitrogen. The residue is diluted with ether (30 mL) and filtered. The resulting filtrate is concentrated to afford 8.2 g of an oil which is dissolved in THF (100 mL) and treated with of 3 N hydrochloric acid (10 mL). After 5 h the volume of this mixture is reduced by two thirds by evaporation at reduced pressure. The residue is diluted with dichloromethane (100 mL). The phases are separated and the organic layer dried over $MgSO_4$. The mixture is filtered and dissolved in toluene. The solvent was evaporated and the process was repeated until TBDMS is no longer detectable in the mixture by $^1H$ NMR. The residual oil is purified by column chromatography (gradient 30–45% dichloromethane in hexanes) to afford 7.9 g of butyl 3-(2-chloro-5-iodophenyl)-3-oxopropanoate as an orange oil.

A mixture of the above ketoester (3.3 g) and ethyl orthoformate (2.2 mL) in acetic anhydride (2 mL) is refluxed for 2 h. The excess triethyl orthoformate and acetic anhydride are removed by evaporation at reduced pressure followed by concentration from xylene (75 mL) to afford butyl 2-(2-chloro-5-iodobenzoyl)-3-ethoxy-2-propenoate as a crude oil.

Dimethylhydrazine (1.1 mL) is added to a solution of the above crude enol ether (4.0 g) in ethanol (10 mL). The mixture is allowed to stirr for 4 h. The reaction mixture is then concentrated to afford 4 g of butyl 2-(2-chloro-5-iodobenzoyl)-3-(2,2-dimethylhydrazino)-2-propenoate as an amber oil.

The above hydrazide is dissolved in dioxane (50 mL) and treated with sodium hydride (0.6 g, 60% in mineral oil). The mixture is refluxed 2 hours, cooled to room temperature, and is filtered washing with absolute ethanol (2×10 mL). The combined filtrate and washes are briefly refluxed with 5 g of DARCO, and the solution is filtered through Celite. The solvent was evaporated at reduced pressure, and the residue is purified by column chromatography (gradient 5–15% ethyl acetate in dichloromethane) to afford 1.2 g of the title compound as a white solid.

Physical characteristics are as follows:

$^1H$ NMR (DMSO-$d_6$) δ8.87, 8.43, 8.06, 7.86, 4.18, 2.85, 1.70–1.55, 1.50–1.30, 0.91; MS (ESI+) m/z 415 (M+H$^+$).

152

Example 120

N-(4-Chlorobenzyl)-1-(dimethylamino)-6-(3-hydroxy-1-propynyl)-4-oxo-1,4-dihydro-3-quinolinecarboxamide

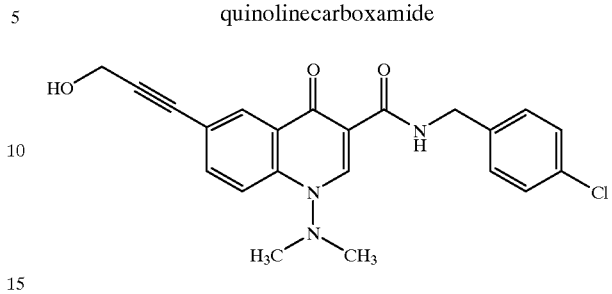

Butyl 1-(dimethylamino)-6-iodo-4-oxo-1,4-dihydro-3-quinolinecarboxylate (0.50 g) from Preparation No. 58 and 4-chlorobenzylamine (0.29 mL) are heated to 170° C. for 7 hours. The reaction is cooled to rt, and the crude solid is recrystallized in acetic acid yielding 0.54 g of the amide. The resulting amide (0.25 g), copper (I) iodide (30 mg), and bis(triphenylphosphine)palladium (II) chloride (18 mg) are suspended in diethylamine (8 mL). Propargyl alcohol (36 μL) is added and the mixture is allowed to stir at room temperature for 16 h. The mixture is diluted with ethanol and then concentrated in vacuo. The crude solid is triturated with dichloromethane and purified by column chromatography (2% MeOH/$CH_2Cl_2$), affording 9 mg of the title compound as a beige solid.

Physical properties are as follows:

Mp 210–214° C.; $^1H$ NMR (DMSO-$d_6$) δ10.52, 9.34, 8.50, 8.39, 8.05, 7.62, 5.64, 4.83, 4.63, 3.19; IR (drift) 2225, 1928, 1912, 1646, 1592, 1572, 1549, 1486, 1462, 1357, 1346, 1032, 1026, 836, 806 cm$^{-1}$; HRMS (FAB) calcd for $C_{22}H_{20}ClN_3O_3$+H 410.1271, found 410.1283.

Preparation 59

Ethyl 1-(Dimethylamino)-4-oxo-1,4-dihydro-3-quinolinecarboxylate

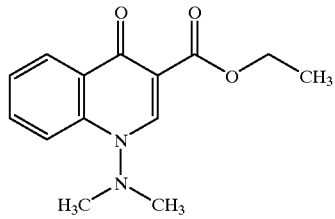

Ethyl 3-(2-fluorophenyl)-3-oxopropanoate (15.0 g) is refluxed with triethylorthoformate (17.8 mL) in acetic anhydride (16.8 mL) for 4 hrs. The reaction mixture is diluted with xylenes (75 mL) and is concentrated under reduced pressure to give 19.1 g of an amber oil. A solution of this oil (4.0 g) in ethanol (10 mL) is treated with 1,1-dimethylhydrazine (1.1 mL) and stirred for 10 min. The reaction mixture is concentrated and agitated with 4:1 hexanes/ether. The solvent is decanted, and the final traces of solvent are removed at high vacuum to leave an amber oil of ethyl 3-(2,2-dimethylhydrazino)-2-(2-fluorobenzoyl)-2-propenoate.

The resulting hydrazide (4.0 g) is dissolved in dioxane (20 mL) and treated with 60% sodium hydride in oil (0.60 g).

The mixture is refluxed under nitrogen for 2 hrs and then cooled to 25° C. The reaction mixture is diluted with ethanol (10 mL) and water (75 mL) and is then extracted with ethyl acetate (3×75 mL). The organic phases are combined, washed with brine, dried with calcium chloride and filtered. The volume of the filtrate is reduced by evaporation at reduced pressure almost to dryness, and the residue is diluted with diethyl ether (150 mL). The solid is filtered and washed with diethyl ether (2×20 mL) to afford 0.75 g of ethyl 1-(dimethylamino)-4-oxo-1,4-dihydro-3-quinolinecarboxylate as an orange solid.

Physical characteristics are as follows:

Mp 119–120° C.; $^1$H NMR (DMSO-d$_6$) δ8.89, 8.19, 8.09, 7.79, 7.47, 4.24, 3.30, 1.29; MS (ESI+) m/z 283 (M+Na$^+$); HRMS (FAB): calcd for $C_{14}H_{17}N_2O_3$+H$^+$: 261.1239. Found: 261.1234.

Example 121

N-(4-Chlorobenzyl)-1-(dimethylamino)-4-oxo-1,4-dihydro-3-quinolinecarboxamide

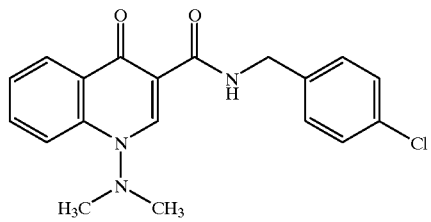

Ethyl 1-(dimethylamino-4-oxo-1,4-dihydro-3-quinolinecarboxylate (0.21 g) of Preparation No. 59 and 4-chlorobenzylamine (1.2 mL) are heated to 180° C. for 10 hrs under nitrogen. The product is precipitated from the cooled reaction mixture by dilution with a mixture of toluene and hexanes. The crude product is then recrystallized from aqueous acetic acid to give 0.030 g of the title compound.

Physical characteristics are as follows:

Mp 170–172° C.; $^1$H NMR (DMSO-d$_6$) δ10.3, 9.1, 8.3, 8.2, 7.9, 7.5, 7.4, 4.6, 2.9; MS (FAB)(M+H)$^+$: calcd 356.1165, found 356.1173.

Preparation 60

Ethyl 1-(Allyloxy-4-oxo-1,4-dihydro-3-quinolinecarboxylate

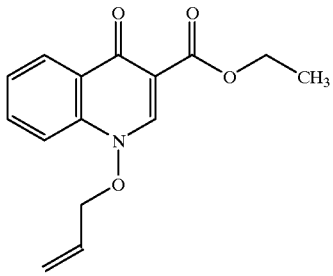

O-Allylhydroxylamine hydrate (1.52 g) is dissolved in ethanol (50 mL) and treated with 3 N aqueous sodium hydroxide until a phenolphthalien endpoint is achieved. Ethyl 3-ethoxy-2-(2-fluorobenzoyl)-2-propenoate (3.7 g, prepared from ethyl 3-(2-fluorophenyl)-3-oxopropanoate as in Preparation No. 59) is added, and the mixture is stirred for 3 h. The mixture is filtered and the resulting filtrate is concentrated. The crude enamine intemediate is treated with sodium hydride in refluxing dioxane according to the procedures analogous to those described in Preparation No. 58. The crude product is is purified by column chromatography (30–40% ethyl acetate in dichloromethane). Fractions containing the major product are combined and concentrated at reduced pressure. The residue is dissolved in a minimum volume of ethyl acetate and stored at −15° C. overnight followed by the addition of ether (20 mL) and cyclohexane (20 mL). The solid is collected by filtration and washed with two portions of ether to afford 1.0 g of the title compound as a pale yellow solid.

Physical characteristics are as follows:

Mp 98–100° C. $^1$H NMR (DMSO-d$_6$) δ8.89, 8.20, 7.85, 7.76, 7.51, 6.3–6.1, 5.50, 5.42, 4.88, 4.22, 1.28; MS (ESI+) m/z 296 (M +H$^+$). Anal. Found for $C_{15}H_{15}NO_4$: C, 65.80; H, 5.64; N, 5.09.

Example 122

1-(Allyloxy)-N-(4-chlorobenzyl)-4-oxo-1,4-dihydro-3-quinolinecarboxamide

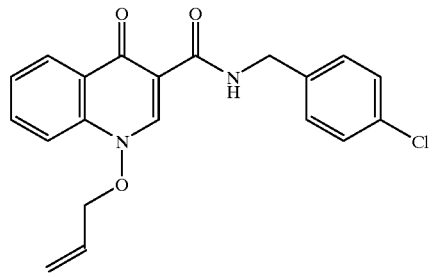

Ethyl 1-(allyloxy)-4-oxo-1,4-dihydro-3-quinolinecarboxylate (0.5 g) of Preparation No. 60 is treated with sodium hydroxide (3 N, 2 mL) in ethanol (2 mL) and stirred for 30 min. The reaction mixture is neutralized with hydrochloric acid and filtered, washing the filtrant with water (3×) and ether (1×). The crude carboxylic acid is dried in a stream of air to give 0.31 g of a white powder which is suspended in DMF (15 mL) and treated with 1,1'-carbonyldiimidazole (0.46 g). The reaction mixture is heated to 65° C. for 5 hrs, cooled and treated with H$_2$O (0.03 mL). After 5 minutes, 4-chiorobenzylamine (0.19 mL) is added. The mixture is stirred for 3 days, diluted with water (15 mL) and filtered to afforded 0.19 g of the title compound as a white solid.

Physical characteristics are as follows:

Mp 113–114° C.; $^1$H NMR (DMSO-d$_6$) δ10.3, 9.0, 8.3, 7.9, 7.6, 7.4, 6.2, 5.5, 5.4, 4.9, 4.5; MS (FAB)(M+H)$^+$: calcd 369.1006, found 369.1000.

Example 123

N-(4-Chlorobenzyl)-1-methoxy-4-oxo-1,4-dihydro-3-quinolinecarboxamide

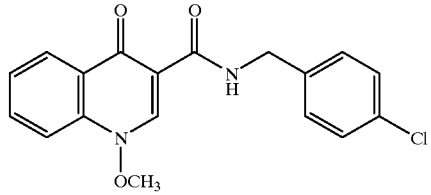

Ethyl 3-ethoxy-2-(2-fluorobenzoyl)-2-propenoate (4.0 g, prepared from ethyl 3-(2-fluorophenyl)-3-oxopropanoate as in Preparation No. 59) and O-methylhydroxylamine (16 mmol, prepared by mixing 1 eq of sodium ethoxide with 1 eq of O-methylhydroxylamine hydrochloride in ethanol) are stirred in ethanol (20 mL) for 1 hour at rt. The mixture is concentrated, diluted with dioxane (75 mL) and re-concentrated to remove any remaining ethanol. The resulting enamine is diluted in dioxane (70 mL) and sodium hydride (60% dispersion, 0.64 g) is added. The mixture is heated to reflux for 2.5 hours, cooled to rt and concentrated in vacuo. The remaining residue is partially dissolved in ethanol (100 mL) and filtered. The filtrate is concentrated in vacuo and chromatographed (7% MeOH/CH$_2$Cl$_2$). The combined fractions are concentrated, leaving a residue which is recrystallized in a 1:1 ether/hexanes mixture to afford 0.95 g of ethyl 1-methoxy-4-oxo-1,4-dihydro-3-quinolinecarboxylate (Mp 120–121° C.) as a white solid.

The resulting carboxylate ester (0.48 g) is stirred with a solution of 3 N NaOH (aqueous, 5 mL) in ethanol (6 mL) for 15 minutes. The reaction mixture is neutralized with 3 N HCl, filtered, and washed with ethanol to give the carboxylic acid as a white solid. The carboxylic acid (0.16 g) and N,N'-carbonyldiimidazole (0.18 g) are dissolved in DMF (10 mL) and heated to 65° C. for 5 hours. The reaction mixture is cooled to 0° C., quenched with water (0.01 mL) and stirred for 5 minutes. After warming to room temperature, 4-chlorobenzylamine (0.10 mL) is added. The reaction mixture is then stirred for 16 hours at room temperature. Water (15 mL) is added, and the precipitate is filtered off and washed with 1:1 DMF/H$_2$O (2×25 mL) and H$_2$O (2×25 mL) to afford 50 mg of the title compound as a white solid.

Physical properties are as follows:

Mp 155–160° C.; $^1$H NMR (DMSO-d$_6$) δ10.30, 9.08, 8.32, 7.91, 7.62, 7.39, 4.56, 4.21; IR (drift) 1941, 1920, 1650, 1603, 1549, 1489, 1463, 1350, 1221, 1013, 954, 840, 801, 751, 713 cm$^{-1}$; HRMS (FAB) calcd for C$_{18}$H$_{15}$ClN$_2$O$_3$+H 343.0849, found 343.0867.

Example 124

N-(4-Bromobenzy)-1-(4-morpholinyl)-6-(4-morpholinylmethyl)-4-oxo-1,4-dihydro-3-quinolinecarboxamide

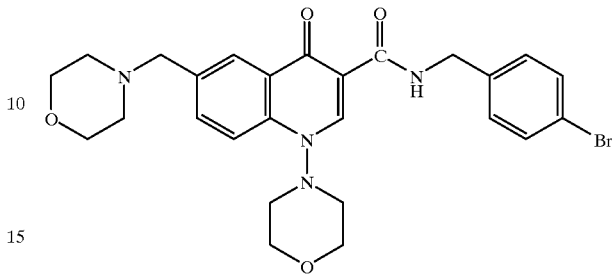

4-Bromobenzylamine hydrochloride (2.22 g) is suspended in water (5 mL) and neutralized with 2N aqueous NaOH (5 mL). The free amine is extracted with dichloromethane (2×25 mL). The organic layers are combined, washed with brine (5 mL), and dried with Na$_2$SO$_4$. The solution is concentrated in vacuo to afford 1.48 g of a clear, colorless oil which is then combined with ethyl 1-(4-morpholinyl)-6-(4-morpholinylmethyl)-4-oxo-1,4-dihydro-3-quinolinecarboxylate (0.48 g) from Preparation No. 56 and heated to 190° C. for 3 hours. The reaction mixture is allowed to cool to room temperature, and the resulting solid is recrystallized in ethyl acetate to afford 0.44 g of the title compound as a white solid.

Physical properties are as follows:

Mp 200–202° C. $^1$H NMR (DMSO-d$_6$) δ) 10.35, 9.03, 8.28, 8.21, 7.81, 7.54, 7.31, 4.55, 3.96, 3.80, 3.62, 3.59, 3.28, 3.08, 2.37. IR (drift) 1966, 1926, 1652, 1597, 1585, 1549, 1522, 1487, 1359, 1351, 1283, 1111, 862, 807, 799 cm$^{-1}$. MS (ESI+) m/z 541 (M+H)$^+$; HRMS (FAB) calcd for C$_{26}$H$_{29}$BrN$_4$O$_4$+H 541.1451, found 541.1447.

Example 125

N-(4-Fluorobenzyl)-1-(4-morpholinyl)-6-(4-morpholinylmethyl)-4-oxo-1,4-dihydro-3-quinolinecarboxamide

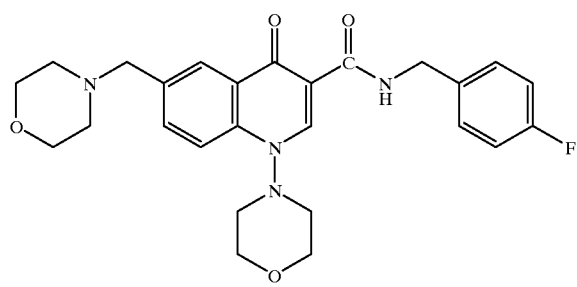

Ethyl 1-(4-morpholinyl)-6-(4-morpbolinylmethyl-4-oxo-1,4-dihydro-3-quinolinecarboxylate (0.33 g) from Preparation No. 56 and 4-fluorobenzylamine (0.55 mL) are combined and heated to 180° C. for 3 hours. The reaction is allowed to cool to room temperature. The crude solid is triturated with ether, filtered, and recrystallized in methanol to afford 0.14 g of the title compound as a white solid.

Physical properties are as follows:

Mp 165–167° C. $^1$H NMR (DMSO-d$_6$) δ10.33, 9.06, 8.27, 8.21, 7.81, 7.39, 7.17, 5.76, 4.57, 3.97, 3.80, 3.62, 3.57, 3.08, 2.37. IR (drift) 1661, 1598, 1549, 1510, 1488, 1355, 1324, 1288, 1269, 1223, 1110, 864, 842, 829, 809 cm$^{-1}$. MS (ESI+) m/z 481 (M+H)$^+$; HRMS (FAB) calcd for $C_{26}H_{29}FN_4O_4$+H 481.2251, found 481.2245.

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:

1. A compound of formula I,

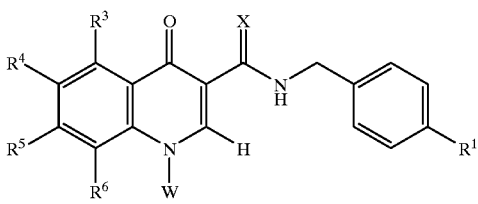

or a pharmaceutically acceptable salt thereof wherein,

X is
  a) O, or
  b) S;

W is
  a) $R^2$;
  b) $NR^7R^8$,
  c) $OR^9$, or
  d) $SO_iR^9$;

$R^1$ is
  a) Cl,
  b) F,
  c) Br,
  d) CN, or
  e) $NO_2$;

$R^2$ is
  a) $(CH_2CH_2O)_mR^{10}$,
  b) het, wherein said het is bonded via a carbon atom,
  c) $C_{1-7}$ alkyl which may be partially unsaturated and is optionally substituted by one or more substituents selected from a group consisting of $NR^7R^8$, $R^{11}$, CN, $SO_iR^9$, or $OC_{2-4}$ alkyl which is further substituted by het, $OR^{10}$, OC(=O)aryl, or $NR^7R^8$, or
  d) $C_{3-8}$ cycloalkyl, which may be partially unsaturated and is optionally substituted by $R^{11}$, $NR^7R^8$, $SO_iR^9$, or $C_{1-7}$ alkyl optionally substituted by $R^{11}$, $NR^7R^8$, or $SO_iR^9$;

$R^3$ is
  a) H,
  b) halo, or
  c) $C_{1-4}$ alkyl, optionally substituted by one to three halo;

$R^4$ is
  a) H,
  b) aryl,
  c) het,
  d) $SO_2NHR^{12}$,
  e) $CONHR^{12}$,
  f) $NR^7R^8$,
  g) $NHCOR^{12}$,
  h) $NHSO_2R^{12}$,
  i) $OC_{2-7}$ alkyl optionally substituted by —OH,
  j) $SC_{2-7}$ alkyl optionally substituted by OH, or
  k) $C_{1-8}$ alkyl which may be partially unsaturated and is optionally substituted by one or more substituents selected from a group consisting of $N_3$, $OR^{10}$, $NR^7R^8$, halo, $SO_iR^9$, $OR^{13}$ or $R^{11}$;

$R^5$ is
  a) H,
  b) halo,
  c) C≡$CR^{14}$,
  d) $NR^7R^8$,
  e) $SO_2NHR^{12}$,
  f) het, or
  g) $C_{1-7}$ alkyl, optionally substituted by OH;

$R^6$ is
  a) H,
  b) halo,
  c) $SC_{1-7}$ alkyl,
  e) $C_{1-7}$ alkoxy, optionally substituted by one or more halo or OH, or
  f) $C_{1-7}$ alkyl, which may be partially unsaturated and is optionally substituted by halo, $NR^{10}R^{10}$, $(CH_2)_nOR^{13}$, $R^{11}$, $OC_{1-7}$ alkyl which is further substituted with het, $NR^7R^8$, or $SO_iR^9$;

$R^7$ and $R^8$ are independently
  a) H,
  b) aryl,
  c) $C_{1-7}$alkyl which may be partially unsaturated and is optionally substituted by one or more substituents selected from a group consisting of $NR^{10}R^{10}$, $CONR^{10}R^{10}$, $R^{11}$, $SO_iR^9$, halo; or
  d) $R^7$ and $R^8$ together with the nitrogen to which they are attached to form a het;

$R^9$ is
  a) aryl,
  b) het,
  c) $C_{3-8}$cycloalkyl, or
  d) $C_{1-7}$alkyl which may be partially unsaturated and optionally substituted by one or more $OR^{10}$, Oaryl, het, aryl, $NR^{10}R^{10}$, CN, SH, $SO_iC_{1-6}$ alkyl, $SO_i$ aryl, halo, or $CONR^{10}R^{10}$;

$R^{10}$ is
  a) H, or
  b) $C_{1-7}$ alkyl, optionally substituted by OH;

$R^{11}$ is
  a) $OR^{10}$,
  b) Ohet,
  c) Oaryl,
  d) $CO_2R^{10}$,
  e) het,
  f) aryl, or
  g) CN;

$R^{12}$ is
  a) H,
  b) het,
  c) aryl,
  d) $C_{3-8}$ cycloalkyl, or
  e) $C_{1-7}$ alkyl optionally substituted by $NR^7R^8$, or $R^{11}$;

$R^{13}$ is
  a) (P=O)(OH)$_2$,
  b) (P=O)($C_{1-7}$ alkoxy)$_2$,
  c) $CO(CH_2)_nCON(CH_3)(CH_2)_nSO_3^-M^+$,
  d) an amino acid,
  e) C(=O)aryl,
  f) C(=O)$C_{1-6}$alkyl, optionally substituted by $NR^{10}R^{10}$, or
  g) $CO(CH_2)_nCO_2H$;

$R^{14}$ is
- a) het,
- b) $(CH_2)_nOR^{13}$, or
- c) $C_{1-7}$ alkyl substituted by one or more substituents selected from a group consisting of $R^{11}$, $OC_{1-7}$ alkyl which is further substituted with het, $NR^7R^8$, or $SO_iR^9$; aryl is a phenyl radical or an ortho-fused bicyclic carbocyclic radical wherein at least one ring is aromatic;
  - het is a four- (4), five- (5), six- (6), or seven- (7) membered saturated or unsaturated heterocyclic ring having 1, 2, or 3 heteroatoms selected from the group consisting of oxygen, sulfur, and nitrogen, which is optionally fused to a benzene ring, or any bicyclic heterocycle group;
  - wherein any aryl is optionally substituted with one or more substituents selected from the group consisting of halo, OH, $CF_3$, $C_{1-6}$alkoxy, and $C_{1-6}$ alkyl which maybe further substituted by one to three $SR^{10}$, $NR^{10}R^{10}$, $OR^{10}$, or $CO_2R^{10}$;
  - wherein any het is optionally substituted with one or more substituents selected from the group consisting of halo, OH, $CF_3$, $C_{1-6}$alkoxy, oxo, oxine, and $C_{1-6}$ alkyl which maybe further substituted by one to three $SR^{10}$, $NR^{10}R^{10}$, $OR^{10}$, or $CO_2R^{10}$;
  - i is 0, 1, or 2;
  - m is 1, 2, or 3;
  - n is 1, 2, 3, 4, 5, or 6; and
  - M is sodium, potassium, or lithium;

With the proviso that $R^1$ is not Cl, Br, F, or CN; when X is O;
$R^2$ is $C_{1-7}$ alkyl optionally substituted by $R^{15}$;
$R^3$ is H, methyl, or halo;
$R^4$ is H, $CONH(C_{1-7}alkyl)$, $NR^{16}R^{17}$, or $C_{1-7}$ alkyl optionally substituted by $OR^{10}$, CN, COOH, or $NR^{16}R^{17}$;
$R^5$ is H, halo, $SO_2NHR^{10}$, $NR^{16}R^{17}$, or $C_{1-7}$ alkyl optionally substituted by $OR^{10}$;
$R^6$ is H, halo, $C_{1-7}$ alkoxy, or $C_{1-7}$ alkyl optionally substituted by halo, $OR^{10}$, $CO_2R^{10}$ or $NR^{16}R^{17}$;
$R^{15}$ is $NR^{16}R^{17}$, $OR^{10}$, CN, or $CO_2R^{10}$; and
$R^{16}$ and $R^{17}$ are independently H or $C_{1-7}$alkyl; or $NR^{16}R^{17}$ together with the nitrogen to which they are attached form a 5- or 6-membered ring selected from pyrrolidine, piperidine, morpholine, or piperazine.

2. A compound of claim 1 wherein $R^1$ is Cl.

3. A compound of claim 1 wherein $R^1$ is F.

4. A compound of claim 1 wherein $R^1$ is CN, or $NO_2$.

5. A compound of claim 1 wherein $R^2$ is $(CH_2CH_2O)_mH$, or $(CH_2CH_2O)_mC_{1-4}$ alkyl, wherein m is 2, or 3.

6. A compound of claim 1 wherein $R^2$ is $C_{3-8}$cycloalkyl optionally substituted by $R^{11}$, $NR^7R^8$, $SO_iR^9$, or $C_{1-7}$ alkyl optionally substituted by $R^{11}$, $NR^7R^8$, or $SO_iR^9$; wherein $R^7$, $R^8$, $R^9$, $R^{11}$ and i are the same as defined in claim 1.

7. A compound of claim 1 wherein $R^2$ is cyclopropyl.

8. A compound of claim 1 wherein $R^2$ is het wherein said het is bonded via a carbon atom and is the same as defined in claim 1.

9. A compound of claim 8 wherein het is tetrahydro-2H-pyranyl, piperdinyl, 1-methyl-piperidinyl, or 1,1-dioxo-tetrahydro-2H-thiopyran.

10. A compound of claim 1 wherein $R^2$ is $C_{2-7}$ alkyl which is partially unsaturated and optionally substituted by $NR^7R^8$, $R^{11}$, $SO_iR^9$, or $OC_{2-4}$ alkyl which is further substituted by het, $OR^{10}$, or $OC(=O)aryl$; wherein $R^7$, $R^8$, $R^9$, $R^{10}$ are the same as defined in claim 1.

11. A compound of claim 10 wherein $R^2$ is (Z or E)-$CH=CHR^{10}$, or $-C-C\equiv CR^{10}$; wherein said $R^{10}$ is H, or $C_{1-7}$ alkyl optionally substituted by OH.

12. A compound of claim 1 wherein $R^2$ is $C_{1-7}$ alkyl substituted by $NR^7R^8$, $R^{11}$, $SO_iR^9$, or $OC_{2-4}$ alkyl which is further substituted by het, $OR^{10}$, or $OC(=O)aryl$ wherein $R^7$, $R^8$, $R^9$, $R^{10}$ and $R^{11}$ are the same as defined in claim 1.

13. A compound of claim 1 wherein $R^2$ is $C_{1-7}$ alkyl substituted by $OC_{2-4}$ alkyl which is further substituted by het, OH, $OC_{1-4}$ alkyl, or $OC(=O)aryl$.

14. A compound of claim 1 wherein $R^2$ is $C_{1-7}$ alkyl substituted by $SO_iR^9$ wherein $R^9$ and I are the same as defined in claim 1.

15. A compound of claim 1 wherein $R^2$ is $C_{1-7}$ alkyl substituted by $SO_iR^9$; wherein $R^9$ is $C_{1-4}$ alkyl, optionally substituted by OH, or $R^9$ is phenyl, optionally substituted by Cl; wherein i is 0, 1, or 2.

16. A compound of claim 1 wherein $R^2$ is methyl.

17. A compound of claim 1 wherein W is $NR^7R^8$, wherein $R^7$ and $R^8$ are the same as defined in claim 1.

18. A compound of claim 1 wherein W is $NR^7R^8$, wherein $R^7$ and $R^8$ together with the nitrogen to which they are attached to form a het, wherein said het is the same as defined in claim 1.

19. A compound of claim 18 wherein het is morpholine, piperidine, pyrrolidine, piperazine, or 4-methyl-piperazine.

20. A compound of claim 1 wherein W is $NR^7R^8$, wherein $R^7$ and $R^8$ are independently H or $C_{1-4}$ alkyl optionally substituted by OH.

21. A compound of claim 18 wherein het is morpholine.

22. A compound of claim 1 wherein W is $OR^9$, or $SO_iR^9$ wherein $R^9$ is $C_{1-6}$alkyl which may be partially unsaturated and optionally substituted by $OR^{10}$, Oaryl, het, aryl, $NR^{10}R^{10}$, CN, $CONR^{10}R^{10}$, or halo; wherein $R^{10}$ is H or $C_{1-4}$ alkyl.

23. A compound of claim 1 wherein $R^3$ is H.

24. A compound of claim 1 wherein $R^3$ is $CF_3$, or halo.

25. A compound of claim 1 wherein $R^4$ is aryl or het.

26. A compound of claim 1 wherein $R^4$ is $SO_2NHR^{12}$, $CONHR^{12}$, $NHCOR^{12}$, or $NHSO_2R^{12}$, wherein $R^{12}$ is the same as defined in claim 1.

27. A compound of claim 1 wherein $R^4$ is $C_{2-8}$ alkyl which is partially unsaturated and optionally substituted by $OR^{10}$, $NR^7R^8$, halo, $SO_iR^9$, $OR^{13}$ or $R^{11}$, wherein $R^7$, $R^8$, $R^9$, $R^{10}$, $R^{11}$ and $R^{13}$ are the same as defined in claim 1.

28. A compound of claim 1 wherein $R^4$ is (Z or E)-$CH\equiv CHC_{1-4}$ alkyl, optionally substituted by OH.

29. A compound of claim 1 wherein $R^4$ is $-C\equiv CC_{1-4}$ alkyl, optionally substituted by OH or $OR^{13}$, wherein $R^{13}$ is $(P=O)(OH)_2$, $(P=O)(C_{1-7}$ alkoxy$)_2$, or $CO(CH_2)_6CON(CH_3)(CH_2)_nSO_3^-M^+$.

30. A compound of claim 1 wherein $R^4$ is $C_{1-8}$ alkyl substituted by $OR^{13}$ wherein $R^{13}$ is $(P=O)(OH)_2$, $(P=O)(C_{1-7}$ alkoxy$)_2$, or $CO(CH_2)_nCON(CH_3)(CH_2)_nSO_3^-M^+$.

31. A compound of claim 1 wherein $R^4$ is $C_{1-8}$ alkyl substituted by $SO_iR^9$, wherein $R^9$ is the same as defined in claim 1.

32. A compound of claim 1 wherein $R^4$ is $NR^7R^8$, wherein $R^7$ and $R^8$ are the same as defined in claim 1.

33. A compound of claim 1 wherein $R^4$ is $C_{1-8}$ alkyl substituted by $NR^7R^8$, wherein $R^7$ and $R^8$ are the same as defined in claim 1.

34. A compound of claim 33 wherein $R^7$ and $R^8$ together with the nitrogen to which they are attached to form a het, wherein het is the same as defined in claim 1.

35. A compound of claim 33 wherein $R^7$ and $R^8$ are independently $C_{1-6}$ alkyl, optionally substituted by one or more substituents selected from a group consisting of OH, aryl, or CN wherein aryl is the same as defined in claim 1.

36. A compound of claim 1 wherein $R^4$ is $C_{1-8}$ alkyl substituted by $N_3$.

37. A compound of claim 1 wherein $R^4$ is $C_{1-8}$ alkyl substituted by het wherein het is the same as defined in claim 1.

38. A compound of claim 1 wherein $R^4$ is 4-morpholine methyl.

39. A compound of claim 1 wherein $R^4$ is $C_{1-7}$ alkyl substituted by $R^{11}$, wherein $R^{11}$ is the same as defined in claim 1.

40. A compound of claim 1 wherein $R^5$ is H or $C_{1-7}$ alkyl optionally substituted by OH.

41. A compound of claim 1 wherein $R^6$ is $OC_{1-7}$ alkyl optionally substituted by one or more OH.

42. A compound of claim 1 wherein $R^6$ is halo.

43. A compound of claim 1 wherein $R^6$ is $C\equiv CC_{1-7}$ alkyl substituted by one or more OH, or $C_{2-7}$ alkoxy substituted by one or more OH.

44. A compound of claim 1 wherein $R^6$ is H or $C_{1-7}$ alkyl, optionally substituted by halo, $NR^{10}R^{10}$, OH, $CO_2R^{10}$, or het; wherein $R^{10}$ and het are the same as defined in claim 1.

45. A compound of claim 1 wherein M is sodium, potassium, or lithium.

46. A compound of claim 1 wherein X is S; W, $R^1$, $R^2$, $R^3$, $R^4$, $R^5$, $R^6$ are the same as defined in claim 1.

47. A compound of claim 1 wherein X is O; $R^1$, $R^3$, $R^4$, $R^5$, $R^6$ are the same as defined in claim 1, W is $NR^7R^8$, $OR^9$, $SO_rR^9$ or $R^2$; wherein $R^2$ is:
a) $(CH_2CH_2O)_nR^{10}$,
b) het, wherein said het is bonded via a carbon atom,
c) $C_{1-7}$ alkyl which is partially unsaturated and optionally substituted by OH,
d) $C_{3-8}$ cycloalkyl, or
e) $C_{1-7}$ alkyl which is optionally substituted by one or more substituents selected from a group consisting of Ohet, Oaryl, $SO_rR^9$, or $OC_{2-4}$ alkyl which is further substituted by het, $OR^{10}$, or $OC(=O)$aryl;
wherein $R^7$, $R^8$, $R^9$, $R^{10}$ and n are the same as defined in claim 1.

48. A compound of claim 1 wherein X is O or S; $R^1$ is Cl; $R^3$ is H; $R^5$ is H; $R^6$ is H or F; $R^4$ is 4-morpholinylmethyl; and $R^2$ is:
a) $C_{1-4}$ alkyl substituted by $SO_rR^9$, or $C_{1-4}$ alkoxy which is further substituted by OH, het, $OC_{1-4}$ alkyl, or $OC(=O)$pheyl,
b) $(CH_2CH_2O)_2C_{1-4}$alkyl,
c) $C_{1-6}$alkyl which is partially unsaturated and optionally substituted by OH,
d) cyclopropyl,
e) tetrahydro-2H-pyranyl,
f) piperdinyl,
g) mopholinyl,
h) 1-methyl-piperidinyl, or
i) 1,1-dioxo-tetrahydro-2H-thiopyran;
wherein $R^9$ is phenyl optionally substituted by Cl, or $R^9$ is $C_{1-6}$alkyl optionally substituted by OH.

49. A compound of claim 1 wherein X is O or S; $R^1$ is Cl; $R^3$ is H; $R^5$ is H; $R^6$ is H or F; $R^4$ is $C_{1-6}$alkyl which is partially unsaturated and optionally substituted by OH or $OR^{13}$; or $R^4$ is $C_{1-4}$alkyl substituted with $OR^{13}$; W is $NR^{10}R^{10}$, cyclopropyl, $(CH_2CH_2O)_2OR^{10}$, or $C_{1-6}$ alkyl which may be partially unsaturated and is optionally substituted by OH, mopholinyl, $NR^{10}R^{10}$; $C(=O)OC_{1-4}$alkyl, wherein $R^{10}$ is H or $C_{1-4}$alkyl; $R^{13}$ is $(P=O)(C_7$ alkoxy$)_2$, $CO(CH_2)_nCON(CH_3)(CH_2)_nSO_3^-M^+$, or $(P=O)(OH)_2$.

50. A compound of claim 1 wherein X is O or S; $R^1$ is Cl; $R^3$ is H; $R^5$ is H; $R^6$ is $C\equiv CC_{1-4}$ alkyl optionally substituted by OH; $R^4$ is H or $C_{1-4}$alkyl which may be partially unsaturated and optionally substituted by OH, and W is $C_{1-4}$ alkyl optionally substituted by OH.

51. A compound of claim 1 which is

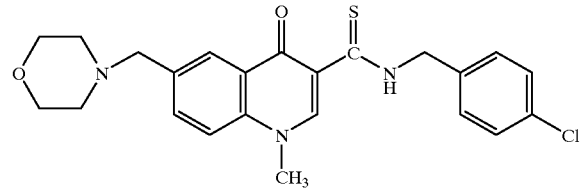

or a pharmaceutically acceptable salt.

52. A compound of claim 1 which is

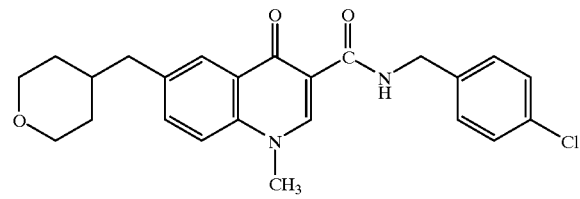

or a pharmaceutically acceptable salt.

53. A compound of claim 1 which is

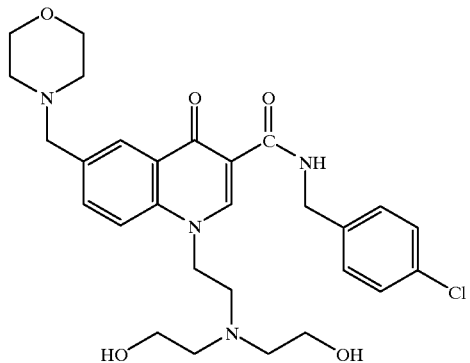

or a pharmaceutically acceptable salt.

54. A compound of claim 1 which is

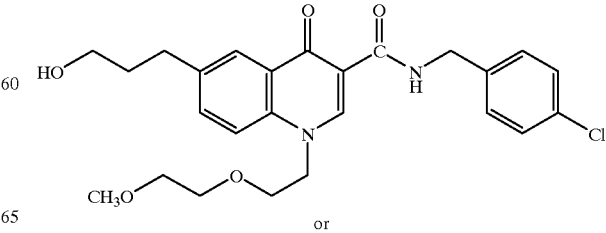

or

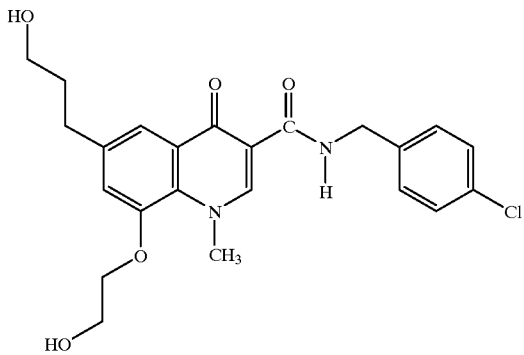

or a pharmaceutically acceptable salt.

55. A compound of claim 1 which is

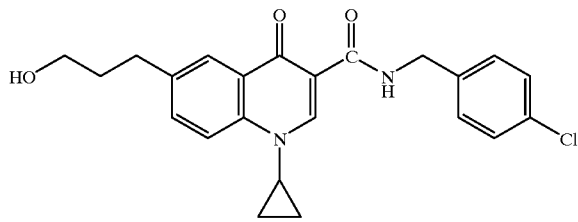

or a pharmaceutically acceptable salt.

56. A compound of claim 1 which is

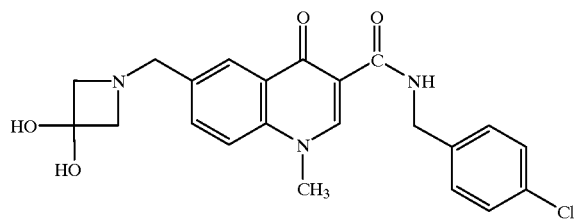

or a pharmaceutically acceptable salt.

57. A compound of claim 1 which is

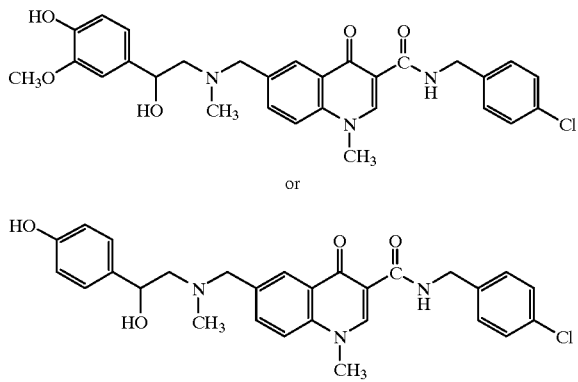

or a pharmaceutically acceptable salt.

58. A compound claim 1 which is

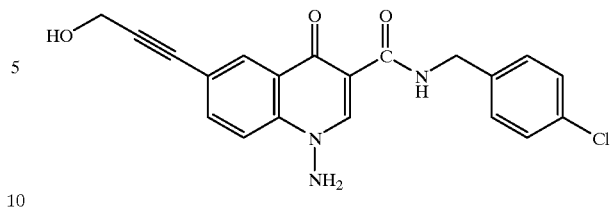

or a pharmaceutically acceptable salt.

59. A compound claim 1 which is

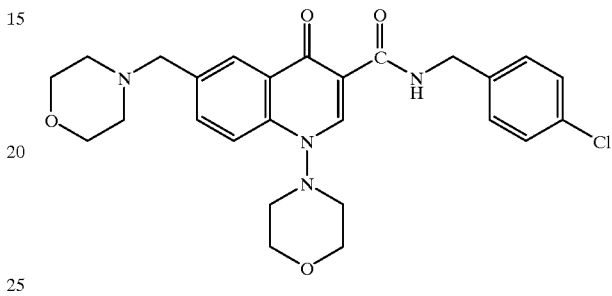

or a pharmaceutically acceptable salt.

60. A compound of claim 1 wherein $R^2$ is methyl, ethyl, propyl, isopropyl, butyl, tert-butyl, cyclopropyl, carboxymethyl, ($C_{1-7}$ alkoxy)carbonylmethyl, 2-hydroxyethyl, 2-(2-methoxyethoxy)ethyl, 3-(2-tetrahydropyranyloxy)propyl, 2-morpholinoethyl, 2-(diethylamino)ethyl, 2-(dimethylamino)ethyl, 2-piperidinoethyl, 3-piperidinopropyl, 2-(1-methylpyrrolidin-2-yl)ethyl, 2-(diisopropylamino)ethyl, 2-pyrrolidin-1-ylethyl, 3-(dimethylamino)propyl, or vinyl.

61. A compound of claim 1 wherein $R^4$ is 3-hydroxy-1-propynyl, 3-hydroxypropyl, hydroxymethyl, cis-4-hydroxy-1-butenyl, trans-4-hydroxy-1-butenyl, (2-hydroxyethyl)(ethyl)amino, morpholinomethyl, $(CH_2)_2O(P=O)(OH)_2$, $(CH_2)_3O(P=O)((tert-butoxy)_2$, 3-[di(tert-butyl)phosphoryl]propyl, 3-phosphorylpropyl, $Na^{+-}OS(O)_2CH_2CH_2N-CH_3)C(=O)(CH_2)_6C(=O)O(CH_2)_3$, or $Na^{+-}OS(O)_2CH_2CH_2N(CH_3)C(=O)-(CH_2)_6C(=O)OCH_2C\equiv C-$.

62. A compound of claim 1 which is:
(1) N-(4-chlorobenzyl)-6-(3-hydroxy-1-propynyl)-1-isopropyl-4-oxo-1,4-dihydro-3-quinolinecarboxamide;
(2) 1-(sec-butyl)-N-(4-chlorobenzyl)-6-(3-hydroxy-1-propynyl)-4-oxo-1,4-dihydro-3-quinolinecarboxamide;
(3) 1-(sec-butyl)-N-(4-chlorobenzyl)-6-(3-hydroxy-1-propynyl)-8-methoxy-4-oxo-1,4-dihydro-3-quinolinecarboxamide;
(4) N-(4-chlorobenzyl)-6-[3-hydroxy-1-propenyl]-1-[2-(4-morpholinyl)ethyl]-4-oxo-1,4-dihydro-3-quinolinecarboxamide;
(5) N-(4-chlorobenzyl)-8-fluoro-6-(3-hydroxy-1-propynyl)-1-methyl-4-oxo-1,4-dihydro-3-quinolinecarboxamide;
(6) N-(4-chlorobenzyl)-8-fluoro-6-[(Z)-3-hydroxy-1-propenyl]-1-methyl-4-oxo-1,4-dihydro-3-quinolinecarboxamide;
(7) N-(4-chlorobenzyl)-1-[2-(diethylamino)ethyl]-8-fluoro-6-(3-hydroxy-1-propynyl)-4-oxo-1,4-dihydro-3-quinolinecarboxamide;
(8) N-(4-chlorobenzyl)-6-(3-hydroxy-1-propynyl)-4-oxo-1-propyl-1,4-dihydro-3-quinolinecarboxamide;
(9) N-(4-chlorobenzyl)-1-[2-(diethylamino)ethyl]-6-(3-hydroxy-1-propynyl)-4-oxo-1,4-dihydro-3-quinolinecarboxarmide;

(10) N-(4-chlorobenzyl)-1-[2-(dimethylamino)ethyl]-6-(3-hydroxy-1-propynyl)-4-oxo-1,4-dihydro-3-quinolinecarboxamide hydrochloride;
(11) N-(4-chlorobenzyl)-6-(3-hydroxy-1-propynyl)-4-oxo-1-[2-(1-piperidinyl)ethyl]-1,4-dihydro-3-quinolinecarboxamide;
(12) N-(4-chlorobenzyl)-6-(3-hydroxy-1-propynyl)-4-oxo-1-[3-(1-piperidinyl)propyl]-1,4-dihydro-3-quinolinecarboxamide;
(13) N-(4-chlorobenzyl)-6-(3-hydroxy-1-propynyl)-1-[2-(1-methyl-2-pyrrolidinyl)ethyl-4-oxo-1,4-dihydro-3-quinolinecarboxamide;
(14) N-(4-chlorobenzyl)-1-[2-(diisopropylamino)ethyl]-6-(3-hydroxy-1-propynyl)-4-oxo-1,4-dihydro-3-quinolinecarboxamide;
(15) N-(4-chlorobenzyl)-6-(3-hydroxy-1-propynyl)-4-oxo-1-[2-(1-pyrrolidinyl)ethyl]-1,4-dihydro-3-quinolinecarboxamide;
(16) N-(4-chlorobenzyl)-6-(3-hydroxy-1-propynyl)-1-[2-(4-morpholinyl)ethyl]-4-oxo-1,4-dihydro-3-quinolinecarboxamide;
(17) N-(4-chlorobenzyl)-1-[3-(dimethylamino)propyl]-6-(3-hydroxy-1-propynyl)-4-oxo-1,4-dihydro-3-quinolinecarboxamide;
(18) N-(4-chlorobenzyl)-6-(3-hydroxy-1-propynyl)-oxo-1-vinyl-1,4-dihydro-3-quinolinecarboxamide;
(19) N-(4-chlorobenzyl)-6-[(E)-3-hydroxy-1-propenyl]-1-methyl-4-oxo-1,4-dihydro-3-quinolinecarboxamide;
(20) N-(4-chlorobenzyl)-6-[(Z)-3-hydroxy-1-propenyl]-1-methyl-4-oxo-1,4-dihydro-3-quinolinecarboxamide;
(21) N-(4-chlorobenzyl)-1-cyclopropyl-6-(3-hydroxy-1-propynyl)-4-oxo-4-dihydro-3-quinolinecarboxamide;
(22) tert-butyl 2-[3-{[(4-chlorobenzyl)amino]carbonyl}-6-(3-hydroxy-1-propynyl)-4-oxo-1(4H)-quinolinyl]acetate;
(23) 2-[3-{[(4-chlorobenzyl)amino]carbonyl}-6-(3-hydroxy-1-propynyl)-4-oxo-1(4H)-quinolinyl]acetic acid;
(24) N-(4-chlorobenzyl)-1-(2-hydroxyethyl)-6-(3-hydroxy-1-propynyl)-4-oxo-1,4-dihydro-3-quinolinecarboxamide;
(25) N-(4-chlorobenzyl)-6-(3-hydroxy-1-propynyl)-1-methyl-4-oxo-1,4-dihydro-3-quinolinecarboxamide;
(26) di(tert-butyl) 3-(3-{[(4-chlorobenzyl)amino]carbonyl}-1-methyl-4-oxo-1,4-dihydro-6-quinolinyl)propyl phosphate;
(27) 3-(3-{[(4-chlorobenzyl)amino]carbonyl}-1-methyl-4-oxo-1,4-dihydro-6-quinolinyl)propyl dihydrogen phosphate;
(28) di(tert-butyl) 3-(3-{[(4-chlorobenzyl)amino]carbonyl}-1-cyclopropyl-4-oxo-1,4-dihydro-6-quinolinyl)propyl phosphate;
(29) sodium 2-[{8-[3-(3-{[(4-chlorobenzyl)amino]carbonyl}-1-cyclopropyl-4-oxo-1,4-dihydro-6-quinolinyl)propoxy]-8-oxooctanoyl}(metbyl)amino]-1-ethanesulfonate;
(30) sodium 2-[(8-{[3-(3-{[(4-chlorobenzyl)amino]carbonyl}-1-methyl-4-oxo-1,4-dihydro-6-quinolinyl)-2-propynyl]oxy}-8-oxooctanoyl)(methyl)amino]-1-ethanesulfonate;
(31) sodium 2-[(8-{[3-(3-{[(4-chlorobenzyl)amino]carbonyl}-1-methyl-4-oxo-1,4-dihydro-6-quinolinyl)-2-propynyl]oxy}-8-oxooctanoyl)(methyl)amino]-1-ethanesulfonate;
(32) sodium 2-[(8-{[3-(3-{[(4-chlorobenzyl)amino]carbonyl}-1-cyclopropyl-4-oxo-1,4-dihydro-6-quinolinyl)-2-propynyl]oxy}-8-oxooctanoyl)(methyl)amino]-1-ethanesulfonate;
(33) 1-(tert-butyl)-N-(4-chlorobenzyl)-6-(3-hydroxy-1-propynyl)-4-oxo-1,4-dihydro-3-quinolinecarboxamide;
(34) sodium 2-[{8-[3-(1-(tert-butyl)-3-{[(4-chlorobenzyl)amino]-carbonyl}-4-oxo-1,4-dihydro-6-quinolinyl)propoxy]-8-oxooctanoyl}(methyl)amino]-1-ethanesulfonate;
(35) sodium 2-[(8-{[3-(1-(tert-butyl)-3-{[(4-chlorobenzyl)amino]-carbonyl}-4-oxo-1,4-dihydro-6-quinolinyl)-2-propynyl]oxy}-8-oxooctanoyl)(methyl)amino]-1-ethanesulfonate;
(36) N-(4-chlorobenzyl)-6-(3-hydroxy-1-propynyl)-1-[2-(2-methoxyethoxy)-ethyl]-4-oxo-1,4-dihydro-3-quinolinecarboxamide;
(37) N-(4-cyanobenzyl)-6-(3-hydroxy-1-propynyl)-1-methyl-4-oxo-1,4-dihydro-3-quinolinecarboxamide;
(38) N-(4-chlorobenzyl)-1-methyl-6-(1,4-oxazepan-4-ylmethyl)-4-oxo-1,4-dihydro-3-quinolinecarboxamide;
(39) N-(4-chlorobenzyl)-1-methyl-4-oxo-6-(1,4-thiazepan-4-ylmethyl)-1,4-dihydro-3-quinolinecarboxamide;
(40) N-(4-chlorobenzyl)-1-methyl-6-(2-oxa-5-azabicyclo[2.2.1]hept-5-ylmethyl)-4-oxo-1,4-dihydro-3-quinolinecarboxamide;
(41) N-(4-chlorobenzyl)-6-(2,3-dihydro-4H-1,4-benzoxazin-4-ylmethyl)-1-methyl-4-oxo-1,4-dihydro-3-quinolinecarboxamide;
(42) 6-(azidomethyl)-N-(4-chlorobenzyl)-1-methyl-4-oxo-1,4-dihydro-3-quinolinecarboxamide;
(43) N-(4-chlorobenzyl)-1-methyl-4oxo-6-vinyl-1,4-dihydro-3-quinolinecarboxamide;
(44) N-(4-chlorobenzyl)-1-[2-(2-hydroxyethoxy)ethyl]-6-(3-hydroxy-1-propynyl)-4-oxo-1,4-dihydro-3-quinolinecarboxamide;
(45) N-(4-chlorobenzyl)-1-{2-[2-(2-methoxyethoxy)ethoxy]ethyl}-6-(4-morpholinylmethyl)-4-oxo-1,4-dihydro-3-quinolinecarboxamide;
(46) N-(4-chlorobenzyl)-1-[2-(2-hydroxyethoxy)ethyl]-6-(4-morpholinylmethyl)-4-oxo-1,4-dihydro-3-quinolinecarboxamide;
(47) N-(4-chlorobenzyl)-1-[2-(2-ethoxyethoxy)ethyl]-6-(4-morpholinylmethyl)-4-oxo-1,4-dihydro-3-quinolinecarboxamide;
(48) N-(4-chlorobenzyl)-6-(4-morpholinylmethyl)-4-oxo-1-(2-propynyl)-1,4-dihydro-3-quinolinecarboxamide;
(49) N-(4-chlorobenzyl)-1-[2-(ethylsulfanyl)ethyl]-6-(4-morpholinylmethyl)-4-oxo-1,4-dihydro-3-quinolinecarboxamide;
(50) N-(4-chlorobenzyl)-1-[3-(methylsulfanyl)propyl]-6-(4-morpholinylmethyl)-4-oxo-1,4-dihydro-3-quinolinecarboxamide;
(51) N-(4-chlorobenzyl)-1-(4-hydroxy-2-butynyl)-6-(4-morpholinylmethyl)-4-oxo-1,4-dihydro-3-quinolinecarboxamide;
(52) N-(4-chlorobenzyl)-6-{[(2-hydroxy-2-phenylethyl)(methyl)amino]methyl}-1-methyl-4-oxo-1,4-dihydro-3-quinolinecarboxamide;
(53) N-(4-chlorobenzyl)-1-[3-(methylsulfinyl)propyl]-6-(4-morpholinylmethyl)-4-oxo-1,4-dihydro-3-quinolinecarboxamide;
(54) N-(4-chlorobenzyl)-1-{3-[(3-hydroxypropyl)sulfanyl]propyl}-6-(4-morpholinylmethyl)-4-oxo-1,4-dihydro-3-quinolinecarboxamide;
(55) N-(4chlorobenzyl)-1-[3-(methylsulfonyl)propyl]-6-(4-morpholinylmethyl)-4-oxo-1,4-dihydro-3-quinolinecarboxamide;
(56) N-(4-chlorobenzyl)-1-[2-(ethylsulfinyl)ethyl]-6-(4-morpholinylmethyl)-4-oxo-1,4-dihydro-3-quinolinecarboxamide;
(57) N-(4-chlorobenzyl)-1-[2-(ethylsulfonyl)ethyl]-6-(4-morpholinylmethyl)-4-oxo-1,4-dihydro-3-quinolinecarboxamide;

(58) N-(4-chlorobenzyl)-1-{3-[(3-hydroxypropyl)sulfinyl]propyl}-6-(4-morpholinylmethyl)-4oxo-1,4-dihydro-3-quinolinecarboxamide;

(59) N-(4-chlorobenzyl)-1-{3-[(3-hydroxypropyl)sulfonyl]propyl}-6-(4-morpholinylmethyl)-4-oxo-1,4-dihydro-3-quinolinecarboxamide;

(60) N-(4-chlorobenzyl)-6-(4-morpholinylmethyl)-4-oxo-1-[2-(phenylsulfanyl)ethyl]-1,4-dihydro-3-quinolinecarboxamide;

(61) N-(4-chlorobenzyl)-1-[(methylsulfanyl)methyl]-6-(4-morpholinylmethyl)-4-oxo-1,4-dihydro-3-quinolinecarboxamide;

(62) N-(4-chlorobenzyl)-6-{[[2-hydroxy-2-(4-hydroxyphenyl)ethyl](methyl)amino]methyl}-1-methyl-4-oxo-1,4-dihydro-3-quinolinecarboxamide;

(63) N-(4-chlorobenzyl)-6-[(3-hydroxy-1-azetidinyl)methyl]-1-methyl-4-oxo-1,4-dihydro-3-quinolinecarboxamide;

(64) N-(4-chlorobenzyl)-6-(4-morpholinylmethyl)-4-oxo-1-[(phenylsulfanyl)-methyl]-1,4-dihydro-3-quinolinecarboxamide;

(65) N-(4-chlorobenzyl)-6-{[[2-hydroxy-2-(4-hydroxy-3-methoxyphenyl)ethyl](methyl)amino]methyl}-1-methyl-4-oxo-1,4-dihydro-3-quinolinecarboxamide;

(66) N-(4-chlorobenzyl)-6-[(3,3-dihydroxy-1-azetidinyl)methyl]-1-methyl-4-oxo-1,4-dihydro-3-quinolinecarboxamide;

(67) N-(4-chlorobenzyl)-1-[(methylsulfinyl)methyl]-6-(4-morpholinylmethyl)-4-oxo-1,4-dihydro-3-quinolinecarboxamide;

(68) N-(4-chlorobenzyl)-1-[(methylsulfonyl)methyl]-6-(4-morpholinylmethyl)-4-oxo-1,4-dihydro-3-quinolinecarboxamide;

(69) N-(4-chlorobenzyl)-6-(4-morpholinylmethyl)-4-oxo-1-[(phenylsulfinyl)-methyl]-1,4-dihydro-3-quinolinecarboxamide;

(70) N-(4-chlorobenzyl)-6-(4-morpholinylmethyl)-4-oxo-1-[(phenylsulfonyl)-methyl]-1,4-dihydro-3-quinolinecarboxamide;

(71) N-(4-chlorobenzyl)-6-(3-hydroxypropyl)-1-[2-(2-methoxyethoxy)ethyl]-4-oxo-1,4-oxo-1,4-dihydro-3-quinolinecarboxamide;

(72) N-(4-chlorobenzyl)-1-[2-(2-methoxyethoxy)ethyl]-6-(4-morpholinylmethyl)-4-oxo-1,4-dihydro-3-quinolinecarboxamide;

(73) N-(4-chlorobenzyl)-1-[2-(2-methoxyethoxy)ethyl]-4-oxo-6-[(4-oxo-1-piperidinyl)methyl]-1,4-dihydro-3-quinolinecarboxamide;

(74) N-(4-chlorobenzyl)-6-{[(cyanomethyl)(methyl)amino]methyl}-1-[2-(2-methoxyethoxy)ethyl]-4-oxo-1,4-dihydro-3-quinolinecarboxamide;

(75) N-(4-chlorobenzyl)-6-{[(3R)-3-hydroxypyrrolidinyl]methyl}-1-[2-(2-methoxyethoxy)ethyl]-4-oxo-1,4-dihydro-3-quinolinecarboxamide;

(76) N-(4-chlorobenzyl)-1-[2-(2-methoxyethoxy)ethyl]-6-[(methylsulfanyl)methyl]-4-oxo-1,4-dihydro-3-quinolinecarboxamide;

(77) N-(4-chlorobenzyl)-6-{[[(1R,2S)-2-hydroxy-1-methyl-2-phenylethyl](methyl)amino]methyl}-1-[2-(2-methoxyethoxy)ethyl]-4-oxo-1,4-dihydro-3-quinolinecarboxamide;

(78) N-(4-chlorobenzyl)-6-{[(2-hydroxy-2-phenylethyl)(methyl)amino]methyl}-1-[2-(2-methoxyethoxy)ethyl]-4-oxo-1,4-dihydro-3-quinolinecarboxamide;

(79) N-(4-chlorobenzyl)-6-{[[2-hydroxy-2-(4-hydroxyphenyl)ethyl](methyl)amino]methyl}-1-[2-(2-methoxyethoxy)ethyl]-4-oxo-1,4-dihydro-3-quinolinecarboxamide;

(80) 1-{2-[2-(tert-butoxy)ethoxy]ethyl-N-(4-chlorobenzyl)-6-(4-morpholinyl-methyl)-4-oxo-1,4-dihydro-3-quinolinecarboxamide;

(81) 1-{2-[2-(tert-butoxy)ethoxy]ethyl-N-(4-chlorobenzyl)-6-{[[2-hydroxy-2-(4-hydroxyphenyl)ethyl](methyl)amino]methyl-4-oxo-1,4-dihydro-3-quinolinecarboxamide;

(82) N-(4-chlorobenzyl)-6-(3-hydroxy-1-propynyl)-1-methyl-4-oxo-1,4-dihydro-3-quinolinecarbothioamide;

(83) N-(4-chlorobenzyl)-8-(3-hydroxy-1-propynyl)-1-methyl-4-oxo-1,4-dihydro-3-quinolinecarboxamide;

(84) N-(4-chlorobenzyl)-8-(4-hydroxy-1-butynyl)-1-methyl-4-oxo-1,4-dihydro-3-quinolinecarboxamide;

(85) N-(4-chlorobenzyl)-6-{[3-(hydroxymino)-1-azetidinyl]methyl}-1-methyl-4-oxo-1,4-dihydro-3-quinolinecarboxamide;

(86) N-(4-chlorobenzyl)-1-{2-[2-(4-morpholinyl)ethoxy]ethyl}-6-(4-morpholinylmethyl)-4-oxo-1,4-dihydro-3-quinolinecarboxamide;

(87) N-(4-chlorobenzyl)-1-([(4-chlorophenyl)sulfanyl]methyl)-6-(4-morpholinylmethyl)-4-oxo-1,4-dihydro-3-quinolinecarboxamide;

(88) N-(4-chlorobenzyl)-1-([(4-chlorophenyl)sulfinyl]methyl)-6-(4-morpholinylmethyl)-4-oxo-1,4-dihydro-3-quinolinecarboxamide;

(89) N-(4-chlorobenzyl)-1-([(4-chlorophenyl)sulfonyl]methyl)-6-(4-morpholinylmethyl)-4-oxo-1,4-dihydro-3-quinolinecarboxamide;

(90) N-(4-chlorobenzyl)-1-[(4-chlorophenoxy)methyl]-6-(4-morpholinylmethyl)-4-oxo-1,4-dihydro-3-quinolinecarboxamide;

(91) N-(4-chlorobenzyl)-1-[(2-methoxyethoxy)methyl]-6-(4-morpholinylmethyl)-4-oxo-1,4-dihydro-3-quinolinecarboxamide;

(92) 2-{[3-{[(4-chlorobenzyl)amino]carbonyl}-6-(4-morpholinylmethyl)-4-oxo-1(4H)quinolinyl]methoxy}ethyl benzoate;

(93) N-(4-chlorobenzyl)-1-[(2-hydroxyethoxy)methyl]-6-(4-morpholinylmethyl)-4-oxo-1,4-dihydro-3-quinolinecarboxamide;

(94) N-(4-chlorobenzyl)-6-(4-morpholinylmethyl)-4-oxo-1-tetrahydro-2H-pyran-4-yl-1,4-dihydro-3-quinolinecarboxamide;

(95) N-(4-chlorobenzyl)-1-(1-methyl-4-piperidinyl)-6-(4-morpholinylmethyl)-4-oxo-1,4-dihydro-3-quinolinecarboxamide;

(96) N-(4-chlorobenzyl)-6-(4-morpholinylmethyl)-4-oxo-1-(4-piperidinyl)-1,4-dihydro-3-quinolinecarboxamide;

(97) N-(4-chlorobenzyl)-1-(1,1-dioxohexahydrothiopyran-4-yl)-6-(4-morpholinylmethyl)-4-oxo-1,4-dihydro-3-quinolinecarboxamide;

(98) N-(4-chlorobenzyl)-1-(4-morpholinyl)-6-(4-morpholinylmethyl)-4-oxo-1,4-dihydro-3-quinolinecarboxamide;

(99) N-(4-chlorobenzyl)-1-(4-methyl-1-piperazinyl)-6-(4-morpholinylmethyl)-4-oxo-1,4-dihydro-3-quinolinecarboxamide;

(100) N-(4-chlorobenzyl)-6-(4-morpholinylmethyl)-4-oxo-1-(1-piperidinyl)-1,4-dihydro-3-quinolinecarboxamide;

(101) N-(4-chlorobenzyl)-6-(4-morpholinylmethyl)-4-oxo-1-(1-pyrrolidinyl)-1,4-dihydro-3-quinolinecarboxamide;

(102) N-(4-chlorobenzyl)-1-[(2R)-2-(methoxymethyl)pyrrolidinyl]-6-(4-morpholinylmethyl)-4-oxo-1,4-dihydro-3-quinolinecarboxamide;

(103) N-(4-chlorobenzyl)-1-(dimethylamino)-6-(4-morpholinylmethyl)-4-oxo-1,4-dihydro-3-quinolinecarboxamide;

(104) 1-Amino-N-(4-chlorobenzyl)-6-(3-hydroxy-1-propynyl)-4-oxo-1,4-dihydro-3-quinolinecarboxamide;
(105) 1-Anino-N-(4-chlorobenzyl)-6-(3-hydroxypropyl)-4-oxo-1,4-dihydro-3-quinolinecarboxamide;
(106) N-(4-chlorobenzyl)-1-(dimethylamino)-6-(3-hydroxy-1-propynyl)-4-oxo-1,4-dihydro-3-quinolinecarboxamide;
(107) N-(4-chlorobenzyl)-1-(dimethylamino)-4-oxo-1,4-dihydro-3-quinolinecarboxamide;
(108) 1-(allyloxy)-N-(4-chlorobenzyl)-4-oxo-1,4-dihydro-3-quinolinecarboxamide;
(109) N-(4-chlorobenzyl)-1-methoxy-4-oxo-1,4-dihydro-3-quinolinecarboxamide;
(110) N-(4-bromobenzyl)-1-(4-morpholinyl)-6-(4-morpholinylmethyl)-4-oxo-1,4-dihydro-3-quinolinecarboxamide;
(111) N-(4-fluorobenzyl)-1-(4-morpholinyl)-6-(4-morpholinylmethyl)-4-oxo-1,4-dihydro-3-quinolinecarboxamide;
(112) N-(4-chlorobenzyl)-1-{[2-(4-morpholinyl)ethoxy]methyl}-6-(4-morpholinylmethyl)-4-oxo-1,4-dihydro-3-quinolinecarboxamide;
(113) N-(4-chlorobenzyl)-1-{[2-(dimethylamino)etboxy]methyl}-6-(4-morpholinylmethyl)-4-oxo-1,4-dihydro-3-quinolinecarboxamide;
(114) N-(4-chlorobenzyl)-1-{[2-(4-methyl-1-piperazinyl)ethoxy]methyl}-6-4-morpholinylmethyl)-4-oxo-1,4-dihydro-3-quinolinecarboxamide;
(115) N-(4-chlorobenzyl)-6-(4-morpholinylmethyl)-4-oxo-1-{[2-(1-piperidinyl)ethoxy]methyl}-1,4-dihydro-3-quinolinecarboxamide;
(116) N-(4-chlorobenzyl)-6-(4-morpholinylmethyl-4-oxo-1-{[2-(1-pyrrolidinyl)ethoxy]methyl}-1,4-dihydro-3-quinolinecarboxamide; or a pharmaceutically acceptable salt thereof.

63. A compound of claim 1 which is:

(1) 1-(sec-butyl)-N-(4-chlorobenzyl)-6-(3-hydroxy-1-propynyl)-4-oxo-1,4-dihydro-3-quinolinecarboxamide;
(2) 1-(sec-butyl)-N-(4-chlorobenzyl)-6-(3-hydroxy-1-propynyl)-8-methoxy4-oxo-1,4-dihydro-3-quinolinecarboxamide;
(3) N-(4-chlorobenzyl)-6-[3-hydroxy-1-propenyl]-1-[2-(4-morpholinyl)ethyl]4-oxo-1,4-dihydro-3-quinolinecarboxamide;
(4) N-(4-chlorobenzyl)-8-fluoro-6-(3-hydroxy-1-propynyl)-1-methyl-4-oxo-1,4-dihydro-3-quinolinecarboxamide;
(5) N-(4-chlorobenzyl)-8-fluoro-6-[(Z)-3-hydroxy-1-propenyl]-1-methyl-4-oxo-1,4-dihydro-3-quinolinecarboxamide;
(6) N-(4-chlorobenzyl)-1-[2-(diethylamino)ethyl]-6-(3-hydroxy-1-propynyl-4-oxo-1,4-dihydro-3-quinolinecarboxamide;
(7) N-(4-chlorobenzyl)-1-[2-(dimethylamino)ethyl]-6-(3-hydroxy-1-propynyl)-4-oxo-1,4-dihydro-3-quinolinecarboxamide hydrochloride;
(8) N-(4-chlorobenzyl)-6-(3-hydroxy-1-propynyl)-4-oxo-1-[2-(1-piperidinyl)ethyl]-1,4-dihydro-3-quinolinecarboxamide;
(9) N-(4-chlorobenzyl)-6-(3-hydroxy-1-propynyl)-4-oxo-1-[3-(1-piperidinyl)propyl]-1,4-dihydro-3-quinolinecarboxamide;
(10) N-(4-chlorobenzyl)-6-(3-hydroxy-1-propynyl)-1-[2-(1-methyl-2-pyrrolidinyl)ethyl]-4-oxo-1,4-dihydro-3-quinolinecarboxamide;
(11) N-(4-chlorobenzyl)-1-[2-(diisopropylamino)ethyl]-6-(3-hydroxy-1-propynyl)-4-oxo-1,4-dihydro-3-quinolinecarboxamide;
(12) N-(4-chlorobenzyl)-6-(3-hydroxy-1-propynyl)-4-oxo-1-[2-(1-pyrrolidinyl)ethyl]-1,4-dihydro-3-quinolinecarboxamide;
(13) N-(4-chlorobenzyl)-6-(3-hydroxy-1-propynyl)-1-[2-(4-morpholinyl)ethyl]-4-oxo-1,4-dihydro-3-quinolinecarboxamide;
(14) N-(4-chlorobenzyl)-1-[3-(dimethylamino)propyl]-6(3-hydroxy-1-propynyl)-4-oxo-1,4-dihydro-3-quinolinecarboxamide;
(15) N-(4-chlorobenzyl)-6-(3-hydroxy-1-propynyl)-4-oxo-1-vinyl-1,4-dihydro-3-quinolinecarboxamide;
(16) N-(4-chlorobenzyl)-6-[(E)-3-hydroxy-1-propenyl]-1-methyl-4-oxo-1,4-dihydro-3-quinolinecarboxamide;
(17) N-(4-chlorobenzyl)-6-[(Z)-3-hydroxy-1-propenyl]-1-methyl-4-oxo-1,4-dihydro-3-quinolinecarboxamide;
(18) N-(4-chlorobenzyl)-1-cyclopropyl-6-(3-hydroxy-1-propynyl)-4-oxo-1,4-dihydro-3-quinolinecarboxamide;
(19) tert-butyl 2-[3-{[(4-chlorobenzyl)amino]carbonyl}-6-(3-hydroxy-1-propynyl-4-oxo-1(4H)-quinolinyl]acetate;
(20) N-(4-chlorobenzyl)-1-(2-hydroxyethyl)-6-(3-hydroxy-1-propynyl)-4-oxo-1,4-dihydro-3-quinolinecarboxamide;
(21) N-(4-chlorobenzyl)-6-(3-hydroxy-1-propynyl)-1-methyl-4-oxo-1,4-dihydro-3-quinolinecarboxamide;
(22) 3-(3-{[(4-chlorobenzyl)amino]carbonyl}-1-methyl-4-oxo-1,4-dihydro-6-quinolinyl)propyl dihydrogen phosphate;
(23) di(tert-butyl) 3-(3-{[(4-chlorobenzyl)amino]carbonyl}-1-cyclopropyl-4-oxo-1,4-dihydro-6-quinolinyl)propyl phosphate;
(24) sodium 2-[{8-[3-(3-{[(4-chlorobenzyl)amino]carbonyl}-1-cyclopropyl-4-oxo-1,4-dihydro-6-quinolinyl)propoxy]-8-oxooctanoyl}(methyl)amino]-1-ethanesulfonate;
(25) sodium 2-[(8-{13-(3-{[(4-chlorobenzyl)amino]carbonyl}-1-methyl-4oxo-1,4-dihydro-6-quinolinyl)-2-propynyl]oxy)-8-oxooctanoyl)(methyl)amino]-1-ethanesulfonate;
(26) N-(4-chlorobenzyl)-6-(3-hydroxy-1-propynyl)-1-[2-(2-methoxyethoxy)-ethyl]-4-oxo-1,4-dihydro-3-quinolinecarboxamide;
(27) N-(4-cyanobenzyl)-6-(3-hydroxy-1-propynyl)-1-methyl-4-oxo-1,4-dihydro-3-quinolinecarboxamide;
(28) N-(4-chlorobenzyl)-6-(3-hydroxy-1-propynyl)-4-oxo-1-propyl-1,4-dihydro-3-quinolinecarboxamide;
(29) N-(4-chlorobenzyl)-1-methyl-6-(1,4-oxazepan-4-ylmethyl)-4-oxo-1,4-dihydro-3-quinolinecarboxamide;
(30) N-(4-chlorobenzyl)-1-methyl-4-oxo-6-(1,4-thiazepan-4-ylmethyl)-1,4-dihydro-3-quinolinecarboxamide;
(31) 6-(azidomethyl)-N-(4-chlorobenzyl)-1-methyl-4-oxo-1,4-dihydro-3-quinolinecarboxamide;
(32) N-(4-chlorobenzyl)-6-[(4,4-difluoro-1-piperidinyl)methyl]-1-methyl-4-oxo-1,4-dihydro-3-quinolinecarboxamide;
(33) N-(4-chlorobenzyl)-4-hydroxy-6-iodo-3-quinolinecarbothioamide;
(34) N-(4-chlorobenzyl)-6-(2,3-dihydro-4H-1,4-benzoxazin-4-ylmethyl)-1-methyl-4-oxo-1,4-dihydro-3-quinolinecarboxamide.
(35) N-(4-chlorobenzyl)-1-methyl-4-oxo-6-vinyl-1,4-dihydro-3-quinoline-carboxamide;
(36) N-(4-chlorobenzyl)-1-[2-(2-hydroxyethoxy)ethyl]-6-(3-hydroxy-1-propynyl)-4-oxo-1,4-dihydro-3-quinolinecarboxamide;
(37) N-(4-chlorobenzyl)-1-{2-[2-(2-methoxyethoxy)ethoxy]ethyl}-6-(4-morpholinylmethyl)-4-oxo-1,4-dihydro-3-quinolinecarboxamide;
(38) N-(4-chlorobenzyl)-1-[2-(2-hydroxyethoxy)ethyl]-6-(4-morpholinylmethyl-4-oxo-1,4-dihydro-3-quinolinecarboxamide;

(39) N-(4-chlorobenzyl)-1-[2-(2-ethoxyethoxy)ethyl]-6-(4-morpholinylmethyl)-4-oxo-1,4-dihydro-3-quinolinecarboxamide;

(40) N-(4-chlorobenzyl)-1-[2-(ethylsulfanyl)ethyl]-6-(4-morpholinylmethyl)-4-oxo-1,4-dihydro-3-quinolinecarboxamide;

(41) N-(4-chlorobenzyl)-1-[3-(methylsulfanyl)propyl]-6-(4-morpholinylmethyl)-4-oxo-1,4-dihydro-3-quinolinecarboxamide;k

(42) N-(4-chlorobenzyl)-1-(4-hydroxy-2-butynyl)-6-(4-morpholinylmethyl)-4-oxo-1,4-dihydro-3-quinolinecarboxamide;

(43) N-(4-chlorobenzyl)-6-[(2-hydroxy-2-phenylethyl)(methyl)amino]methyl}-1-methyl-4-oxo-1,4-dihydro-3-quinolinecarboxamide;

(44) N-(4-chlorobenzyl)-1-[3-(methylsulfinyl)propyl]-6-(4-morpholinylmethyl)-4-oxo-1,4-dihydro-3-quinolinecarboxamide;

(45) N-(4-chlorobenzyl)-1-{3-[(3-hydroxypropyl)sulfanyl]propyl}-6-(4-morpholinylmethyl)-4-oxo-1,4-dihydro-3-quinolinecarboxamide;

(46) N-(4-chlorobenzyl)-1-[3-(methylsulfonyl)propyl]-6-(4-morpholinylmethyl-4-oxo-1,4-dihydro-3-quinolinecarboxamide;

(47) N-(4-chlorobenzyl)-1-[2-(ethylsulfinyl)ethyl]-6-(4-morpholinylmethyl)-4-oxo-1,4-dihydro-3-quinolinecarboxamide;

(48) N-(4-chlorobenzyl)-1-[2-(ethylsulfonyl)ethyl]-6-(4-morpholinylmethyl)-4-oxo-1,4-dihydro-3-quinolinecarboxamide;

(49) N-(4-chlorobenzyl)-1-{3-[(3-hydroxypropyl)sulfinyl]propyl}-6-(4-morpholinylmethyl)-4-oxo-1,4-dihydro-3-quinolinecarboxamide;

(50) N-(4-chlorobenzyl)-1-{3-[(3-hydroxypropyl)sulfonyl]propyl}-6-(4-morpholinylmethyl)-4-oxo-1,4-dihydro-3-quinolinecarboxamide;

(51) N-(4-chlorobenzyl)-6-(4-morpholinylmethyl)-4-oxo-1-[2-(phenylsulfanyl)ethyl]-1,4-dihydro-3-quinolinecarboxamide;

(52) N-(4-chlorobenzyl)-1-[(methylsulfanyl)methyl]-6-(4-morpholinylmethyl)-4-oxo-1,4-dihydro-3-quinolinecarboxamide;

(53) N-(4-chlorobenzyl)-6-{[[2-hydroxy-2-(4-hydroxyphenyl)ethyl](methyl)amino]methyl}l-1-methyl-4-oxo-1,4-dihydro-3-quinolinecarboxamide;

(54) N-(4-chlorobenzyl)-6-[(3-hydroxy-1-azetidinyl)methyl]-1-methyl-4-oxo-1,4-dihydro-3-quinolinecarboxamide;

(55) N-(4-chlorobenzyl)-6-(4-morpholinylmethyl-4-oxo-1-[(phenylsulfanyl)-methyl]-1,4-dihydro-3-quinolinecarboxamide

(56) N-(4-chlorobenzyl)-6-{[[2-hydroxy-2-(4-hydroxy-3-methoxyphenyl)ethyl](methyl)amino]methyl}-1-methyl4-oxo-1,4-dihydro-3-quinolinecarboxamide;

(57) N-(4-chlorobenzyl)-6-[(3,3-dihydroxy-1-azetidinyl)methyl]-1-methyl-4-oxo-1,4-dihydro-3-quinolinecarboxamide;

(58) N-(4-chlorobenzyl)-1-[(methylsulfinyl)methyl]-6-(4-morpholinylmethyl)-4-oxo-1,4-dihydro-3-quinolinecarboxamide;

(59) N-(4-chlorobenzyl)-1-[(methylsulfonyl)methyl]-6-(4-morpholinylmethyl)-4-oxo-1,4-dihydro-3-quinolinecarboxamide;

(60) N-(4chlorobenzyl)-6-(4-morpholinylmethyl)-4-oxo-1-[(phenylsulfinyl)-methyl]-1,4-dihydro-3-quinolinecarboxamide;

(61) N-(4-chlorobenzyl)-6-(4-morpholinylmethyl)-4-oxo-1-[(phenylsulfonyl)-methyl]-1,4-dihydro-3-quinolinecarboxamide;

(62) N-(4-chlorobenzyl)-6-(3-hydroxypropyl)-1-[2-(2-methoxyethoxy)ethyl]-4-oxo-1,4-dihydro-3-quinolinecarboxamide;

(63) N-(4-chlorobenzyl)-1-[2-(2-methoxyethoxy)ethyl]-6-(4-morpholinylmethyl)-4-oxo-1,4-dihydro-3-quinolinecarboxamide;

(64) N-(4-chlorobenzyl)-1-[2-(2-methoxyethoxy)ethyl]-4-oxo-6-[(4-oxo-1-piperidinyl)methyl]-1,4-dihydro-3-quinolinecarboxamide;

(65) N-(4-chlorobenzyl)-6-{[(3R)-3-hydroxypyrrolidinyl]methyl}-1-[2-(2-methoxyethoxy)ethyl]-4-oxo-1,4-dihydro-3-quinolinecarboxamide;k

(66) N-(4-chlorobenzyl)-6-{[[(1R,2S)-2-hydroxy-1-methyl-2-phenylethyl](methyl)amino]methyl}-1-[2-(2-methoxyethoxy)ethyl]-4-oxo-1,4-dihydro-3-quinolinecarboxamide;

(67) N-(4-chlorobenzyl)-6-{[[2-hydroxy-2-(4-hydroxyphenyl)ethyl](methyl)amino]methyl}-1-[2-(2-methoxyethoxy)ethyl]-4-oxo-1,4-dihydro-3-quinolinecarboxamide;

(68) 1-{2-[2-(tert-butoxy)ethoxy]ethyl-N-(4-chlorobenzyl)-6-(4-morpholinyl-methyl)-4-oxo-1,4-dihydro-3-quinolinecarboxamide;

(69) 1-{2-[2-(tert-butoxy)ethoxy]ethyl-N-(4-chlorobenzyl)-6-{[[2-hydroxy-2-(4-hydroxyphenyl)ethyl](methyl)amino]methyl-4-oxo-1,4-dihydro-3-quinolinecarboxamide;

(70) N-(4-chlorobenzyl)-6-(3-hydroxy-1-propynyl)-1-methyl-4-oxo-1,4-dihydro-3-quinolinecarbothioamide;

(71) N-(4-chlorobenzyl)-8-(3-hydroxy-1-propynyl)-1-methyl-4-oxo-1,4-dihydro-3-quinolinecarboxamide;

(72) N-(4-chlorobenzyl)-8-(4-hydroxy-1-butynyl)-1-methyl-4-oxo-1,4-dihydro-3-quinolinecarboxamide;

(73) N-(4-chlorobenzyl)-6-{[3-(hydroxyimino)-1-azetidinyl]methyl}-1-methyl-4-oxo-1,4-dihydro-3-quinolinecarboxamide;

(74) N-(4-chlorobenzyl)-1-{2-[2-(4-morpholinyl)ethoxy]ethyl}-6-(4-morpholinylmethyl)-4-oxo-1,4-dihydro-3-quinolinecarboxamide;

(75) N-(4-chlorobenzyl)-1-([(4-chlorophenyl)sulfanyl]methyl)-6-(4-morpholinylmethyl)-4-oxo-1,4-dihydro-3-quinolinecarboxamide;

(76) N-(4-chlorobenzyl)-1-([(4-chlorophenyl)sulfinyl]methyl)-6-(4-morpholinylmethyl)-4-oxo-1,4-dihydro-3-quinolinecarboxamide;

(77) N-(4-chlorobenzyl)-1-([(4-chlorophenyl)sulfonyl]methyl)-6-(4-morpholinylmethyl)-4-oxo-1,4-dihydro-3-quinolinecarboxamide;

(78) N-(4-chlorobenzyl)-1-[(4-chlorophenoxy)methyl]-6-(4-morpholinylmethyl)-4-oxo-1,4-dihydro-3-quinolinecarboxamide;

(79) N-(4-chlorobenzyl)-1-[(2-methoxyethoxy)methyl]-6-(4-morpholinylmethyl)-4-oxo-1,4-dihydro-3-quinolinecarboxamide;

(80) 2-{([3-{[(4-chlorobenzyl)amino]carbonyl}-6-(4-morpholinylmethyl)-4-oxo-1(4H)quinolinyl]methoxy}ethyl benzoate;

(81) N-(4-chlorobenzyl)-1-[(2-hydroxyethoxy)methyl]-6-(4-morpholinylmethyl)-4-oxo-1,4-dihydro-3-quinolinecarboxamide;

(82) N-(4-chlorobenzyl)-6-(4-morpholinylmethyl)-4-oxo-1-tetrahydro-2H-pyran-4-yl-1,4-dihydro-3-quinolinecarboxamide;

(83) N-(4-chlorobenzyl)-1-(1-methyl-4-piperidinyl)-6-(4-morpholinylmethyl)-4-oxo-1,4-dihydro-3-quinolinecarboxamide;

(84) N-(4-chlorobenzyl)-6-(4-morpholinylmethyl-4-oxo-1-(4-piperidinyl)-1,4-dihydro-3-quinolinecarboxamide;

(85) N-(4-chlorobenzyl-1-(1,1-dioxohexahydrothiopyran-4-yl)-6-(4-morpholinylmethyl)-4-oxo-1,4-dihydro-3-quinolinecarboxamide;
(86) N-(4-chlorobenzyl)-1-(4-morpholinyl)-6-(4-morpholinylmethyl)-4-oxo-1,4-dihydro-3-quinolinecarboxamide;
(87) N-(4-chlorobenzyl)-1-(4-methyl-1-piperazinyl)-6-(4-morpholinylmethyl)-4-oxo-1,4-dihydro-3-quinolinecarboxamide;
(88) N-(4-chlorobenzyl)-6-(4-morpholinylmethyl)-4-oxo-1-(1-piperidinyl)-1,4-dihydro-3-quinolinecarboxamide;
(89) N-(4-chlorobenzyl)-6-(4-morpholinylmethyl)-4-oxo-1-(1-pyrolidinyl)-1,4-dihydro-3-quinolinecarboxamide;
(90) N-(4-chlorobenzyl)-1-[(2R)-2-(methoxymethyl)pyrrolidinyl]-6-(4-morpholinylmethyl)-4-oxo-1,4-dihydro-3-quinolinecarboxamide;
(91) N-(4-chlorobenzyl)-1-(dimethylamino)-6-(4-morpholinylmethyl)-4-oxo-1,4-dihydro-3-quinolinecarboxamide;
(92) 1-amino-N-(4-chlorobenzyl)-6-(3-hydroxy-1-propynyl)-4-oxo-1,4-dihydro-3-quinolinecarboxamide;
(93) 1-amino-N-(4-chlorobenzyl)-6-(3-hydroxypropyl)-4-oxo-1,4-dihydro-3-quinolinecarboxamide;
(94) N-(4-chlorobenzyl)-1-(dimethylamino)-6-(3-hydroxy-1-propynyl)-4-oxo-1,4-dihydro-3-quinolinecarboxamide;
(95) 1-(allyloxy)-N-(4-chlorobenzyl)-4-oxo-1,4-dihydro-3-quinolinecarboxamide; or a pharmaceutically acceptable salt thereof.

64. A compound of claim 1 which is:
(1) 1-(sec-butyl)-N-(4-chlorobenzyl)-6-(3-hydroxy-1-propynyl)-4-oxo-1,4-dihydro-3-quinolinecarboxamide;
(2) 1-(sec-butyl)-N-(4-chlorobenzyl)-6-(3-hydroxy-1-propynyl)-8-methoxy-4-oxo-1,4-dihydro-3-quinolinecarboxamide;
(3) N-(4-chlorobenzyl)-6-[3-hydroxy-1-propenyl]-1-[2-(4-morpholinyl)ethyl]-4-oxo-1,4-dihydro-3-quinolinecarboxamide;
(4) N-(4-chlorobenzyl)-8-fluoro-6-(3-hydroxy-1-propynyl)-1-methyl-4-oxo-1,4-dihydro-3-quinolinecarboxamide;
(5) N-(4chlorobenzyl)-8-fluoro-6-[(Z)-3-hydroxy-1-propenyl]-1-methyl-4-oxo-1,4-dihydro-3-quinolinecarboxamide;
(6) N-(4-chlorobenzyl)-1-[2-(dimethylamino)ethyl]-6-(3-hydroxy-1-propynyl)-4-oxo-1,4-dihydro-3-quinolinecarboxamide hydrochloride;
(7) N-(4-chlorobenzyl)-6-(3-hydroxy-1-propynyl-4-oxo-1-[2-(1-piperidinyl)ethyl]-1,4-dihydro-3-quinolinecarboxamide;
(8) N-(4-chlorobenzyl)-6-(3-hydroxy-1-propynyl-4-oxo-1-[3-(1-piperidinyl)propyl]-1,4-dihydro-3-quinolinecarboxamide;
(9) N-(4-chlorobenzyl)-6-(3-hydroxy-1-propynyl)-1-[2-(1-methyl-2-pyrrolidinyl)ethyl]-4-oxo-1,4-dihydro-3-quinolinecarboxamide;
(10) N-(4-chlorobenzyl)-1-[2-(diisopropylamino)ethyl]-6-(3-hydroxy-1-propynyl)-4-oxo-1,4-dihydro-3-quinolinecarboxamide;
(11) N-(4-chlorobenzyl)-6-(3-hydroxy-1-propynyl)-4-oxo-1-[2-(1-pyrrolidinyl)ethyl]-1,4-dihydro-3-quinolinecarboxamide;
(12) N-(4-chlorobenzyl)-6-(3-hydroxy-1-propynyl)-1-[2-(4-morpholinyl)ethyl]-4-oxo-1,4-dihydro-3-quinolinecarboxamide;
(13) N-(4-chlorobenzyl)-1-[3-(dimethylamino)propyl]-6-(3-hydroxy-1-propynyl)-4-oxo-1,4-dihydro-3-quinolinecarboxamide;
(14) N-(4-chlorobenzyl)-6-(3-hydroxy-1-propynyl)-4-oxo-1-vinyl-1,4-dihydro-3-quinolinecarboxamide;
(15) N-(4-chlorobenzyl)-6-[(E)-3-hydroxy-1-propenyl]-1-methyl-4-oxo-1,4-dihydro-3-quinolinecarboxamide;
(16) N-(4-chlorobenzyl)-6-[(Z)-3-hydroxy-1-propenyl]-1-methyl-4-oxo-1,4-dihydro-3-quinolinecarboxamide;
(17) N-(4-chlorobenzyl)-1-cyclopropyl-6-(3-hydroxy-1-propynyl)-4-oxo-1,4-dihydro-3-quinolinecarboxamide;
(18) tert-butyl 2-[3-{[(4-chlorobenzyl)amino]carbonyl}-6-(3-hydroxy-1-propynyl)-4-oxo-1(4H)-quinolinyl]acetate;
(19) N-(4-chlorobenzyl)-1-(2-hydroxyethyl)-6-(3-hydroxy-1-propynyl)-4-oxo-1,4-dihydro-3-quinolinecarboxamide;
(20) N-(4-chlorobenzyl)-6-(3-hydroxy-1-propynyl)-1-methyl-4-oxo-1,4-dihydro-3-quinolinecarboxamide;
(21) 3-(3-{[(4-chlorobenzyl)amino]carbonyl}-1-methyl-4-oxo-1,4-dihydro-6-quinolinyl)propyl dihydrogen phosphate;
(22) di(tert-butyl) 3-(3-{[(4-chlorobenzyl)amino]carbonyl}-1-cyclopropyl-4-oxo-1,4-dihydro-6-quinolinyl)propyl phosphate;
(23) sodium 2-[{8-[3-(3-{[(4-chlorobenzyl)amino]carbonyl}-1-cyclopropyl-4-oxo-1,4-dihydro-6-quinolinyl)propoxy]-8-oxooctanoyl}(methyl)amino]-1-ethanesulfonate;
(24) sodium 2-[(8-{[3-(3-{[(4-chlorobenzyl)amino]carbonyl}-1-methyl-4-oxo-1,4-dihydro-6-quinolinyl)-2-propynyl]oxy}-8-oxooctanoyl)(methyl)amino]-1-ethanesulfonate;
(25) N-(4-chlorobenzyl)-6-(3-hydroxy-1-propynyl)-1-[2-(2-methoxyethoxy)ethyl]-4-oxo-1,4-dihydro-3-quinolinecarboxamide;
(26) N-(4-cyanobenzyl)-6-(3-hydroxy-1-propynyl)-1-methyl-4-oxo-1,4-dihydro-3-quinolinecarboxamide;
(27) N-(4-chlorobenzyl)-6-(3-hydroxy-1-propynyl)-4-oxo-1-propyl-1,4-dihydro-3-quinolinecarboxamide;
(28) 6-(azidomethyl)-N-(4-chlorobenzyl)-1-methyl-4-oxo-1,4-dihydro-3-quinolinecarboxamide;
(29) N-(4-chlorobenzyl)-6-(2,3-dihydro-4H-1,4-benzoxazin-4-ylmethyl)-1-methyl-4-oxo-1,4-dihydro-3-quinolinecarboxamide;
(30) N-(4-chlorobenzyl)-1-methyl-4-oxo-6-vinyl-1,4-dihydro-3-quinoline-carboxamide;
(31) N-(4-chlorobenzyl)-1-[2-(2-hydroxyethoxy)ethyl]-6-(3-hydroxy-1-propynyl)-4-oxo-1,4-dihydro-3-quinolinecarboxamide;
(32) N-(4-chlorobenzyl)-1-{2-[2-(2-methoxyethoxy)ethoxy]ethyl}-6-(4-morpholinylmethyl)-4-oxo-1,4-dihydro-3-quinolinecarboxamide;
(33) N-(4-chlorobenzyl)-1-[2-(2-hydroxyethoxy)ethyl]-6-(4-morpholinylmethyl-4-oxo-1,4-dihydro-3-quinolinecarboxamide;
(34) N-(4-chlorobenzyl)-1-[2-(2-ethoxyethoxy)ethyl]-6-(4-morpholinylmethyl)-4-oxo-1,4-dihydro-3-quinolinecarboxamide;
(35) N-(4-chlorobenzyl)-1-[2-(ethylsulfanyl)ethyl]-6-(4-morpholinylmethyl)-4-oxo-1,4-dihydro-3-quinolinecarboxamide;
(36) N-(4-chlorobenzyl)-1-[3-(methylsulfanyl)propyl]-6-(4-morpholinylmethyl)-4-oxo-1,4-dihydro-3-quinolinecarboxamide;
(37) N-(4-chlorobenzyl)-1-(4-hydroxy-2-butynyl)-6-(4-morpholinylmethyl)-4-oxo-1,4-dihydro-3-quinolinecarboxamide;
(38) N-(4-chlorobenzyl)-1-[3-(methylsulfinyl)propyl]-6-(4-morpholinylmethyl)-4-oxo-1,4-dihydro-3-quinolinecarboxamide;
(39) N-(4chlorobenzyl)-1-{3-[(3-hydroxypropyl)sulfanyl]propyl}-6-(4-morpholinylmethyl)-4-oxo-1,4-dihydro-3-quinolinecarboxamide;

(40) N-(4-chlorobenzyl)-1-[3-(methylsulfonyl)propyl]-6-(4-morpholinylmethyl)-4-oxo-1,4-dihydro-3-quinolinecarboxanide;
(41) N-(4-chlorobenzyl)-1-[2-(ethylsulfinyl)ethyl]-6-(4-morpholinylmethyl)-4-oxo-1,4-dihydro-3-quinolinecarboxamide;
(42) N-(4-chlorobenzyl)-1-[2-(ethylsulfonyl)ethyl]-6-(4-morpholinylmethyl)-4-oxo-1,4-dihydro-3-quinolinecarboxamide;
(43) N-(4-chlorobenzyl)-1-{3-[(3-hydroxypropyl)sulfinyl]propyl}-6-(4-morpholinylmethyl)-4-oxo-1,4-dihydro-3-quinolinecarboxamide;
(44) N-(4-chlorobenzyl)-1-{3-[(3-hydroxypropyl)sulfonyl]propyl}-6-(4-morpholinylmethyl)-4-oxo-1,4-dihydro-3-quinolinecarboxamide;
(45) N-(4-chlorobenzyl)-6-(4-morpholinylmethyl)-4-oxo-1-[2-(phenylsulfanyl)ethyl]-1,4-dihydro-3-quinolinecarboxamide;
(46) N-(4-chlorobenzyl)-1-[(methylsulfanyl)methyl]-6-(4-morpholinylmethyl)-4-oxo-1,4-dihydro-3-quinolinecarboxamide;
(47) N-(4-chlorobenzyl)-6-{[[2-hydroxy-2-(4-hydroxyphenyl)ethyl](methyl)amino]methyl}-1-methyl-4-oxo-1,4-dihydro-3-quinolinecarboxamide;
(48) N-(4-chlorobenzyl)-6-[(3-hydroxy-1-azetidinyl)methyl]-1-methyl-4-oxo-1,4-dihydro-3-quinolinecarboxamide;
(49) N-(4-chlorobenzyl)-6-(4-morpholinylmethyl-4-oxo-1-[(phenylsulfanyl)-methyl]-1,4-dihydro-3-quinolinecarboxamide;
(50) N-(4-chlorobenzyl)-6-{[[2-hydroxy-2-(4-hydroxy-3-methoxyphenyl)ethyl]-(methyl)amino]methyl}-1-methyl-4-oxo-1,4-dihydro-3-quinolinecarboxamide;
(51) N-(4-chlorobenzyl)-6-[(3,3-dihydroxy-1-azetidinyl)methyl]-1-methyl-4-oxo-1,4-dihydro-3-quinolinecarboxamide;
(52) N-(4-chlorobenzyl)-1-[(methylsulfinyl)methyl]-6-(4-morpholinylmethyl)-4-oxo-1,4-dihydro-3-quinolinecarboxamide;
(53) N-(4-chlorobenzyl)-1-[(methylsulfonyl)methyl]-6-(4-morpholinylmethyl)-4-oxo-1,4-dihydro-3-quinolinecarboxamide;
(54) N-(4-chlorobenzyl)-6-(4-morpholinylmethyl-4-oxo-1-[(phenylsulfinyl)-methyl]-1,4-dihydro-3-quinolinecarboxamide;
(55) N-(4-chlorobenzyl)-6-(4-morpholinylmethyl-4-oxo-1-[(phenylsulfonyl)-methyl]-1,4-dihydro-3-quinolinecarboxamide;
(56) N-(4-chlorobenzyl)-6-(3-hydroxypropyl)-1-[2-(2-methoxyethoxy)ethyl]-4-oxo-1,4-dihydro-3-quinolinecarboxamide;
(57) N-(4-chlorobenzyl)-1-[2-(2-methoxyethoxy)ethyl]-6-(4-morpholinylmethyl)-4-oxo-1,4-dihydro-3-quinolinecarboxamide;
(58) N-(4-chlorobenzyl)-1-[2-(2-methoxyethoxy)ethyl]-4-oxo-6-[(4-oxo-1-piperidinyl)methyl]-1,4-dihydro-3-quinolinecarboxamide;
(59) N-(4-chlorobenzyl)-6-{[(3R)-3-hydroxypyrrolidinyl]methyl}-1-[2-(2-methoxyethoxy)ethyl]-4-oxo-1,4-dihydro-3-quinolinecarboxanide;
(60) N-(4-chlorobenzyl)-6-{[[2-hydroxy-2-(4-hydroxyphenyl)ethyl](methyl)amino]methyl}-1-[2-(2-methoxyethoxy)ethyl]-4-oxo-1,4-dihydro-3-quinolinecarboxamide;
(61) 1-{2-[2-(tert-butoxy)ethoxy]ethyl-N-(4-chlorobenzyl)-6-(4-morpholinyl-methyl)-4-oxo-1,4-dihydro-3-quinolinecarboxamide;
(62) 1-{2-[2-(tert-butoxy)ethoxy]ethyl-N-(4-chlorobenzyl)-6-{[[2-hydroxy-2-(4-hydroxyphenyl)ethyl](methyl)amino]methyl-4-oxo-1,4-dihydro-3-quinolinecarboxamide;
(63) N-(4-chlorobenzyl)-6-(3-hydroxy-1-propynyl)-1-methyl-4-oxo-1,4-dihydro-3-quinolinecarbothioamide;
(64) N-(4-chlorobenzyl)-8-(3-hydroxy-1-propynyl)-1-methyl-4-oxo-1,4-dihydro-3-quinolinecarboxamide;
(65) N-(4-chlorobenzyl)-8-(4-hydroxy-1-butynyl)-1-methyl-4-oxo-1,4-dihydro-3-quinolinecarboxamide;
(66) N-(4-chlorobenzyl)-6-{[3-(hydroxyimino)-1-azetidinyl]methyl}-1-methyl-4-oxo-1,4-dihydro-3-quinolinecarboxamide;
(67) N-(4-chlorobenzyl)-1-{2-[2-(4-morpholinyl)ethoxy]ethyl}-6-(4-morpholinylmethyl)-4-oxo-1,4-dihydro-3-quinolinecarboxamide;
(68) N-(4-chlorobenzyl)-1-([(4-chlorophenyl)sulfanyl]methyl)-6-(4-morpholinylmethyl)-4-oxo-1,4-dihydro-3-quinolinecarboxamide;
(69) N-(4-chlorobenzyl)-1-([(4-chlorophenyl)sulfinyl]methyl)-6-(4-morpholinylmethyl)-4-oxo-1,4-dihydro-3-quinolinecarboxamide;
(70) N-(4-chlorobenzyl)-1-([(4-chlorophenyl)sulfonyl]methyl)-6-(4-morpholinylmethyl)-4-oxo-1,4-dihydro-3-quinolinecarboxamide;
(71) N-(4-chlorobenzyl)-1-[(2-methoxyethoxy)methyl]-6-(4-morpholinylmethyl)-4-oxo-1,4-dihydro-3-quinolinecarboxamide;
(72) 2-{[3-{[(4-chlorobenzyl)amino]carbonyl}-6-(4-morpholinylmethyl)-4-oxo-1(4H)quinolinyl]methoxy}ethyl benzoate;
(73) N-(4-chlorobenzyl)-1-[(2-hydroxyethoxy)methyl]-6-(4-morpholinylmethyl)-4-oxo-1,4-dihydro-3-quinolinecarboxamide;
(74) N-(4-chlorobenzyl)-6-(4-morpbolinylmethyl)-4-oxo-1-tetrahydro-2H-pyran-4-yl-1,4-dihydro-3-quinolinecarboxamide;
(75) N-(4-chlorobenzyl)-1-(1-methyl-4-piperidinyl)-6-(4-morpholinylmethyl-4-oxo-1,4-dihydro-3-quinolinecarboxamide;
(76) N-(4-chlorobenzyl)-6-(4-morpholinylmethyl)-4-oxo-1-(4-piperidinyl)-1,4-dihydro-3-quinolinecarboxamide;
(77) N-(4-chlorobenzyl)-1-(1,1-dioxohexahydrothiopyran-4-yl)-6-(4-morpholinylmethyl)-4-oxo-1,4-dihydro-3-quinolinecarboxamide;
(78) N-(4-chlorobenzyl)-1-(4-morpholinyl)-6-(4-morpholinylmethyl)-4-oxo-1,4-dihydro-3-quinolinecarboxamide;
(89) N-(4-chlorobenzyl)-1-(4-methyl-1-piperazinyl)-6-(4-morpholinylmethyl)-4-oxo-1,4-dihydro-3-quinolinecarboxamide;
(80) N-(4-chlorobenzyl)-6-(4-morpholinylmethyl)-4-oxo-1-(1-piperidinyl)-1,4-dihydro-3-quinolinecarboxamide;
(81) N-(4-chlorobenzyl)-1-(dimethylamino)-6-(4-morpholinylmethyl)-4-oxo-1,4-dihydro-3-quinolinecarboxamide;
(82) 1-amino-N-(4-chlorobenzyl)-6-(3-hydroxy-1-propynyl)-4-oxo-1,4-dihydro-3-quinolinecarboxamide;
(83) 1-amino-N-(4-chlorobenzyl)-6-(3-hydroxypropyl)-4-oxo-1,4-dihydro-3-quinolinecarboxamide; or a pharmaceutically acceptable salt thereof.
65. A compound of claim 1 which is
(1) N-(4-chlorobenzyl)-8-fluoro-6-[(Z)-3-hydroxy-1-propenyl]-1-methyl-4-oxo-1,4-dihydro-3-quinolinecarboxamide;
(2) N-(4-chlorobenzyl)-6-(3-hydroxy-1-propynyl)-1-[2-(4-morpholinyl)ethyl]4-oxo-1,4-dihydro-3-quinolinecarboxamide;

(3) N-(4-chlorobenzyl)-6-(3-hydroxy-1-propynyl)-4-oxo-1-vinyl-1,4-dihydro-3-quinolinecarboxamide;

(4) N-(4-chlorobenzyl)-6-[(Z)-3-hydroxy-1-propenyl]-1-methyl-4-oxo-1,4-dihydro-3-quinolinecarboxamide;

(5) N-(4-chlorobenzyl)-1-cyclopropyl-6-(3-hydroxy-1-propynyl)-4-oxo-1,4-dihydro-3-quinolinecarboxamide;

(6) N-(4-chlorobenzyl)-1-(2-hydroxyethyl)-6-(3-hydroxy-1-propynyl)-4-oxo-1,4-dihydro-3-quinolinecarboxamide;

(7) N-(4-chlorobenzyl)-6-(3-hydroxy-1-propynyl)-1-methyl-4-oxo-1,4-dihydro-3-quinolinecarboxamide;

(8) 3-(3-{[(4-chlorobenzyl)amino]carbonyl I -1-methyl-4-oxo-1,4-dihydro-6-quinolinyl)propyl dihydrogen phosphate;

(9) sodium 2-[(8-{[3-(3-{[(4-chlorobenzyl)amino]carbonyl}-1-methyl-4-oxo-1,4-dihydro-6-quinolinyl)-2-propynyl]oxy}-8-oxooctanoyl)(methyl)amino]-1-ethanesulfonate;

(10) N-(4-chlorobenzyl)-6-(3-hydroxy-1-propynyl)-1-[2-(2-methoxyethoxy)-ethyl]-4-oxo-1,4-dihydro-3-quinolinecarboxamide;

(11) N-(4-chlorobenzyl)-1-methyl-4-oxo-6-vinyl-1,4-dihydro-3-quinolinecarboxamide;

(12) N-(4-chlorobenzyl)-1-[2-(2-hydroxyethoxy)ethyl]-6-(3-hydroxy-1-propynyl)-4-oxo-1,4-dihydro-3-quinolinecarboxamide;

(13) N-(4-chlorobenzyl)-1-[2-(2-hydroxyethoxy)ethyl]-6-(4-morpholinylmethyl)-4-oxo-1,4-dihydro-3-quinolinecarboxamide;

(14) N-(4-chlorobenzyl)-1-[2-(2-ethoxyethoxy)ethyl]-6-(4-morpholinylmethyl)-4-oxo-1,4-dihydro-3-quinolinecarboxamide;

(15) N-(4-chlorobenzyl)-1-[2-(ethylsulfanyl)ethyl]-6-(4-morpholinylmethyl)-4-oxo-1,4-dihydro-3-quinolinecarboxamide;

(16) N-(4-chlorobenzyl)-1-[3-(methylsulfanyl)propyl]-6-(4-morpholinylmethyl)-4-oxo-1,4-dihydro-3-quinolinecarboxamide;

(17) N-(4-chlorobenzyl)-1-(4-hydroxy-2-butynyl)-6-(4-morpholinylmethyl)-4-oxo-1,4-dihydro-3-quinolinecarboxamide;

(18) N-(4-chlorobenzyl)-1-[3-(methylsulfinyl)propyl]-6-(4-morpholinylmethyl)-4-oxo-1,4-dihydro-3-quinolinecarboxamide;

(19) N-(4-chlorobenzyl)-1-(3-[(3-hydroxypropyl)sulfanyl]propyl}-6-(4-morpholinylmethyl)-4-oxo-1,4-dihydro-3-quinolinecarboxamide;

(20) N-(4-chlorobenzyl)-1-[3-(methylsulfonyl)propyl]-6-(4-morpholinylmethyl)-4-oxo-1,4-dihydro-3-quinolinecarboxamide;

(21) N-(4-chlorobenzyl)-1-[2-(ethylsulfinyl)ethyl]-6-(4-morpholinylmethyl)-4-oxo-1,4-dihydro-3-quinolinecarboxamide;

(22) N-(4-chlorobenzyl)-1-[2-(ethylsulfonyl)ethyl]-6-(4-morpholinylmethyl)-4-oxo-1,4-dihydro-3-quinolinecarboxamide;

(23) N-(4-chlorobenzyl)-1-{3-[(3-hydroxypropyl)sulfonyl]propyl}-6-(4-morpholinylmethyl)-4-oxo-1,4-dihydro-3-quinolinecarboxamide;

(24) N-(4-chlorobenzyl)-6-(4-morpholinylmethyl)-4-oxo-1-[2-(phenylsulfanyl)ethyl]-1,4-dihydro-3-quinolinecarboxamide;

(25) N-(4-chlorobenzyl)-1-[(methylsulfanyl)methyl]-6-(4-morpholinylmethyl)-4-oxo-1,4-dihydro-3-quinolinecarboxamide;

(26) N-(4-chlorobenzyl)-6-{[[2-hydroxy-2-(4-hydroxyphenyl)ethyl](methyl)amino]methyl}-1-methyl-4-oxo-1,4-dihydro-3-quinolinecarboxamide;

(27) N-(4-chlorobenzyl)-6-(4-morpholinylmethyl)-4-oxo-1-[(phenylsulfanyl)-methyl]-1,4-dihydro-3-quinolinecarboxamide;

(28) N-(4-chlorobenzyl)-6-{[[2-hydroxy-2-(4-hydroxy-3-methoxyphenyl)ethyl](methyl)amino]methyl}-1-methyl-4-oxo-1,4-dihydro-3-quinolinecarboxamide;

(29) N-(4-chlorobenzyl)-6-[(3,3-dihydroxy-1-azetidinyl)methyl]-1-methyl-4-oxo-1,4-dihydro-3-quinolinecarboxamide;

(30) N-(4-chlorobenzyl)-1-[(methylsulfinyl)methyl]-6-(4-morpholinylmethyl)-4-oxo-1,4-dihydro-3-quinolinecarboxamide;

(31) N-(4-chlorobenzyl)-1-[(methylsulfonyl)methyl]-6-(4-morpholinylmethyl)-4-oxo-1,4-dihydro-3-quinolinecarboxamide;

(32) N-(4-chlorobenzyl)-6-(4-morpholinylmethyl)-4-oxo-1-[(phenylsulfinyl)-methyl]-1,4-dihydro-3-quinolinecarboxamide;

(33) N-(4-chlorobenzyl)-6-(4-morpholinylmethyl)-4-oxo-1-[(phenylsulfonyl)-methyl]-1,4-dihydro-3-quinolinecarboxamide;

(34) N-(4-chlorobenzyl)-6-(3-hydroxypropyl)-1-[2-(2-methoxyethoxy)ethyl]-4-oxo-1,4-dihydro-3-quinolinecarboxamide;

(35) N-(4-chlorobenzyl)-1-[2-(2-methoxyethoxy)ethyl]-6-(4-morpholinylmethyl)-4-oxo-1,4-dihydro-3-quinolinecarboxamide;

(36) 1-{2-[2-(tert-butoxy)ethoxy]ethyl-N-(4-chlorobenzyl)-6-(4-morpholinyl-methyl)-4-oxo-1,4-dihydro-3-quinolinecarboxamide;

(37) N-(4-chlorobenzyl)-6-(3-hydroxy-1-propynyl)-1-methyl-4-oxo-1,4-dihydro-3-quinolinecarbothioamide;

(38) N-(4-chlorobenzyl)-8-(3-hydroxy-1-propynyl)-1-methyl-4-oxo-1,4-dihydro-3-quinolinecarboxamide;

(39) N-(4-chlorobenzyl)-8-(4-hydroxy-1-butynyl)-1-methyl-4-oxo-1,4-dihydro-3-quinolinecarboxamide;

(40) N-(4-chlorobenzyl)-1-([(4-chlorophenyl)sulfanyl]methyl)-6-(4-morpholinylmethyl)-4-oxo-1,4-dihydro-3-quinolinecarboxamide;

(41) N-(4-chlorobenzyl)-1-([(4-chlorophenyl)sulfinyl]methyl)-6-(4-morpholinylmethyl)-4-oxo-1,4-dihydro-3-quinolinecarboxamide;

(42) N-(4-chlorobenzyl)-1-[(2-methoxyethoxy)methyl]-6-(4-morpholinylmethyl)-4-oxo-1,4-dihydro-3-quinolinecarboxamide;

(43) 2-{[3-{[(4-chlorobenzyl)amino]carbonyl}-6-(4-morpholinylmethyl)-4-oxo-1-(4H)quinolinyl]methoxy}ethyl benzoate;

(44) N-(4-chlorobenzyl)-1-[(2-hydroxyethoxy)methyl]-6-(4-morpholinylmethyl)-4-oxo-1,4-dihydro-3-quinolinecarboxamide;

(45) N-(4-chlorobenzyl)-6-(4-morpholinylmethyl-4-oxo-1-tetrahydro-2H-pyran-4-yl-1,4-dihydro-3-quinolinecarboxamide;

(46) N-(4-chlorobenzyl)-1-(1-methyl-4-piperidinyl)-6-(4-morpholinylmethyl)-4-oxo-1,4-dihydro-3-quinolinecarboxamide;

(47) N-(4-chlorobenzyl)-6-(4-morpholinylmethyl-4-oxo-1-(4-piperidinyl)-1,4-dihydro-3-quinolinecarboxamide;

(48) N-(4-chlorobenzyl)-1-(1,1-dioxohexahydrothiopyran-4-yl)-6-(4-morpholinylmethyl)-4-oxo-1,4-dihydro-3-quinolinecarboxamide;

(49) N-(4-chlorobenzyl)-1-(4-morpholinyl)-6-(4-morpholinylmethyl)-4-oxo-1,4-dihydro-3-quinolinecarboxamide;

(50) 1-amino-N-(4-chlorobenzyl)-6-(3-hydroxy-1-propynyl)-4-oxo-1,4-dihydro-3-quinolinecarboxamide;

(51) 1-amino-N-(4-chlorobenzyl)-6-(3-hydroxypropyl)-4-oxo-1,4-dihydro-3-quinolinecarboxamide; or a pharmaceutically acceptable salt thereof.

66. A compound claim 1 which is
(5) N-(4-chlorobenzyl)-1-methyl-4-oxo-6-(tetrahydro-2H-pyran-4-ylmethyl)-1,4-dihydro-3-quinolinecarboxamide;
(5) N-(4-chlorobenzyl)-1-methyl-6-(4-morpholinylmethyl)-4-oxo-1,4-dihydro-3-quinolinecarbothioamide;
(5) N-(4-chlorobenzyl)-8-(2-hydroxyethoxy)-6-(3-hydroxypropyl)-1-methyl-4-oxo-1,4-dihydro-3-quinolinecarboxamide;
(5) N-(4-chlorobenzyl)-1-cyclopropyl-6-(3-hydroxypropyl)-4-oxo-1,4-dihydro-3-quinolinecarboxamid;
(5) 1-{2-[bis(2-hydroxyethyl)amino]ethyl}-N-(4-chlorobenzyl)-6-(4-morpholinylmethyl)-4-oxo-1,4-dihydro-3-quinolinecarboxamide; or a pharmaceutically acceptable salt thereof.

67. A compound of claim 1 which is:
(1) N-(4-chlorobenzyl)-8-[2-hydroxy-1-(hydroxymethyl)ethoxy]-6-(3-hydroxypropyl)-1-methyl-4-oxo-1,4-dihydro-3-quinolinecarboxamide;
(2) N-(4-chlorobenzyl)-8-fluoro-6-(hydroxymethyl)-4-oxo-1-[3-(tetrahydro-2H-pyran-2-yloxy)propyl]-1,4-dihydro-3-quinolinecarboxamide;
(3) N-(4-chlorobenzyl)-6-[ethyl(2-hydroxyethyl)amino]-1-methyl-4-oxo 1,4-dihydro-3-quinolinecarboxamide;
(4) N-(4-chlorobenzyl)-1-cyclopropyl-6-(4-morpholinylmethyl)-4-oxo-1,4-dihydro-3-quinolinecarboxamide;
(5) 6-{[bis(2-hydroxyethyl)amino]methyl}-N-(4-chlorobenzyl)-1-methyl-4-oxo-1,4-dihydro-3-quinolinecarboxamide;
(6) N-(4-chlorobenzyl)-6-{[(2-hydroxyethyl)(methyl)amino]methyl}-1-methyl-4-oxo-1,4-dihydro-3-quinolinecarboxamide;
(7) 6-((benzyl(2-hydroxyethyl)amino)methyl)-N-(4-chlorobenzyl)-1-methyl-4-oxo-1,4-dihydro-3-quinolinecarboxamide;
(8) N-(4-chlorobenzyl)-6-[(4,4-difluoro-1-piperidinyl)methyl]-1-methyl-4oxo-1,4-dihydro-3-quinolinecarboxamide;
(9) N-(4-chlorobenzyl)-6-{[4-fluoro-3,6-dihydro-1(2H)-pyridinyl]methyl}-1methyl-4-oxo-1,4-dihydro-3-quinolinecarboxamide; or a pharmaceutically acceptable salt thereof.

68. A compound of claim 1 which is:
(1) N-(4-chlorobenzyl)-1-[2-(2-hydroxyethoxy)ethyl]-6-(3-hydroxy-1-propynyl)-4-oxo-1,4-dihydro-3-quinolinecarboxamide;
(2) N-(4-chlorobenzyl)-6-{[[2-hydroxy-2-(4-hydroxyphenyl)ethyl](methyl)amino]methyl}-1-methyl-4-oxo-1,4-dihydro-3-quinolinecarboxamide;
(3) N-(4-chlorobenzyl)-6-{[[2-hydroxy-2-(4-hydroxy-3-methoxyphenyl)ethyl](methyl)amino]methyl}-1-methyl-4-oxo-1,4-dihydro-3-quinolinecarboxamide;
(4) N-(4-chlorobenzyl)-6-[(3,3-dihydroxy-1-azetidinyl)methyl]-1-methyl-4-oxo-1,4-dihydro-3-quinolinecarboxamide;
(5) N-(4-chlorobenzyl)-8-fluoro-6-[(Z)-3-hydroxy-1-propenyl]-1-methyl-4-oxo-1,4-dihydro-3-quinolinecarboxamide;
(6) N-(4-chlorobenzyl)-6-(3-hydroxy-1-propynyl)-1-[2-(4-morpholinyl)ethyl]-4-oxo-1,4-dihydro-3-quinolinecarboxamide;
(7) N-(4-chlorobenzyl)-6-[(Z)-3-hydroxy-1-propenyl]-1-methyl-4-oxo-1,4-dihydro-3-quinolinecarboxamide;
(8) N-(4-chlorobenzyl)-1-cyclopropyl-6-(3-hydroxy-1-propynyl)-4-oxo-1,4-dihydro-3-quinolinecarboxamide;
(9) N-(4-chlorobenzyl)-1-(2-hydroxyethyl)-6-(3-hydroxy-1-propynyl)-4-oxo-1,4-dihydro-3-quinolinecarboxamide;
(10) N-(4-chlorobenzyl)-6-(3-hydroxy-1-propynyl)-1-methyl-4-oxo-1,4-dihydro-3-quinolinecarboxamide;
(11) N-(4-chlorobenzyl)-6-(3-hydroxy-1-propynyl)-1-[2-(2-methoxyethoxy)ethyl]-4-oxo-1,4-dihydro-3-quinolinecarboxamide;
(12) N-(4-chlorobenzyl)-6-(3-hydroxy-1-propynyl)-1-methyl-4-oxo-1,4-dihydro-3-quinolinecarbothioamide;
(13) N-(4-chlorobenzyl)-8-(3-hydroxy-1-propynyl)-1-methyl-4-oxo-1,4-dihydro-3-quinolinecarboxamide;
(14) N-(4-chlorobenzyl)-8-(4-hydroxy-1-butynyl)-1-methyl-4-oxo-1,4-dihydro-3-quinolinecarboxamide;
(15) N-(4-chlorobenzyl)-1-methyl-4-oxo-6-(tetrahydro-2H-pyran-4-ylmethyl)-1,4-dihydro-3-quinolinecarboxamide; or a pharmaceutically acceptable salt thereof.

69. The compound of claim 1 which is:
(1) N-(4-chlorobenzyl)-1-(4-morpholinyl)-6-(4-morpholinylmethyl)-4-oxo-1,4-dihydro-3-quinolinecarboxamide;
(2) 1-amino-N-(4-chlorobenzyl)-6-(3-hydroxy-1-propynyl)-4-oxo-1,4-dihydro-3-quinolinecarboxamide;
(3) 1-amino-N-(4-chlorobenzyl)-6-(3-hydroxypropyl)-4-oxo-1,4-dihydro-3-quinolinecarboxamide;
(4) N-(4-bromobenzyl)-1-(4-morpholinyl)-6-(4-morpholinylmethyl)-4-oxo-1,4-dihydro-3-quinolinecarboxamide;
(5) N-(4-fluorobenzyl)-1-(4-morpholinyl)-6-(4-morpholinylmethyl)-4-oxo-1,4-dihydro-3-quinolinecarboxamide; or a pharmaceutically acceptable salt thereof.

70. The compound of claim 1 which is:
(1) N-(4-chlorobenzyl)-1-{[(4-chlorophenyl)sulfanyl]methyl}-6-(4-morpholinylmethyl)-4-oxo-1,4-dihydro-3-quinolinecarboxamide;
(2) N-(4-chlorobenzyl)-1-{[(4-chlorophenyl)sulfinyl]methyl}-6-(4-morpholinylmethyl)-4-oxo-1,4-dihydro-3-quinolinecarboxamide;
(3) N-(4-chlorobenzyl)-1-[(2-methoxyethoxy)methyl]-6-(4-morpholinylmethyl-4-oxo-1,4-dihydro-3-quinolinecarboxamide;
(4) 2-{[3-{[(4-chlorobenzyl)amino]carbonyl}-6-(4-morpholinylmethyl)-4-oxo-1(4H)quinolinyl]methoxy}ethyl benzoate;
(5) N-(4-chlorobenzyl)-1-[(2-hydroxyethoxy)methyl]-6-(4-morpholinylmethyl)-4-oxo-1,4-dihydro-3-quinolinecarboxamide;
(6) N-(4-chlorobenzyl)-6-(4-morpholinylmethyl)-4-oxo-1-tetrahydro-2H-pyran-4-yl-1,4-dihydro-3-quinolinecarboxamide;
(7) N-(4-chlorobenzyl)-1-(1-methyl)-4-piperidinyl)-6-(4-morpholinylmethyl-4-oxo-1,4-dihydro-3-quinolinecarboxamide;
(8) N-(4-chlorobenzyl)-6-(4-morpholinylmethyl)-4-oxo-1-(4-piperidinyl)-1,4-dihydro-3-quinolinecarboxamide;
(9) N-(4-chlorobenzyl)-1-(1,1-dioxohexahydro-1lambda~6~-thiopyran-4-yl)-6-(4-morpholinylmethyl)-4-oxo-1,4-dihydro-3-quinolinecarboxamide;
(10) N-(4-chlorobenzyl)-1-(4-morpholinyl)-6-(4-morpholinylmethyl)-4-oxo-1,4-dihydro-3-quinolinecarboxamide;
(11) N-(4-chlorobenzyl) 1-[2-(2-hydroxyethoxy)ethyl]-6-(4-morpholinylmethyl)-4-oxo-1,4-dihydro-3-quinolinecarboxamide;
(12) N-(4-chlorobenzyl)-1-[2-(2-ethoxyethoxy)ethyl]-6-(4-morpholinylmethyl)-4-oxo-1,4-dihydro-3-quinolinecarboxamide:

(13) N-(4-chlorobenzyl)-1-[2-(ethylsulfanyl)ethyl]-6-(4-morpholinylmethyl)-4-oxo-1,4-dihydro-3-quinolinecarboxamide;
(14) N-(4-chlorobenzyl)-1-[3-(methylsulfanyl)propyl]-6-(4-morpholinylmethyl)-4-oxo-1,4-dihydro-3-quinolinecarboxamide;
(15) N-(4-chlorobenzyl)-1-(4-hydroxy-2-butynyl)-6-(4-morpholinylmethyl)-4-oxo-1,4-dihydro-3-quinolinecarboxamide;
(16) 1-{2-[bis(2-hydroxyethyl)amino]ethyl}-N-(4-chlorobenzyl)-6-(4-morpholinylmethyl)-4-oxo-1,4-dihydro-3-quinolinecarboxamide;
(17) N-(4-chlorobenzyl)-1-[3-(methylsulfinyl)propyl]-6-(4-morpholinylmethyl)-4-oxo-1,4-dihydro-3-quinolinecarboxamide;
(18) N-(4-chlorobenzyl)-1-{(3-[(3-hydroxypropyl)sulfanyl]propyl}-6-(4-morpholinylmethyl)-4-oxo-1,4-dihydro-3-quinolinecarboxamide;
(19) N-(4-chlorobenzyl)-1-[3-(methylsulfonyl)propyl]-6-(4-morpholinylmethyl)-4-oxo-1,4-dihydro-3-quinolinecarboxamide;
(20) N-(4-chlorobenzyl)-1-[2-(ethylsulfinyl)ethyl]-6-(4-morpholinylmethyl)-4-oxo-1,4-dihydro-3-quinolinecarboxamide;
(21) N-(4-chlorobenzyl)-1-[2-(ethylsulfonyl)ethyl]-6-(4-morpholinylmethyl)-4-oxo-1,4-dihydro-3-quinolinecarboxamide;
(22) N-(4-chlorobenzyl)-1-{3-[(3-hydroxypropyl)sulfonyl]propyl}-6-(4-morpholinylmethyl)-4-oxo-1,4-dihydro-3-quinolinecarboxamide;
(23) N-(4-chlorobenzyl)-6-(4-morpholinylmethyl)-4-oxo-1-[2-(phenylsulfanyl)ethyl]-1,4-dihydro-3-quinolinecarboxamide;
(24) N-(4-chlorobenzyl)-1-[(methylsulfanyl)methyl]-6-(4-morpholinylmethyl)-4-oxo-1,4-dihydro-3-quinolinecarboxamide;
(25) N-(4-chlorobenzyl)-6-(4-morpholinylmethyl)-4-oxo-1-[(phenylsulfanyl)methyl]-1,4-dihydro-3-quinolinecarboxamide;
(26) N-(4-chlorobenzyl)-1-[(methylsulfinyl)methyl]-6-(4-morpholinylmethyl)-4-oxo-1,4-dihydro-3-quinolinecarboxamide;
(27) N-(4-chlorobenzyl)-1-[(methylsulfonyl)methyl]-6-(4-morpholinylmethyl)-4-oxo-1,4-dihydro-3-quinolinecarboxamide;
(28) N-(4-chlorobenzyl)-6-(4-morpholinylmethyl)-4-oxo-1-[(phenylsulfinyl)methyl]-1,4-dihydro-3-quinolinecarboxamide;
(29) N-(4-chlorobenzyl)-6-(4-morpholinylmethyl)-4-oxo-1-[(phenylsulfonyl)methyl]-1,4-dihydro-3-quinolinecarboxamide;
(30) N-(4-chlorobenzyl)-1-[2-(2-methoxyethoxy)ethyl]-6-(4-morpholinylmethyl)-4-oxo-1,4-dihydro-3-quinolinecarboxamide;
(31) 1-{2-[2-(tert-butoxy)ethoxy]ethyl}-N-(4-chlorobenzyl)-6-(4-morpholinylmethyl)-4-oxo-1,4-dihydro-3-quinolinecarboxamide;
(32) N-(4-chlorobenzyl)-1-cyclopropyl-6-(4-morpholinylmethyl)-4-oxo-1,4-dihydro-3-quinolinecarboxamide; or a pharmaceutically acceptable salt thereof.

71. A pharmaceutical composition comprising a compound of claim 1 and a pharmaceutically acceptable carrier.

72. A method for inhibiting a viral DNA polymerase, comprising contacting the polymerase with an effective inhibitory amount of a compound of claim 1.

73. The method of claim 72 wherein the polymerase and the compound are contacted in vitro.

74. The method of claim 72 wherein the polymerase and the compound are contacted in vivo.

75. A method of treating infections from herpesviruses which comprises administering to a patient in need thereof an effective amount of a compound of formula I as shown in claim 1.

76. The method of claim 75 wherein said herpesviruses is herpes simplex virus types 1, herpes simplex virus types 2, varicella zoster virus, cytomegalovirus, Epstein-Barr virus, human herpes viruses 6, human herpes viruses 7 or human herpes viruses.

77. The method of claim 75 wherein said herpesviruses is herpes simplex virus types 1, herpes simplex virus types 2, varicella zoster virus, cytomegalovirus, Epstein-Barr virus, human herpes viruses 7 or human herpes viruses.

78. The method of claim 75 wherein said herpesviruses is human cytomegalovirus.

79. The method of claim 75 wherein the effective amount of a compound of claim 1 is administered orally, parenterally or topically.

80. The method of claim 75 wherein the effective amount of a compound of claim 1 is in an amount of from about 0.1 to about 300 mg/kg of body weight.

81. The method of claim 75 wherein the effective amount of a compound of claim 1 is in an amount of from about 1 to about 30 mg/kg of body weight.

* * * * *

UNITED STATES PATENT AND TRADEMARK OFFICE
CERTIFICATE OF CORRECTION

PATENT NO. : 6,248,739 B1  Page 1 of 1
DATED : June 19, 2001
INVENTOR(S) : Turner et al.

It is certified that error appears in the above-identified patent and that said Letters Patent is hereby corrected as shown below:

<u>Column 160,</u>
Line 47, change "E)-CH ≡ CHC" to -- E)-CH = CHC --

Signed and Sealed this

Nineteenth Day of October, 2004

JON W. DUDAS
*Director of the United States Patent and Trademark Office*